United States Patent
Jørgensen et al.

(10) Patent No.: US 12,055,537 B2
(45) Date of Patent: Aug. 6, 2024

(54) EXTRACELLULAR VESICLES PURIFIED FROM DRIED BLOOD CARDS

(71) Applicant: REGION NORDJYLLAND, AALBORG UNIVERSITY HOSPITAL, Aalborg Øst (DK)

(72) Inventors: Malene Møller Jørgensen, Suldrup (DK); Rikke Bæk, Aalborg (DK)

(73) Assignee: Region Nordjylland, Aalborg University Hospital, Aalborg Øst (DK)

( * ) Notice: Subject to any disclaimer, the term of this patent is extended or adjusted under 35 U.S.C. 154(b) by 1092 days.

(21) Appl. No.: 16/771,927

(22) PCT Filed: Dec. 13, 2018

(86) PCT No.: PCT/EP2018/084789
§ 371 (c)(1),
(2) Date: Jun. 11, 2020

(87) PCT Pub. No.: WO2019/115705
PCT Pub. Date: Jun. 20, 2019

(65) Prior Publication Data
US 2020/0393444 A1    Dec. 17, 2020

(30) Foreign Application Priority Data
Dec. 13, 2017   (EP) .................................. 17206867

(51) Int. Cl.
*G01N 33/50*    (2006.01)
*G01N 33/48*    (2006.01)
*G01N 33/68*    (2006.01)

(52) U.S. Cl.
CPC ......... *G01N 33/5002* (2013.01); *G01N 33/48* (2013.01); *G01N 33/68* (2013.01)

(58) Field of Classification Search
None
See application file for complete search history.

(56) References Cited

PUBLICATIONS

Baek, Rikke et al, "The impact of various preanalytical treatments on the phenotype of small extracellular vesicles in blood analyzed by protein microarray", Journal of Immunological Methods, vol. 438; 11-20, 2016.

Baek, Rikke et al., "Does smoking, age or gender affect the protein phenotype of extracellular vesicles in plasma?", Transfususion and Apheresis Science, vol. 55; 44-52, 2016.

Baek, Rikke et Jorgensen, Malene Moller, "Multiplexed Phenotyping of Small Extracellular Vesicles Using Protein Microarray (EV Array)", In the book: Hill A. (eds) Exosomes and Microvesicles: Methods in Molecular Biology, chapter 8, vol. 1545; Year 2016.

Jorgensen, Malene et al., "Extracellular Vesicle (EV) Array: microarray capturing of exosomes and other extracellular vesicles for multiplexed phenotyping", Journal Extracellular Vesicles, vol. 2, 2013.

Chen, Chihchen et al; "Paper-based Devices of Isolation and Characterization of Extracellular Vesicles"; Journal of Visualized Experiments; No. 98, Apr. 3, 2015.

Hsiao, Yi-Hsing et al; "Paper-Based for Isolation of Extracellular Vesicles"; Methods in Molecular Biology; 2018, vol. 1660, Aug. 22, 2017, pp. 43-54.

Lefterova, Martina I. et al; "Next-Generation Molecular Testing of Newbord Dried Blood Spots for Cystic Fibrosis"; The Journal of Molecular Diagnostics, vol. 18, No. 2, Mar. 1, 2016, pp. 267-282.

Neo et al; "Trehalose significantly enhances the recovery of serum and serum exosomal miRNA from a paperbased matrix"; Scientific Reports, vol. 7, No. 1; Nov. 30, 2017.

*Primary Examiner* — Allison M Fox
(74) *Attorney, Agent, or Firm* — Dinsmore & Shohl LLP

(57) ABSTRACT

A method is provided, which comprises providing a dried body fluid card sample, extracting body fluid from said dried body fluid card sample, and detecting gene products associated with extracellular vesicles. An application of the method is also applied for diagnosing and/or prognosing a clinical condition, where gene products associated with a population of extracellular vesicles and gene products associated with the clinical condition are detected.

18 Claims, 24 Drawing Sheets

Specification includes a Sequence Listing.

SEQUENCE LISTING

<160> NUMBER OF SEQ ID NOS: 87

<210> SEQ ID NO 1
<211> LENGTH: 377
<212> TYPE: PRT
<213> ORGANISM: Homo sapiens

<400> SEQUENCE: 1

Met Cys Asp Glu Asp Glu Thr Thr Ala Leu Val Cys Asp Asn Gly Ser
1               5                   10                  15

Gly Leu Val Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly

```
            35                  40                  45
Met Gly Gln Lys Asp Ser Tyr Val Gly Asp Glu Ala Gln Ser Lys Arg
             50                  55                  60

Gly Ile Leu Thr Leu Lys Tyr Pro Ile Glu His Gly Ile Ile Thr Asn
 65                  70                  75                  80

Trp Asp Asp Met Glu Lys Ile Trp His His Thr Phe Tyr Asn Glu Leu
                 85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
        275                 280                 285

Ile Asp Ile Arg Lys Asp Leu Tyr Ala Asn Asn Val Met Ser Gly Gly
290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Thr Lys Gln Glu Tyr Asp Glu Ala Gly
        355                 360                 365

Pro Ser Ile Val His Arg Lys Cys Phe
370                 375

<210> SEQ ID NO 2
<211> LENGTH: 853
<212> TYPE: PRT
<213> ORGANISM: Homo sapiens

<400> SEQUENCE: 2

Met Ser Glu Lys Val Asp Trp Leu Gln Ser Gln Asn Gly Val Cys Lys
  1               5                  10                  15

Val Asp Val Tyr Ser Pro Gly Asp Asn Gln Ala Gln Asp Trp Lys Met
             20                  25                  30
```

-continued

```
Asp Thr Ser Thr Asp Pro Val Arg Val Leu Ser Trp Leu Arg Arg Asp
         35                  40                  45
Leu Glu Lys Ser Thr Ala Glu Phe Gln Asp Val Arg Phe Lys Pro Gly
 50                  55                  60
Glu Ser Phe Gly Gly Glu Thr Ser Asn Ser Gly Asp Pro His Lys Gly
 65                  70                  75                  80
Phe Ser Val Asp Tyr Tyr Asn Thr Thr Thr Lys Gly Thr Pro Glu Arg
                 85                  90                  95
Leu His Phe Glu Met Thr His Lys Glu Ile Pro Cys Gln Gly Pro Arg
                100                 105                 110
Ala Gln Leu Gly Asn Gly Ser Ser Val Asp Glu Val Ser Phe Tyr Ala
            115                 120                 125
Asn Arg Leu Thr Asn Leu Val Ile Ala Met Ala Arg Lys Glu Ile Asn
        130                 135                 140
Glu Lys Ile Asp Gly Ser Glu Asn Lys Cys Val Tyr Gln Ser Leu Tyr
145                 150                 155                 160
Met Gly Asn Glu Pro Thr Pro Thr Lys Ser Leu Ser Lys Ile Ala Ser
                165                 170                 175
Glu Leu Val Asn Glu Thr Val Ser Ala Cys Ser Arg Asn Ala Ala Pro
            180                 185                 190
Asp Lys Ala Pro Gly Ser Gly Asp Arg Val Ser Gly Ser Ser Gln Ser
        195                 200                 205
Pro Pro Asn Leu Lys Tyr Lys Ser Thr Leu Lys Ile Lys Glu Ser Thr
210                 215                 220
Lys Glu Arg Gln Gly Pro Asp Asp Lys Pro Pro Ser Lys Lys Ser Phe
225                 230                 235                 240
Phe Tyr Lys Glu Val Phe Glu Ser Arg Asn Gly Asp Tyr Ala Arg Glu
                245                 250                 255
Gly Gly Arg Phe Phe Pro Arg Glu Arg Lys Arg Phe Arg Gly Gln Glu
            260                 265                 270
Arg Pro Asp Asp Phe Thr Ala Ser Val Ser Glu Gly Ile Met Thr Tyr
        275                 280                 285
Ala Asn Ser Val Val Ser Asp Met Met Val Ser Ile Met Lys Thr Leu
        290                 295                 300
Lys Ile Gln Val Lys Asp Thr Thr Ile Ala Thr Ile Leu Leu Lys Lys
305                 310                 315                 320
Val Leu Leu Lys His Ala Lys Glu Val Val Ser Asp Leu Ile Asp Ser
                325                 330                 335
Phe Leu Arg Asn Leu His Ser Val Thr Gly Thr Leu Met Thr Asp Thr
            340                 345                 350
Gln Phe Val Ser Ala Val Lys Arg Thr Val Phe Ser His Gly Ser Gln
        355                 360                 365
Lys Ala Thr Asp Ile Met Asp Ala Met Leu Arg Lys Leu Tyr Asn Val
370                 375                 380
Met Phe Ala Lys Lys Val Pro Glu His Val Arg Lys Ala Gln Asp Lys
385                 390                 395                 400
Ala Glu Ser Tyr Ser Leu Ile Ser Met Lys Gly Met Gly Asp Pro Lys
                405                 410                 415
Asn Arg Asn Val Asn Phe Ala Met Lys Ser Glu Thr Lys Leu Arg Glu
            420                 425                 430
Lys Met Tyr Ser Glu Pro Lys Ser Glu Glu Thr Cys Ala Lys Thr
        435                 440                 445
Leu Gly Glu His Ile Ile Lys Glu Gly Leu Thr Leu Trp His Lys Thr
```

```
            450                 455                 460
Gln Gln Lys Glu Cys Lys Ser Leu Gly Phe Gln His Ala Ala Phe Glu
465                 470                 475                 480

Ala Pro Asn Thr Gln Arg Lys Pro Ala Ser Asp Ile Ser Phe Glu Tyr
                485                 490                 495

Pro Glu Asp Ile Gly Asn Leu Ser Leu Pro Pro Tyr Pro Pro Glu Lys
                500                 505                 510

Pro Glu Asn Phe Met Tyr Asp Ser Asp Ser Trp Ala Glu Asp Leu Ile
                515                 520                 525

Val Ser Ala Leu Leu Leu Ile Gln Tyr His Leu Ala Gln Gly Gly Arg
                530                 535                 540

Arg Asp Ala Arg Ser Phe Val Glu Ala Ala Gly Thr Thr Asn Phe Pro
545                 550                 555                 560

Ala Asn Glu Pro Pro Val Ala Pro Asp Glu Ser Cys Leu Lys Ser Ala
                565                 570                 575

Pro Ile Val Gly Asp Gln Glu Gln Ala Glu Lys Lys Asp Leu Arg Ser
                580                 585                 590

Val Phe Phe Asn Phe Ile Arg Asn Leu Leu Ser Glu Thr Ile Phe Lys
                595                 600                 605

Arg Asp Gln Ser Pro Glu Pro Lys Val Pro Glu Gln Pro Val Lys Glu
610                 615                 620

Asp Arg Lys Leu Cys Glu Arg Pro Leu Ala Ser Ser Pro Pro Arg Leu
625                 630                 635                 640

Tyr Glu Asp Asp Glu Thr Pro Gly Ala Leu Ser Gly Leu Thr Lys Met
                645                 650                 655

Ala Val Ser Gln Ile Asp Gly His Met Ser Gly Gln Met Val Glu His
                660                 665                 670

Leu Met Asn Ser Val Met Lys Leu Cys Val Ile Ile Ala Lys Ser Cys
                675                 680                 685

Asp Ala Ser Leu Ala Glu Leu Gly Asp Asp Lys Ser Gly Asp Ala Ser
                690                 695                 700

Arg Leu Thr Ser Ala Phe Pro Asp Ser Leu Tyr Glu Cys Leu Pro Ala
705                 710                 715                 720

Lys Gly Thr Gly Ser Ala Glu Ala Val Leu Gln Asn Ala Tyr Gln Ala
                725                 730                 735

Ile His Asn Glu Met Arg Gly Thr Ser Gly Gln Pro Pro Glu Gly Cys
                740                 745                 750

Ala Ala Pro Thr Val Ile Val Ser Asn His Asn Leu Thr Asp Thr Val
                755                 760                 765

Gln Asn Lys Gln Leu Gln Ala Val Leu Gln Trp Val Ala Ala Ser Glu
                770                 775                 780

Leu Asn Val Pro Ile Leu Tyr Phe Ala Gly Asp Glu Gly Ile Gln
785                 790                 795                 800

Glu Lys Leu Leu Gln Leu Ser Ala Ala Val Asp Lys Gly Cys Ser
                805                 810                 815

Val Gly Glu Val Leu Gln Ser Val Leu Arg Tyr Glu Lys Glu Arg Gln
                820                 825                 830

Leu Asn Glu Ala Val Gly Asn Val Thr Pro Leu Gln Leu Leu Asp Trp
                835                 840                 845

Leu Met Val Asn Leu
                850

<210> SEQ ID NO 3
```

```
<211> LENGTH: 868
<212> TYPE: PRT
<213> ORGANISM: Homo sapiens

<400> SEQUENCE: 3

Met Ala Thr Phe Ile Ser Val Gln Leu Lys Lys Thr Ser Glu Val Asp
1               5                   10                  15

Leu Ala Lys Pro Leu Val Lys Phe Ile Gln Gln Thr Tyr Pro Ser Gly
                20                  25                  30

Gly Glu Glu Gln Ala Gln Tyr Cys Arg Ala Ala Glu Leu Ser Lys
        35                  40                  45

Leu Arg Arg Ala Ala Val Gly Arg Pro Leu Asp Lys His Glu Gly Ala
50                  55                  60

Leu Glu Thr Leu Leu Arg Tyr Tyr Asp Gln Ile Cys Ser Ile Glu Pro
65                  70                  75                  80

Lys Phe Pro Phe Ser Glu Asn Gln Ile Cys Leu Thr Phe Thr Trp Lys
                85                  90                  95

Asp Ala Phe Asp Lys Gly Ser Leu Phe Gly Gly Ser Val Lys Leu Ala
                100                 105                 110

Leu Ala Ser Leu Gly Tyr Glu Lys Ser Cys Val Leu Phe Asn Cys Ala
            115                 120                 125

Ala Leu Ala Ser Gln Ile Ala Ala Glu Gln Asn Leu Asp Asn Asp Glu
130                 135                 140

Gly Leu Lys Ile Ala Ala Lys His Tyr Gln Phe Ala Ser Gly Ala Phe
145                 150                 155                 160

Leu His Ile Lys Glu Thr Val Leu Ser Ala Leu Ser Arg Glu Pro Thr
                165                 170                 175

Val Asp Ile Ser Pro Asp Thr Val Gly Thr Leu Ser Leu Ile Met Leu
                180                 185                 190

Ala Gln Ala Gln Glu Val Phe Phe Leu Lys Ala Thr Arg Asp Lys Met
            195                 200                 205

Lys Asp Ala Ile Ile Ala Lys Leu Ala Asn Gln Ala Ala Asp Tyr Phe
210                 215                 220

Gly Asp Ala Phe Lys Gln Cys Gln Tyr Lys Asp Thr Leu Pro Lys Glu
225                 230                 235                 240

Val Phe Pro Val Leu Ala Ala Lys His Cys Ile Met Gln Ala Asn Ala
                245                 250                 255

Glu Tyr His Gln Ser Ile Leu Ala Lys Gln Gln Lys Lys Phe Gly Glu
                260                 265                 270

Glu Ile Ala Arg Leu Gln His Ala Ala Glu Leu Ile Lys Thr Val Ala
            275                 280                 285

Ser Arg Tyr Asp Glu Tyr Val Asn Val Lys Asp Phe Ser Asp Lys Ile
290                 295                 300

Asn Arg Ala Leu Ala Ala Lys Lys Asp Asn Asp Phe Ile Tyr His
305                 310                 315                 320

Asp Arg Val Pro Asp Leu Lys Asp Leu Asp Pro Ile Gly Lys Ala Thr
                325                 330                 335

Leu Val Lys Ser Thr Pro Val Asn Val Pro Ile Ser Gln Lys Phe Thr
                340                 345                 350

Asp Leu Phe Glu Lys Met Val Pro Val Ser Val Gln Gln Ser Leu Ala
            355                 360                 365

Ala Tyr Asn Gln Arg Lys Ala Asp Leu Val Asn Arg Ser Ile Ala Gln
370                 375                 380

Met Arg Glu Ala Thr Thr Leu Ala Asn Gly Val Leu Ala Ser Leu Asn
```

```
            385                 390                 395                 400
Leu Pro Ala Ala Ile Glu Asp Val Ser Gly Asp Thr Val Pro Gln Ser
                405                 410                 415
Ile Leu Thr Lys Ser Arg Ser Val Ile Glu Gln Gly Gly Ile Gln Thr
                420                 425                 430
Val Asp Gln Leu Ile Lys Glu Leu Pro Glu Leu Leu Gln Arg Asn Arg
                435                 440                 445
Glu Ile Leu Asp Glu Ser Leu Arg Leu Leu Asp Glu Glu Ala Thr
                450                 455                 460
Asp Asn Asp Leu Arg Ala Lys Phe Lys Glu Arg Trp Gln Arg Thr Pro
465                 470                 475                 480
Ser Asn Glu Leu Tyr Lys Pro Leu Arg Ala Glu Gly Thr Asn Phe Arg
                485                 490                 495
Thr Val Leu Asp Lys Ala Val Gln Ala Asp Gly Gln Val Lys Glu Cys
                500                 505                 510
Tyr Gln Ser His Arg Asp Thr Ile Val Leu Leu Cys Lys Pro Glu Pro
                515                 520                 525
Glu Leu Asn Ala Ala Ile Pro Ser Ala Asn Pro Ala Lys Thr Met Gln
                530                 535                 540
Gly Ser Glu Val Val Asn Val Leu Lys Ser Leu Leu Ser Asn Leu Asp
545                 550                 555                 560
Glu Val Lys Lys Glu Arg Glu Gly Leu Glu Asn Asp Leu Lys Ser Val
                565                 570                 575
Asn Phe Asp Met Thr Ser Lys Phe Leu Thr Ala Leu Ala Gln Asp Gly
                580                 585                 590
Val Ile Asn Glu Glu Ala Leu Ser Val Thr Glu Leu Asp Arg Val Tyr
                595                 600                 605
Gly Gly Leu Thr Thr Lys Val Gln Glu Ser Leu Lys Lys Gln Glu Gly
                610                 615                 620
Leu Leu Lys Asn Ile Gln Val Ser His Gln Glu Phe Ser Lys Met Lys
625                 630                 635                 640
Gln Ser Asn Asn Glu Ala Asn Leu Arg Glu Glu Val Leu Lys Asn Leu
                645                 650                 655
Ala Thr Ala Tyr Asp Asn Phe Val Glu Leu Val Ala Asn Leu Lys Glu
                660                 665                 670
Gly Thr Lys Phe Tyr Asn Glu Leu Thr Glu Ile Leu Val Arg Phe Gln
                675                 680                 685
Asn Lys Cys Ser Asp Ile Val Phe Ala Arg Lys Thr Glu Arg Asp Glu
                690                 695                 700
Leu Leu Lys Asp Leu Gln Gln Ser Ile Ala Arg Glu Pro Ser Ala Pro
705                 710                 715                 720
Ser Ile Pro Thr Pro Ala Tyr Gln Ser Ser Pro Ala Gly Gly His Ala
                725                 730                 735
Pro Thr Pro Pro Thr Pro Ala Pro Arg Thr Met Pro Pro Thr Lys Pro
                740                 745                 750
Gln Pro Pro Ala Arg Pro Pro Pro Val Leu Pro Ala Asn Arg Ala
                755                 760                 765
Pro Ser Ala Thr Ala Pro Ser Pro Val Gly Ala Gly Thr Ala Ala Pro
                770                 775                 780
Ala Pro Ser Gln Thr Pro Gly Ser Ala Pro Pro Gln Ala Gln Gly
785                 790                 795                 800
Pro Pro Tyr Pro Thr Tyr Pro Gly Tyr Pro Gly Tyr Cys Gln Met Pro
                805                 810                 815
```

```
Met Pro Met Gly Tyr Asn Pro Tyr Ala Tyr Gly Gln Tyr Asn Met Pro
            820                 825                 830

Tyr Pro Pro Val Tyr His Gln Ser Pro Gly Gln Ala Pro Tyr Pro Gly
            835                 840                 845

Pro Gln Gln Pro Ser Tyr Pro Phe Pro Gln Pro Pro Gln Gln Ser Tyr
            850                 855                 860

Tyr Pro Gln Gln
865

<210> SEQ ID NO 4
<211> LENGTH: 320
<212> TYPE: PRT
<213> ORGANISM: Homo sapiens

<400> SEQUENCE: 4

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
```

-continued

```
305                310                315                320
```

<210> SEQ ID NO 5
<211> LENGTH: 252
<212> TYPE: PRT
<213> ORGANISM: Homo sapiens

<400> SEQUENCE: 5

```
Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250
```

<210> SEQ ID NO 6
<211> LENGTH: 375
<212> TYPE: PRT
<213> ORGANISM: Homo sapiens

<400> SEQUENCE: 6

```
Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
```

```
                65                  70                  75                  80
        Asp Met Glu Lys Ile Trp His His Thr Phe Tyr Asn Glu Leu Arg Val
                        85                  90                  95

Ala Pro Glu Glu His Pro Val Leu Leu Thr Glu Ala Pro Leu Asn Pro
                        100                 105                 110

Lys Ala Asn Arg Glu Lys Met Thr Gln Ile Met Phe Glu Thr Phe Asn
                        115                 120                 125

Thr Pro Ala Met Tyr Val Ala Ile Gln Ala Val Leu Ser Leu Tyr Ala
                        130                 135                 140

Ser Gly Arg Thr Thr Gly Ile Val Met Asp Ser Gly Asp Gly Val Thr
        145                 150                 155                 160

His Thr Val Pro Ile Tyr Glu Gly Tyr Ala Leu Pro His Ala Ile Leu
                            165                 170                 175

Arg Leu Asp Leu Ala Gly Arg Asp Leu Thr Asp Tyr Leu Met Lys Ile
                        180                 185                 190

Leu Thr Glu Arg Gly Tyr Ser Phe Thr Thr Thr Ala Glu Arg Glu Ile
                        195                 200                 205

Val Arg Asp Ile Lys Glu Lys Leu Cys Tyr Val Ala Leu Asp Phe Glu
        210                 215                 220

Gln Glu Met Ala Thr Ala Ala Ser Ser Ser Ser Leu Glu Lys Ser Tyr
        225                 230                 235                 240

Glu Leu Pro Asp Gly Gln Val Ile Thr Ile Gly Asn Glu Arg Phe Arg
                        245                 250                 255

Cys Pro Glu Ala Leu Phe Gln Pro Ser Phe Leu Gly Met Glu Ser Cys
                        260                 265                 270

Gly Ile His Glu Thr Thr Phe Asn Ser Ile Met Lys Cys Asp Val Asp
                        275                 280                 285

Ile Arg Lys Asp Leu Tyr Ala Asn Thr Val Leu Ser Gly Gly Thr Thr
                        290                 295                 300

Met Tyr Pro Gly Ile Ala Asp Arg Met Gln Lys Glu Ile Thr Ala Leu
        305                 310                 315                 320

Ala Pro Ser Thr Met Lys Ile Lys Ile Ile Ala Pro Pro Glu Arg Lys
                        325                 330                 335

Tyr Ser Val Trp Ile Gly Gly Ser Ile Leu Ala Ser Leu Ser Thr Phe
                        340                 345                 350

Gln Gln Met Trp Ile Ser Lys Gln Glu Tyr Asp Glu Ser Gly Pro Ser
                        355                 360                 365

Ile Val His Arg Lys Cys Phe
                        370                 375

<210> SEQ ID NO 7
<211> LENGTH: 361
<212> TYPE: PRT
<213> ORGANISM: Homo sapiens

<400> SEQUENCE: 7

Met Asp Pro Leu Gly Ala Ala Lys Pro Gln Trp Pro Trp Arg Arg Cys
        1               5                   10                  15

Leu Ala Ala Leu Leu Phe Gln Leu Leu Val Ala Val Cys Phe Phe Ser
                        20                  25                  30

Tyr Leu Arg Val Ser Arg Asp Asp Ala Thr Gly Ser Pro Arg Ala Pro
                        35                  40                  45

Ser Gly Ser Ser Arg Gln Asp Thr Thr Pro Thr Arg Pro Thr Leu Leu
        50                  55                  60
```

```
Ile Leu Leu Trp Thr Trp Pro Phe His Ile Pro Val Ala Leu Ser Arg
 65                  70                  75                  80

Cys Ser Glu Met Val Pro Gly Thr Ala Asp Cys His Ile Thr Ala Asp
                 85                  90                  95

Arg Lys Val Tyr Pro Gln Ala Asp Thr Val Ile Val His His Trp Asp
            100                 105                 110

Ile Met Ser Asn Pro Lys Ser Arg Leu Pro Ser Pro Arg Pro Gln
        115                 120                 125

Gly Gln Arg Trp Ile Trp Phe Asn Leu Glu Pro Pro Asn Cys Gln
    130                 135                 140

His Leu Glu Ala Leu Asp Arg Tyr Phe Asn Leu Thr Met Ser Tyr Arg
145                 150                 155                 160

Ser Asp Ser Asp Ile Phe Thr Pro Tyr Gly Trp Leu Glu Pro Trp Ser
                165                 170                 175

Gly Gln Pro Ala His Pro Pro Leu Asn Leu Ser Ala Lys Thr Glu Leu
            180                 185                 190

Val Ala Trp Ala Val Ser Asn Trp Lys Pro Asp Ser Ala Arg Val Arg
        195                 200                 205

Tyr Tyr Gln Ser Leu Gln Ala His Leu Lys Val Asp Val Tyr Gly Arg
    210                 215                 220

Ser His Lys Pro Leu Pro Lys Gly Thr Met Met Glu Thr Leu Ser Arg
225                 230                 235                 240

Tyr Lys Phe Tyr Leu Ala Phe Glu Asn Ser Leu His Pro Asp Tyr Ile
                245                 250                 255

Thr Glu Lys Leu Trp Arg Asn Ala Leu Glu Ala Trp Ala Val Pro Val
            260                 265                 270

Val Leu Gly Pro Ser Arg Ser Asn Tyr Glu Arg Phe Leu Pro Pro Asp
        275                 280                 285

Ala Phe Ile His Val Asp Asp Phe Gln Ser Pro Lys Asp Leu Ala Arg
    290                 295                 300

Tyr Leu Gln Glu Leu Asp Lys Asp His Ala Arg Tyr Leu Ser Tyr Phe
305                 310                 315                 320

Arg Trp Arg Glu Thr Leu Arg Pro Arg Ser Phe Ser Trp Ala Leu Asp
                325                 330                 335

Phe Cys Lys Ala Cys Trp Lys Leu Gln Gln Glu Ser Arg Tyr Gln Thr
            340                 345                 350

Val Arg Ser Ile Ala Ala Trp Phe Thr
            355                 360

<210> SEQ ID NO 8
<211> LENGTH: 354
<212> TYPE: PRT
<213> ORGANISM: Homo sapiens

<400> SEQUENCE: 8

Met Pro Arg Arg Ser Leu His Ala Ala Val Leu Leu Val Ile
 1               5                  10                  15

Leu Lys Glu Gln Pro Ser Ser Pro Ala Pro Val Asn Gly Ser Lys Trp
            20                  25                  30

Thr Tyr Phe Gly Pro Asp Gly Glu Asn Ser Trp Ser Lys Lys Tyr Pro
        35                  40                  45

Ser Cys Gly Gly Leu Leu Gln Ser Pro Ile Asp Leu His Ser Asp Ile
    50                  55                  60

Leu Gln Tyr Asp Ala Ser Leu Thr Pro Leu Glu Phe Gln Gly Tyr Asn
 65                  70                  75                  80
```

-continued

Leu Ser Ala Asn Lys Gln Phe Leu Leu Thr Asn Asn Gly His Ser Val
                85                  90                  95

Lys Leu Asn Leu Pro Ser Asp Met His Ile Gln Gly Leu Gln Ser Arg
            100                 105                 110

Tyr Ser Ala Thr Gln Leu His Leu His Trp Gly Asn Pro Asn Asp Pro
        115                 120                 125

His Gly Ser Glu His Thr Val Ser Gly Gln His Phe Ala Ala Glu Leu
    130                 135                 140

His Ile Val His Tyr Asn Ser Asp Leu Tyr Pro Asp Ala Ser Thr Ala
145                 150                 155                 160

Ser Asn Lys Ser Glu Gly Leu Ala Val Leu Ala Val Leu Ile Glu Met
                165                 170                 175

Gly Ser Phe Asn Pro Ser Tyr Asp Lys Ile Phe Ser His Leu Gln His
            180                 185                 190

Val Lys Tyr Lys Gly Gln Glu Ala Phe Val Pro Gly Phe Asn Ile Glu
        195                 200                 205

Glu Leu Leu Pro Glu Arg Thr Ala Glu Tyr Tyr Arg Tyr Arg Gly Ser
    210                 215                 220

Leu Thr Thr Pro Pro Cys Asn Pro Thr Val Leu Trp Thr Val Phe Arg
225                 230                 235                 240

Asn Pro Val Gln Ile Ser Gln Glu Gln Leu Leu Ala Leu Glu Thr Ala
                245                 250                 255

Leu Tyr Cys Thr His Met Asp Asp Pro Ser Pro Arg Glu Met Ile Asn
            260                 265                 270

Asn Phe Arg Gln Val Gln Lys Phe Asp Glu Arg Leu Val Tyr Thr Ser
        275                 280                 285

Phe Ser Gln Val Gln Val Cys Thr Ala Ala Gly Leu Ser Leu Gly Ile
    290                 295                 300

Ile Leu Ser Leu Ala Leu Ala Gly Ile Leu Gly Ile Cys Ile Val Val
305                 310                 315                 320

Val Val Ser Ile Trp Leu Phe Arg Arg Lys Ser Ile Lys Lys Gly Asp
                325                 330                 335

Asn Lys Gly Val Ile Tyr Lys Pro Ala Thr Lys Met Glu Thr Glu Ala
            340                 345                 350

His Ala

<210> SEQ ID NO 9
<211> LENGTH: 658
<212> TYPE: PRT
<213> ORGANISM: Homo sapiens

<400> SEQUENCE: 9

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

```
Leu Val Leu Ser Val Asn Ser Ser Val Phe Leu His Leu Gln Ala Leu
            100                 105                 110
Gly Ile Pro Leu His Leu Ala Tyr Asn Ser Ser Leu Val Thr Phe Gln
            115                 120                 125
Glu Pro Pro Gly Val Asn Thr Thr Glu Leu Pro Ser Phe Pro Lys Thr
            130                 135                 140
Gln Ile Leu Glu Trp Ala Ala Glu Arg Gly Pro Ile Thr Ser Ala Ala
145                 150                 155                 160
Glu Leu Asn Asp Pro Gln Ser Ile Leu Leu Arg Leu Gly Gln Ala Gln
                165                 170                 175
Gly Ser Leu Ser Phe Cys Met Leu Glu Ala Ser Gln Asp Met Gly Arg
            180                 185                 190
Thr Leu Glu Trp Arg Pro Arg Thr Pro Ala Leu Val Arg Gly Cys His
            195                 200                 205
Leu Glu Gly Val Ala Gly His Lys Glu Ala His Ile Leu Arg Val Leu
            210                 215                 220
Pro Gly His Ser Ala Gly Pro Arg Thr Val Thr Val Lys Val Glu Leu
225                 230                 235                 240
Ser Cys Ala Pro Gly Asp Leu Asp Ala Val Leu Ile Leu Gln Gly Pro
                245                 250                 255
Pro Tyr Val Ser Trp Leu Ile Asp Ala Asn His Asn Met Gln Ile Trp
            260                 265                 270
Thr Thr Gly Glu Tyr Ser Phe Lys Ile Phe Pro Glu Lys Asn Ile Arg
            275                 280                 285
Gly Phe Lys Leu Pro Asp Thr Pro Gln Gly Leu Leu Gly Glu Ala Arg
            290                 295                 300
Met Leu Asn Ala Ser Ile Val Ala Ser Phe Val Glu Leu Pro Leu Ala
305                 310                 315                 320
Ser Ile Val Ser Leu His Ala Ser Ser Cys Gly Gly Arg Leu Gln Thr
                325                 330                 335
Ser Pro Ala Pro Ile Gln Thr Thr Pro Pro Lys Asp Thr Cys Ser Pro
            340                 345                 350
Glu Leu Leu Met Ser Leu Ile Gln Thr Lys Cys Ala Asp Asp Ala Met
            355                 360                 365
Thr Leu Val Leu Lys Lys Glu Leu Val Ala His Leu Lys Cys Thr Ile
370                 375                 380
Thr Gly Leu Thr Phe Trp Asp Pro Ser Cys Glu Ala Glu Asp Arg Gly
385                 390                 395                 400
Asp Lys Phe Val Leu Arg Ser Ala Tyr Ser Ser Cys Gly Met Gln Val
                405                 410                 415
Ser Ala Ser Met Ile Ser Asn Glu Ala Val Val Asn Ile Leu Ser Ser
            420                 425                 430
Ser Ser Pro Gln Arg Lys Lys Val His Cys Leu Asn Met Asp Ser Leu
            435                 440                 445
Ser Phe Gln Leu Gly Leu Tyr Leu Ser Pro His Phe Leu Gln Ala Ser
            450                 455                 460
Asn Thr Ile Glu Pro Gly Gln Gln Ser Phe Val Gln Val Arg Val Ser
465                 470                 475                 480
Pro Ser Val Ser Glu Phe Leu Leu Gln Leu Asp Ser Cys His Leu Asp
                485                 490                 495
Leu Gly Pro Glu Gly Gly Thr Val Glu Leu Ile Gln Gly Arg Ala Ala
            500                 505                 510
```

-continued

```
Lys Gly Asn Cys Val Ser Leu Leu Ser Pro Ser Pro Glu Gly Asp Pro
            515                 520                 525

Arg Phe Ser Phe Leu Leu His Phe Tyr Thr Val Pro Ile Pro Lys Thr
530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
        595                 600                 605

Ala Leu Trp Tyr Ile Tyr Ser His Thr Arg Ser Pro Ser Lys Arg Glu
    610                 615                 620

Pro Val Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                645                 650                 655

Met Ala

<210> SEQ ID NO 10
<211> LENGTH: 739
<212> TYPE: PRT
<213> ORGANISM: Homo sapiens

<400> SEQUENCE: 10

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220
```

```
Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
            245                 250                 255

Phe Trp Ser Lys Lys Leu Asp Asn Gly Asn Leu Gln His Leu Ser Gly
        260                 265                 270

Asn Ala Thr Leu Thr Leu Ile Ala Met Arg Met Glu Asp Ser Gly Ile
    275                 280                 285

Tyr Val Cys Glu Gly Val Asn Leu Ile Gly Lys Asn Arg Lys Glu Val
290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
            325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
            435                 440                 445

Asn Ile Glu Phe Leu Glu Asp Thr Asp Met Lys Ser Leu Glu Asn Lys
        450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
```

```
                    645                 650                 655
Lys Ala Gln Leu Lys Asp Ala Gly Val Tyr Glu Cys Glu Ser Lys Asn
                660                 665                 670

Lys Val Gly Ser Gln Leu Arg Ser Leu Thr Leu Asp Val Gln Gly Arg
            675                 680                 685

Glu Asn Asn Lys Asp Tyr Phe Ser Pro Glu Leu Leu Val Leu Tyr Phe
        690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 11
<211> LENGTH: 967
<212> TYPE: PRT
<213> ORGANISM: Homo sapiens

<400> SEQUENCE: 11

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
```

```
                275                 280                 285
Tyr Val Glu Lys Gln Ala Ser Asn Gly Val Leu Ile Arg Ile Trp Ala
290                 295                 300
Arg Pro Ser Ala Ile Ala Ala Gly His Gly Asp Tyr Ala Leu Asn Val
305                 310                 315                 320
Thr Gly Pro Ile Leu Asn Phe Phe Ala Gly His Tyr Asp Thr Pro Tyr
                325                 330                 335
Pro Leu Pro Lys Ser Asp Gln Ile Gly Leu Pro Asp Phe Asn Ala Gly
                340                 345                 350
Ala Met Glu Asn Trp Gly Leu Val Thr Tyr Arg Glu Asn Ser Leu Leu
                355                 360                 365
Phe Asp Pro Leu Ser Ser Ser Ser Asn Lys Glu Arg Val Val Thr
370                 375                 380
Val Ile Ala His Glu Leu Ala His Gln Trp Phe Gly Asn Leu Val Thr
385                 390                 395                 400
Ile Glu Trp Trp Asn Asp Leu Trp Leu Asn Glu Gly Phe Ala Ser Tyr
                405                 410                 415
Val Glu Tyr Leu Gly Ala Asp Tyr Ala Glu Pro Thr Trp Asn Leu Lys
                420                 425                 430
Asp Leu Met Val Leu Asn Asp Val Tyr Arg Val Met Ala Val Asp Ala
                435                 440                 445
Leu Ala Ser Ser His Pro Leu Ser Thr Pro Ala Ser Glu Ile Asn Thr
450                 455                 460
Pro Ala Gln Ile Ser Glu Leu Phe Asp Ala Ile Ser Tyr Ser Lys Gly
465                 470                 475                 480
Ala Ser Val Leu Arg Met Leu Ser Ser Phe Leu Ser Glu Asp Val Phe
                485                 490                 495
Lys Gln Gly Leu Ala Ser Tyr Leu His Thr Phe Ala Tyr Gln Asn Thr
                500                 505                 510
Ile Tyr Leu Asn Leu Trp Asp His Leu Gln Glu Ala Val Asn Asn Arg
                515                 520                 525
Ser Ile Gln Leu Pro Thr Thr Val Arg Asp Ile Met Asn Arg Trp Thr
530                 535                 540
Leu Gln Met Gly Phe Pro Val Ile Thr Val Asp Thr Ser Thr Gly Thr
545                 550                 555                 560
Leu Ser Gln Glu His Phe Leu Leu Asp Pro Asp Ser Asn Val Thr Arg
                565                 570                 575
Pro Ser Glu Phe Asn Tyr Val Trp Ile Val Pro Ile Thr Ser Ile Arg
                580                 585                 590
Asp Gly Arg Gln Gln Asp Tyr Trp Leu Ile Asp Val Arg Ala Gln
                595                 600                 605
Asn Asp Leu Phe Ser Thr Ser Gly Asn Glu Trp Val Leu Leu Asn Leu
                610                 615                 620
Asn Val Thr Gly Tyr Tyr Arg Val Asn Tyr Asp Glu Glu Asn Trp Arg
625                 630                 635                 640
Lys Ile Gln Thr Gln Leu Gln Arg Asp His Ser Ala Ile Pro Val Ile
                645                 650                 655
Asn Arg Ala Gln Ile Ile Asn Asp Ala Phe Asn Leu Ala Ser Ala His
                660                 665                 670
Lys Val Pro Val Thr Leu Ala Leu Asn Asn Thr Leu Phe Leu Ile Glu
                675                 680                 685
Glu Arg Gln Tyr Met Pro Trp Glu Ala Ala Leu Ser Ser Leu Ser Tyr
                690                 695                 700
```

```
Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Glu Gln Phe
                805                 810                 815

Arg Asn Ala Thr Leu Val Asn Glu Ala Asp Lys Leu Arg Ala Ala Leu
                820                 825                 830

Ala Cys Ser Lys Glu Leu Trp Ile Leu Asn Arg Tyr Leu Ser Tyr Thr
            835                 840                 845

Leu Asn Pro Asp Leu Ile Arg Lys Gln Asp Ala Thr Ser Thr Ile Ile
        850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 12
<211> LENGTH: 310
<212> TYPE: PRT
<213> ORGANISM: Homo sapiens

<400> SEQUENCE: 12

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
        50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
```

```
            100                 105                 110
Gly Leu Thr Ala Arg Glu Gln Glu Ala Thr Pro Arg Pro Arg Glu Thr
            115                 120                 125

Thr Gln Leu Pro Thr Thr His Leu Ala Ser Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Pro Ser Ala Thr Glu Arg Ala Ala
            180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
            210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
            275                 280                 285

Glu Glu Pro Lys Gln Ala Asn Gly Gly Ala Tyr Gln Lys Pro Thr Lys
            290                 295                 300

Gln Glu Glu Phe Tyr Ala
305                 310

<210> SEQ ID NO 13
<211> LENGTH: 375
<212> TYPE: PRT
<213> ORGANISM: Homo sapiens

<400> SEQUENCE: 13

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
                20                  25                  30

Arg Cys Val Cys Asn Phe Ser Glu Pro Gln Pro Asp Trp Ser Glu Ala
            35                  40                  45

Phe Gln Cys Val Ser Ala Val Glu Val Glu Ile His Ala Gly Gly Leu
            50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
            130                 135                 140

Ser Ser Leu Arg Leu Arg Asn Val Ser Trp Ala Thr Gly Arg Ser Trp
145                 150                 155                 160
```

```
Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

Cys Ala Ala Leu Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
    370                 375

<210> SEQ ID NO 14
<211> LENGTH: 575
<212> TYPE: PRT
<213> ORGANISM: Homo sapiens

<400> SEQUENCE: 14

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160
```

```
Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Cys Glu His Ala Cys
                245                 250                 255

Asn Ala Ile Pro Gly Ala Pro Arg Cys Gln Cys Pro Ala Gly Ala Ala
                260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
        290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
                340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
        370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
    450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575
```

<210> SEQ ID NO 15
<211> LENGTH: 295
<212> TYPE: PRT
<213> ORGANISM: Homo sapiens

<400> SEQUENCE: 15

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
            275                 280                 285

Asn Ser Pro Leu Asn Val Ser
    290                 295

<210> SEQ ID NO 16
<211> LENGTH: 646
<212> TYPE: PRT
<213> ORGANISM: Homo sapiens

<400> SEQUENCE: 16

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

```
Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
 50                  55                  60

Val His Lys Glu Lys Arg Thr Leu Ile Phe Arg Val Arg Gln Gly Gln
 65                  70                  75                  80

Gly Gln Ser Glu Pro Gly Glu Tyr Glu Gln Arg Leu Ser Leu Gln Asp
                 85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
                115                 120                 125

Gln Leu Arg Val Tyr Lys Ala Pro Glu Glu Pro Asn Ile Gln Val Asn
            130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
            210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
            275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Gly Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
```

```
                450             455             460
Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
            530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
                580                 585                 590

Ser Gly Lys Gln Glu Ile Thr Leu Pro Pro Ser Arg Lys Ser Glu Leu
            595                 600                 605

Val Val Glu Val Lys Ser Asp Lys Leu Pro Glu Glu Met Gly Leu Leu
            610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 17
<211> LENGTH: 253
<212> TYPE: PRT
<213> ORGANISM: Homo sapiens

<400> SEQUENCE: 17

Met Gly Glu Phe Asn Glu Lys Lys Thr Thr Cys Gly Thr Val Cys Leu
1               5                   10                  15

Lys Tyr Leu Leu Phe Thr Tyr Asn Cys Cys Phe Trp Leu Ala Gly Leu
                20                  25                  30

Ala Val Met Ala Val Gly Ile Trp Thr Leu Ala Leu Lys Ser Asp Tyr
            35                  40                  45

Ile Ser Leu Leu Ala Ser Gly Thr Tyr Leu Ala Thr Ala Tyr Ile Leu
        50                  55                  60

Val Val Ala Gly Thr Val Val Met Val Thr Gly Val Leu Gly Cys Cys
65                  70                  75                  80

Ala Thr Phe Lys Glu Arg Arg Asn Leu Leu Arg Leu Tyr Phe Ile Leu
                85                  90                  95

Leu Leu Ile Ile Phe Leu Leu Glu Ile Ile Ala Gly Ile Leu Ala Tyr
                100                 105                 110

Ala Tyr Tyr Gln Gln Leu Asn Thr Glu Leu Lys Glu Asn Leu Lys Asp
            115                 120                 125

Thr Met Thr Lys Arg Tyr His Gln Pro Gly His Glu Ala Val Thr Ser
130                 135                 140

Ala Val Asp Gln Leu Gln Gln Glu Phe His Cys Cys Gly Ser Asn Asn
145                 150                 155                 160

Ser Gln Asp Trp Arg Asp Ser Glu Trp Ile Arg Ser Gln Glu Ala Gly
                165                 170                 175
```

```
Gly Arg Val Val Pro Asp Ser Cys Cys Lys Thr Val Val Ala Leu Cys
            180                 185                 190

Gly Gln Arg Asp His Ala Ser Asn Ile Tyr Lys Val Glu Gly Gly Cys
        195                 200                 205

Ile Thr Lys Leu Glu Thr Phe Ile Gln Glu His Leu Arg Val Ile Gly
    210                 215                 220

Ala Val Gly Ile Gly Ile Ala Cys Val Gln Val Phe Gly Met Ile Phe
225                 230                 235                 240

Thr Cys Cys Leu Tyr Arg Ser Leu Lys Leu Glu His Tyr
            245                 250
```

<210> SEQ ID NO 18
<211> LENGTH: 254
<212> TYPE: PRT
<213> ORGANISM: Homo sapiens

<400> SEQUENCE: 18

```
Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 19
<211> LENGTH: 233
<212> TYPE: PRT
<213> ORGANISM: Homo sapiens

<400> SEQUENCE: 19

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230

<210> SEQ ID NO 20
<211> LENGTH: 412
<212> TYPE: PRT
<213> ORGANISM: Homo sapiens

<400> SEQUENCE: 20

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
            130                 135                 140
```

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
            165                 170                 175

Ala Ala Thr Glu Ala Gln Thr Thr Gln Pro Thr Gly Leu Glu Ala Gln
        180                 185                 190

Thr Thr Ala Pro Ala Ala Met Glu Ala Gln Thr Thr Ala Pro Ala Ala
    195                 200                 205

Met Glu Ala Gln Thr Thr Pro Pro Ala Ala Met Glu Ala Gln Thr Thr
210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
            245                 250                 255

Ala Ala Met Glu Ala Leu Ser Thr Glu Pro Ser Ala Thr Glu Ala Leu
        260                 265                 270

Ser Met Glu Pro Thr Thr Lys Arg Gly Leu Phe Ile Pro Phe Ser Val
    275                 280                 285

Ser Ser Val Thr His Lys Gly Ile Pro Met Ala Ala Ser Asn Leu Ser
290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
            325                 330                 335

Cys Thr Val Val Leu Ala Val Arg Leu Ser Arg Lys Gly His Met Tyr
        340                 345                 350

Pro Val Arg Asn Tyr Ser Pro Thr Glu Met Val Cys Ile Ser Ser Leu
    355                 360                 365

Leu Pro Asp Gly Gly Glu Gly Pro Ser Ala Thr Ala Asn Gly Gly Leu
370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
            405                 410

<210> SEQ ID NO 21
<211> LENGTH: 1156
<212> TYPE: PRT
<213> ORGANISM: Homo sapiens

<400> SEQUENCE: 21

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Trp Gly Thr Val Cys Asn Asn Gly Trp
65                  70                  75                  80

Ser Met Glu Ala Val Ser Val Ile Cys Asn Gln Leu Gly Cys Pro Thr
            85                  90                  95

Ala Ile Lys Ala Pro Gly Trp Ala Asn Ser Ser Ala Gly Ser Gly Arg

```
            100             105             110
Ile Trp Met Asp His Val Ser Cys Arg Gly Asn Glu Ser Ala Leu Trp
            115             120             125

Asp Cys Lys His Asp Gly Trp Gly Lys His Ser Asn Cys Thr His Gln
    130             135             140

Gln Asp Ala Gly Val Thr Cys Ser Asp Gly Ser Asn Leu Glu Met Arg
145             150             155             160

Leu Thr Arg Gly Gly Asn Met Cys Ser Gly Arg Ile Glu Ile Lys Phe
                165             170             175

Gln Gly Arg Trp Gly Thr Val Cys Asp Asp Asn Phe Asn Ile Asp His
            180             185             190

Ala Ser Val Ile Cys Arg Gln Leu Glu Cys Gly Ser Ala Val Ser Phe
        195             200             205

Ser Gly Ser Ser Asn Phe Gly Glu Gly Ser Gly Pro Ile Trp Phe Asp
    210             215             220

Asp Leu Ile Cys Asn Gly Asn Glu Ser Ala Leu Trp Asn Cys Lys His
225             230             235             240

Gln Gly Trp Gly Lys His Asn Cys Asp His Ala Glu Asp Ala Gly Val
                245             250             255

Ile Cys Ser Lys Gly Ala Asp Leu Ser Leu Arg Leu Val Asp Gly Val
            260             265             270

Thr Glu Cys Ser Gly Arg Leu Glu Val Arg Phe Gln Gly Glu Trp Gly
        275             280             285

Thr Ile Cys Asp Asp Gly Trp Asp Ser Tyr Asp Ala Ala Val Ala Cys
    290             295             300

Lys Gln Leu Gly Cys Pro Thr Ala Val Thr Ala Ile Gly Arg Val Asn
305             310             315             320

Ala Ser Lys Gly Phe Gly His Ile Trp Leu Asp Ser Val Ser Cys Gln
                325             330             335

Gly His Glu Pro Ala Ile Trp Gln Cys Lys His His Glu Trp Gly Lys
            340             345             350

His Tyr Cys Asn His Asn Glu Asp Ala Gly Val Thr Cys Ser Asp Gly
        355             360             365

Ser Asp Leu Glu Leu Arg Leu Arg Gly Gly Ser Arg Cys Ala Gly
    370             375             380

Thr Val Glu Val Glu Ile Gln Arg Leu Leu Gly Lys Val Cys Asp Arg
385             390             395             400

Gly Trp Gly Leu Lys Glu Ala Asp Val Val Cys Arg Gln Leu Gly Cys
                405             410             415

Gly Ser Ala Leu Lys Thr Ser Tyr Gln Val Tyr Ser Lys Ile Gln Ala
            420             425             430

Thr Asn Thr Trp Leu Phe Leu Ser Cys Asn Gly Asn Glu Thr Ser
        435             440             445

Leu Trp Asp Cys Lys Asn Trp Gln Trp Gly Gly Leu Thr Cys Asp His
    450             455             460

Tyr Glu Glu Ala Lys Ile Thr Cys Ser Ala His Arg Glu Pro Arg Leu
465             470             475             480

Val Gly Gly Asp Ile Pro Cys Ser Gly Arg Val Glu Val Lys His Gly
                485             490             495

Asp Thr Trp Gly Ser Ile Cys Asp Ser Asp Phe Ser Leu Glu Ala Ala
            500             505             510

Ser Val Leu Cys Arg Glu Leu Gln Cys Gly Thr Val Val Ser Ile Leu
        515             520             525
```

```
Gly Gly Ala His Phe Gly Glu Gly Asn Gly Gln Ile Trp Ala Glu Glu
        530                 535                 540
Phe Gln Cys Glu Gly His Glu Ser His Leu Ser Leu Cys Pro Val Ala
545                 550                 555                 560
Pro Arg Pro Glu Gly Thr Cys Ser His Ser Arg Asp Val Gly Val Val
                565                 570                 575
Cys Ser Arg Tyr Thr Glu Ile Arg Leu Val Asn Gly Lys Thr Pro Cys
            580                 585                 590
Glu Gly Arg Val Glu Leu Lys Thr Leu Gly Ala Trp Gly Ser Leu Cys
        595                 600                 605
Asn Ser His Trp Asp Ile Glu Asp Ala His Val Leu Cys Gln Gln Leu
    610                 615                 620
Lys Cys Gly Val Ala Leu Ser Thr Pro Gly Gly Ala Arg Phe Gly Lys
625                 630                 635                 640
Gly Asn Gly Gln Ile Trp Arg His Met Phe His Cys Thr Gly Thr Glu
                645                 650                 655
Gln His Met Gly Asp Cys Pro Val Thr Ala Leu Gly Ala Ser Leu Cys
            660                 665                 670
Pro Ser Glu Gln Val Ala Ser Val Ile Cys Ser Gly Asn Gln Ser Gln
        675                 680                 685
Thr Leu Ser Ser Cys Asn Ser Ser Ser Leu Gly Pro Thr Arg Pro Thr
    690                 695                 700
Ile Pro Glu Glu Ser Ala Val Ala Cys Ile Glu Ser Gly Gln Leu Arg
705                 710                 715                 720
Leu Val Asn Gly Gly Arg Cys Ala Gly Arg Val Glu Ile Tyr His
                725                 730                 735
Glu Gly Ser Trp Gly Thr Ile Cys Asp Asp Ser Trp Asp Leu Ser Asp
            740                 745                 750
Ala His Val Val Cys Arg Gln Leu Gly Cys Gly Glu Ala Ile Asn Ala
        755                 760                 765
Thr Gly Ser Ala His Phe Gly Glu Gly Thr Gly Pro Ile Trp Leu Asp
    770                 775                 780
Glu Met Lys Cys Asn Gly Lys Glu Ser Arg Ile Trp Gln Cys His Ser
785                 790                 795                 800
His Gly Trp Gly Gln Gln Asn Cys Arg His Lys Glu Asp Ala Gly Val
                805                 810                 815
Ile Cys Ser Glu Phe Met Ser Leu Arg Leu Thr Ser Glu Ala Ser Arg
            820                 825                 830
Glu Ala Cys Ala Gly Arg Leu Glu Val Phe Tyr Asn Gly Ala Trp Gly
        835                 840                 845
Thr Val Gly Lys Ser Ser Met Ser Glu Thr Thr Val Gly Val Val Cys
    850                 855                 860
Arg Gln Leu Gly Cys Ala Asp Lys Gly Lys Ile Asn Pro Ala Ser Leu
865                 870                 875                 880
Asp Lys Ala Met Ser Ile Pro Met Trp Val Asp Asn Val Gln Cys Pro
                885                 890                 895
Lys Gly Pro Asp Thr Leu Trp Gln Cys Pro Ser Ser Pro Trp Glu Lys
            900                 905                 910
Arg Leu Ala Ser Pro Ser Glu Glu Thr Trp Ile Thr Cys Asp Asn Lys
        915                 920                 925
Ile Arg Leu Gln Glu Gly Pro Thr Ser Cys Ser Gly Arg Val Glu Ile
    930                 935                 940
```

```
Trp His Gly Gly Ser Trp Gly Thr Val Cys Asp Ser Trp Asp Leu
945                 950                 955                 960

Asp Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
        995                 1000                1005

Pro Ala Arg Arg Trp Gly His Ser Glu Cys Gly His Lys Glu Asp
    1010                1015                1020

Ala Ala Val Asn Cys Thr Asp Ile Ser Val Gln Lys Thr Pro Gln
    1025                1030                1035

Lys Ala Thr Thr Gly Arg Ser Arg Gln Ser Ser Phe Ile Ala
    1040                1045                1050

Val Gly Ile Leu Gly Val Val Leu Leu Ala Ile Phe Val Ala Leu
    1055                1060                1065

Phe Phe Leu Thr Lys Lys Arg Arg Gln Arg Gln Arg Leu Ala Val
    1070                1075                1080

Ser Ser Arg Gly Glu Asn Leu Val His Gln Ile Gln Tyr Arg Glu
    1085                1090                1095

Met Asn Ser Cys Leu Asn Ala Asp Asp Leu Asp Leu Met Asn Ser
    1100                1105                1110

Ser Glu Asn Ser His Glu Ser Ala Asp Phe Ser Ala Ala Glu Leu
    1115                1120                1125

Ile Ser Val Ser Lys Phe Leu Pro Ile Ser Gly Met Glu Lys Glu
    1130                1135                1140

Ala Ile Leu Ser His Thr Glu Lys Glu Asn Gly Asn Leu
    1145                1150                1155

<210> SEQ ID NO 22
<211> LENGTH: 1257
<212> TYPE: PRT
<213> ORGANISM: Homo sapiens

<400> SEQUENCE: 22

Met Val Val Ala Leu Arg Tyr Val Trp Pro Leu Leu Leu Cys Ser Pro
1               5                   10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
    50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
                100                 105                 110

Arg Cys Phe Ala Ser Asn Lys Leu Gly Thr Ala Met Ser His Glu Ile
            115                 120                 125

Arg Leu Met Ala Glu Gly Ala Pro Lys Trp Pro Lys Glu Thr Val Lys
    130                 135                 140

Pro Val Glu Val Glu Glu Gly Glu Ser Val Val Leu Pro Cys Asn Pro
145                 150                 155                 160
```

```
Pro Pro Ser Ala Glu Pro Leu Arg Ile Tyr Trp Met Asn Ser Lys Ile
            165                 170                 175

Leu His Ile Lys Gln Asp Glu Arg Val Thr Met Gly Gln Asn Gly Asn
            180                 185                 190

Leu Tyr Phe Ala Asn Val Leu Thr Ser Asp Asn His Ser Asp Tyr Ile
            195                 200                 205

Cys His Ala His Phe Pro Gly Thr Arg Thr Ile Ile Gln Lys Glu Pro
            210                 215                 220

Ile Asp Leu Arg Val Lys Ala Thr Asn Ser Met Ile Asp Arg Lys Pro
225                 230                 235                 240

Arg Leu Leu Phe Pro Thr Asn Ser Ser Ser His Leu Val Ala Leu Gln
            245                 250                 255

Gly Gln Pro Leu Val Leu Glu Cys Ile Ala Glu Gly Phe Pro Thr Pro
            260                 265                 270

Thr Ile Lys Trp Leu Arg Pro Ser Gly Pro Met Pro Ala Asp Arg Val
            275                 280                 285

Thr Tyr Gln Asn His Asn Lys Thr Leu Gln Leu Leu Lys Val Gly Glu
            290                 295                 300

Glu Asp Asp Gly Glu Tyr Arg Cys Leu Ala Glu Asn Ser Leu Gly Ser
305                 310                 315                 320

Ala Arg His Ala Tyr Tyr Val Thr Val Glu Ala Ala Pro Tyr Trp Leu
            325                 330                 335

His Lys Pro Gln Ser His Leu Tyr Gly Pro Gly Glu Thr Ala Arg Leu
            340                 345                 350

Asp Cys Gln Val Gln Gly Arg Pro Gln Pro Glu Val Thr Trp Arg Ile
            355                 360                 365

Asn Gly Ile Pro Val Glu Glu Leu Ala Lys Asp Gln Lys Tyr Arg Ile
            370                 375                 380

Gln Arg Gly Ala Leu Ile Leu Ser Asn Val Gln Pro Ser Asp Thr Met
385                 390                 395                 400

Val Thr Gln Cys Glu Ala Arg Asn Arg His Gly Leu Leu Leu Ala Asn
            405                 410                 415

Ala Tyr Ile Tyr Val Val Gln Leu Pro Ala Lys Ile Leu Thr Ala Asp
            420                 425                 430

Asn Gln Thr Tyr Met Ala Val Gln Gly Ser Thr Ala Tyr Leu Leu Cys
            435                 440                 445

Lys Ala Phe Gly Ala Pro Val Pro Ser Val Gln Trp Leu Asp Glu Asp
            450                 455                 460

Gly Thr Thr Val Leu Gln Asp Glu Arg Phe Phe Pro Tyr Ala Asn Gly
465                 470                 475                 480

Thr Leu Gly Ile Arg Asp Leu Gln Ala Asn Asp Thr Gly Arg Tyr Phe
            485                 490                 495

Cys Leu Ala Ala Asn Asp Gln Asn Asn Val Thr Ile Met Ala Asn Leu
            500                 505                 510

Lys Val Lys Asp Ala Thr Gln Ile Thr Gln Gly Pro Arg Ser Thr Ile
            515                 520                 525

Glu Lys Lys Gly Ser Arg Val Thr Phe Thr Cys Gln Ala Ser Phe Asp
530                 535                 540

Pro Ser Leu Gln Pro Ser Ile Thr Trp Arg Gly Asp Gly Arg Asp Leu
545                 550                 555                 560

Gln Glu Leu Gly Asp Ser Asp Lys Tyr Phe Ile Glu Asp Gly Arg Leu
            565                 570                 575
```

-continued

Val Ile His Ser Leu Asp Tyr Ser Asp Gln Gly Asn Tyr Ser Cys Val
              580                 585                 590

Ala Ser Thr Glu Leu Asp Val Val Glu Ser Arg Ala Gln Leu Leu Val
          595                 600                 605

Val Gly Ser Pro Gly Pro Val Pro Arg Leu Val Leu Ser Asp Leu His
      610                 615                 620

Leu Leu Thr Gln Ser Gln Val Arg Val Ser Trp Ser Pro Ala Glu Asp
625                 630                 635                 640

His Asn Ala Pro Ile Glu Lys Tyr Asp Ile Glu Phe Glu Asp Lys Glu
                  645                 650                 655

Met Ala Pro Glu Lys Trp Tyr Ser Leu Gly Lys Val Pro Gly Asn Gln
              660                 665                 670

Thr Ser Thr Thr Leu Lys Leu Ser Pro Tyr Val His Tyr Thr Phe Arg
          675                 680                 685

Val Thr Ala Ile Asn Lys Tyr Gly Pro Gly Glu Pro Ser Pro Val Ser
      690                 695                 700

Glu Thr Val Val Thr Pro Glu Ala Ala Pro Glu Lys Asn Pro Val Asp
705                 710                 715                 720

Val Lys Gly Glu Gly Asn Glu Thr Thr Asn Met Val Ile Thr Trp Lys
                  725                 730                 735

Pro Leu Arg Trp Met Asp Trp Asn Ala Pro Gln Val Gln Tyr Arg Val
              740                 745                 750

Gln Trp Arg Pro Gln Gly Thr Arg Gly Pro Trp Gln Glu Gln Ile Val
          755                 760                 765

Ser Asp Pro Phe Leu Val Val Ser Asn Thr Ser Thr Phe Val Pro Tyr
      770                 775                 780

Glu Ile Lys Val Gln Ala Val Asn Ser Gln Gly Lys Gly Pro Glu Pro
785                 790                 795                 800

Gln Val Thr Ile Gly Tyr Ser Gly Glu Asp Tyr Pro Gln Ala Ile Pro
                  805                 810                 815

Glu Leu Glu Gly Ile Glu Ile Leu Asn Ser Ser Ala Val Leu Val Lys
              820                 825                 830

Trp Arg Pro Val Asp Leu Ala Gln Val Lys Gly His Leu Arg Gly Tyr
          835                 840                 845

Asn Val Thr Tyr Trp Arg Glu Gly Ser Gln Arg Lys His Ser Lys Arg
      850                 855                 860

His Ile His Lys Asp His Val Val Pro Ala Asn Thr Thr Ser Val
865                 870                 875                 880

Ile Leu Ser Gly Leu Arg Pro Tyr Ser Ser Tyr His Leu Glu Val Gln
                  885                 890                 895

Ala Phe Asn Gly Arg Gly Ser Gly Pro Ala Ser Glu Phe Thr Phe Ser
              900                 905                 910

Thr Pro Glu Gly Val Pro Gly His Pro Glu Ala Leu His Leu Glu Cys
          915                 920                 925

Gln Ser Asn Thr Ser Leu Leu Leu Arg Trp Gln Pro Pro Leu Ser His
      930                 935                 940

Asn Gly Val Leu Thr Gly Tyr Val Leu Ser Tyr His Pro Leu Asp Glu
945                 950                 955                 960

Gly Gly Lys Gly Gln Leu Ser Phe Asn Leu Arg Asp Pro Glu Leu Arg
                  965                 970                 975

Thr His Asn Leu Thr Asp Leu Ser Pro His Leu Arg Tyr Arg Phe Gln
              980                 985                 990

Leu Gln Ala Thr Thr Lys Glu Gly Pro Gly Glu Ala Ile Val Arg Glu

```
              995                 1000                1005
     Gly  Gly  Thr  Met  Ala  Leu  Ser  Gly  Ile  Ser  Asp  Phe  Gly  Asn  Ile
               1010                1015                     1020

Ser  Ala  Thr  Ala  Gly  Glu  Asn  Tyr  Ser  Val  Val  Ser  Trp  Val  Pro
          1025                1030                     1035

Lys  Glu  Gly  Gln  Cys  Asn  Phe  Arg  Phe  His  Ile  Leu  Phe  Lys  Ala
          1040                1045                     1050

Leu  Gly  Glu  Glu  Lys  Gly  Gly  Ala  Ser  Leu  Ser  Pro  Gln  Tyr  Val
          1055                1060                     1065

Ser  Tyr  Asn  Gln  Ser  Ser  Tyr  Thr  Gln  Trp  Asp  Leu  Gln  Pro  Asp
          1070                1075                     1080

Thr  Asp  Tyr  Glu  Ile  His  Leu  Phe  Lys  Glu  Arg  Met  Phe  Arg  His
          1085                1090                     1095

Gln  Met  Ala  Val  Lys  Thr  Asn  Gly  Thr  Gly  Arg  Val  Arg  Leu  Pro
          1100                1105                     1110

Pro  Ala  Gly  Phe  Ala  Thr  Glu  Gly  Trp  Phe  Ile  Gly  Phe  Val  Ser
          1115                1120                     1125

Ala  Ile  Ile  Leu  Leu  Leu  Leu  Val  Leu  Leu  Ile  Leu  Cys  Phe  Ile
          1130                1135                     1140

Lys  Arg  Ser  Lys  Gly  Gly  Lys  Tyr  Ser  Val  Lys  Asp  Lys  Glu  Asp
          1145                1150                     1155

Thr  Gln  Val  Asp  Ser  Glu  Ala  Arg  Pro  Met  Lys  Asp  Glu  Thr  Phe
          1160                1165                     1170

Gly  Glu  Tyr  Arg  Ser  Leu  Glu  Ser  Asp  Asn  Glu  Glu  Lys  Ala  Phe
          1175                1180                     1185

Gly  Ser  Ser  Gln  Pro  Ser  Leu  Asn  Gly  Asp  Ile  Lys  Pro  Leu  Gly
          1190                1195                     1200

Ser  Asp  Asp  Ser  Leu  Ala  Asp  Tyr  Gly  Gly  Ser  Val  Asp  Val  Gln
          1205                1210                     1215

Phe  Asn  Glu  Asp  Gly  Ser  Phe  Ile  Gly  Gln  Tyr  Ser  Gly  Lys  Lys
          1220                1225                     1230

Glu  Lys  Glu  Ala  Ala  Gly  Gly  Asn  Asp  Ser  Ser  Gly  Ala  Thr  Ser
          1235                1240                     1245

Pro  Ile  Asn  Pro  Ala  Val  Ala  Leu  Glu
          1250                1255

<210> SEQ ID NO 23
<211> LENGTH: 556
<212> TYPE: PRT
<213> ORGANISM: Homo sapiens

<400> SEQUENCE: 23

Met  Pro  Pro  Pro  Arg  Leu  Leu  Phe  Phe  Leu  Leu  Phe  Leu  Thr  Pro  Met
 1                  5                   10                  15

Glu  Val  Arg  Pro  Glu  Glu  Pro  Leu  Val  Val  Lys  Val  Glu  Glu  Gly  Asp
               20                  25                  30

Asn  Ala  Val  Leu  Gln  Cys  Leu  Lys  Gly  Thr  Ser  Asp  Gly  Pro  Thr  Gln
          35                  40                  45

Gln  Leu  Thr  Trp  Ser  Arg  Glu  Ser  Pro  Leu  Lys  Pro  Phe  Leu  Lys  Leu
     50                  55                  60

Ser  Leu  Gly  Leu  Pro  Gly  Leu  Gly  Ile  His  Met  Arg  Pro  Leu  Ala  Ile
 65                  70                  75                  80

Trp  Leu  Phe  Ile  Phe  Asn  Val  Ser  Gln  Gln  Met  Gly  Gly  Phe  Tyr  Leu
                85                  90                  95
```

```
Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
```

```
                515                 520                 525
Asp Ser Tyr Glu Asn Met Asp Asn Pro Asp Gly Pro Asp Pro Ala Trp
        530                 535                 540

Gly Gly Gly Gly Arg Met Gly Thr Trp Ser Thr Arg
545                 550                 555

<210> SEQ ID NO 24
<211> LENGTH: 1456
<212> TYPE: PRT
<213> ORGANISM: Homo sapiens

<400> SEQUENCE: 24

Met Arg Leu Pro Leu Leu Leu Val Phe Ala Ser Val Ile Pro Gly Ala
1               5                   10                  15

Val Leu Leu Leu Asp Thr Arg Gln Phe Leu Ile Tyr Asn Glu Asp His
                20                  25                  30

Lys Arg Cys Val Asp Ala Val Ser Pro Ser Ala Val Gln Thr Ala Ala
            35                  40                  45

Cys Asn Gln Asp Ala Glu Ser Gln Lys Phe Arg Trp Val Ser Glu Ser
        50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335
```

```
Gly Tyr Ile Cys Lys Lys Gly Asn Thr Thr Leu Asn Ser Phe Val Ile
                340                 345                 350

Pro Ser Glu Ser Asp Val Pro Thr His Cys Pro Ser Gln Trp Trp Pro
            355                 360                 365

Tyr Ala Gly His Cys Tyr Lys Ile His Arg Asp Glu Lys Lys Ile Gln
        370                 375                 380

Arg Asp Ala Leu Thr Thr Cys Arg Lys Glu Gly Asp Leu Thr Ser
385                 390                 395                 400

Ile His Thr Ile Glu Glu Leu Asp Phe Ile Ile Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
        435                 440                 445

Leu Arg Gly Glu Pro Ser His Glu Asn Asn Arg Gln Glu Asp Cys Val
    450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
            500                 505                 510

Phe Tyr Cys Tyr Met Ile Gly His Thr Leu Ser Thr Phe Ala Glu Ala
        515                 520                 525

Asn Gln Thr Cys Asn Asn Glu Asn Ala Tyr Leu Thr Thr Ile Glu Asp
    530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
            580                 585                 590

Met Pro Gly Arg Lys Pro Gly Cys Val Ala Met Arg Thr Gly Ile Ala
        595                 600                 605

Gly Gly Leu Trp Asp Val Leu Lys Cys Asp Glu Lys Ala Lys Phe Val
    610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
        675                 680                 685

Ser Ile Asn Asn Lys Glu Glu Gln Gln Thr Ile Trp Arg Leu Ile Thr
    690                 695                 700

Ala Ser Gly Ser Tyr His Lys Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Thr Met Ser Trp Asn Asp Ile Asn
```

-continued

```
            755                 760                 765
Cys Glu His Leu Asn Asn Trp Ile Cys Gln Ile Gln Lys Gly Gln Thr
            770                 775                 780
Pro Lys Pro Glu Pro Thr Pro Ala Pro Gln Asp Asn Pro Val Thr
785                 790                 795                 800
Glu Asp Gly Trp Val Ile Tyr Lys Asp Tyr Gln Tyr Tyr Phe Ser Lys
                        805                 810                 815
Glu Lys Glu Thr Met Asp Asn Ala Arg Ala Phe Cys Lys Arg Asn Phe
                820                 825                 830
Gly Asp Leu Val Ser Ile Gln Ser Glu Ser Glu Lys Lys Phe Leu Trp
                835                 840                 845
Lys Tyr Val Asn Arg Asn Asp Ala Gln Ser Ala Tyr Phe Ile Gly Leu
            850                 855                 860
Leu Ile Ser Leu Asp Lys Lys Phe Ala Trp Met Asp Gly Ser Lys Val
865                 870                 875                 880
Asp Tyr Val Ser Trp Ala Thr Gly Glu Pro Asn Phe Ala Asn Glu Asp
                        885                 890                 895
Glu Asn Cys Val Thr Met Tyr Ser Asn Ser Gly Phe Trp Asn Asp Ile
                900                 905                 910
Asn Cys Gly Tyr Pro Asn Ala Phe Ile Cys Gln Arg His Asn Ser Ser
            915                 920                 925
Ile Asn Ala Thr Thr Val Met Pro Thr Met Pro Ser Val Pro Ser Gly
            930                 935                 940
Cys Lys Glu Gly Trp Asn Phe Tyr Ser Asn Lys Cys Phe Lys Ile Phe
945                 950                 955                 960
Gly Phe Met Glu Glu Glu Arg Lys Asn Trp Gln Glu Ala Arg Lys Ala
                        965                 970                 975
Cys Ile Gly Phe Gly Gly Asn Leu Val Ser Ile Gln Asn Glu Lys Glu
                980                 985                 990
Gln Ala Phe Leu Thr Tyr His Met  Lys Asp Ser Thr Phe  Ser Ala Trp
            995                 1000                1005
Thr Gly Leu Asn Asp Val Asn  Ser Glu His Thr Phe  Leu Trp Thr
1010                1015                1020
Asp Gly Arg Gly Val His Tyr  Thr Asn Trp Gly Lys  Gly Tyr Pro
        1025                1030                1035
Gly Gly Arg Arg Ser Ser Leu  Ser Tyr Glu Asp Ala  Asp Cys Val
        1040                1045                1050
Val Ile Ile Gly Gly Ala Ser  Asn Glu Ala Gly Lys  Trp Met Asp
        1055                1060                1065
Asp Thr Cys Asp Ser Lys Arg  Gly Tyr Ile Cys Gln  Thr Arg Ser
        1070                1075                1080
Asp Pro Ser Leu Thr Asn Pro  Pro Ala Thr Ile Gln  Thr Asp Gly
        1085                1090                1095
Phe Val Lys Tyr Gly Lys Ser  Ser Tyr Ser Leu Met  Arg Gln Lys
        1100                1105                1110
Phe Gln Trp His Glu Ala Glu  Thr Tyr Cys Lys Leu  His Asn Ser
        1115                1120                1125
Leu Ile Ala Ser Ile Leu Asp Pro Tyr Ser Asn Ala  Phe Ala Trp
        1130                1135                1140
Leu Gln Met Glu Thr Ser Asn  Glu Arg Val Trp Ile  Ala Leu Asn
        1145                1150                1155
Ser Asn Leu Thr Asp Asn Gln  Tyr Thr Trp Thr Asp  Lys Trp Arg
        1160                1165                1170
```

```
Val Arg Tyr Thr Asn Trp Ala Ala Asp Glu Pro Lys Leu Lys Ser
    1175                1180                1185

Ala Cys Val Tyr Leu Asp Leu Asp Gly Tyr Trp Lys Thr Ala His
    1190                1195                1200

Cys Asn Glu Ser Phe Tyr Phe Leu Cys Lys Arg Ser Asp Glu Ile
    1205                1210                1215

Pro Ala Thr Glu Pro Pro Gln Leu Pro Gly Arg Cys Pro Glu Ser
    1220                1225                1230

Asp His Thr Ala Trp Ile Pro Phe His Gly His Cys Tyr Tyr Ile
    1235                1240                1245

Glu Ser Ser Tyr Thr Arg Asn Trp Gly Gln Ala Ser Leu Glu Cys
    1250                1255                1260

Leu Arg Met Gly Ser Ser Leu Val Ser Ile Glu Ser Ala Ala Glu
    1265                1270                1275

Ser Ser Phe Leu Ser Tyr Arg Val Glu Pro Leu Lys Ser Lys Thr
    1280                1285                1290

Asn Phe Trp Ile Gly Leu Phe Arg Asn Val Glu Gly Thr Trp Leu
    1295                1300                1305

Trp Ile Asn Asn Ser Pro Val Ser Phe Val Asn Trp Asn Thr Gly
    1310                1315                1320

Asp Pro Ser Gly Glu Arg Asn Asp Cys Val Ala Leu His Ala Ser
    1325                1330                1335

Ser Gly Phe Trp Ser Asn Ile His Cys Ser Ser Tyr Lys Gly Tyr
    1340                1345                1350

Ile Cys Lys Arg Pro Lys Ile Ile Asp Ala Lys Pro Thr His Glu
    1355                1360                1365

Leu Leu Thr Thr Lys Ala Asp Thr Arg Lys Met Asp Pro Ser Lys
    1370                1375                1380

Pro Ser Ser Asn Val Ala Gly Val Val Ile Ile Val Ile Leu Leu
    1385                1390                1395

Ile Leu Thr Gly Ala Gly Leu Ala Ala Tyr Phe Phe Tyr Lys Lys
    1400                1405                1410

Arg Arg Val His Leu Pro Gln Glu Gly Ala Phe Glu Asn Thr Leu
    1415                1420                1425

Tyr Phe Asn Ser Gln Ser Ser Pro Gly Thr Ser Asp Met Lys Asp
    1430                1435                1440

Leu Val Gly Asn Ile Glu Gln Asn Glu His Ser Val Ile
    1445                1450                1455

<210> SEQ ID NO 25
<211> LENGTH: 150
<212> TYPE: PRT
<213> ORGANISM: Homo sapiens

<400> SEQUENCE: 25

Met Tyr Gly Lys Ile Ile Phe Val Leu Leu Leu Ser Glu Ile Val Ser
1               5                   10                  15

Ile Ser Ala Ser Ser Thr Thr Gly Val Ala Met His Thr Ser Thr Ser
                20                  25                  30

Ser Ser Val Thr Lys Ser Tyr Ile Ser Ser Gln Thr Asn Asp Thr His
            35                  40                  45

Lys Arg Asp Thr Tyr Ala Ala Thr Pro Arg Ala His Glu Val Ser Glu
        50                  55                  60

Ile Ser Val Arg Thr Val Tyr Pro Pro Glu Glu Glu Thr Gly Glu Arg
```

```
                65                  70                  75                  80
Val Gln Leu Ala His His Phe Ser Glu Pro Glu Ile Thr Leu Ile Ile
                    85                  90                  95

Phe Gly Val Met Ala Val Ile Gly Thr Ile Leu Leu Ile Ser Tyr
                100                 105                 110

Gly Ile Arg Arg Leu Ile Lys Lys Ser Pro Ser Asp Val Lys Pro Leu
                115                 120                 125

Pro Ser Pro Asp Thr Asp Val Pro Leu Ser Ser Val Glu Ile Glu Asn
130                 135                 140

Pro Glu Thr Ser Asp Gln
145                 150

<210> SEQ ID NO 26
<211> LENGTH: 534
<212> TYPE: PRT
<213> ORGANISM: Homo sapiens

<400> SEQUENCE: 26

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
                35                  40                  45

Cys Cys Ser Phe Ser Pro Glu Pro Gly Phe Ser Leu Ala Gln Leu Asn
            50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
        210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
            275                 280                 285
```

-continued

```
Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530

<210> SEQ ID NO 27
<211> LENGTH: 220
<212> TYPE: PRT
<213> ORGANISM: Homo sapiens

<400> SEQUENCE: 27

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125
```

```
Asn Gly Thr Ile Ile His Val Lys Gly Lys His Leu Cys Pro Ser Pro
            130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
210                 215                 220

<210> SEQ ID NO 28
<211> LENGTH: 207
<212> TYPE: PRT
<213> ORGANISM: Homo sapiens

<400> SEQUENCE: 28

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 29
<211> LENGTH: 281
<212> TYPE: PRT
<213> ORGANISM: Homo sapiens

<400> SEQUENCE: 29

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30
```

```
Gly Ile Trp Ile Leu Ile Asp Lys Thr Ser Phe Val Ser Phe Val Gly
            35                  40                  45

Leu Ala Phe Val Pro Leu Gln Ile Trp Ser Lys Val Leu Ala Ile Ser
        50                  55                  60

Gly Ile Phe Thr Met Gly Ile Ala Leu Leu Gly Cys Val Gly Ala Leu
 65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
               100                 105                 110

Ala Gln Leu Glu Arg Ser Leu Arg Asp Val Val Glu Lys Thr Ile Gln
               115                 120                 125

Lys Tyr Gly Thr Asn Pro Glu Glu Thr Ala Ala Glu Glu Ser Trp Asp
               130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                    165                 170                 175

Val Pro Cys Ser Cys Tyr Asn Leu Ser Ala Thr Asn Asp Ser Thr Ile
                180                 185                 190

Leu Asp Lys Val Ile Leu Pro Gln Leu Ser Arg Leu Gly His Leu Ala
                195                 200                 205

Arg Ser Arg His Ser Ala Asp Ile Cys Ala Val Pro Ala Glu Ser His
                210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                    245                 250                 255

Leu Gly Phe Met Thr Leu Ser Ile Phe Leu Cys Arg Asn Leu Asp His
                260                 265                 270

Val Tyr Asn Arg Leu Ala Arg Tyr Arg
                275                 280

<210> SEQ ID NO 30
<211> LENGTH: 458
<212> TYPE: PRT
<213> ORGANISM: Homo sapiens

<400> SEQUENCE: 30

Met Asn Arg Gly Val Pro Phe Arg His Leu Leu Leu Val Leu Gln Leu
 1               5                  10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
                35                  40                  45

Ile Gln Phe His Trp Lys Asn Ser Asn Gln Ile Lys Ile Leu Gly Asn
                50                  55                  60

Gln Gly Ser Phe Leu Thr Lys Gly Pro Ser Lys Leu Asn Asp Arg Ala
 65                 70                  75                  80

Asp Ser Arg Arg Ser Leu Trp Asp Gln Gly Asn Phe Pro Leu Ile Ile
                    85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
```

```
            115                 120                 125
Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Gln Lys Ala Ser
        195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
450                 455
```

<210> SEQ ID NO 31
<211> LENGTH: 1039
<212> TYPE: PRT
<213> ORGANISM: Homo sapiens

<400> SEQUENCE: 31

```
Met Ala Arg Ala Leu Cys Pro Leu Gln Ala Leu Trp Leu Leu Glu Trp
1               5                   10                  15

Val Leu Leu Leu Leu Gly Pro Cys Ala Ala Pro Pro Ala Trp Ala Leu
            20                  25                  30
```

```
Asn Leu Asp Pro Val Gln Leu Thr Phe Tyr Ala Gly Pro Asn Gly Ser
         35                  40                  45

Gln Phe Gly Phe Ser Leu Asp Phe His Lys Asp Ser His Gly Arg Val
 50                  55                  60

Ala Ile Val Val Gly Ala Pro Arg Thr Leu Gly Pro Ser Gln Glu Glu
 65                  70                  75                  80

Thr Gly Gly Val Phe Leu Cys Pro Trp Arg Ala Glu Gly Gly Gln Cys
                 85                  90                  95

Pro Ser Leu Leu Phe Asp Leu Arg Asp Glu Thr Arg Asn Val Gly Ser
             100                 105                 110

Gln Thr Leu Gln Thr Phe Lys Ala Arg Gln Gly Leu Gly Ala Ser Val
         115                 120                 125

Val Ser Trp Ser Asp Val Ile Val Ala Cys Ala Pro Trp Gln His Trp
 130                 135                 140

Asn Val Leu Glu Lys Thr Glu Glu Ala Glu Lys Thr Pro Val Gly Ser
 145                 150                 155                 160

Cys Phe Leu Ala Gln Pro Glu Ser Gly Arg Arg Ala Glu Tyr Ser Pro
             165                 170                 175

Cys Arg Gly Asn Thr Leu Ser Arg Ile Tyr Val Glu Asn Asp Phe Ser
             180                 185                 190

Trp Asp Lys Arg Tyr Cys Glu Ala Gly Phe Ser Ser Val Val Thr Gln
         195                 200                 205

Ala Gly Glu Leu Val Leu Gly Ala Pro Gly Gly Tyr Tyr Phe Leu Gly
 210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Ser Gln Ser Leu Ser Phe Asp Ser
                 245                 250                 255

Ser Asn Pro Glu Tyr Phe Asp Gly Tyr Trp Gly Tyr Ser Val Ala Val
             260                 265                 270

Gly Glu Phe Asp Gly Asp Leu Asn Thr Thr Glu Tyr Val Val Gly Ala
             275                 280                 285

Pro Thr Trp Ser Trp Thr Leu Gly Ala Val Glu Ile Leu Asp Ser Tyr
         290                 295                 300

Tyr Gln Arg Leu His Arg Leu Arg Gly Glu Gln Met Ala Ser Tyr Phe
305                 310                 315                 320

Gly His Ser Val Ala Val Thr Asp Val Asn Gly Asp Gly Arg His Asp
                 325                 330                 335

Leu Leu Val Gly Ala Pro Leu Tyr Met Glu Ser Arg Ala Asp Arg Lys
             340                 345                 350

Leu Ala Glu Val Gly Arg Val Tyr Leu Phe Leu Gln Pro Arg Gly Pro
         355                 360                 365

His Ala Leu Gly Ala Pro Ser Leu Leu Leu Thr Gly Thr Gln Leu Tyr
         370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                 405                 410                 415

Arg Gly Gln Val Leu Val Phe Leu Gly Gln Ser Glu Gly Leu Arg Ser
             420                 425                 430

Arg Pro Ser Gln Val Leu Asp Ser Pro Phe Pro Thr Gly Ser Ala Phe
             435                 440                 445

Gly Phe Ser Leu Arg Gly Ala Val Asp Ile Asp Asp Asn Gly Tyr Pro
```

-continued

```
                450                 455                 460
Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
                500                 505                 510

Val Ser Cys Phe Asn Ile Gln Met Cys Val Gly Ala Thr Gly His Asn
                515                 520                 525

Ile Pro Gln Lys Leu Ser Leu Asn Ala Glu Leu Gln Leu Asp Arg Gln
                530                 535                 540

Lys Pro Arg Gln Gly Arg Val Leu Leu Gly Ser Gln Gln Ala
545                 550                 555                 560

Gly Thr Thr Leu Asn Leu Asp Leu Gly Lys His Ser Pro Ile Cys
                565                 570                 575

His Thr Thr Met Ala Phe Leu Arg Asp Glu Ala Asp Phe Arg Asp Lys
                580                 585                 590

Leu Ser Pro Ile Val Leu Ser Leu Asn Val Ser Leu Pro Pro Thr Glu
                595                 600                 605

Ala Gly Met Ala Pro Ala Val Val Leu His Gly Asp Thr His Val Gln
                610                 615                 620

Glu Gln Thr Arg Ile Val Leu Asp Cys Gly Glu Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
                660                 665                 670

Glu Gly Ala Tyr Glu Ala Glu Leu Ala Val His Leu Pro Gln Gly Ala
                675                 680                 685

His Tyr Met Arg Ala Leu Ser Asn Val Glu Gly Phe Glu Arg Leu Ile
                690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
                740                 745                 750

Gln Ile Arg Ser Lys Asn Ser Gln Asn Pro Asn Ser Lys Ile Val Leu
                755                 760                 765

Leu Asp Val Pro Val Arg Ala Glu Ala Gln Val Glu Leu Arg Gly Asn
                770                 775                 780

Ser Phe Pro Ala Ser Leu Val Val Ala Ala Glu Glu Gly Glu Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
                820                 825                 830

His Leu Pro Gly Gln Ser Gln Pro Ser Asp Leu Leu Tyr Ile Leu Asp
                835                 840                 845

Ile Gln Pro Gln Gly Gly Leu Gln Cys Phe Pro Gln Pro Val Asn
                850                 855                 860

Pro Leu Lys Val Asp Trp Gly Leu Pro Ile Pro Ser Pro Ser Pro Ile
865                 870                 875                 880
```

His Pro Ala His His Lys Arg Asp Arg Arg Gln Ile Phe Leu Pro Glu
            885                 890                 895

Pro Glu Gln Pro Ser Arg Leu Gln Asp Pro Val Leu Val Ser Cys Asp
            900                 905                 910

Ser Ala Pro Cys Thr Val Val Gln Cys Asp Leu Gln Glu Met Ala Arg
            915                 920                 925

Gly Gln Arg Ala Met Val Thr Val Leu Ala Phe Leu Trp Leu Pro Ser
        930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
            980                 985                 990

Arg Ala Ile Pro Ile Trp Trp Val Leu Val Gly Val Leu Gly Gly Leu
            995                 1000                1005

Leu Leu Leu Thr Ile Leu Val Leu Ala Met Trp Lys Val Gly Phe
        1010                1015                1020

Phe Lys Arg Asn Arg Pro Pro Leu Glu Glu Asp Asp Glu Glu Gly
        1025                1030                1035

Glu

<210> SEQ ID NO 32
<211> LENGTH: 177
<212> TYPE: PRT
<213> ORGANISM: Homo sapiens

<400> SEQUENCE: 32

Met Pro Ala Trp Gly Ala Leu Phe Leu Leu Trp Ala Thr Ala Glu Ala
1               5                   10                  15

Thr Lys Asp Cys Pro Ser Pro Cys Thr Cys Arg Ala Leu Glu Thr Met
            20                  25                  30

Gly Leu Trp Val Asp Cys Arg Gly His Gly Leu Thr Ala Leu Pro Ala
        35                  40                  45

Leu Pro Ala Arg Thr Arg His Leu Leu Leu Ala Asn Asn Ser Leu Gln
    50                  55                  60

Ser Val Pro Pro Gly Ala Phe Asp His Leu Pro Gln Leu Gln Thr Leu
65                  70                  75                  80

Asp Val Thr Gln Asn Pro Trp His Cys Asp Cys Ser Leu Thr Tyr Leu
                85                  90                  95

Arg Leu Trp Leu Glu Asp Arg Thr Pro Glu Ala Leu Leu Gln Val Arg
            100                 105                 110

Cys Ala Ser Pro Ser Leu Ala Ala His Gly Pro Leu Gly Arg Leu Thr
        115                 120                 125

Gly Tyr Gln Leu Gly Ser Cys Gly Trp Gln Leu Gln Ala Ser Trp Val
    130                 135                 140

Arg Pro Gly Val Leu Trp Asp Val Ala Leu Val Ala Val Ala Ala Leu
145                 150                 155                 160

Gly Leu Ala Leu Leu Ala Gly Leu Leu Cys Ala Thr Thr Glu Ala Leu
                165                 170                 175

Asp

<210> SEQ ID NO 33
<211> LENGTH: 1304

```
<212> TYPE: PRT
<213> ORGANISM: Homo sapiens

<400> SEQUENCE: 33

Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30

Leu Thr Thr Ala Lys Met Pro Ser Val Pro Leu Ser Ser Asp Pro Leu
            35                  40                  45

Pro Thr His Thr Thr Ala Phe Ser Pro Ala Ser Thr Phe Glu Arg Glu
        50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
            85                  90                  95

Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
            115                 120                 125

Ala Ala Asn Ala Lys Leu Asn Pro Thr Pro Gly Ser Asn Ala Ile Ser
        130                 135                 140

Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
            165                 170                 175

Ala Leu Pro Ala Arg Thr Ser Asn Thr Thr Ile Thr Ala Asn Thr Ser
            180                 185                 190

Asp Ala Tyr Leu Asn Ala Ser Glu Thr Thr Thr Leu Ser Pro Ser Gly
            195                 200                 205

Ser Ala Val Ile Ser Thr Thr Thr Ile Ala Thr Thr Pro Ser Lys Pro
        210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
            245                 250                 255

Glu Cys Gly Asn Asn Thr Cys Thr Asn Asn Glu Val His Asn Leu Thr
            260                 265                 270

Glu Cys Lys Asn Ala Ser Val Ser Ile Ser His Asn Ser Cys Thr Ala
            275                 280                 285

Pro Asp Lys Thr Leu Ile Leu Asp Val Pro Pro Gly Val Glu Lys Phe
        290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
            325                 330                 335

Thr Tyr Arg Phe Gln Cys Gly Asn Met Ile Phe Asp Asn Lys Glu Ile
            340                 345                 350

Lys Leu Glu Asn Leu Glu Pro Glu His Glu Tyr Lys Cys Asp Ser Glu
            355                 360                 365

Ile Leu Tyr Asn Asn His Lys Phe Thr Asn Ala Ser Lys Ile Ile Lys
        370                 375                 380

Thr Asp Phe Gly Ser Pro Gly Glu Pro Gln Ile Ile Phe Cys Arg Ser
385                 390                 395                 400
```

```
Glu Ala Ala His Gln Gly Val Ile Thr Trp Asn Pro Pro Gln Arg Ser
                405                 410                 415

Phe His Asn Phe Thr Leu Cys Tyr Ile Lys Glu Thr Glu Lys Asp Cys
                420                 425                 430

Leu Asn Leu Asp Lys Asn Leu Ile Lys Tyr Asp Leu Gln Asn Leu Lys
                435                 440                 445

Pro Tyr Thr Lys Tyr Val Leu Ser Leu His Ala Tyr Ile Ile Ala Lys
            450                 455                 460

Val Gln Arg Asn Gly Ser Ala Ala Met Cys His Phe Thr Thr Lys Ser
465                 470                 475                 480

Ala Pro Pro Ser Gln Val Trp Asn Met Thr Val Ser Met Thr Ser Asp
                485                 490                 495

Asn Ser Met His Val Lys Cys Arg Pro Pro Arg Asp Arg Asn Gly Pro
                500                 505                 510

His Glu Arg Tyr His Leu Glu Val Glu Ala Gly Asn Thr Leu Val Arg
            515                 520                 525

Asn Glu Ser His Lys Asn Cys Asp Phe Arg Val Lys Asp Leu Gln Tyr
530                 535                 540

Ser Thr Asp Tyr Thr Phe Lys Ala Tyr Phe His Asn Gly Asp Tyr Pro
545                 550                 555                 560

Gly Glu Pro Phe Ile Leu His His Ser Thr Ser Tyr Asn Ser Lys Ala
                565                 570                 575

Leu Ile Ala Phe Leu Ala Phe Leu Ile Ile Val Thr Ser Ile Ala Leu
                580                 585                 590

Leu Val Val Leu Tyr Lys Ile Tyr Asp Leu His Lys Lys Arg Ser Cys
                595                 600                 605

Asn Leu Asp Glu Gln Gln Glu Leu Val Glu Arg Asp Asp Glu Lys Gln
            610                 615                 620

Leu Met Asn Val Glu Pro Ile His Ala Asp Ile Leu Leu Glu Thr Tyr
625                 630                 635                 640

Lys Arg Lys Ile Ala Asp Glu Gly Arg Leu Phe Leu Ala Glu Phe Gln
                645                 650                 655

Ser Ile Pro Arg Val Phe Ser Lys Phe Pro Ile Lys Glu Ala Arg Lys
                660                 665                 670

Pro Phe Asn Gln Asn Lys Asn Arg Tyr Val Asp Ile Leu Pro Tyr Asp
            675                 680                 685

Tyr Asn Arg Val Glu Leu Ser Glu Ile Asn Gly Asp Ala Gly Ser Asn
            690                 695                 700

Tyr Ile Asn Ala Ser Tyr Ile Asp Gly Phe Lys Glu Pro Arg Lys Tyr
705                 710                 715                 720

Ile Ala Ala Gln Gly Pro Arg Asp Glu Thr Val Asp Asp Phe Trp Arg
                725                 730                 735

Met Ile Trp Glu Gln Lys Ala Thr Val Ile Val Met Val Thr Arg Cys
                740                 745                 750

Glu Glu Gly Asn Arg Asn Lys Cys Ala Glu Tyr Trp Pro Ser Met Glu
                755                 760                 765

Glu Gly Thr Arg Ala Phe Gly Asp Val Val Lys Ile Asn Gln His
            770                 775                 780

Lys Arg Cys Pro Asp Tyr Ile Ile Gln Lys Leu Asn Ile Val Asn Lys
785                 790                 795                 800

Lys Glu Lys Ala Thr Gly Arg Glu Val Thr His Ile Gln Phe Thr Ser
                805                 810                 815
```

-continued

Trp Pro Asp His Gly Val Pro Glu Asp Pro His Leu Leu Leu Lys Leu
            820                 825                 830

Arg Arg Arg Val Asn Ala Phe Ser Asn Phe Phe Ser Gly Pro Ile Val
        835                 840                 845

Val His Cys Ser Ala Gly Val Gly Arg Thr Gly Thr Tyr Ile Gly Ile
    850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
            885                 890                 895

Glu Ala Gln Tyr Ile Leu Ile His Gln Ala Leu Val Glu Tyr Asn Gln
        900                 905                 910

Phe Gly Glu Thr Glu Val Asn Leu Ser Glu Leu His Pro Tyr Leu His
    915                 920                 925

Asn Met Lys Lys Arg Asp Pro Pro Ser Glu Pro Ser Pro Leu Glu Ala
930                 935                 940

Glu Phe Gln Arg Leu Pro Ser Tyr Arg Ser Trp Arg Thr Gln His Ile
945                 950                 955                 960

Gly Asn Gln Glu Glu Asn Lys Ser Lys Asn Arg Asn Ser Asn Val Ile
            965                 970                 975

Pro Tyr Asp Tyr Asn Arg Val Pro Leu Lys His Glu Leu Glu Met Ser
        980                 985                 990

Lys Glu Ser Glu His Asp Ser Asp Glu Ser Ser Asp Asp Ser Asp
            995                 1000                1005

Ser Glu Glu Pro Ser Lys Tyr Ile Asn Ala Ser Phe Ile Met Ser
    1010                1015                1020

Tyr Trp Lys Pro Glu Val Met Ile Ala Ala Gln Gly Pro Leu Lys
    1025                1030                1035

Glu Thr Ile Gly Asp Phe Trp Gln Met Ile Phe Gln Arg Lys Val
    1040                1045                1050

Lys Val Ile Val Met Leu Thr Glu Leu Lys His Gly Asp Gln Glu
    1055                1060                1065

Ile Cys Ala Gln Tyr Trp Gly Glu Gly Lys Gln Thr Tyr Gly Asp
    1070                1075                1080

Ile Glu Val Asp Leu Lys Asp Thr Asp Lys Ser Ser Thr Tyr Thr
    1085                1090                1095

Leu Arg Val Phe Glu Leu Arg His Ser Lys Arg Lys Asp Ser Arg
    1100                1105                1110

Thr Val Tyr Gln Tyr Gln Tyr Thr Asn Trp Ser Val Glu Gln Leu
    1115                1120                1125

Pro Ala Glu Pro Lys Glu Leu Ile Ser Met Ile Gln Val Val Lys
    1130                1135                1140

Gln Lys Leu Pro Gln Lys Asn Ser Ser Glu Gly Asn Lys His His
    1145                1150                1155

Lys Ser Thr Pro Leu Leu Ile His Cys Arg Asp Gly Ser Gln Gln
    1160                1165                1170

Thr Gly Ile Phe Cys Ala Leu Leu Asn Leu Leu Glu Ser Ala Glu
    1175                1180                1185

Thr Glu Glu Val Val Asp Ile Phe Gln Val Val Lys Ala Leu Arg
    1190                1195                1200

Lys Ala Arg Pro Gly Met Val Ser Thr Phe Glu Gln Tyr Gln Phe
    1205                1210                1215

Leu Tyr Asp Val Ile Ala Ser Thr Tyr Pro Ala Gln Asn Gly Gln

```
                1220                1225                1230
Val Lys Lys Asn Asn His Gln Glu Asp Lys Ile Glu Phe Asp Asn
            1235                1240                1245
Glu Val Asp Lys Val Lys Gln Asp Ala Asn Cys Val Asn Pro Leu
            1250                1255                1260
Gly Ala Pro Glu Lys Leu Pro Glu Ala Lys Glu Gln Ala Glu Gly
            1265                1270                1275
Ser Glu Pro Thr Ser Gly Thr Glu Gly Pro Glu His Ser Val Asn
            1280                1285                1290
Gly Pro Ala Ser Pro Ala Leu Asn Gln Gly Ser
            1295                1300

<210> SEQ ID NO 34
<211> LENGTH: 1032
<212> TYPE: PRT
<213> ORGANISM: Homo sapiens

<400> SEQUENCE: 34

Met Ala Trp Glu Ala Arg Arg Glu Pro Gly Pro Arg Arg Ala Val
1               5                   10                  15
Arg Glu Thr Val Met Leu Leu Leu Cys Leu Gly Val Pro Thr Gly
            20                  25                  30
Pro Tyr Asn Val Asp Thr Glu Ser Ala Leu Leu Tyr Gln Gly Pro His
            35                  40                  45
Asn Thr Leu Phe Gly Tyr Ser Val Val Leu His Ser His Gly Ala Asn
        50                  55                  60
Arg Trp Leu Leu Val Gly Ala Pro Thr Ala Asn Trp Leu Ala Asn Ala
65                  70                  75                  80
Ser Val Ile Asn Pro Gly Ala Ile Tyr Arg Cys Arg Ile Gly Lys Asn
                85                  90                  95
Pro Gly Gln Thr Cys Glu Gln Leu Gln Leu Gly Ser Pro Asn Gly Glu
            100                 105                 110
Pro Cys Gly Lys Thr Cys Leu Glu Glu Arg Asp Asn Gln Trp Leu Gly
            115                 120                 125
Val Thr Leu Ser Arg Gln Pro Gly Glu Asn Gly Ser Ile Val Thr Cys
        130                 135                 140
Gly His Arg Trp Lys Asn Ile Phe Tyr Ile Lys Asn Glu Asn Lys Leu
145                 150                 155                 160
Pro Thr Gly Gly Cys Tyr Gly Val Pro Pro Asp Leu Arg Thr Glu Leu
                165                 170                 175
Ser Lys Arg Ile Ala Pro Cys Tyr Gln Asp Tyr Val Lys Lys Phe Gly
            180                 185                 190
Glu Asn Phe Ala Ser Cys Gln Ala Gly Ile Ser Ser Phe Tyr Thr Lys
            195                 200                 205
Asp Leu Ile Val Met Gly Ala Pro Gly Ser Ser Tyr Trp Thr Gly Ser
        210                 215                 220
Leu Phe Val Tyr Asn Ile Thr Thr Asn Lys Tyr Lys Ala Phe Leu Asp
225                 230                 235                 240
Lys Gln Asn Gln Val Lys Phe Gly Ser Tyr Leu Gly Tyr Ser Val Gly
                245                 250                 255
Ala Gly His Phe Arg Ser Gln His Thr Thr Glu Val Val Gly Gly Ala
            260                 265                 270
Pro Gln His Glu Gln Ile Gly Lys Ala Tyr Ile Phe Ser Ile Asp Glu
            275                 280                 285
```

```
Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
                340                 345                 350

Ala Met Glu Thr Asn Leu Val Gly Ser Asp Lys Tyr Ala Ala Arg Phe
        355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
                420                 425                 430

Ser Ile Ser Gly Gln Ile Asp Ala Asp Asn Asn Gly Tyr Val Asp Val
        435                 440                 445

Ala Val Gly Ala Phe Arg Ser Asp Ser Ala Val Leu Leu Arg Thr Arg
    450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
                500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
                580                 585                 590

Thr Glu Glu Phe Pro Pro Leu Gln Pro Ile Leu Gln Gln Lys Lys Glu
        595                 600                 605

Lys Asp Ile Met Lys Lys Thr Ile Asn Phe Ala Arg Phe Cys Ala His
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
                660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
    690                 695                 700

Gly Val Val Gln Leu Asp Cys Ser Ile Gly Tyr Ile Tyr Val Asp His
```

```
        705                 710                 715                 720
Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
    770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
            820                 825                 830

Ser Pro Gln Thr Asp Lys Leu Phe Asn Ile Leu Asp Val Gln Thr Thr
        835                 840                 845

Thr Gly Glu Cys His Phe Glu Asn Tyr Gln Arg Val Cys Ala Leu Glu
    850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
            900                 905                 910

Ala Ser Val His Ile Gln Leu Glu Gly Arg Pro Ser Ile Leu Glu Met
        915                 920                 925

Asp Glu Thr Ser Ala Leu Lys Phe Glu Ile Arg Ala Thr Gly Phe Pro
    930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Ser Leu Leu Leu Gly Leu Ile Val Leu
            980                 985                 990

Leu Leu Ile Ser Tyr Val Met Trp Lys Ala Gly Phe Phe Lys Arg Gln
        995                 1000                1005

Tyr Lys Ser Ile Leu Gln Glu Glu Asn Arg Arg Asp Ser Trp Ser
    1010                1015                1020

Tyr Ile Asn Ser Lys Ser Asn Asp Asp
    1025                1030

<210> SEQ ID NO 35
<211> LENGTH: 858
<212> TYPE: PRT
<213> ORGANISM: Homo sapiens

<400> SEQUENCE: 35

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45
```

```
Asp Lys Asp Ile Ser Trp Phe Ser Pro Asn Gly Glu Lys Leu Thr Pro
 50                  55                  60

Asn Gln Gln Arg Ile Ser Val Val Trp Asn Asp Asp Ser Ser Ser Thr
 65                  70                  75                  80

Leu Thr Ile Tyr Asn Ala Asn Ile Asp Asp Ala Gly Ile Tyr Lys Cys
                 85                  90                  95

Val Val Thr Gly Glu Asp Gly Ser Glu Ser Glu Ala Thr Val Asn Val
                100                 105                 110

Lys Ile Phe Gln Lys Leu Met Phe Lys Asn Ala Pro Thr Pro Gln Glu
            115                 120                 125

Phe Arg Glu Gly Glu Asp Ala Val Ile Val Cys Asp Val Val Ser Ser
        130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
                180                 185                 190

Ile Leu Ala Arg Gly Glu Ile Asn Phe Lys Asp Ile Gln Val Ile Val
            195                 200                 205

Asn Val Pro Pro Thr Ile Gln Ala Arg Gln Asn Ile Val Asn Ala Thr
210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Ala Ser Trp Thr Arg Pro Glu Lys Gln Glu Thr Leu Asp Gly His
        355                 360                 365

Met Val Val Arg Ser His Ala Arg Val Ser Ser Leu Thr Leu Lys Ser
    370                 375                 380

Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
                405                 410                 415

Lys Leu Gln Gly Pro Val Ala Val Tyr Thr Trp Glu Gly Asn Gln Val
            420                 425                 430

Asn Ile Thr Cys Glu Val Phe Ala Tyr Pro Ser Ala Thr Ile Ser Trp
        435                 440                 445

Phe Arg Asp Gly Gln Leu Leu Pro Ser Ser Asn Tyr Ser Asn Ile Lys
450                 455                 460

Ile Tyr Asn Thr Pro Ser Ala Ser Tyr Leu Glu Val Thr Pro Asp Ser
```

```
              465                 470                 475                 480
Glu Asn Asp Phe Gly Asn Tyr Asn Cys Thr Ala Val Asn Arg Ile Gly
                    485                 490                 495

Gln Glu Ser Leu Glu Phe Ile Leu Val Gln Ala Asp Thr Pro Ser Ser
                500                 505                 510

Pro Ser Ile Asp Gln Val Glu Pro Tyr Ser Ser Thr Ala Gln Val Gln
            515                 520                 525

Phe Asp Glu Pro Glu Ala Thr Gly Gly Val Pro Ile Leu Lys Tyr Lys
        530                 535                 540

Ala Glu Trp Arg Ala Val Gly Glu Val Trp His Ser Lys Trp Tyr
545                 550                 555                 560

Asp Ala Lys Glu Ala Ser Met Glu Gly Ile Val Thr Ile Val Gly Leu
                565                 570                 575

Lys Pro Glu Thr Thr Tyr Ala Val Arg Leu Ala Ala Leu Asn Gly Lys
                580                 585                 590

Gly Leu Gly Glu Ile Ser Ala Ala Ser Glu Phe Lys Thr Gln Pro Val
        595                 600                 605

Gln Gly Glu Pro Ser Ala Pro Lys Leu Glu Gly Gln Met Gly Glu Asp
    610                 615                 620

Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
                645                 650                 655

Lys Pro Glu Ile Arg Leu Pro Ser Gly Ser Asp His Val Met Leu Lys
                660                 665                 670

Ser Leu Asp Trp Asn Ala Glu Tyr Glu Val Tyr Val Val Ala Glu Asn
            675                 680                 685

Gln Gln Gly Lys Ser Lys Ala Ala His Phe Val Phe Arg Thr Ser Ala
        690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
                725                 730                 735

Val Val Val Asp Ile Thr Cys Tyr Phe Leu Asn Lys Cys Gly Leu Phe
                740                 745                 750

Met Cys Ile Ala Val Asn Leu Cys Gly Lys Ala Gly Pro Gly Ala Lys
            755                 760                 765

Gly Lys Asp Met Glu Glu Gly Lys Ala Ala Phe Ser Lys Asp Glu Ser
        770                 775                 780

Lys Glu Pro Ile Val Glu Val Arg Thr Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Glu Ala Lys Pro Glu Cys Gln Glu Thr
                820                 825                 830

Glu Thr Lys Pro Ala Pro Ala Glu Val Lys Thr Val Pro Asn Asp Ala
            835                 840                 845

Thr Gln Thr Lys Glu Asn Glu Ser Lys Ala
        850                 855

<210> SEQ ID NO 36
<211> LENGTH: 610
<212> TYPE: PRT
<213> ORGANISM: Homo sapiens
```

<400> SEQUENCE: 36

```
Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Leu Ala Leu Cys Tyr Thr Ala Ala Cys Thr
130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
    290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
    370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
```

```
                405                 410                 415
Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
            435                 440                 445

Gly Glu Phe Thr Tyr Lys Ser Ser Cys Ala Phe Ser Cys Glu Glu Gly
            450                 455                 460

Phe Glu Leu His Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
            515                 520                 525

Ser Ala Ala Arg Thr Cys Gly Ala Thr Gly His Trp Ser Gly Leu Leu
            530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
            595                 600                 605

Ile Leu
610

<210> SEQ ID NO 37
<211> LENGTH: 830
<212> TYPE: PRT
<213> ORGANISM: Homo sapiens

<400> SEQUENCE: 37

Met Ala Asn Cys Gln Ile Ala Ile Leu Tyr Gln Arg Phe Gln Arg Val
1               5                   10                  15

Val Phe Gly Ile Ser Gln Leu Leu Cys Phe Ser Ala Leu Ile Ser Glu
            20                  25                  30

Leu Thr Asn Gln Lys Glu Val Ala Ala Trp Thr Tyr His Tyr Ser Thr
        35                  40                  45

Lys Ala Tyr Ser Trp Asn Ile Ser Arg Lys Tyr Cys Gln Asn Arg Tyr
    50                  55                  60

Thr Asp Leu Val Ala Ile Gln Asn Lys Asn Glu Ile Asp Tyr Leu Asn
65                  70                  75                  80

Lys Val Leu Pro Tyr Tyr Ser Ser Tyr Trp Ile Gly Ile Arg Lys
                85                  90                  95

Asn Asn Lys Thr Trp Thr Trp Val Gly Thr Lys Lys Ala Leu Thr Asn
            100                 105                 110

Glu Ala Glu Asn Trp Ala Asp Asn Glu Pro Asn Asn Lys Arg Asn Asn
            115                 120                 125

Glu Asp Cys Val Glu Ile Tyr Ile Lys Ser Pro Ser Ala Pro Gly Lys
            130                 135                 140

Trp Asn Asp Glu His Cys Leu Lys Lys Lys His Ala Leu Cys Tyr Thr
145                 150                 155                 160
```

```
Ala Ser Cys Gln Asp Met Ser Cys Ser Lys Gln Gly Glu Cys Leu Glu
            165                 170                 175
Thr Ile Gly Asn Tyr Thr Cys Ser Cys Tyr Pro Gly Phe Tyr Gly Pro
            180                 185                 190
Glu Cys Glu Tyr Val Arg Glu Cys Gly Glu Leu Glu Leu Pro Gln His
            195                 200                 205
Val Leu Met Asn Cys Ser His Pro Leu Gly Asn Phe Ser Phe Asn Ser
        210                 215                 220
Gln Cys Ser Phe His Cys Thr Asp Gly Tyr Gln Val Asn Gly Pro Ser
225                 230                 235                 240
Lys Leu Glu Cys Leu Ala Ser Gly Ile Trp Thr Asn Lys Pro Pro Gln
                245                 250                 255
Cys Leu Ala Ala Gln Cys Pro Pro Leu Lys Ile Pro Glu Arg Gly Asn
            260                 265                 270
Met Thr Cys Leu His Ser Ala Lys Ala Phe Gln His Gln Ser Ser Cys
        275                 280                 285
Ser Phe Ser Cys Glu Glu Gly Phe Ala Leu Val Gly Pro Glu Val Val
        290                 295                 300
Gln Cys Thr Ala Ser Gly Val Trp Thr Ala Pro Ala Pro Val Cys Lys
305                 310                 315                 320
Ala Val Gln Cys Gln His Leu Glu Ala Pro Ser Glu Gly Thr Met Asp
                325                 330                 335
Cys Val His Pro Leu Thr Ala Phe Ala Tyr Gly Ser Ser Cys Lys Phe
            340                 345                 350
Glu Cys Gln Pro Gly Tyr Arg Val Arg Gly Leu Asp Met Leu Arg Cys
            355                 360                 365
Ile Asp Ser Gly His Trp Ser Ala Pro Leu Pro Thr Cys Glu Ala Ile
        370                 375                 380
Ser Cys Glu Pro Leu Glu Ser Pro Val His Gly Ser Met Asp Cys Ser
385                 390                 395                 400
Pro Ser Leu Arg Ala Phe Gln Tyr Asp Thr Asn Cys Ser Phe Arg Cys
                405                 410                 415
Ala Glu Gly Phe Met Leu Arg Gly Ala Asp Ile Val Arg Cys Asp Asn
            420                 425                 430
Leu Gly Gln Trp Thr Ala Pro Ala Pro Val Cys Gln Ala Leu Gln Cys
        435                 440                 445
Gln Asp Leu Pro Val Pro Asn Glu Ala Arg Val Asn Cys Ser His Pro
450                 455                 460
Phe Gly Ala Phe Arg Tyr Gln Ser Val Cys Ser Phe Thr Cys Asn Glu
465                 470                 475                 480
Gly Leu Leu Leu Val Gly Ala Ser Val Leu Gln Cys Leu Ala Thr Gly
                485                 490                 495
Asn Trp Asn Ser Val Pro Pro Glu Cys Gln Ala Ile Pro Cys Thr Pro
            500                 505                 510
Leu Leu Ser Pro Gln Asn Gly Thr Met Thr Cys Val Gln Pro Leu Gly
            515                 520                 525
Ser Ser Ser Tyr Lys Ser Thr Cys Gln Phe Ile Cys Asp Glu Gly Tyr
        530                 535                 540
Ser Leu Ser Gly Pro Glu Arg Leu Asp Cys Thr Arg Ser Gly Arg Trp
545                 550                 555                 560
Thr Asp Ser Pro Pro Met Cys Glu Ala Ile Lys Cys Pro Glu Leu Phe
                565                 570                 575
Ala Pro Glu Gln Gly Ser Leu Asp Cys Ser Asp Thr Arg Gly Glu Phe
```

```
                    580                 585                 590
Asn Val Gly Ser Thr Cys His Phe Ser Cys Asp Asn Gly Phe Lys Leu
            595                 600                 605

Glu Gly Pro Asn Asn Val Glu Cys Thr Thr Ser Gly Arg Trp Ser Ala
    610                 615                 620

Thr Pro Pro Thr Cys Lys Gly Ile Ala Ser Leu Pro Thr Pro Gly Leu
625                 630                 635                 640

Gln Cys Pro Ala Leu Thr Thr Pro Gly Gln Gly Thr Met Tyr Cys Arg
                645                 650                 655

His His Pro Gly Thr Phe Gly Phe Asn Thr Thr Cys Tyr Phe Gly Cys
            660                 665                 670

Asn Ala Gly Phe Thr Leu Ile Gly Asp Ser Thr Leu Ser Cys Arg Pro
        675                 680                 685

Ser Gly Gln Trp Thr Ala Val Thr Pro Ala Cys Arg Ala Val Lys Cys
    690                 695                 700

Ser Glu Leu His Val Asn Lys Pro Ile Ala Met Asn Cys Ser Asn Leu
705                 710                 715                 720

Trp Gly Asn Phe Ser Tyr Gly Ser Ile Cys Ser Phe His Cys Leu Glu
                725                 730                 735

Gly Gln Leu Leu Asn Gly Ser Ala Gln Thr Ala Cys Gln Glu Asn Gly
            740                 745                 750

His Trp Ser Thr Thr Val Pro Thr Cys Gln Ala Gly Pro Leu Thr Ile
        755                 760                 765

Gln Glu Ala Leu Thr Tyr Phe Gly Gly Ala Val Ala Ser Thr Ile Gly
    770                 775                 780

Leu Ile Met Gly Gly Thr Leu Leu Ala Leu Leu Arg Lys Arg Phe Arg
785                 790                 795                 800

Gln Lys Asp Asp Gly Lys Cys Pro Leu Asn Pro His Ser His Leu Gly
                805                 810                 815

Thr Tyr Gly Val Phe Thr Asn Ala Ala Phe Asp Pro Ser Pro
            820                 825                 830

<210> SEQ ID NO 38
<211> LENGTH: 238
<212> TYPE: PRT
<213> ORGANISM: Homo sapiens

<400> SEQUENCE: 38

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Phe Arg Gln Gln Met Glu Asn Tyr Pro Lys
        115                 120                 125
```

```
Asn Asn His Thr Ala Ser Ile Leu Asp Arg Met Gln Ala Asp Phe Lys
    130                 135                 140
Cys Cys Gly Ala Ala Asn Tyr Thr Asp Trp Glu Lys Ile Pro Ser Met
145                 150                 155                 160
Ser Lys Asn Arg Val Pro Asp Ser Cys Cys Ile Asn Val Thr Val Gly
            165                 170                 175
Cys Gly Ile Asn Phe Asn Glu Lys Ala Ile His Lys Glu Gly Cys Val
            180                 185                 190
Glu Lys Ile Gly Gly Trp Leu Arg Lys Asn Val Leu Val Ala Ala
        195                 200                 205
Ala Ala Leu Gly Ile Ala Phe Val Glu Val Leu Gly Ile Val Phe Ala
    210                 215                 220
Cys Cys Leu Val Lys Ser Ile Arg Ser Gly Tyr Glu Val Met
225                 230                 235

<210> SEQ ID NO 39
<211> LENGTH: 288
<212> TYPE: PRT
<213> ORGANISM: Homo sapiens

<400> SEQUENCE: 39

Met Gly His Thr Arg Arg Gln Gly Thr Ser Pro Ser Lys Cys Pro Tyr
1               5                   10                  15
Leu Asn Phe Phe Gln Leu Leu Val Leu Ala Gly Leu Ser His Phe Cys
                20                  25                  30
Ser Gly Val Ile His Val Thr Lys Glu Val Lys Glu Val Ala Thr Leu
            35                  40                  45
Ser Cys Gly His Asn Val Ser Val Glu Glu Leu Ala Gln Thr Arg Ile
50                  55                  60
Tyr Trp Gln Lys Glu Lys Lys Met Val Leu Thr Met Met Ser Gly Asp
65                  70                  75                  80
Met Asn Ile Trp Pro Glu Tyr Lys Asn Arg Thr Ile Phe Asp Ile Thr
                85                  90                  95
Asn Asn Leu Ser Ile Val Ile Leu Ala Leu Arg Pro Ser Asp Glu Gly
            100                 105                 110
Thr Tyr Glu Cys Val Val Leu Lys Tyr Glu Lys Asp Ala Phe Lys Arg
        115                 120                 125
Glu His Leu Ala Glu Val Thr Leu Ser Val Lys Ala Asp Phe Pro Thr
    130                 135                 140
Pro Ser Ile Ser Asp Phe Glu Ile Pro Thr Ser Asn Ile Arg Arg Ile
145                 150                 155                 160
Ile Cys Ser Thr Ser Gly Gly Phe Pro Glu Pro His Leu Ser Trp Leu
                165                 170                 175
Glu Asn Gly Glu Glu Leu Asn Ala Ile Asn Thr Thr Val Ser Gln Asp
            180                 185                 190
Pro Glu Thr Glu Leu Tyr Ala Val Ser Ser Lys Leu Asp Phe Asn Met
        195                 200                 205
Thr Thr Asn His Ser Phe Met Cys Leu Ile Lys Tyr Gly His Leu Arg
    210                 215                 220
Val Asn Gln Thr Phe Asn Trp Asn Thr Thr Lys Gln Glu His Phe Pro
225                 230                 235                 240
Asp Asn Leu Leu Pro Ser Trp Ala Ile Thr Leu Ile Ser Val Asn Gly
                245                 250                 255
Ile Phe Val Ile Cys Cys Leu Thr Tyr Cys Phe Ala Pro Arg Cys Arg
            260                 265                 270
```

```
Glu Arg Arg Arg Asn Glu Arg Leu Arg Arg Glu Ser Val Arg Pro Val
        275                 280                 285

<210> SEQ ID NO 40
<211> LENGTH: 236
<212> TYPE: PRT
<213> ORGANISM: Homo sapiens

<400> SEQUENCE: 40

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Ala Asn Asn Ala Lys
    130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235

<210> SEQ ID NO 41
<211> LENGTH: 267
<212> TYPE: PRT
<213> ORGANISM: Homo sapiens

<400> SEQUENCE: 41

Met Gly Ser Ala Cys Ile Lys Val Thr Lys Tyr Phe Leu Phe Leu Phe
1               5                   10                  15

Asn Leu Ile Phe Phe Ile Leu Gly Ala Val Ile Leu Gly Phe Gly Val
            20                  25                  30

Trp Ile Leu Ala Asp Lys Ser Ser Phe Ile Ser Val Leu Gln Thr Ser
        35                  40                  45

Ser Ser Ser Leu Arg Met Gly Ala Tyr Val Phe Ile Gly Val Gly Ala
    50                  55                  60

Val Thr Met Leu Met Gly Phe Leu Gly Cys Ile Gly Ala Val Asn Glu
65                  70                  75                  80
```

-continued

```
Val Arg Cys Leu Leu Gly Leu Tyr Phe Ala Phe Leu Leu Ile Leu
                85                  90                  95

Ile Ala Gln Val Thr Ala Gly Ala Leu Phe Tyr Phe Asn Met Gly Lys
            100                 105                 110

Leu Lys Gln Glu Met Gly Gly Ile Val Thr Glu Leu Ile Arg Asp Tyr
            115                 120                 125

Asn Ser Ser Arg Glu Asp Ser Leu Gln Asp Ala Trp Asp Tyr Val Gln
    130                 135                 140

Ala Gln Val Lys Cys Cys Gly Trp Val Ser Phe Tyr Asn Trp Thr Asp
145                 150                 155                 160

Asn Ala Glu Leu Met Asn Arg Pro Glu Val Thr Tyr Pro Cys Ser Cys
                165                 170                 175

Glu Val Lys Gly Glu Glu Asp Asn Ser Leu Ser Val Arg Lys Gly Phe
            180                 185                 190

Cys Glu Ala Pro Gly Asn Arg Thr Gln Ser Gly Asn His Pro Glu Asp
        195                 200                 205

Trp Pro Val Tyr Gln Glu Gly Cys Met Glu Lys Val Gln Ala Trp Leu
    210                 215                 220

Gln Glu Asn Leu Gly Ile Ile Leu Gly Val Gly Val Gly Val Ala Ile
225                 230                 235                 240

Ile Glu Leu Leu Gly Met Val Leu Ser Ile Cys Leu Cys Arg His Val
                245                 250                 255

His Ser Glu Asp Tyr Ser Lys Val Pro Lys Tyr
            260                 265

<210> SEQ ID NO 42
<211> LENGTH: 205
<212> TYPE: PRT
<213> ORGANISM: Homo sapiens

<400> SEQUENCE: 42

Met Ser Arg Gly Leu Gln Leu Leu Leu Leu Ser Cys Ala Tyr Ser Leu
1               5                   10                  15

Ala Pro Ala Thr Pro Glu Val Lys Val Ala Cys Ser Glu Asp Val Asp
                20                  25                  30

Leu Pro Cys Thr Ala Pro Trp Asp Pro Gln Val Pro Tyr Thr Val Ser
            35                  40                  45

Trp Val Lys Leu Leu Glu Gly Gly Glu Glu Arg Met Glu Thr Pro Gln
    50                  55                  60

Glu Asp His Leu Arg Gly Gln His Tyr His Gln Lys Gly Gln Asn Gly
65                  70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
            100                 105                 110

Asp Gly Gln Arg Asn Leu Ser Gly Lys Val Ile Leu Arg Val Thr Gly
        115                 120                 125

Cys Pro Ala Gln Arg Lys Glu Glu Thr Phe Lys Lys Tyr Arg Ala Glu
    130                 135                 140

Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
```

```
                    180                 185                 190

His Leu Gly Leu Val Thr Pro His Lys Thr Glu Leu Val
            195                 200                 205

<210> SEQ ID NO 43
<211> LENGTH: 235
<212> TYPE: PRT
<213> ORGANISM: Homo sapiens

<400> SEQUENCE: 43

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 44
<211> LENGTH: 228
<212> TYPE: PRT
<213> ORGANISM: Homo sapiens

<400> SEQUENCE: 44

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
```

-continued

```
             65                  70                  75                  80
Ala Val Gln Glu Ser Gln Cys Met Leu Gly Leu Phe Gly Phe Leu
                    85                  90                  95

Leu Val Ile Phe Ala Ile Glu Ile Ala Ala Ile Trp Gly Tyr Ser
                100                 105                 110

His Lys Asp Glu Val Ile Lys Glu Val Gln Glu Phe Tyr Lys Asp Thr
                115                 120                 125

Tyr Asn Lys Leu Lys Thr Lys Asp Glu Pro Gln Arg Glu Thr Leu Lys
            130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                    165                 170                 175

Thr Val Lys Ser Cys Pro Asp Ala Ile Lys Glu Val Phe Asp Asn Lys
                180                 185                 190

Phe His Ile Ile Gly Ala Val Gly Ile Gly Ile Ala Val Val Met Ile
                195                 200                 205

Phe Gly Met Ile Phe Ser Met Ile Leu Cys Cys Ala Ile Arg Arg Asn
    210                 215                 220

Arg Glu Met Val
225

<210> SEQ ID NO 45
<211> LENGTH: 702
<212> TYPE: PRT
<213> ORGANISM: Homo sapiens

<400> SEQUENCE: 45

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                    85                  90                  95

Gly Arg Glu Ile Ile Tyr Pro Asn Ala Ser Leu Leu Ile Gln Asn Ile
                100                 105                 110

Ile Gln Asn Asp Thr Gly Phe Tyr Thr Leu His Val Ile Lys Ser Asp
            115                 120                 125

Leu Val Asn Glu Glu Ala Thr Gly Gln Phe Arg Val Tyr Pro Glu Leu
        130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                    165                 170                 175

Leu Trp Trp Val Asn Asn Gln Ser Leu Pro Val Ser Pro Arg Leu Gln
                180                 185                 190

Leu Ser Asn Gly Asn Arg Thr Leu Thr Leu Phe Asn Val Thr Arg Asn
            195                 200                 205
```

Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu

```
            625                 630                 635                 640

Phe Ile Ala Lys Ile Thr Pro Asn Asn Gly Thr Tyr Ala Cys Phe
                        645                 650                 655

Val Ser Asn Leu Ala Thr Gly Arg Asn Asn Ser Ile Val Lys Ser Ile
                    660                 665                 670

Thr Val Ser Ala Ser Gly Thr Ser Pro Gly Leu Ser Ala Gly Ala Thr
                    675                 680                 685

Val Gly Ile Met Ile Gly Val Leu Val Gly Val Ala Leu Ile
                    690                 695                 700

<210> SEQ ID NO 46
<211> LENGTH: 1390
<212> TYPE: PRT
<213> ORGANISM: Homo sapiens

<400> SEQUENCE: 46

Met Lys Ala Pro Ala Val Leu Ala Pro Gly Ile Leu Val Leu Leu Phe
        1               5                   10                  15

Thr Leu Val Gln Arg Ser Asn Gly Glu Cys Lys Glu Ala Leu Ala Lys
                    20                  25                  30

Ser Glu Met Asn Val Asn Met Lys Tyr Gln Leu Pro Asn Phe Thr Ala
                35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
        65                  70                  75                  80

Val Ala Glu Tyr Lys Thr Gly Pro Val Leu Glu His Pro Asp Cys Phe
                        85                  90                  95

Pro Cys Gln Asp Cys Ser Ser Lys Ala Asn Leu Ser Gly Gly Val Trp
                    100                 105                 110

Lys Asp Asn Ile Asn Met Ala Leu Val Val Asp Thr Tyr Tyr Asp Asp
                115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
        145                 150                 155                 160

Ile Phe Ser Pro Gln Ile Glu Glu Pro Ser Gln Cys Pro Asp Cys Val
                        165                 170                 175

Val Ser Ala Leu Gly Ala Lys Val Leu Ser Ser Val Lys Asp Arg Phe
                    180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
        210                 215                 220

Gly Phe Met Phe Leu Thr Asp Gln Ser Tyr Ile Asp Val Leu Pro Glu
        225                 230                 235                 240

Phe Arg Asp Ser Tyr Pro Ile Lys Tyr Val His Ala Phe Glu Ser Asn
                        245                 250                 255

Asn Phe Ile Tyr Phe Leu Thr Val Gln Arg Glu Thr Leu Asp Ala Gln
                    260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
        290                 295                 300
```

```
Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
            325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
            485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
            565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
```

```
                725                 730                 735
Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
                915                 920                 925

Gln Asn Phe Thr Gly Leu Ile Ala Gly Val Val Ser Ile Ser Thr Ala
930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser Val Asp Tyr Arg Ala Thr Phe Pro
                995                 1000                1005

Glu Asp Gln Phe Pro Asn Ser Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140
```

```
Gly Ile Cys Leu Arg Ser Glu Gly Ser Pro Leu Val Val Leu Pro
    1145                1150               1155

Tyr Met Lys His Gly Asp Leu Arg Asn Phe Ile Arg Asn Glu Thr
    1160                1165               1170

His Asn Pro Thr Val Lys Asp Leu Ile Gly Phe Gly Leu Gln Val
    1175                1180               1185

Ala Lys Gly Met Lys Tyr Leu Ala Ser Lys Lys Phe Val His Arg
    1190                1195               1200

Asp Leu Ala Ala Arg Asn Cys Met Leu Asp Glu Lys Phe Thr Val
    1205                1210               1215

Lys Val Ala Asp Phe Gly Leu Ala Arg Asp Met Tyr Asp Lys Glu
    1220                1225               1230

Tyr Tyr Ser Val His Asn Lys Thr Gly Ala Lys Leu Pro Val Lys
    1235                1240               1245

Trp Met Ala Leu Glu Ser Leu Gln Thr Gln Lys Phe Thr Thr Lys
    1250                1255               1260

Ser Asp Val Trp Ser Phe Gly Val Leu Leu Trp Glu Leu Met Thr
    1265                1270               1275

Arg Gly Ala Pro Pro Tyr Pro Asp Val Asn Thr Phe Asp Ile Thr
    1280                1285               1290

Val Tyr Leu Leu Gln Gly Arg Arg Leu Leu Gln Pro Glu Tyr Cys
    1295                1300               1305

Pro Asp Pro Leu Tyr Glu Val Met Leu Lys Cys Trp His Pro Lys
    1310                1315               1320

Ala Glu Met Arg Pro Ser Phe Ser Glu Leu Val Ser Arg Ile Ser
    1325                1330               1335

Ala Ile Phe Ser Thr Phe Ile Gly Glu His Tyr Val His Val Asn
    1340                1345               1350

Ala Thr Tyr Val Asn Val Lys Cys Val Ala Pro Tyr Pro Ser Leu
    1355                1360               1365

Leu Ser Ser Glu Asp Asn Ala Asp Asp Glu Val Asp Thr Arg Pro
    1370                1375               1380

Ala Ser Phe Trp Glu Thr Ser
    1385                1390

<210> SEQ ID NO 47
<211> LENGTH: 576
<212> TYPE: PRT
<213> ORGANISM: Homo sapiens

<400> SEQUENCE: 47

Met Ala Ala Ser Glu Thr Val Arg Leu Arg Leu Gln Phe Asp Tyr Pro
1               5                   10                  15

Pro Pro Ala Thr Pro His Cys Thr Ala Phe Trp Leu Leu Val Asp Leu
                20                  25                  30

Asn Arg Cys Arg Val Val Thr Asp Leu Ile Ser Leu Ile Arg Gln Arg
            35                  40                  45

Phe Gly Phe Ser Ser Gly Ala Phe Leu Gly Leu Tyr Leu Glu Gly Gly
        50                  55                  60

Leu Leu Pro Pro Ala Glu Ser Ala Arg Leu Val Arg Asp Asn Asp Cys
65                  70                  75                  80

Leu Arg Val Lys Leu Glu Glu Arg Gly Val Ala Glu Asn Ser Val Val
                85                  90                  95

Ile Ser Asn Gly Asp Ile Asn Leu Ser Leu Arg Lys Ala Lys Lys Arg
```

```
            100                 105                 110
Ala Phe Gln Leu Glu Glu Gly Glu Thr Glu Pro Asp Cys Lys Tyr
            115                 120                 125

Ser Lys Lys His Trp Lys Ser Arg Glu Asn Asn Asn Asn Glu Lys
            130                 135             140

Val Leu Asp Leu Glu Pro Lys Ala Val Thr Asp Gln Thr Val Ser Lys
145                 150                 155                 160

Lys Asn Lys Arg Lys Asn Lys Ala Thr Cys Gly Thr Val Gly Asp Asp
                165                 170                 175

Asn Glu Glu Ala Lys Arg Lys Ser Pro Lys Lys Glu Lys Cys Glu
            180                 185                 190

Tyr Lys Lys Lys Ala Lys Asn Pro Lys Ser Pro Lys Val Gln Ala Val
            195                 200                 205

Lys Asp Trp Ala Asn Gln Arg Cys Ser Ser Pro Lys Gly Ser Ala Arg
            210                 215                 220

Asn Ser Leu Val Lys Ala Lys Arg Lys Gly Ser Val Ser Val Cys Ser
225                 230                 235                 240

Lys Glu Ser Pro Ser Ser Ser Glu Ser Glu Ser Cys Asp Glu Ser
                245                 250                 255

Ile Ser Asp Gly Pro Ser Lys Val Thr Leu Glu Ala Arg Asn Ser Ser
            260                 265                 270

Glu Lys Leu Pro Thr Glu Leu Ser Lys Glu Glu Pro Ser Thr Lys Asn
            275                 280                 285

Thr Thr Ala Asp Lys Leu Ala Ile Lys Leu Gly Phe Ser Leu Thr Pro
            290                 295                 300

Ser Lys Gly Lys Thr Ser Gly Thr Thr Ser Ser Ser Asp Ser Ser
305                 310                 315                 320

Ala Glu Ser Asp Asp Gln Cys Leu Met Ser Ser Thr Pro Glu Cys
                325                 330                 335

Ala Ala Gly Phe Leu Lys Thr Val Gly Leu Phe Ala Gly Arg Gly Arg
            340                 345                 350

Pro Gly Pro Gly Leu Ser Ser Gln Thr Ala Gly Ala Gly Trp Arg
            355                 360                 365

Arg Ser Gly Ser Asn Gly Gly Gly Gln Ala Pro Gly Ala Ser Pro Ser
            370                 375                 380

Val Ser Leu Pro Ala Ser Leu Gly Arg Gly Trp Gly Arg Glu Glu Asn
385                 390                 395                 400

Leu Phe Ser Trp Lys Gly Ala Lys Gly Arg Gly Met Arg Gly Arg Gly
                405                 410                 415

Arg Gly Arg Gly His Pro Val Ser Cys Val Val Asn Arg Ser Thr Asp
                420                 425                 430

Asn Gln Arg Gln Gln Leu Asn Asp Val Val Lys Asn Ser Ser Thr
            435                 440                 445

Ile Ile Gln Asn Pro Val Glu Thr Pro Lys Lys Asp Tyr Ser Leu Leu
            450                 455                 460

Pro Leu Leu Ala Ala Ala Pro Gln Val Gly Glu Lys Ile Ala Phe Lys
465                 470                 475                 480

Leu Leu Glu Leu Thr Ser Ser Tyr Ser Pro Asp Val Ser Asp Tyr Lys
                485                 490                 495

Glu Gly Arg Ile Leu Ser His Asn Pro Glu Thr Gln Gln Val Asp Ile
            500                 505                 510

Glu Ile Leu Ser Ser Leu Pro Ala Leu Arg Glu Pro Gly Lys Phe Asp
            515                 520                 525
```

Leu Val Tyr His Asn Glu Asn Gly Ala Glu Val Val Glu Tyr Ala Val
            530                 535                 540

Thr Gln Glu Ser Lys Ile Thr Val Phe Trp Lys Glu Leu Ile Asp Pro
545                 550                 555                 560

Arg Leu Ile Ile Glu Ser Pro Ser Asn Thr Ser Ser Thr Glu Pro Ala
                565                 570                 575

<210> SEQ ID NO 48
<211> LENGTH: 223
<212> TYPE: PRT
<213> ORGANISM: Homo sapiens

<400> SEQUENCE: 48

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
210                 215                 220

<210> SEQ ID NO 49
<211> LENGTH: 1210
<212> TYPE: PRT
<213> ORGANISM: Homo sapiens

<400> SEQUENCE: 49

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

```
Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480
```

-continued

Phe Gly Thr Ser Gly Gln Lys Thr Lys Ile Ile Ser Asn Arg Gly Glu
              485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
        580                 585                 590

Lys Thr Cys Pro Ala Gly Val Met Gly Glu Asn Asn Thr Leu Val Trp
    595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
    755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser

```
                900             905             910
Lys Pro Tyr Asp Gly Ile Pro Ala Ser Glu Ile Ser Ile Leu Glu
            915             920             925

Lys Gly Glu Arg Leu Pro Gln Pro Ile Cys Thr Ile Asp Val Tyr
            930             935             940

Met Ile Met Val Lys Cys Trp Met Ile Asp Ala Asp Ser Arg Pro Lys
945             950             955             960

Phe Arg Glu Leu Ile Ile Glu Phe Ser Lys Met Ala Arg Asp Pro Gln
                965             970             975

Arg Tyr Leu Val Ile Gln Gly Asp Glu Arg Met His Leu Pro Ser Pro
            980             985             990

Thr Asp Ser Asn Phe Tyr Arg Ala Leu Met Asp Glu Glu Asp Met Asp
            995             1000            1005

Asp Val Val Asp Ala Asp Glu Tyr Leu Ile Pro Gln Gln Gly Phe
    1010            1015            1020

Phe Ser Ser Pro Ser Thr Ser Arg Thr Pro Leu Leu Ser Ser Leu
    1025            1030            1035

Ser Ala Thr Ser Asn Asn Ser Thr Val Ala Cys Ile Asp Arg Asn
    1040            1045            1050

Gly Leu Gln Ser Cys Pro Ile Lys Glu Asp Ser Phe Leu Gln Arg
    1055            1060            1065

Tyr Ser Ser Asp Pro Thr Gly Ala Leu Thr Glu Asp Ser Ile Asp
    1070            1075            1080

Asp Thr Phe Leu Pro Val Pro Glu Tyr Ile Asn Gln Ser Val Pro
    1085            1090            1095

Lys Arg Pro Ala Gly Ser Val Gln Asn Pro Val Tyr His Asn Gln
    1100            1105            1110

Pro Leu Asn Pro Ala Pro Ser Arg Asp Pro His Tyr Gln Asp Pro
    1115            1120            1125

His Ser Thr Ala Val Gly Asn Pro Glu Tyr Leu Asn Thr Val Gln
    1130            1135            1140

Pro Thr Cys Val Asn Ser Thr Phe Asp Ser Pro Ala His Trp Ala
    1145            1150            1155

Gln Lys Gly Ser His Gln Ile Ser Leu Asp Asn Pro Asp Tyr Gln
    1160            1165            1170

Gln Asp Phe Phe Pro Lys Glu Ala Lys Pro Asn Gly Ile Phe Lys
    1175            1180            1185

Gly Ser Thr Ala Glu Asn Ala Glu Tyr Leu Arg Val Ala Pro Gln
    1190            1195            1200

Ser Ser Glu Phe Ile Gly Ala
    1205            1210

<210> SEQ ID NO 50
<211> LENGTH: 314
<212> TYPE: PRT
<213> ORGANISM: Homo sapiens

<400> SEQUENCE: 50

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
            35                  40                  45
```

Thr Ser Val Gly Ala Gln Asn Thr Val Ile Cys Ser Lys Leu Ala Ala
 50                  55                  60

Lys Cys Leu Val Met Lys Ala Glu Met Asn Gly Ser Lys Leu Gly Arg
 65                  70                  75                  80

Arg Ala Lys Pro Glu Gly Ala Leu Gln Asn Asn Asp Gly Leu Tyr Asp
                 85                  90                  95

Pro Asp Cys Asp Glu Ser Gly Leu Phe Lys Ala Lys Gln Cys Asn Gly
                100                 105                 110

Thr Ser Met Cys Trp Cys Val Asn Thr Ala Gly Val Arg Arg Thr Asp
                115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
                180                 185                 190

Ile Asp Leu Val Gln Asn Ser Ser Gln Lys Thr Gln Asn Asp Val Asp
                195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
                260                 265                 270

Val Val Val Val Ile Ala Val Val Ala Gly Ile Val Val Leu Val Ile
                275                 280                 285

Ser Arg Lys Lys Arg Met Ala Lys Tyr Glu Lys Ala Glu Ile Lys Glu
                290                 295                 300

Met Gly Glu Met His Arg Glu Leu Asn Ala
305                 310

<210> SEQ ID NO 51
<211> LENGTH: 281
<212> TYPE: PRT
<213> ORGANISM: Homo sapiens

<400> SEQUENCE: 51

Met Gln Gln Pro Phe Asn Tyr Pro Tyr Pro Gln Ile Tyr Trp Val Asp
 1                   5                  10                  15

Ser Ser Ala Ser Ser Pro Trp Ala Pro Pro Gly Thr Val Leu Pro Cys
                 20                  25                  30

Pro Thr Ser Val Pro Arg Arg Pro Gly Gln Arg Arg Pro Pro Pro Pro
                 35                  40                  45

Pro Pro Pro Pro Pro Leu Pro Pro Pro Pro Pro Pro Pro Pro Leu Pro
 50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Gln Ile Gly His Pro Ser Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
            275                 280

<210> SEQ ID NO 52
<211> LENGTH: 427
<212> TYPE: PRT
<213> ORGANISM: Homo sapiens

<400> SEQUENCE: 52

Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
                20                  25                  30

Pro Cys Ile Gln Gln Ile Gln Arg Ile Ser Leu Asn Thr Leu Thr Leu
            35                  40                  45

Asn Val Lys Ser Glu Lys Val Tyr Thr Arg His Gly Val Pro Ile Ser
    50                  55                  60

Val Thr Gly Ile Ala Gln Val Lys Ile Gln Gly Gln Asn Lys Glu Met
65                  70                  75                  80

Leu Ala Ala Ala Cys Gln Met Phe Leu Gly Lys Thr Glu Ala Glu Ile
                85                  90                  95

Ala His Ile Ala Leu Glu Thr Leu Glu Gly His Gln Arg Ala Ile Met
            100                 105                 110

Ala His Met Thr Val Glu Glu Ile Tyr Lys Asp Arg Gln Lys Phe Ser
    115                 120                 125

Glu Gln Val Phe Lys Val Ala Ser Ser Asp Leu Val Asn Met Gly Ile
    130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
            180                 185                 190

Lys Ala Lys Gln Glu Lys Val Ser Ala Gln Tyr Leu Ser Glu Ile Glu

```
              195                 200                 205
Met Ala Lys Ala Gln Arg Asp Tyr Glu Leu Lys Lys Ala Ala Tyr Asp
    210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Arg Val Gln Val
                245                 250                 255

Gln Val Val Glu Arg Ala Gln Gln Val Ala Val Gln Glu Gln Glu Ile
            260                 265                 270

Ala Arg Arg Glu Lys Glu Leu Glu Ala Arg Val Arg Lys Pro Ala Glu
        275                 280                 285

Ala Glu Arg Tyr Lys Leu Glu Arg Leu Ala Glu Ala Glu Lys Ser Gln
        290                 295                 300

Leu Ile Met Gln Ala Glu Ala Glu Ala Ala Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Leu Tyr Gln Glu Ala Ala
            340                 345                 350

Gln Leu Asp Met Leu Leu Glu Lys Leu Pro Gln Val Ala Glu Glu Ile
        355                 360                 365

Ser Gly Pro Leu Thr Ser Ala Asn Lys Ile Thr Leu Val Ser Ser Gly
370                 375                 380

Ser Gly Thr Met Gly Ala Ala Lys Val Thr Gly Glu Val Leu Asp Ile
385                 390                 395                 400

Leu Thr Arg Leu Pro Glu Ser Val Glu Arg Leu Thr Gly Val Ser Ile
                405                 410                 415

Ser Gln Val Asn His Lys Pro Leu Arg Thr Ala
            420                 425

<210> SEQ ID NO 53
<211> LENGTH: 654
<212> TYPE: PRT
<213> ORGANISM: Homo sapiens

<400> SEQUENCE: 53

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140
```

-continued

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile 565                 570                 575
Gly Asp Lys Glu Lys Leu Gly Gly Lys Leu Ser Ser Glu Asp Lys Glu
                580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Glu Leu Glu
        610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 54
<211> LENGTH: 208
<212> TYPE: PRT
<213> ORGANISM: Homo sapiens

<400> SEQUENCE: 54

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205

<210> SEQ ID NO 55
<211> LENGTH: 1255
<212> TYPE: PRT
<213> ORGANISM: Homo sapiens

<400> SEQUENCE: 55

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His

```
                35                  40                  45
Leu Tyr Gln Gly Cys Gln Val Gln Gly Asn Leu Glu Leu Thr Tyr
 50                  55                  60
Leu Pro Thr Asn Ala Ser Leu Ser Phe Leu Gln Asp Ile Gln Glu Val
 65                      70                  75                  80
Gln Gly Tyr Val Leu Ile Ala His Asn Gln Val Arg Gln Val Pro Leu
                     85                  90                  95
Gln Arg Leu Arg Ile Val Arg Gly Thr Gln Leu Phe Glu Asp Asn Tyr
                100                 105                 110
Ala Leu Ala Val Leu Asp Asn Gly Asp Pro Leu Asn Asn Thr Thr Pro
                115                 120                 125
Val Thr Gly Ala Ser Pro Gly Gly Leu Arg Glu Leu Gln Leu Arg Ser
130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
                370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
                435                 440                 445
Gly Ile Ser Trp Leu Gly Leu Arg Ser Leu Arg Glu Leu Gly Ser Gly
                450                 455                 460
```

```
Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880
```

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Pro Thr Ala Glu Asn Pro Glu Tyr
    1235                1240                1245

Leu Gly Leu Asp Val Pro Val
    1250                1255

<210> SEQ ID NO 56
<211> LENGTH: 1342
<212> TYPE: PRT

<213> ORGANISM: Homo sapiens

<400> SEQUENCE: 56

```
Met Arg Ala Asn Asp Ala Leu Gln Val Leu Gly Leu Leu Phe Ser Leu
1               5                   10                  15
Ala Arg Gly Ser Glu Val Gly Asn Ser Gln Ala Val Cys Pro Gly Thr
            20                  25                  30
Leu Asn Gly Leu Ser Val Thr Gly Asp Ala Glu Asn Gln Tyr Gln Thr
        35                  40                  45
Leu Tyr Lys Leu Tyr Glu Arg Cys Glu Val Val Met Gly Asn Leu Glu
    50                  55                  60
Ile Val Leu Thr Gly His Asn Ala Asp Leu Ser Phe Leu Gln Trp Ile
65                  70                  75                  80
Arg Glu Val Thr Gly Tyr Val Leu Val Ala Met Asn Glu Phe Ser Thr
                85                  90                  95
Leu Pro Leu Pro Asn Leu Arg Val Val Arg Gly Thr Gln Val Tyr Asp
            100                 105                 110
Gly Lys Phe Ala Ile Phe Val Met Leu Asn Tyr Asn Thr Asn Ser Ser
        115                 120                 125
His Ala Leu Arg Gln Leu Arg Leu Thr Gln Leu Thr Glu Ile Leu Ser
    130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys Lys Gly
            180                 185                 190
Arg Cys Trp Gly Pro Gly Ser Glu Asp Cys Gln Thr Leu Thr Lys Thr
        195                 200                 205
Ile Cys Ala Pro Gln Cys Asn Gly His Cys Phe Gly Pro Asn Pro Asn
    210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
```

```
Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
```

```
                820             825             830
Arg Asn Leu Ala Ala Arg Asn Val Leu Leu Lys Ser Pro Ser Gln Val
            835             840             845
Gln Val Ala Asp Phe Gly Val Ala Asp Leu Leu Pro Pro Asp Asp Lys
    850             855             860
Gln Leu Leu Tyr Ser Glu Ala Lys Thr Pro Ile Lys Trp Met Ala Leu
865             870             875             880
Glu Ser Ile His Phe Gly Lys Tyr Thr His Gln Ser Asp Val Trp Ser
                885             890             895
Tyr Gly Val Thr Val Trp Glu Leu Met Thr Phe Gly Ala Glu Pro Tyr
            900             905             910
Ala Gly Leu Arg Leu Ala Glu Val Pro Asp Leu Leu Glu Lys Gly Glu
            915             920             925
Arg Leu Ala Gln Pro Gln Ile Cys Thr Ile Asp Val Tyr Met Val Met
            930             935             940
Val Lys Cys Trp Met Ile Asp Glu Asn Ile Arg Pro Thr Phe Lys Glu
945             950             955             960
Leu Ala Asn Glu Phe Thr Arg Met Ala Arg Asp Pro Pro Arg Tyr Leu
            965             970             975
Val Ile Lys Arg Glu Ser Gly Pro Gly Ile Ala Pro Gly Pro Glu Pro
            980             985             990
His Gly Leu Thr Asn Lys Lys Leu Glu Glu Val Glu Leu Glu Pro Glu
            995             1000            1005
Leu Asp Leu Asp Leu Asp Leu Glu Ala Glu Glu Asp Asn Leu Ala
    1010            1015            1020
Thr Thr Thr Leu Gly Ser Ala Leu Ser Leu Pro Val Gly Thr Leu
    1025            1030            1035
Asn Arg Pro Arg Gly Ser Gln Ser Leu Leu Ser Pro Ser Ser Gly
    1040            1045            1050
Tyr Met Pro Met Asn Gln Gly Asn Leu Gly Glu Ser Cys Gln Glu
    1055            1060            1065
Ser Ala Val Ser Gly Ser Ser Glu Arg Cys Pro Arg Pro Val Ser
    1070            1075            1080
Leu His Pro Met Pro Arg Gly Cys Leu Ala Ser Glu Ser Ser Glu
    1085            1090            1095
Gly His Val Thr Gly Ser Glu Ala Glu Leu Gln Glu Lys Val Ser
    1100            1105            1110
Met Cys Arg Ser Arg Ser Arg Ser Arg Ser Pro Arg Pro Arg Gly
    1115            1120            1125
Asp Ser Ala Tyr His Ser Gln Arg His Ser Leu Leu Thr Pro Val
    1130            1135            1140
Thr Pro Leu Ser Pro Pro Gly Leu Glu Glu Glu Asp Val Asn Gly
    1145            1150            1155
Tyr Val Met Pro Asp Thr His Leu Lys Gly Thr Pro Ser Ser Arg
    1160            1165            1170
Glu Gly Thr Leu Ser Ser Val Gly Leu Ser Ser Val Leu Gly Thr
    1175            1180            1185
Glu Glu Glu Asp Glu Asp Glu Tyr Glu Tyr Met Asn Arg Arg
    1190            1195            1200
Arg Arg His Ser Pro Pro His Pro Pro Arg Pro Ser Ser Leu Glu
    1205            1210            1215
Glu Leu Gly Tyr Glu Tyr Met Asp Val Gly Ser Asp Leu Ser Ala
    1220            1225            1230
```

```
Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 57
<211> LENGTH: 1308
<212> TYPE: PRT
<213> ORGANISM: Homo sapiens

<400> SEQUENCE: 57

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
```

-continued

```
                245                 250                 255
Ala Cys Val Thr Gln Cys Pro Gln Thr Phe Val Tyr Asn Pro Thr Thr
            260                 265                 270
Phe Gln Leu Glu His Asn Phe Asn Ala Lys Tyr Thr Tyr Gly Ala Phe
        275                 280                 285
Cys Val Lys Lys Cys Pro His Asn Phe Val Val Asp Ser Ser Ser Cys
    290                 295                 300
Val Arg Ala Cys Pro Ser Ser Lys Met Glu Val Glu Glu Asn Gly Ile
305                 310                 315                 320
Lys Met Cys Lys Pro Cys Thr Asp Ile Cys Pro Lys Ala Cys Asp Gly
                325                 330                 335
Ile Gly Thr Gly Ser Leu Met Ser Ala Gln Thr Val Asp Ser Ser Asn
            340                 345                 350
Ile Asp Lys Phe Ile Asn Cys Thr Lys Ile Asn Gly Asn Leu Ile Phe
        355                 360                 365
Leu Val Thr Gly Ile His Gly Asp Pro Tyr Asn Ala Ile Glu Ala Ile
    370                 375                 380
Asp Pro Glu Lys Leu Asn Val Phe Arg Thr Val Arg Glu Ile Thr Gly
385                 390                 395                 400
Phe Leu Asn Ile Gln Ser Trp Pro Pro Asn Met Thr Asp Phe Ser Val
                405                 410                 415
Phe Ser Asn Leu Val Thr Ile Gly Gly Arg Val Leu Tyr Ser Gly Leu
            420                 425                 430
Ser Leu Leu Ile Leu Lys Gln Gln Gly Ile Thr Ser Leu Gln Phe Gln
        435                 440                 445
Ser Leu Lys Glu Ile Ser Ala Gly Asn Ile Tyr Ile Thr Asp Asn Ser
    450                 455                 460
Asn Leu Cys Tyr Tyr His Thr Ile Asn Trp Thr Thr Leu Phe Ser Thr
465                 470                 475                 480
Ile Asn Gln Arg Ile Val Ile Arg Asp Asn Arg Lys Ala Glu Asn Cys
                485                 490                 495
Thr Ala Glu Gly Met Val Cys Asn His Leu Cys Ser Ser Asp Gly Cys
            500                 505                 510
Trp Gly Pro Gly Pro Asp Gln Cys Leu Ser Cys Arg Arg Phe Ser Arg
        515                 520                 525
Gly Arg Ile Cys Ile Glu Ser Cys Asn Leu Tyr Asp Gly Glu Phe Arg
    530                 535                 540
Glu Phe Glu Asn Gly Ser Ile Cys Val Glu Cys Asp Pro Gln Cys Glu
545                 550                 555                 560
Lys Met Glu Asp Gly Leu Leu Thr Cys His Gly Pro Gly Pro Asp Asn
                565                 570                 575
Cys Thr Lys Cys Ser His Phe Lys Asp Gly Pro Asn Cys Val Glu Lys
            580                 585                 590
Cys Pro Asp Gly Leu Gln Gly Ala Asn Ser Phe Ile Phe Lys Tyr Ala
        595                 600                 605
Asp Pro Asp Arg Glu Cys His Pro Cys His Pro Asn Cys Thr Gln Gly
    610                 615                 620
Cys Asn Gly Pro Thr Ser His Asp Cys Ile Tyr Tyr Pro Trp Thr Gly
625                 630                 635                 640
His Ser Thr Leu Pro Gln His Ala Arg Thr Pro Leu Ile Ala Ala Gly
                645                 650                 655
Val Ile Gly Gly Leu Phe Ile Leu Val Ile Val Gly Leu Thr Phe Ala
            660                 665                 670
```

```
Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
        690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                    725                 730                 735

Trp Val Pro Glu Gly Glu Thr Val Lys Ile Pro Val Ala Ile Lys Ile
                    740                 745                 750

Leu Asn Glu Thr Thr Gly Pro Lys Ala Asn Val Glu Phe Met Asp Glu
                    755                 760                 765

Ala Leu Ile Met Ala Ser Met Asp His Pro His Leu Val Arg Leu Leu
        770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                    805                 810                 815

Ser Gln Leu Leu Leu Asn Trp Cys Val Gln Ile Ala Lys Gly Met Met
                    820                 825                 830

Tyr Leu Glu Glu Arg Arg Leu Val His Arg Asp Leu Ala Ala Arg Asn
        835                 840                 845

Val Leu Val Lys Ser Pro Asn His Val Lys Ile Thr Asp Phe Gly Leu
850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                    885                 890                 895

Phe Thr His Gln Ser Asp Val Trp Ser Tyr Gly Val Thr Ile Trp Glu
        900                 905                 910

Leu Met Thr Phe Gly Gly Lys Pro Tyr Asp Gly Ile Pro Thr Arg Glu
        915                 920                 925

Ile Pro Asp Leu Leu Glu Lys Gly Glu Arg Leu Pro Gln Pro Pro Ile
        930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                    965                 970                 975

Met Ala Arg Asp Pro Gln Arg Tyr Leu Val Ile Gln Gly Asp Asp Arg
                    980                 985                 990

Met Lys Leu Pro Ser Pro Asn Asp Ser Lys Phe Phe Gln Asn Leu Leu
        995                 1000                1005

Asp Glu Glu Asp Leu Glu Asp Met Met Asp Ala Glu Glu Tyr Leu
        1010                1015                1020

Val Pro Gln Ala Phe Asn Ile Pro Pro Pro Ile Tyr Thr Ser Arg
        1025                1030                1035

Ala Arg Ile Asp Ser Asn Arg Ser Glu Ile Gly His Ser Pro Pro
        1040                1045                1050

Pro Ala Tyr Thr Pro Met Ser Gly Asn Gln Phe Val Tyr Arg Asp
        1055                1060                1065

Gly Gly Phe Ala Ala Glu Gln Gly Val Ser Val Pro Tyr Arg Ala
        1070                1075                1080
```

```
Pro Thr Ser Thr Ile Pro Glu Ala Pro Val Ala Gln Gly Ala Thr
    1085                1090                1095

Ala Glu Ile Phe Asp Asp Ser Cys Cys Asn Gly Thr Leu Arg Lys
    1100                1105                1110

Pro Val Ala Pro His Val Gln Glu Asp Ser Ser Thr Gln Arg Tyr
    1115                1120                1125

Ser Ala Asp Pro Thr Val Phe Ala Pro Glu Arg Ser Pro Arg Gly
    1130                1135                1140

Glu Leu Asp Glu Glu Gly Tyr Met Thr Pro Met Arg Asp Lys Pro
    1145                1150                1155

Lys Gln Glu Tyr Leu Asn Pro Val Glu Glu Asn Pro Phe Val Ser
    1160                1165                1170

Arg Arg Lys Asn Gly Asp Leu Gln Ala Leu Asp Asn Pro Glu Tyr
    1175                1180                1185

His Asn Ala Ser Asn Gly Pro Pro Lys Ala Glu Asp Glu Tyr Val
    1190                1195                1200

Asn Glu Pro Leu Tyr Leu Asn Thr Phe Ala Asn Thr Leu Gly Lys
    1205                1210                1215

Ala Glu Tyr Leu Lys Asn Asn Ile Leu Ser Met Pro Glu Lys Ala
    1220                1225                1230

Lys Lys Ala Phe Asp Asn Pro Asp Tyr Trp Asn His Ser Leu Pro
    1235                1240                1245

Pro Arg Ser Thr Leu Gln His Pro Asp Tyr Leu Gln Glu Tyr Ser
    1250                1255                1260

Thr Lys Tyr Phe Tyr Lys Gln Asn Gly Arg Ile Arg Pro Ile Val
    1265                1270                1275

Ala Glu Asn Pro Glu Tyr Leu Ser Glu Phe Ser Leu Lys Pro Gly
    1280                1285                1290

Thr Val Leu Pro Pro Pro Tyr Arg His Arg Asn Thr Val Val
    1295                1300                1305

<210> SEQ ID NO 58
<211> LENGTH: 230
<212> TYPE: PRT
<213> ORGANISM: Homo sapiens

<400> SEQUENCE: 58

Met Ser Ser Tyr Tyr Val Asn Ala Leu Phe Ser Lys Tyr Thr Ala
1               5                   10                  15

Gly Ala Ser Leu Phe Gln Asn Ala Glu Pro Thr Ser Cys Ser Phe Ala
                20                  25                  30

Pro Asn Ser Gln Arg Ser Gly Tyr Gly Ala Gly Ala Phe Ala
        35                  40                  45

Ser Thr Val Pro Gly Leu Tyr Asn Val Asn Ser Pro Leu Tyr Gln Ser
    50                  55                  60

Pro Phe Ala Ser Gly Tyr Gly Leu Gly Ala Asp Ala Tyr Gly Asn Leu
65                  70                  75                  80

Pro Cys Ala Ser Tyr Asp Gln Asn Ile Pro Gly Leu Cys Ser Asp Leu
                85                  90                  95

Ala Lys Gly Ala Cys Asp Lys Thr Asp Glu Gly Ala Leu His Gly Ala
                100                 105                 110

Ala Glu Ala Asn Phe Arg Ile Tyr Pro Trp Met Arg Ser Ser Gly Pro
                115                 120                 125

Asp Arg Lys Arg Gly Arg Gln Thr Tyr Thr Arg Tyr Gln Thr Leu Glu
                130                 135                 140
```

```
Leu Glu Lys Glu Phe His Phe Asn Arg Tyr Leu Thr Arg Arg Arg
145                 150                 155                 160

Ile Glu Ile Ala His Ala Leu Cys Leu Thr Glu Arg Gln Ile Lys Ile
                165                 170                 175

Trp Phe Gln Asn Arg Arg Met Lys Trp Lys Lys Glu His Lys Asp Glu
            180                 185                 190

Gly Pro Thr Ala Ala Ala Pro Glu Gly Ala Val Pro Ser Ala Ala
            195                 200                 205

Ala Thr Ala Ala Ala Asp Lys Ala Asp Glu Glu Asp Asp Glu Glu
    210                 215                 220

Glu Glu Asp Glu Glu Glu
225                 230

<210> SEQ ID NO 59
<211> LENGTH: 724
<212> TYPE: PRT
<213> ORGANISM: Homo sapiens

<400> SEQUENCE: 59

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
            35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
            115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
            195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
```

```
            275                 280                 285
Trp Thr Arg Asn Pro Asp Asp Ile Thr Gln Glu Glu Tyr Gly Glu Phe
290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
                340                 345                 350

Ile Lys Leu Tyr Val Arg Arg Val Phe Ile Met Asp Ser Cys Asp Glu
                355                 360                 365

Leu Ile Pro Glu Tyr Leu Asn Phe Ile Arg Gly Val Val Asp Ser Glu
370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
                420                 425                 430

Phe Ser Lys Asn Leu Lys Leu Gly Ile His Glu Asp Ser Thr Asn Arg
                435                 440                 445

Arg Arg Leu Ser Glu Leu Leu Arg Tyr His Thr Ser Gln Ser Gly Asp
450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
                500                 505                 510

Met Thr Glu Pro Ile Asp Glu Tyr Cys Val Gln Gln Leu Lys Glu Phe
                515                 520                 525

Asp Gly Lys Ser Leu Val Ser Val Thr Lys Glu Gly Leu Glu Leu Pro
530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
                580                 585                 590

Thr Ser Thr Tyr Gly Trp Thr Ala Asn Met Glu Arg Ile Met Lys Ala
                595                 600                 605

Gln Ala Leu Arg Asp Asn Ser Thr Met Gly Tyr Met Met Ala Lys Lys
610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
                660                 665                 670

Pro Gln Thr His Ser Asn Arg Ile Tyr Arg Met Ile Lys Leu Gly Leu
                675                 680                 685

Gly Ile Asp Glu Asp Glu Val Ala Ala Glu Glu Pro Asn Ala Ala Val
690                 695                 700
```

```
Pro Asp Glu Ile Pro Pro Leu Glu Gly Asp Glu Asp Ala Ser Arg Met
705                 710                 715                 720

Glu Glu Val Asp

<210> SEQ ID NO 60
<211> LENGTH: 532
<212> TYPE: PRT
<213> ORGANISM: Homo sapiens

<400> SEQUENCE: 60

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
                20                  25                  30

Pro Ser Lys Val Ile Leu Pro Arg Gly Gly Ser Val Leu Val Thr Cys
            35                  40                  45

Ser Thr Ser Cys Asp Gln Pro Lys Leu Leu Gly Ile Glu Thr Pro Leu
        50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350
```

Arg Ala Gln Leu Leu Lys Ala Thr Pro Glu Asp Asn Gly Arg Ser
            355                 360                 365

Phe Ser Cys Ser Ala Thr Leu Glu Val Ala Gly Gln Leu Ile His Lys
            370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
            435                 440                 445

Arg Asp Leu Glu Gly Thr Tyr Leu Cys Arg Ala Arg Ser Thr Gln Gly
            450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
            515                 520                 525

Ala Thr Pro Pro
            530

<210> SEQ ID NO 61
<211> LENGTH: 387
<212> TYPE: PRT
<213> ORGANISM: Homo sapiens

<400> SEQUENCE: 61

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
            50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
            115                 120                 125

Gln Val Asn Leu Leu Arg Arg Met Trp Val Thr Gly Val Val Thr Gln
            130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His

```
                180             185             190
Val Asn Leu Phe Glu Thr Pro Val Glu Ala Gln Tyr Val Arg Leu Tyr
            195             200             205

Pro Thr Ser Cys His Thr Ala Cys Thr Leu Arg Phe Glu Leu Leu Gly
        210             215             220

Cys Glu Leu Asn Gly Cys Ala Asn Pro Leu Gly Leu Lys Asn Asn Ser
225             230             235             240

Ile Pro Asp Lys Gln Ile Thr Ala Ser Ser Tyr Lys Thr Trp Gly
            245             250             255

Leu His Leu Phe Ser Trp Asn Pro Ser Tyr Ala Arg Leu Asp Lys Gln
            260             265             270

Gly Asn Phe Asn Ala Trp Val Ala Gly Ser Tyr Gly Asn Asp Gln Trp
        275             280             285

Leu Gln Val Asp Leu Gly Ser Ser Lys Glu Val Thr Gly Ile Ile Thr
        290             295             300

Gln Gly Ala Arg Asn Phe Gly Ser Val Gln Phe Val Ala Ser Tyr Lys
305             310             315             320

Val Ala Tyr Ser Asn Asp Ser Ala Asn Trp Thr Glu Tyr Gln Asp Pro
                325             330             335

Arg Thr Gly Ser Ser Lys Ile Phe Pro Gly Asn Trp Asp Asn His Ser
            340             345             350

His Lys Lys Asn Leu Phe Glu Thr Pro Ile Leu Ala Arg Tyr Val Arg
            355             360             365

Ile Leu Pro Val Ala Trp His Asn Arg Ile Ala Leu Arg Leu Glu Leu
370             375             380

Leu Gly Cys
385

<210> SEQ ID NO 62
<211> LENGTH: 410
<212> TYPE: PRT
<213> ORGANISM: Homo sapiens

<400> SEQUENCE: 62

Met Val Cys Phe Arg Leu Phe Pro Val Pro Gly Ser Gly Leu Val Leu
1               5               10              15

Val Cys Leu Val Leu Gly Ala Val Arg Ser Tyr Ala Leu Glu Leu Asn
            20              25              30

Leu Thr Asp Ser Glu Asn Ala Thr Cys Leu Tyr Ala Lys Trp Gln Met
        35              40              45

Asn Phe Thr Val Arg Tyr Glu Thr Thr Asn Lys Thr Tyr Lys Thr Val
        50              55              60

Thr Ile Ser Asp His Gly Thr Val Thr Tyr Asn Gly Ser Ile Cys Gly
65              70              75              80

Asp Asp Gln Asn Gly Pro Lys Ile Ala Val Gln Phe Gly Pro Gly Phe
            85              90              95

Ser Trp Ile Ala Asn Phe Thr Lys Ala Ala Ser Thr Tyr Ser Ile Asp
            100             105             110

Ser Val Ser Phe Ser Tyr Asn Thr Gly Asp Asn Thr Thr Phe Pro Asp
            115             120             125

Ala Glu Asp Lys Gly Ile Leu Thr Val Asp Glu Leu Leu Ala Ile Arg
        130             135             140

Ile Pro Leu Asn Asp Leu Phe Arg Cys Asn Ser Leu Ser Thr Leu Glu
145             150             155             160
```

```
Lys Asn Asp Val Val Gln His Tyr Trp Asp Val Leu Val Gln Ala Phe
            165                 170                 175

Val Gln Asn Gly Thr Val Ser Thr Asn Glu Phe Leu Cys Asp Lys Asp
        180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 63
<211> LENGTH: 1170
<212> TYPE: PRT
<213> ORGANISM: Homo sapiens

<400> SEQUENCE: 63

Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
                20                  25                  30

Ala Arg Ser Phe Ser Pro Pro Arg Ala Gly Arg His Phe Gly Tyr Arg
            35                  40                  45

Val Leu Gln Val Gly Asn Gly Val Ile Val Gly Ala Pro Gly Glu Gly
        50                  55                  60

Asn Ser Thr Gly Ser Leu Tyr Gln Cys Gln Ser Gly Thr Gly His Cys
65                  70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Ala Cys Asp
            100                 105                 110

Pro Gly Leu Ser Arg Thr Cys Asp Gln Asn Thr Tyr Leu Ser Gly Leu
        115                 120                 125
```

```
Cys Tyr Leu Phe Arg Gln Asn Leu Gln Gly Pro Met Leu Gln Gly Arg
    130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Arg Lys Asp Pro Asp Ala Leu Leu Lys His Val
    210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Ile Thr Asp Gly Glu Ala Thr Asp Ser Gly Asn
            260                 265                 270

Ile Asp Ala Ala Lys Asp Ile Ile Arg Tyr Ile Gly Ile Gly Lys
        275                 280                 285

His Phe Gln Thr Lys Glu Ser Gln Glu Thr Leu His Lys Phe Ala Ser
    290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
        355                 360                 365

Gly Ala Lys Asp Trp Ala Gly Gly Phe Leu Asp Leu Lys Ala Asp Leu
    370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
        435                 440                 445

Gln Thr Ile His Gly Thr Gln Ile Gly Ser Tyr Phe Gly Gly Glu Leu
    450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
        515                 520                 525

Thr Asp Ile Asn Gly Asp Gly Leu Val Asp Val Ala Val Gly Ala Pro
    530                 535                 540
```

```
Leu Glu Glu Gln Gly Ala Val Tyr Ile Phe Asn Gly Arg His Gly
545                 550                 555                 560
Leu Ser Pro Gln Pro Ser Gln Arg Ile Glu Gly Thr Gln Val Leu Ser
                565                 570                 575
Gly Ile Gln Trp Phe Gly Arg Ser Ile His Gly Val Lys Asp Leu Glu
            580                 585                 590
Gly Asp Gly Leu Ala Asp Val Ala Val Gly Ala Glu Ser Gln Met Ile
        595                 600                 605
Val Leu Ser Ser Arg Pro Val Asp Met Val Thr Leu Met Ser Phe
        610                 615                 620
Ser Pro Ala Glu Ile Pro Val His Glu Val Glu Cys Ser Tyr Ser Thr
625                 630                 635                 640
Ser Asn Lys Met Lys Glu Gly Val Asn Ile Thr Ile Cys Phe Gln Ile
                645                 650                 655
Lys Ser Leu Ile Pro Gln Phe Gln Gly Arg Leu Val Ala Asn Leu Thr
                660                 665                 670
Tyr Thr Leu Gln Leu Asp Gly His Arg Thr Arg Arg Arg Gly Leu Phe
            675                 680                 685
Pro Gly Gly Arg His Glu Leu Arg Arg Asn Ile Ala Val Thr Thr Ser
        690                 695                 700
Met Ser Cys Thr Asp Phe Ser Phe His Phe Pro Val Cys Val Gln Asp
705                 710                 715                 720
Leu Ile Ser Pro Ile Asn Val Ser Leu Asn Phe Ser Leu Trp Glu Glu
                725                 730                 735
Glu Gly Thr Pro Arg Asp Gln Arg Ala Gln Gly Lys Asp Ile Pro Pro
            740                 745                 750
Ile Leu Arg Pro Ser Leu His Ser Glu Thr Trp Glu Ile Pro Phe Glu
        755                 760                 765
Lys Asn Cys Gly Glu Asp Lys Lys Cys Glu Ala Asn Leu Arg Val Ser
        770                 775                 780
Phe Ser Pro Ala Arg Ser Arg Ala Leu Arg Leu Thr Ala Phe Ala Ser
785                 790                 795                 800
Leu Ser Val Glu Leu Ser Leu Ser Asn Leu Glu Glu Asp Ala Tyr Trp
                805                 810                 815
Val Gln Leu Asp Leu His Phe Pro Pro Gly Leu Ser Phe Arg Lys Val
            820                 825                 830
Glu Met Leu Lys Pro His Ser Gln Ile Pro Val Ser Cys Glu Glu Leu
        835                 840                 845
Pro Glu Glu Ser Arg Leu Leu Ser Arg Ala Leu Ser Cys Asn Val Ser
    850                 855                 860
Ser Pro Ile Phe Lys Ala Gly His Ser Val Ala Leu Gln Met Met Phe
865                 870                 875                 880
Asn Thr Leu Val Asn Ser Ser Trp Gly Asp Ser Val Glu Leu His Ala
                885                 890                 895
Asn Val Thr Cys Asn Asn Glu Asp Ser Asp Leu Leu Glu Asp Asn Ser
            900                 905                 910
Ala Thr Thr Ile Ile Pro Ile Leu Tyr Pro Ile Asn Ile Leu Ile Gln
        915                 920                 925
Asp Gln Glu Asp Ser Thr Leu Tyr Val Ser Phe Thr Pro Lys Gly Pro
    930                 935                 940
Lys Ile His Gln Val Lys His Met Tyr Gln Val Arg Ile Gln Pro Ser
945                 950                 955                 960
Ile His Asp His Asn Ile Pro Thr Leu Glu Ala Val Val Gly Val Pro
```

```
                    965                 970                 975
Gln Pro Pro Ser Glu Gly Pro Ile Thr His Gln Trp Ser Val Gln Met
                980                 985                 990

Glu Pro Pro Val Pro Cys His Tyr Glu Asp Leu Glu Arg Leu Pro Asp
            995                1000                1005

Ala Ala Glu Pro Cys Leu Pro Gly Ala Leu Phe Arg Cys Pro Val
       1010                1015                1020

Val Phe Arg Gln Glu Ile Leu Val Gln Val Ile Gly Thr Leu Glu
       1025                1030                1035

Leu Val Gly Glu Ile Glu Ala Ser Ser Met Phe Ser Leu Cys Ser
       1040                1045                1050

Ser Leu Ser Ile Ser Phe Asn Ser Ser Lys His Phe His Leu Tyr
       1055                1060                1065

Gly Ser Asn Ala Ser Leu Ala Gln Val Val Met Lys Val Asp Val
       1070                1075                1080

Val Tyr Glu Lys Gln Met Leu Tyr Leu Tyr Val Leu Ser Gly Ile
       1085                1090                1095

Gly Gly Leu Leu Leu Leu Leu Ile Phe Ile Val Leu Tyr Lys
       1100                1105                1110

Val Gly Phe Phe Lys Arg Asn Leu Lys Glu Lys Met Glu Ala Gly
       1115                1120                1125

Arg Gly Val Pro Asn Gly Ile Pro Ala Glu Asp Ser Glu Gln Leu
       1130                1135                1140

Ala Ser Gly Gln Glu Ala Gly Asp Pro Gly Cys Leu Lys Pro Leu
       1145                1150                1155

His Glu Lys Asp Ser Glu Ser Gly Gly Gly Lys Asp
       1160                1165                1170

<210> SEQ ID NO 64
<211> LENGTH: 383
<212> TYPE: PRT
<213> ORGANISM: Homo sapiens

<400> SEQUENCE: 64

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Thr Glu
        35                  40                  45

Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160
```

```
Leu Ala Met Asn Val Arg Asn Phe Leu Lys Glu Asp Ala Met Lys Thr
            165                 170                 175
Lys Thr His Tyr His Ala Met His Ala Asp Cys Leu Gln Glu Leu Arg
            180                 185                 190
Arg Tyr Leu Lys Ser Gly Val Val Leu Arg Arg Thr Val Pro Pro Met
            195                 200                 205
Val Asn Val Thr Arg Ser Glu Ala Ser Glu Gly Asn Ile Thr Val Thr
            210                 215                 220
Cys Arg Ala Ser Gly Phe Tyr Pro Trp Asn Ile Thr Leu Ser Trp Arg
225                 230                 235                 240
Gln Asp Gly Val Ser Leu Ser His Asp Thr Gln Gln Trp Gly Asp Val
            245                 250                 255
Leu Pro Asp Gly Asn Gly Thr Tyr Gln Thr Trp Val Ala Thr Arg Ile
            260                 265                 270
Cys Gln Gly Glu Glu Gln Arg Phe Thr Cys Tyr Met Glu His Ser Gly
            275                 280                 285
Asn His Ser Thr His Pro Val Pro Ser Gly Lys Val Leu Val Leu Gln
            290                 295                 300
Ser His Trp Gln Thr Phe His Val Ser Ala Val Ala Ala Ala Ala Ile
305                 310                 315                 320
Phe Val Ile Ile Ile Phe Tyr Val Arg Cys Cys Lys Lys Lys Thr Ser
            325                 330                 335
Ala Ala Glu Gly Pro Glu Leu Val Ser Leu Gln Val Leu Asp Gln His
            340                 345                 350
Pro Val Gly Thr Ser Asp His Arg Asp Ala Thr Gln Leu Gly Phe Gln
            355                 360                 365
Pro Leu Met Ser Asp Leu Gly Ser Thr Gly Ser Thr Glu Gly Ala
            370                 375                 380

<210> SEQ ID NO 65
<211> LENGTH: 383
<212> TYPE: PRT
<213> ORGANISM: Homo sapiens

<400> SEQUENCE: 65

Met Gly Leu Gly Arg Val Leu Leu Phe Leu Ala Val Ala Phe Pro Phe
1               5                   10                  15
Ala Pro Pro Ala Ala Ala Glu Pro His Ser Leu Arg Tyr Asn Leu
            20                  25                  30
Met Val Leu Ser Gln Asp Glu Ser Val Gln Ser Gly Phe Leu Ala Glu
            35                  40                  45
Gly His Leu Asp Gly Gln Pro Phe Leu Arg Tyr Asp Arg Gln Lys Arg
            50                  55                  60
Arg Ala Lys Pro Gln Gly Gln Trp Ala Glu Asp Val Leu Gly Ala Lys
65                  70                  75                  80
Thr Trp Asp Thr Glu Thr Glu Asp Leu Thr Glu Asn Gly Gln Asp Leu
            85                  90                  95
Arg Arg Thr Leu Thr His Ile Lys Asp Gln Lys Gly Gly Leu His Ser
            100                 105                 110
Leu Gln Glu Ile Arg Val Cys Glu Ile His Glu Asp Ser Ser Thr Arg
            115                 120                 125
Gly Ser Arg His Phe Tyr Tyr Asp Gly Glu Leu Phe Leu Ser Gln Asn
            130                 135                 140
Leu Glu Thr Gln Glu Ser Thr Val Pro Gln Ser Ser Arg Ala Gln Thr
145                 150                 155                 160
```

```
Leu Ala Met Asn Val Thr Asn Phe Trp Lys Glu Asp Ala Met Lys Thr
                165                 170                 175
Lys Thr His Tyr Arg Ala Met Gln Ala Asp Cys Leu Gln Lys Leu Gln
            180                 185                 190
Arg Tyr Leu Lys Ser Gly Val Ala Ile Arg Thr Val Pro Pro Met
        195                 200                 205
Val Asn Val Thr Cys Ser Glu Val Ser Glu Gly Asn Ile Thr Val Thr
    210                 215                 220
Cys Arg Ala Ser Ser Phe Tyr Pro Arg Asn Ile Thr Leu Thr Trp Arg
225                 230                 235                 240
Gln Asp Gly Val Ser Leu Ser His Asn Thr Gln Gln Trp Gly Asp Val
                245                 250                 255
Leu Pro Asp Gly Asn Gly Thr Tyr Gln Thr Trp Val Ala Thr Arg Ile
            260                 265                 270
Arg Gln Gly Glu Glu Gln Arg Phe Thr Cys Tyr Met Glu His Ser Gly
        275                 280                 285
Asn His Gly Thr His Pro Val Pro Ser Gly Lys Val Leu Val Leu Gln
    290                 295                 300
Ser Gln Arg Thr Asp Phe Pro Tyr Val Ser Ala Ala Met Pro Cys Phe
305                 310                 315                 320
Val Ile Ile Ile Leu Cys Val Pro Cys Cys Lys Lys Thr Ser
                325                 330                 335
Ala Ala Glu Gly Pro Glu Leu Val Ser Leu Gln Val Leu Asp Gln His
            340                 345                 350
Pro Val Gly Thr Gly Asp His Arg Asp Ala Ala Gln Leu Gly Phe Gln
        355                 360                 365
Pro Leu Met Ser Ala Thr Gly Ser Thr Gly Ser Thr Glu Gly Ala
    370                 375                 380

<210> SEQ ID NO 66
<211> LENGTH: 1255
<212> TYPE: PRT
<213> ORGANISM: Homo sapiens

<400> SEQUENCE: 66

Met Thr Pro Gly Thr Gln Ser Pro Phe Phe Leu Leu Leu Leu Leu Thr
1               5                   10                  15
Val Leu Thr Val Val Thr Gly Ser Gly His Ala Ser Ser Thr Pro Gly
                20                  25                  30
Gly Glu Lys Glu Thr Ser Ala Thr Gln Arg Ser Ser Val Pro Ser Ser
            35                  40                  45
Thr Glu Lys Asn Ala Val Ser Met Thr Ser Ser Val Leu Ser Ser His
        50                  55                  60
Ser Pro Gly Ser Gly Ser Ser Thr Thr Gln Gly Gln Asp Val Thr Leu
65                  70                  75                  80
Ala Pro Ala Thr Glu Pro Ala Ser Gly Ser Ala Ala Thr Trp Gly Gln
                85                  90                  95
Asp Val Thr Ser Val Pro Val Thr Arg Pro Ala Leu Gly Ser Thr Thr
            100                 105                 110
Pro Pro Ala His Asp Val Thr Ser Ala Pro Asp Asn Lys Pro Ala Pro
        115                 120                 125
Gly Ser Thr Ala Pro Ala His Gly Val Thr Ser Ala Pro Asp Thr
    130                 135                 140
Arg Pro Ala Pro Gly Ser Thr Ala Pro Pro Ala His Gly Val Thr Ser
```

```
        145                 150                 155                 160
Ala Pro Asp Thr Arg Pro Ala Pro Gly Ser Thr Ala Pro Pro Ala His
                165                 170                 175
Gly Val Thr Ser Ala Pro Asp Thr Arg Pro Ala Pro Gly Ser Thr Ala
                180                 185                 190
Pro Pro Ala His Gly Val Thr Ser Ala Pro Asp Thr Arg Pro Ala Pro
                195                 200                 205
Gly Ser Thr Ala Pro Pro Ala His Gly Val Thr Ser Ala Pro Asp Thr
    210                 215                 220
Arg Pro Ala Pro Gly Ser Thr Ala Pro Pro Ala His Gly Val Thr Ser
225                 230                 235                 240
Ala Pro Asp Thr Arg Pro Ala Pro Gly Ser Thr Ala Pro Pro Ala His
                245                 250                 255
Gly Val Thr Ser Ala Pro Asp Thr Arg Pro Ala Pro Gly Ser Thr Ala
                260                 265                 270
Pro Pro Ala His Gly Val Thr Ser Ala Pro Asp Thr Arg Pro Ala Pro
                275                 280                 285
Gly Ser Thr Ala Pro Pro Ala His Gly Val Thr Ser Ala Pro Asp Thr
    290                 295                 300
Arg Pro Ala Pro Gly Ser Thr Ala Pro Pro Ala His Gly Val Thr Ser
305                 310                 315                 320
Ala Pro Asp Thr Arg Pro Ala Pro Gly Ser Thr Ala Pro Pro Ala His
                325                 330                 335
Gly Val Thr Ser Ala Pro Asp Thr Arg Pro Ala Pro Gly Ser Thr Ala
                340                 345                 350
Pro Pro Ala His Gly Val Thr Ser Ala Pro Asp Thr Arg Pro Ala Pro
                355                 360                 365
Gly Ser Thr Ala Pro Pro Ala His Gly Val Thr Ser Ala Pro Asp Thr
    370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
                420                 425                 430
Pro Pro Ala His Gly Val Thr Ser Ala Pro Asp Thr Arg Pro Ala Pro
                435                 440                 445
Gly Ser Thr Ala Pro Pro Ala His Gly Val Thr Ser Ala Pro Asp Thr
    450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
                500                 505                 510
Pro Pro Ala His Gly Val Thr Ser Ala Pro Asp Thr Arg Pro Ala Pro
                515                 520                 525
Gly Ser Thr Ala Pro Pro Ala His Gly Val Thr Ser Ala Pro Asp Thr
    530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
```

```
Gly Val Thr Ser Ala Pro Asp Thr Arg Pro Ala Pro Gly Ser Thr Ala
                580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
                660                 665                 670
Pro Pro Ala His Gly Val Thr Ser Ala Pro Asp Thr Arg Pro Ala Pro
            675                 680                 685
Gly Ser Thr Ala Pro Pro Ala His Gly Val Thr Ser Ala Pro Asp Thr
            690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
                740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
            770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
                820                 825                 830
Pro Pro Ala His Gly Val Thr Ser Ala Pro Asp Thr Arg Pro Ala Pro
            835                 840                 845
Gly Ser Thr Ala Pro Pro Ala His Gly Val Thr Ser Ala Pro Asp Thr
            850                 855                 860
Arg Pro Ala Pro Gly Ser Thr Ala Pro Pro Ala His Gly Val Thr Ser
865                 870                 875                 880
Ala Pro Asp Thr Arg Pro Ala Pro Gly Ser Thr Ala Pro Pro Ala His
                885                 890                 895
Gly Val Thr Ser Ala Pro Asp Thr Arg Pro Ala Pro Gly Ser Thr Ala
                900                 905                 910
Pro Pro Ala His Gly Val Thr Ser Ala Pro Asp Thr Arg Pro Ala Pro
            915                 920                 925
Gly Ser Thr Ala Pro Pro Ala His Gly Val Thr Ser Ala Pro Asp Asn
            930                 935                 940
Arg Pro Ala Leu Gly Ser Thr Ala Pro Val His Asn Val Thr Ser
945                 950                 955                 960
Ala Ser Gly Ser Ala Ser Gly Ser Ala Ser Thr Leu Val His Asn Gly
                965                 970                 975
Thr Ser Ala Arg Ala Thr Thr Thr Pro Ala Ser Lys Ser Thr Pro Phe
                980                 985                 990
```

```
Ser Ile Pro Ser His His Ser Asp Thr Pro Thr Thr Leu Ala Ser His
        995                1000                1005

Ser Thr Lys Thr Asp Ala Ser Ser Thr His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 67
<211> LENGTH: 14507
<212> TYPE: PRT
<213> ORGANISM: Homo sapiens

<400> SEQUENCE: 67

Met Leu Lys Pro Ser Gly Leu Pro Gly Ser Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95
```

```
Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
            115                 120                 125

Pro Arg Thr Arg Thr Ser Ser Thr Glu Gly Asn Phe Thr Lys Glu Ala
            130                 135                 140

Ser Thr Tyr Thr Leu Thr Val Glu Thr Ser Gly Pro Val Thr Glu
145                 150                 155                 160

Lys Tyr Thr Val Pro Thr Glu Thr Ser Thr Glu Gly Asp Ser Thr
                165                 170                 175

Glu Thr Pro Trp Asp Thr Arg Tyr Ile Pro Val Lys Ile Thr Ser Pro
                180                 185                 190

Met Lys Thr Phe Ala Asp Ser Thr Ala Ser Lys Glu Asn Ala Pro Val
            195                 200                 205

Ser Met Thr Pro Ala Glu Thr Thr Val Thr Asp Ser His Thr Pro Gly
            210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
            275                 280                 285

Ser Val Leu Asp Asn Lys Ile Ser Glu Thr Ser Ile Phe Ser Gly Gln
            290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
            355                 360                 365

Ala Phe Ala Glu Thr Met Asp Ile Pro Ser Thr His Ile Ala Lys Thr
            370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
            450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510
```

```
Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
        530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
        595                 600                 605

Ile Ser Met Thr Gly Gly Ser Ser Thr Arg Gly Ser Gln Gly Thr Thr
        610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
        675                 680                 685

Ala Phe Arg Glu Gly Thr Ser Leu Gly Leu Thr Pro Leu Asn Thr Arg
        690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
        755                 760                 765

Val Leu Ser Ser Met Thr Leu Ser Asn Ala Ala Thr Ser Pro Glu Arg
        770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
        835                 840                 845

Thr Phe Ser Ser Ser Thr Pro Ser Thr His Leu Phe Thr Ser Gly Glu
        850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
        915                 920                 925

Thr Asn Ser Thr Gly Ser Ala Leu Pro Lys Ile Ser His Leu Thr Gly
```

```
                930              935            940
Thr Ala Thr Met Ser Gln Thr Asn Arg Asp Thr Phe Asn Asp Ser Ala
945                 950             955                 960

Ala Pro Gln Ser Thr Thr Trp Pro Glu Thr Ser Pro Arg Phe Lys Thr
                965             970             975

Gly Leu Pro Ser Ala Thr Thr Val Ser Thr Ser Ala Thr Ser Leu
            980             985             990

Ser Ala Thr Val Met Val Ser Lys Phe Thr Ser Pro Ala Thr Ser Ser
        995             1000            1005

Met Glu Ala Thr Ser Ile Arg Glu Pro Ser Thr Thr Ile Leu Thr
    1010            1015            1020

Thr Glu Thr Thr Asn Gly Pro Gly Ser Met Ala Val Ala Ser Thr
    1025            1030            1035

Asn Ile Pro Ile Gly Lys Gly Tyr Ile Thr Glu Gly Arg Leu Asp
    1040            1045            1050

Thr Ser His Leu Pro Ile Gly Thr Thr Ala Ser Ser Glu Thr Ser
    1055            1060            1065

Met Asp Phe Thr Met Ala Lys Glu Ser Val Ser Met Ser Val Ser
    1070            1075            1080

Pro Ser Gln Ser Met Asp Ala Ala Gly Ser Ser Thr Pro Gly Arg
    1085            1090            1095

Thr Ser Gln Phe Val Asp Thr Phe Ser Asp Asp Val Tyr His Leu
    1100            1105            1110

Thr Ser Arg Glu Ile Thr Ile Pro Arg Asp Gly Thr Ser Ser Ala
    1115            1120            1125

Leu Thr Pro Gln Met Thr Ala Thr His Pro Pro Ser Pro Asp Pro
    1130            1135            1140

Gly Ser Ala Arg Ser Thr Trp Leu Gly Ile Leu Ser Ser Ser Pro
    1145            1150            1155

Ser Ser Pro Thr Pro Lys Val Thr Met Ser Ser Thr Phe Ser Thr
    1160            1165            1170

Gln Arg Val Thr Thr Ser Met Ile Met Asp Thr Val Glu Thr Ser
    1175            1180            1185

Arg Trp Asn Met Pro Asn Leu Pro Ser Thr Thr Ser Leu Thr Pro
    1190            1195            1200

Ser Asn Ile Pro Thr Ser Gly Ala Ile Gly Lys Ser Thr Leu Val
    1205            1210            1215

Pro Leu Asp Thr Pro Ser Pro Ala Thr Ser Leu Glu Ala Ser Glu
    1220            1225            1230

Gly Gly Leu Pro Thr Leu Ser Thr Tyr Pro Glu Ser Thr Asn Thr
    1235            1240            1245

Pro Ser Ile His Leu Gly Ala His Ala Ser Ser Glu Ser Pro Ser
    1250            1255            1260

Thr Ile Lys Leu Thr Met Ala Ser Val Val Lys Pro Gly Ser Tyr
    1265            1270            1275

Thr Pro Leu Thr Phe Pro Ser Ile Glu Thr His Ile His Val Ser
    1280            1285            1290

Thr Ala Arg Met Ala Tyr Ser Ser Gly Ser Ser Pro Glu Met Thr
    1295            1300            1305

Ala Pro Gly Glu Thr Asn Thr Gly Ser Thr Trp Asp Pro Thr Thr
    1310            1315            1320

Tyr Ile Thr Thr Thr Asp Pro Lys Asp Thr Ser Ser Ala Gln Val
    1325            1330            1335
```

-continued

```
Ser Thr Pro His Ser Val Arg Thr Leu Arg Thr Thr Glu Asn His
    1340                1345                1350

Pro Lys Thr Glu Ser Ala Thr Pro Ala Ala Tyr Ser Gly Ser Pro
    1355                1360                1365

Lys Ile Ser Ser Ser Pro Asn Leu Thr Ser Pro Ala Thr Lys Ala
    1370                1375                1380

Trp Thr Ile Thr Asp Thr Thr Glu His Ser Thr Gln Leu His Tyr
    1385                1390                1395

Thr Lys Leu Ala Glu Lys Ser Ser Gly Phe Glu Thr Gln Ser Ala
    1400                1405                1410

Pro Gly Pro Val Ser Val Val Ile Pro Thr Ser Pro Thr Ile Gly
    1415                1420                1425

Ser Ser Thr Leu Glu Leu Thr Ser Asp Val Pro Gly Glu Pro Leu
    1430                1435                1440

Val Leu Ala Pro Ser Glu Gln Thr Thr Ile Thr Leu Pro Met Ala
    1445                1450                1455

Thr Trp Leu Ser Thr Ser Leu Thr Glu Glu Met Ala Ser Thr Asp
    1460                1465                1470

Leu Asp Ile Ser Ser Pro Ser Ser Pro Met Ser Thr Phe Ala Ile
    1475                1480                1485

Phe Pro Pro Met Ser Thr Pro Ser His Glu Leu Ser Lys Ser Glu
    1490                1495                1500

Ala Asp Thr Ser Ala Ile Arg Asn Thr Asp Ser Thr Thr Leu Asp
    1505                1510                1515

Gln His Leu Gly Ile Arg Ser Leu Gly Arg Thr Gly Asp Leu Thr
    1520                1525                1530

Thr Val Pro Ile Thr Pro Leu Thr Thr Thr Trp Thr Ser Val Ile
    1535                1540                1545

Glu His Ser Thr Gln Ala Gln Asp Thr Leu Ser Ala Thr Met Ser
    1550                1555                1560

Pro Thr His Val Thr Gln Ser Leu Lys Asp Gln Thr Ser Ile Pro
    1565                1570                1575

Ala Ser Ala Ser Pro Ser His Leu Thr Glu Val Tyr Pro Glu Leu
    1580                1585                1590

Gly Thr Gln Gly Arg Ser Ser Glu Ala Thr Thr Phe Trp Lys
    1595                1600                1605

Pro Ser Thr Asp Thr Leu Ser Arg Glu Ile Glu Thr Gly Pro Thr
    1610                1615                1620

Asn Ile Gln Ser Thr Pro Pro Met Asp Asn Thr Thr Thr Gly Ser
    1625                1630                1635

Ser Ser Ser Gly Val Thr Leu Gly Ile Ala His Leu Pro Ile Gly
    1640                1645                1650

Thr Ser Ser Pro Ala Glu Thr Ser Thr Asn Met Ala Leu Glu Arg
    1655                1660                1665

Arg Ser Ser Thr Ala Thr Val Ser Met Ala Gly Thr Met Gly Leu
    1670                1675                1680

Leu Val Thr Ser Ala Pro Gly Arg Ser Ile Ser Gln Ser Leu Gly
    1685                1690                1695

Arg Val Ser Ser Val Leu Ser Glu Ser Thr Thr Glu Gly Val Thr
    1700                1705                1710

Asp Ser Ser Lys Gly Ser Ser Pro Arg Leu Asn Thr Gln Gly Asn
    1715                1720                1725
```

-continued

Thr Ala Leu Ser Ser Ser Leu Glu Pro Ser Tyr Ala Glu Gly Ser
1730                1735                1740

Gln Met Ser Thr Ser Ile Pro Leu Thr Ser Pro Thr Thr Pro
1745                1750                1755

Asp Val Glu Phe Ile Gly Gly Ser Thr Phe Trp Thr Lys Glu Val
1760                1765                1770

Thr Thr Val Met Thr Ser Asp Ile Ser Lys Ser Ala Arg Thr
1775                1780                1785

Glu Ser Ser Ser Ala Thr Leu Met Ser Thr Ala Leu Gly Ser Thr
1790                1795                1800

Glu Asn Thr Gly Lys Glu Lys Leu Arg Thr Ala Ser Met Asp Leu
1805                1810                1815

Pro Ser Pro Thr Pro Ser Met Glu Val Thr Pro Trp Ile Ser Leu
1820                1825                1830

Thr Leu Ser Asn Ala Pro Asn Thr Thr Asp Ser Leu Asp Leu Ser
1835                1840                1845

His Gly Val His Thr Ser Ser Ala Gly Thr Leu Ala Thr Asp Arg
1850                1855                1860

Ser Leu Asn Thr Gly Val Thr Arg Ala Ser Arg Leu Glu Asn Gly
1865                1870                1875

Ser Asp Thr Ser Ser Lys Ser Leu Ser Met Gly Asn Ser Thr His
1880                1885                1890

Thr Ser Met Thr Tyr Thr Glu Lys Ser Glu Val Ser Ser Ser Ile
1895                1900                1905

His Pro Arg Pro Glu Thr Ser Ala Pro Gly Ala Glu Thr Thr Leu
1910                1915                1920

Thr Ser Thr Pro Gly Asn Arg Ala Ile Ser Leu Thr Leu Pro Phe
1925                1930                1935

Ser Ser Ile Pro Val Glu Glu Val Ile Ser Thr Gly Ile Thr Ser
1940                1945                1950

Gly Pro Asp Ile Asn Ser Ala Pro Met Thr His Ser Pro Ile Thr
1955                1960                1965

Pro Pro Thr Ile Val Trp Thr Ser Thr Gly Thr Ile Glu Gln Ser
1970                1975                1980

Thr Gln Pro Leu His Ala Val Ser Ser Glu Lys Val Ser Val Gln
1985                1990                1995

Thr Gln Ser Thr Pro Tyr Val Asn Ser Val Ala Val Ser Ala Ser
2000                2005                2010

Pro Thr His Glu Asn Ser Val Ser Ser Gly Ser Ser Thr Ser Ser
2015                2020                2025

Pro Tyr Ser Ser Ala Ser Leu Glu Ser Leu Asp Ser Thr Ile Ser
2030                2035                2040

Arg Arg Asn Ala Ile Thr Ser Trp Leu Trp Asp Leu Thr Thr Ser
2045                2050                2055

Leu Pro Thr Thr Thr Trp Pro Ser Thr Ser Leu Ser Glu Ala Leu
2060                2065                2070

Ser Ser Gly His Ser Gly Val Ser Asn Pro Ser Ser Thr Thr Thr
2075                2080                2085

Glu Phe Pro Leu Phe Ser Ala Ala Ser Thr Ser Ala Ala Lys Gln
2090                2095                2100

Arg Asn Pro Glu Thr Glu Thr His Gly Pro Gln Asn Thr Ala Ala
2105                2110                2115

Ser Thr Leu Asn Thr Asp Ala Ser Ser Val Thr Gly Leu Ser Glu

```
                2120                2125                2130

Thr Pro Val Gly Ala Ser Ile Ser Ser Glu Val Pro Leu Pro Met
        2135                2140                2145

Ala Ile Thr Ser Arg Ser Asp Val Ser Gly Leu Thr Ser Glu Ser
        2150                2155                2160

Thr Ala Asn Pro Ser Leu Gly Thr Ala Ser Ser Ala Gly Thr Lys
        2165                2170                2175

Leu Thr Arg Thr Ile Ser Leu Pro Thr Ser Glu Ser Leu Val Ser
        2180                2185                2190

Phe Arg Met Asn Lys Asp Pro Trp Thr Val Ser Ile Pro Leu Gly
        2195                2200                2205

Ser His Pro Thr Thr Asn Thr Glu Thr Ser Ile Pro Val Asn Ser
        2210                2215                2220

Ala Gly Pro Pro Gly Leu Ser Thr Val Ala Ser Asp Val Ile Asp
        2225                2230                2235

Thr Pro Ser Asp Gly Ala Glu Ser Ile Pro Thr Val Ser Phe Ser
        2240                2245                2250

Pro Ser Pro Asp Thr Glu Val Thr Thr Ile Ser His Phe Pro Glu
        2255                2260                2265

Lys Thr Thr His Ser Phe Arg Thr Ile Ser Ser Leu Thr His Glu
        2270                2275                2280

Leu Thr Ser Arg Val Thr Pro Ile Pro Gly Asp Trp Met Ser Ser
        2285                2290                2295

Ala Met Ser Thr Lys Pro Thr Gly Ala Ser Pro Ser Ile Thr Leu
        2300                2305                2310

Gly Glu Arg Arg Thr Ile Thr Ser Ala Ala Pro Thr Thr Ser Pro
        2315                2320                2325

Ile Val Leu Thr Ala Ser Phe Thr Glu Thr Ser Thr Val Ser Leu
        2330                2335                2340

Asp Asn Glu Thr Thr Val Lys Thr Ser Asp Ile Leu Asp Ala Arg
        2345                2350                2355

Lys Thr Asn Glu Leu Pro Ser Asp Ser Ser Ser Ser Ser Asp Leu
        2360                2365                2370

Ile Asn Thr Ser Ile Ala Ser Ser Thr Met Asp Val Thr Lys Thr
        2375                2380                2385

Ala Ser Ile Ser Pro Thr Ser Ile Ser Gly Met Thr Ala Ser Ser
        2390                2395                2400

Ser Pro Ser Leu Phe Ser Ser Asp Arg Pro Gln Val Pro Thr Ser
        2405                2410                2415

Thr Thr Glu Thr Asn Thr Ala Thr Ser Pro Ser Val Ser Ser Asn
        2420                2425                2430

Thr Tyr Ser Leu Asp Gly Gly Ser Asn Val Gly Gly Thr Pro Ser
        2435                2440                2445

Thr Leu Pro Pro Phe Thr Ile Thr His Pro Val Glu Thr Ser Ser
        2450                2455                2460

Ala Leu Leu Ala Trp Ser Arg Pro Val Arg Thr Phe Ser Thr Met
        2465                2470                2475

Val Ser Thr Asp Thr Ala Ser Gly Glu Asn Pro Thr Ser Ser Asn
        2480                2485                2490

Ser Val Val Thr Ser Val Pro Ala Pro Gly Thr Trp Thr Ser Val
        2495                2500                2505

Gly Ser Thr Thr Asp Leu Pro Ala Met Gly Phe Leu Lys Thr Ser
        2510                2515                2520
```

```
Pro Ala Gly Glu Ala His Ser Leu Leu Ala Ser Thr Ile Glu Pro
    2525            2530                2535

Ala Thr Ala Phe Thr Pro His Leu Ser Ala Ala Val Val Thr Gly
    2540            2545                2550

Ser Ser Ala Thr Ser Glu Ala Ser Leu Leu Thr Thr Ser Glu Ser
    2555            2560                2565

Lys Ala Ile His Ser Ser Pro Gln Thr Pro Thr Thr Pro Thr Ser
    2570            2575                2580

Gly Ala Asn Trp Glu Thr Ser Ala Thr Pro Glu Ser Leu Leu Val
    2585            2590                2595

Val Thr Glu Thr Ser Asp Thr Thr Leu Thr Ser Lys Ile Leu Val
    2600            2605                2610

Thr Asp Thr Ile Leu Phe Ser Thr Val Ser Thr Pro Pro Ser Lys
    2615            2620                2625

Phe Pro Ser Thr Gly Thr Leu Ser Gly Ala Ser Phe Pro Thr Leu
    2630            2635                2640

Leu Pro Asp Thr Pro Ala Ile Pro Leu Thr Ala Thr Glu Pro Thr
    2645            2650                2655

Ser Ser Leu Ala Thr Ser Phe Asp Ser Thr Pro Leu Val Thr Ile
    2660            2665                2670

Ala Ser Asp Ser Leu Gly Thr Val Pro Glu Thr Thr Leu Thr Met
    2675            2680                2685

Ser Glu Thr Ser Asn Gly Asp Ala Leu Val Leu Lys Thr Val Ser
    2690            2695                2700

Asn Pro Asp Arg Ser Ile Pro Gly Ile Thr Ile Gln Gly Val Thr
    2705            2710                2715

Glu Ser Pro Leu His Pro Ser Ser Thr Ser Pro Ser Lys Ile Val
    2720            2725                2730

Ala Pro Arg Asn Thr Thr Tyr Glu Gly Ser Ile Thr Val Ala Leu
    2735            2740                2745

Ser Thr Leu Pro Ala Gly Thr Thr Gly Ser Leu Val Phe Ser Gln
    2750            2755                2760

Ser Ser Glu Asn Ser Glu Thr Thr Ala Leu Val Asp Ser Ser Ala
    2765            2770                2775

Gly Leu Glu Arg Ala Ser Val Met Pro Leu Thr Thr Gly Ser Gln
    2780            2785                2790

Gly Met Ala Ser Ser Gly Gly Ile Arg Ser Gly Ser Thr His Ser
    2795            2800                2805

Thr Gly Thr Lys Thr Phe Ser Ser Leu Pro Leu Thr Met Asn Pro
    2810            2815                2820

Gly Glu Val Thr Ala Met Ser Glu Ile Thr Thr Asn Arg Leu Thr
    2825            2830                2835

Ala Thr Gln Ser Thr Ala Pro Lys Gly Ile Pro Val Lys Pro Thr
    2840            2845                2850

Ser Ala Glu Ser Gly Leu Leu Thr Pro Val Ser Ala Ser Ser Ser
    2855            2860                2865

Pro Ser Lys Ala Phe Ala Ser Leu Thr Thr Ala Pro Pro Thr Trp
    2870            2875                2880

Gly Ile Pro Gln Ser Thr Leu Thr Phe Glu Phe Ser Glu Val Pro
    2885            2890                2895

Ser Leu Asp Thr Lys Ser Ala Ser Leu Pro Thr Pro Gly Gln Ser
    2900            2905                2910
```

```
Leu Asn Thr Ile Pro Asp Ser Asp Ala Ser Thr Ala Ser Ser Ser
2915                2920                2925

Leu Ser Lys Ser Pro Glu Lys Asn Pro Arg Ala Arg Met Met Thr
2930                2935                2940

Ser Thr Lys Ala Ile Ser Ala Ser Ser Phe Gln Ser Thr Gly Phe
2945                2950                2955

Thr Glu Thr Pro Glu Gly Ser Ala Ser Pro Ser Met Ala Gly His
2960                2965                2970

Glu Pro Arg Val Pro Thr Ser Gly Thr Gly Asp Pro Arg Tyr Ala
2975                2980                2985

Ser Glu Ser Met Ser Tyr Pro Asp Pro Ser Lys Ala Ser Ser Ala
2990                2995                3000

Met Thr Ser Thr Ser Leu Ala Ser Lys Leu Thr Thr Leu Phe Ser
3005                3010                3015

Thr Gly Gln Ala Ala Arg Ser Gly Ser Ser Ser Pro Ile Ser
3020                3025                3030

Leu Ser Thr Glu Lys Glu Thr Ser Phe Leu Ser Pro Thr Ala Ser
3035                3040                3045

Thr Ser Arg Lys Thr Ser Leu Phe Leu Gly Pro Ser Met Ala Arg
3050                3055                3060

Gln Pro Asn Ile Leu Val His Leu Gln Thr Ser Ala Leu Thr Leu
3065                3070                3075

Ser Pro Thr Ser Thr Leu Asn Met Ser Gln Glu Glu Pro Pro Glu
3080                3085                3090

Leu Thr Ser Ser Gln Thr Ile Ala Glu Glu Gly Thr Thr Ala
3095                3100                3105

Glu Thr Gln Thr Leu Thr Phe Thr Pro Ser Glu Thr Pro Thr Ser
3110                3115                3120

Leu Leu Pro Val Ser Ser Pro Thr Glu Pro Thr Ala Arg Arg Lys
3125                3130                3135

Ser Ser Pro Glu Thr Trp Ala Ser Ser Ile Ser Val Pro Ala Lys
3140                3145                3150

Thr Ser Leu Val Glu Thr Thr Asp Gly Thr Leu Val Thr Thr Ile
3155                3160                3165

Lys Met Ser Ser Gln Ala Ala Gln Gly Asn Ser Thr Trp Pro Ala
3170                3175                3180

Pro Ala Glu Glu Thr Gly Ser Ser Pro Ala Gly Thr Ser Pro Gly
3185                3190                3195

Ser Pro Glu Met Ser Thr Thr Leu Lys Ile Met Ser Ser Lys Glu
3200                3205                3210

Pro Ser Ile Ser Pro Glu Ile Arg Ser Thr Val Arg Asn Ser Pro
3215                3220                3225

Trp Lys Thr Pro Glu Thr Thr Val Pro Met Glu Thr Thr Val Glu
3230                3235                3240

Pro Val Thr Leu Gln Ser Thr Ala Leu Gly Ser Gly Ser Thr Ser
3245                3250                3255

Ile Ser His Leu Pro Thr Gly Thr Thr Ser Pro Thr Lys Ser Pro
3260                3265                3270

Thr Glu Asn Met Leu Ala Thr Glu Arg Val Ser Leu Ser Pro Ser
3275                3280                3285

Pro Pro Glu Ala Trp Thr Asn Leu Tyr Ser Gly Thr Pro Gly Gly
3290                3295                3300

Thr Arg Gln Ser Leu Ala Thr Met Ser Ser Val Ser Leu Glu Ser
```

```
              3305                3310                3315
Pro Thr Ala Arg Ser Ile Thr Gly Thr Gly Gln Gln Ser Ser Pro
              3320                3325                3330
Glu Leu Val Ser Lys Thr Thr Gly Met Glu Phe Ser Met Trp His
              3335                3340                3345
Gly Ser Thr Gly Gly Thr Thr Gly Asp Thr His Val Ser Leu Ser
              3350                3355                3360
Thr Ser Ser Asn Ile Leu Glu Asp Pro Val Thr Ser Pro Asn Ser
              3365                3370                3375
Val Ser Ser Leu Thr Asp Lys Ser Lys His Lys Thr Glu Thr Trp
              3380                3385                3390
Val Ser Thr Thr Ala Ile Pro Ser Thr Val Leu Asn Asn Lys Ile
              3395                3400                3405
Met Ala Ala Glu Gln Gln Thr Ser Arg Ser Val Asp Glu Ala Tyr
              3410                3415                3420
Ser Ser Thr Ser Ser Trp Ser Asp Gln Thr Ser Gly Ser Asp Ile
              3425                3430                3435
Thr Leu Gly Ala Ser Pro Asp Val Thr Asn Thr Leu Tyr Ile Thr
              3440                3445                3450
Ser Thr Ala Gln Thr Thr Ser Leu Val Ser Leu Pro Ser Gly Asp
              3455                3460                3465
Gln Gly Ile Thr Ser Leu Thr Asn Pro Ser Gly Gly Lys Thr Ser
              3470                3475                3480
Ser Ala Ser Ser Val Thr Ser Pro Ser Ile Gly Leu Glu Thr Leu
              3485                3490                3495
Arg Ala Asn Val Ser Ala Val Lys Ser Asp Ile Ala Pro Thr Ala
              3500                3505                3510
Gly His Leu Ser Gln Thr Ser Ser Pro Ala Glu Val Ser Ile Leu
              3515                3520                3525
Asp Val Thr Thr Ala Pro Thr Pro Gly Ile Ser Thr Thr Ile Thr
              3530                3535                3540
Thr Met Gly Thr Asn Ser Ile Ser Thr Thr Thr Pro Asn Pro Glu
              3545                3550                3555
Val Gly Met Ser Thr Met Asp Ser Thr Pro Ala Thr Glu Arg Arg
              3560                3565                3570
Thr Thr Ser Thr Glu His Pro Ser Thr Trp Ser Ser Thr Ala Ala
              3575                3580                3585
Ser Asp Ser Trp Thr Val Thr Asp Met Thr Ser Asn Leu Lys Val
              3590                3595                3600
Ala Arg Ser Pro Gly Thr Ile Ser Thr Met His Thr Thr Ser Phe
              3605                3610                3615
Leu Ala Ser Ser Thr Glu Leu Asp Ser Met Ser Thr Pro His Gly
              3620                3625                3630
Arg Ile Thr Val Ile Gly Thr Ser Leu Val Thr Pro Ser Ser Asp
              3635                3640                3645
Ala Ser Ala Val Lys Thr Glu Thr Ser Thr Ser Glu Arg Thr Leu
              3650                3655                3660
Ser Pro Ser Asp Thr Thr Ala Ser Thr Pro Ile Ser Thr Phe Ser
              3665                3670                3675
Arg Val Gln Arg Met Ser Ile Ser Val Pro Asp Ile Leu Ser Thr
              3680                3685                3690
Ser Trp Thr Pro Ser Ser Thr Glu Ala Glu Asp Val Pro Val Ser
              3695                3700                3705
```

```
Met Val Ser Thr Asp His Ala Ser Thr Lys Thr Asp Pro Asn Thr
    3710            3715                3720

Pro Leu Ser Thr Phe Leu Phe Asp Ser Leu Ser Thr Leu Asp Trp
    3725            3730                3735

Asp Thr Gly Arg Ser Leu Ser Ser Ala Thr Ala Thr Thr Ser Ala
    3740            3745                3750

Pro Gln Gly Ala Thr Thr Pro Gln Glu Leu Thr Leu Glu Thr Met
    3755            3760                3765

Ile Ser Pro Ala Thr Ser Gln Leu Pro Phe Ser Ile Gly His Ile
    3770            3775                3780

Thr Ser Ala Val Thr Pro Ala Ala Met Ala Arg Ser Ser Gly Val
    3785            3790                3795

Thr Phe Ser Arg Pro Asp Pro Thr Ser Lys Lys Ala Glu Gln Thr
    3800            3805                3810

Ser Thr Gln Leu Pro Thr Thr Thr Ser Ala His Pro Gly Gln Val
    3815            3820                3825

Pro Arg Ser Ala Ala Thr Thr Leu Asp Val Ile Pro His Thr Ala
    3830            3835                3840

Lys Thr Pro Asp Ala Thr Phe Gln Arg Gln Gly Gln Thr Ala Leu
    3845            3850                3855

Thr Thr Glu Ala Arg Ala Thr Ser Asp Ser Trp Asn Glu Lys Glu
    3860            3865                3870

Lys Ser Thr Pro Ser Ala Pro Trp Ile Thr Glu Met Met Asn Ser
    3875            3880                3885

Val Ser Glu Asp Thr Ile Lys Glu Val Thr Ser Ser Ser Ser Val
    3890            3895                3900

Leu Arg Thr Leu Asn Thr Leu Asp Ile Asn Leu Glu Ser Gly Thr
    3905            3910                3915

Thr Ser Ser Pro Ser Trp Lys Ser Ser Pro Tyr Glu Arg Ile Ala
    3920            3925                3930

Pro Ser Glu Ser Thr Thr Asp Lys Glu Ala Ile His Pro Ser Thr
    3935            3940                3945

Asn Thr Val Glu Thr Thr Gly Trp Val Thr Ser Ser Glu His Ala
    3950            3955                3960

Ser His Ser Thr Ile Pro Ala His Ser Ala Ser Ser Lys Leu Thr
    3965            3970                3975

Ser Pro Val Val Thr Thr Ser Thr Arg Glu Gln Ala Ile Val Ser
    3980            3985                3990

Met Ser Thr Thr Thr Trp Pro Glu Ser Thr Arg Ala Arg Thr Glu
    3995            4000                4005

Pro Asn Ser Phe Leu Thr Ile Glu Leu Arg Asp Val Ser Pro Tyr
    4010            4015                4020

Met Asp Thr Ser Ser Thr Thr Gln Thr Ser Ile Ile Ser Ser Pro
    4025            4030                4035

Gly Ser Thr Ala Ile Thr Lys Gly Pro Arg Thr Glu Ile Thr Ser
    4040            4045                4050

Ser Lys Arg Ile Ser Ser Ser Phe Leu Ala Gln Ser Met Arg Ser
    4055            4060                4065

Ser Asp Ser Pro Ser Glu Ala Ile Thr Arg Leu Ser Asn Phe Pro
    4070            4075                4080

Ala Met Thr Glu Ser Gly Gly Met Ile Leu Ala Met Gln Thr Ser
    4085            4090                4095
```

```
Pro Pro Gly Ala Thr Ser Leu Ser Ala Pro Thr Leu Asp Thr Ser
    4100            4105            4110

Ala Thr Ala Ser Trp Thr Gly Thr Pro Leu Ala Thr Thr Gln Arg
    4115            4120            4125

Phe Thr Tyr Ser Glu Lys Thr Leu Phe Ser Lys Gly Pro Glu
    4130            4135            4140

Asp Thr Ser Gln Pro Ser Pro Ser Val Glu Glu Thr Ser Ser
    4145            4150            4155

Ser Ser Ser Leu Val Pro Ile His Ala Thr Thr Ser Pro Ser Asn
    4160            4165            4170

Ile Leu Leu Thr Ser Gln Gly His Ser Pro Ser Thr Pro Pro
    4175            4180            4185

Val Thr Ser Val Phe Leu Ser Glu Thr Ser Gly Leu Gly Lys Thr
    4190            4195            4200

Thr Asp Met Ser Arg Ile Ser Leu Glu Pro Gly Thr Ser Leu Pro
    4205            4210            4215

Pro Asn Leu Ser Ser Thr Ala Gly Glu Ala Leu Ser Thr Tyr Glu
    4220            4225            4230

Ala Ser Arg Asp Thr Lys Ala Ile His His Ser Ala Asp Thr Ala
    4235            4240            4245

Val Thr Asn Met Glu Ala Thr Ser Ser Glu Tyr Ser Pro Ile Pro
    4250            4255            4260

Gly His Thr Lys Pro Ser Lys Ala Thr Ser Pro Leu Val Thr Ser
    4265            4270            4275

His Ile Met Gly Asp Ile Thr Ser Ser Thr Ser Val Phe Gly Ser
    4280            4285            4290

Ser Glu Thr Thr Glu Ile Glu Thr Val Ser Ser Val Asn Gln Gly
    4295            4300            4305

Leu Gln Glu Arg Ser Thr Ser Gln Val Ala Ser Ala Thr Glu
    4310            4315            4320

Thr Ser Thr Val Ile Thr His Val Ser Ser Gly Asp Ala Thr Thr
    4325            4330            4335

His Val Thr Lys Thr Gln Ala Thr Phe Ser Ser Gly Thr Ser Ile
    4340            4345            4350

Ser Ser Pro His Gln Phe Ile Thr Ser Thr Asn Thr Phe Thr Asp
    4355            4360            4365

Val Ser Thr Asn Pro Ser Thr Ser Leu Ile Met Thr Glu Ser Ser
    4370            4375            4380

Gly Val Thr Ile Thr Thr Gln Thr Gly Pro Thr Gly Ala Ala Thr
    4385            4390            4395

Gln Gly Pro Tyr Leu Leu Asp Thr Ser Thr Met Pro Tyr Leu Thr
    4400            4405            4410

Glu Thr Pro Leu Ala Val Thr Pro Asp Phe Met Gln Ser Glu Lys
    4415            4420            4425

Thr Thr Leu Ile Ser Lys Gly Pro Lys Asp Val Ser Trp Thr Ser
    4430            4435            4440

Pro Pro Ser Val Ala Glu Ser Ser Tyr Pro Ser Ser Leu Thr Pro
    4445            4450            4455

Phe Leu Val Thr Thr Ile Pro Pro Ala Thr Ser Thr Leu Gln Gly
    4460            4465            4470

Gln His Thr Ser Ser Pro Val Ser Ala Thr Ser Val Leu Thr Ser
    4475            4480            4485

Gly Leu Val Lys Thr Thr Asp Met Leu Asn Thr Ser Met Glu Pro
```

```
                4490            4495             4500
Val Thr Asn Ser Pro Gln Asn Leu Asn Pro Ser Asn Glu Ile
    4505                4510             4515

Leu Ala Thr Leu Ala Ala Thr Thr Asp Ile Glu Thr Ile His Pro
    4520                4525             4530

Ser Ile Asn Lys Ala Val Thr Asn Met Gly Thr Ala Ser Ser Ala
    4535                4540             4545

His Val Leu His Ser Thr Leu Pro Val Ser Ser Glu Pro Ser Thr
    4550                4555             4560

Ala Thr Ser Pro Met Val Pro Ala Ser Ser Met Gly Asp Ala Leu
    4565                4570             4575

Ala Ser Ile Ser Ile Pro Gly Ser Glu Thr Thr Asp Ile Glu Gly
    4580                4585             4590

Glu Pro Thr Ser Ser Leu Thr Ala Gly Arg Lys Glu Asn Ser Thr
    4595                4600             4605

Leu Gln Glu Met Asn Ser Thr Glu Ser Asn Ile Ile Leu Ser
    4610                4615             4620

Asn Val Ser Val Gly Ala Ile Thr Glu Ala Thr Lys Met Glu Val
    4625                4630             4635

Pro Ser Phe Asp Ala Thr Phe Ile Pro Thr Pro Ala Gln Ser Thr
    4640                4645             4650

Lys Phe Pro Asp Ile Phe Ser Val Ala Ser Ser Arg Leu Ser Asn
    4655                4660             4665

Ser Pro Pro Met Thr Ile Ser Thr His Met Thr Thr Gln Thr
    4670                4675             4680

Gly Ser Ser Gly Ala Thr Ser Lys Ile Pro Leu Ala Leu Asp Thr
    4685                4690             4695

Ser Thr Leu Glu Thr Ser Ala Gly Thr Pro Ser Val Val Thr Glu
    4700                4705             4710

Gly Phe Ala His Ser Lys Ile Thr Thr Ala Met Asn Asn Asp Val
    4715                4720             4725

Lys Asp Val Ser Gln Thr Asn Pro Pro Phe Gln Asp Glu Ala Ser
    4730                4735             4740

Ser Pro Ser Ser Gln Ala Pro Val Leu Val Thr Thr Leu Pro Ser
    4745                4750             4755

Ser Val Ala Phe Thr Pro Gln Trp His Ser Thr Ser Pro Val
    4760                4765             4770

Ser Met Ser Ser Val Leu Thr Ser Ser Leu Val Lys Thr Ala Gly
    4775                4780             4785

Lys Val Asp Thr Ser Leu Glu Thr Val Thr Ser Ser Pro Gln Ser
    4790                4795             4800

Met Ser Asn Thr Leu Asp Asp Ile Ser Val Thr Ser Ala Ala Thr
    4805                4810             4815

Thr Asp Ile Glu Thr Thr His Pro Ser Ile Asn Thr Val Val Thr
    4820                4825             4830

Asn Val Gly Thr Thr Gly Ser Ala Phe Glu Ser His Ser Thr Val
    4835                4840             4845

Ser Ala Tyr Pro Glu Pro Ser Lys Val Thr Ser Pro Asn Val Thr
    4850                4855             4860

Thr Ser Thr Met Glu Asp Thr Thr Ile Ser Arg Ser Ile Pro Lys
    4865                4870             4875

Ser Ser Lys Thr Thr Arg Thr Glu Thr Glu Thr Thr Ser Ser Leu
    4880                4885             4890
```

```
Thr Pro Lys Leu Arg Glu Thr Ser Ile Ser Gln Glu Ile Thr Ser
    4895                4900                4905

Ser Thr Glu Thr Ser Thr Val Pro Tyr Lys Glu Leu Thr Gly Ala
    4910                4915                4920

Thr Thr Glu Val Ser Arg Thr Asp Val Thr Ser Ser Ser Ser Thr
    4925                4930                4935

Ser Phe Pro Gly Pro Asp Gln Ser Thr Val Ser Leu Asp Ile Ser
    4940                4945                4950

Thr Glu Thr Asn Thr Arg Leu Ser Thr Ser Pro Ile Met Thr Glu
    4955                4960                4965

Ser Ala Glu Ile Thr Ile Thr Thr Gln Thr Gly Pro His Gly Ala
    4970                4975                4980

Thr Ser Gln Asp Thr Phe Thr Met Asp Pro Ser Asn Thr Thr Pro
    4985                4990                4995

Gln Ala Gly Ile His Ser Ala Met Thr His Gly Phe Ser Gln Leu
    5000                5005                5010

Asp Val Thr Thr Leu Met Ser Arg Ile Pro Gln Asp Val Ser Trp
    5015                5020                5025

Thr Ser Pro Pro Ser Val Asp Lys Thr Ser Ser Pro Ser Ser Phe
    5030                5035                5040

Leu Ser Ser Pro Ala Met Thr Thr Pro Ser Leu Ile Ser Ser Thr
    5045                5050                5055

Leu Pro Glu Asp Lys Leu Ser Ser Pro Met Thr Ser Leu Leu Thr
    5060                5065                5070

Ser Gly Leu Val Lys Ile Thr Asp Ile Leu Arg Thr Arg Leu Glu
    5075                5080                5085

Pro Val Thr Ser Ser Leu Pro Asn Phe Ser Ser Thr Ser Asp Lys
    5090                5095                5100

Ile Leu Ala Thr Ser Lys Asp Ser Lys Asp Thr Lys Glu Ile Phe
    5105                5110                5115

Pro Ser Ile Asn Thr Glu Glu Thr Asn Val Lys Ala Asn Asn Ser
    5120                5125                5130

Gly His Glu Ser His Ser Pro Ala Leu Ala Asp Ser Glu Thr Pro
    5135                5140                5145

Lys Ala Thr Thr Gln Met Val Ile Thr Thr Val Gly Asp Pro
    5150                5155                5160

Ala Pro Ser Thr Ser Met Pro Val His Gly Ser Ser Glu Thr Thr
    5165                5170                5175

Asn Ile Lys Arg Glu Pro Thr Tyr Phe Leu Thr Pro Arg Leu Arg
    5180                5185                5190

Glu Thr Ser Thr Ser Gln Glu Ser Ser Phe Pro Thr Asp Thr Ser
    5195                5200                5205

Phe Leu Leu Ser Lys Val Pro Thr Gly Thr Ile Thr Glu Val Ser
    5210                5215                5220

Ser Thr Gly Val Asn Ser Ser Ser Lys Ile Ser Thr Pro Asp His
    5225                5230                5235

Asp Lys Ser Thr Val Pro Asp Thr Phe Thr Gly Glu Ile Pro
    5240                5245                5250

Arg Val Phe Thr Ser Ser Ile Lys Thr Lys Ser Ala Glu Met Thr
    5255                5260                5265

Ile Thr Thr Gln Ala Ser Pro Pro Glu Ser Ala Ser His Ser Thr
    5270                5275                5280
```

| | | | | | | | | | | |
|---|---|---|---|---|---|---|---|---|---|---|
| Leu | Pro | Leu | Asp | Thr | Ser | Thr | Thr | Leu | Ser | Gln | Gly | Gly | Thr | His |
| 5285 | | | | | 5290 | | | | | 5295 | | | | |

Ser Thr Val Thr Gln Gly Phe Pro Tyr Ser Glu Val Thr Thr Leu
    5300                    5305                    5310

Met Gly Met Gly Pro Gly Asn Val Ser Trp Met Thr Thr Pro Pro
    5315                    5320                    5325

Val Glu Glu Thr Ser Ser Val Ser Ser Leu Met Ser Ser Pro Ala
    5330                    5335                    5340

Met Thr Ser Pro Ser Pro Val Ser Ser Thr Ser Pro Gln Ser Ile
    5345                    5350                    5355

Pro Ser Ser Pro Leu Pro Val Thr Ala Leu Pro Thr Ser Val Leu
    5360                    5365                    5370

Val Thr Thr Thr Asp Val Leu Gly Thr Thr Ser Pro Glu Ser Val
    5375                    5380                    5385

Thr Ser Ser Pro Pro Asn Leu Ser Ser Ile Thr His Glu Arg Pro
    5390                    5395                    5400

Ala Thr Tyr Lys Asp Thr Ala His Thr Glu Ala Ala Met His His
    5405                    5410                    5415

Ser Thr Asn Thr Ala Val Thr Asn Val Gly Thr Ser Gly Ser Gly
    5420                    5425                    5430

His Lys Ser Gln Ser Ser Val Leu Ala Asp Ser Glu Thr Ser Lys
    5435                    5440                    5445

Ala Thr Pro Leu Met Ser Thr Thr Ser Thr Leu Gly Asp Thr Ser
    5450                    5455                    5460

Val Ser Thr Ser Thr Pro Asn Ile Ser Gln Thr Asn Gln Ile Gln
    5465                    5470                    5475

Thr Glu Pro Thr Ala Ser Leu Ser Pro Arg Leu Arg Glu Ser Ser
    5480                    5485                    5490

Thr Ser Glu Lys Thr Ser Ser Thr Thr Glu Thr Asn Thr Ala Phe
    5495                    5500                    5505

Ser Tyr Val Pro Thr Gly Ala Ile Thr Gln Ala Ser Arg Thr Glu
    5510                    5515                    5520

Ile Ser Ser Ser Arg Thr Ser Ile Ser Asp Leu Asp Arg Pro Thr
    5525                    5530                    5535

Ile Ala Pro Asp Ile Ser Thr Gly Met Ile Thr Arg Leu Phe Thr
    5540                    5545                    5550

Ser Pro Ile Met Thr Lys Ser Ala Glu Met Thr Val Thr Thr Gln
    5555                    5560                    5565

Thr Thr Thr Pro Gly Ala Thr Ser Gln Gly Ile Leu Pro Trp Asp
    5570                    5575                    5580

Thr Ser Thr Thr Leu Phe Gln Gly Gly Thr His Ser Thr Val Ser
    5585                    5590                    5595

Gln Gly Phe Pro His Ser Glu Ile Thr Thr Leu Arg Ser Arg Thr
    5600                    5605                    5610

Pro Gly Asp Val Ser Trp Met Thr Thr Pro Pro Val Glu Glu Thr
    5615                    5620                    5625

Ser Ser Gly Phe Ser Leu Met Ser Pro Ser Met Thr Ser Pro Ser
    5630                    5635                    5640

Pro Val Ser Ser Thr Ser Pro Glu Ser Ile Pro Ser Ser Pro Leu
    5645                    5650                    5655

Pro Val Thr Ala Leu Leu Thr Ser Val Leu Val Thr Thr Thr Asn
    5660                    5665                    5670

Val Leu Gly Thr Thr Ser Pro Glu Pro Val Thr Ser Ser Pro Pro

-continued

|     |     |     |     |     |     |     |     |     |     |     |     |
|-----|-----|-----|-----|-----|-----|-----|-----|-----|-----|-----|-----|
|     | 5675 |     |     | 5680 |     |     |     | 5685 |     |     |     |
| Asn | Leu | Ser | Ser | Pro | Thr | Gln | Glu | Arg | Leu | Thr | Thr |
|     | 5690 |     |     |     | 5695 |     |     |     | 5700 |     |     |
| Tyr | Lys | Asp | Thr | Ala | His | Thr | Glu | Ala | Met | His | Ala |
|     | 5705 |     |     |     | 5710 |     |     |     | 5715 |     |     |
| Ser | Met | His | Thr | Asn | Thr | Ala | Val | Ala | Asn | Val | Gly |
|     | 5720 |     |     |     | 5725 |     |     |     | 5730 |     |     |
| Thr | Ser | Ile | Ser | Gly | His | Glu | Ser | Gln | Ser | Ser | Val |
|     | 5735 |     |     |     | 5740 |     |     |     | 5745 |     |     |
| Pro | Ala | Asp | Ser | His | Thr | Ser | Lys | Ala | Thr | Ser | Pro |
|     | 5750 |     |     |     | 5755 |     |     |     | 5760 |     |     |
| Met | Gly | Ile | Thr | Phe | Ala | Met | Gly | Asp | Thr | Ser | Val |
|     | 5765 |     |     |     | 5770 |     |     |     | 5775 |     |     |
| Ser | Thr | Ser | Thr | Pro | Ala | Phe | Phe | Glu | Thr | Arg | Ile |
|     | 5780 |     |     |     | 5785 |     |     |     | 5790 |     |     |
| Gln | Thr | Glu | Ser | Thr | Ser | Ser | Leu | Ile | Pro | Gly | Leu |
|     | 5795 |     |     |     | 5800 |     |     |     | 5805 |     |     |
| Arg | Asp | Thr | Arg | Thr | Ser | Glu | Glu | Ile | Asn | Thr | Val |
|     | 5810 |     |     |     | 5815 |     |     |     | 5820 |     |     |
| Thr | Glu | Thr | Ser | Thr | Val | Leu | Ser | Glu | Val | Pro | Thr |
|     | 5825 |     |     |     | 5830 |     |     |     | 5835 |     |     |
| Thr | Thr | Thr | Thr | Glu | Val | Ser | Arg | Thr | Glu | Val | Ile |
|     | 5840 |     |     |     | 5845 |     |     |     | 5850 |     |     |
| Thr | Ser | Ser | Arg | Thr | Thr | Ile | Ser | Gly | Pro | Asp | His |
|     | 5855 |     |     |     | 5860 |     |     |     | 5865 |     |     |
| Ser | Lys | Met | Ser | Pro | Tyr | Ile | Ser | Thr | Glu | Thr | Ile |
|     | 5870 |     |     |     | 5875 |     |     |     | 5880 |     |     |
| Thr | Arg | Leu | Ser | Thr | Phe | Pro | Phe | Val | Thr | Gly | Ser |
|     | 5885 |     |     |     | 5890 |     |     |     | 5895 |     |     |
| Thr | Glu | Met | Ala | Ile | Thr | Asn | Gln | Thr | Gly | Pro | Ile |
|     | 5900 |     |     |     | 5905 |     |     |     | 5910 |     |     |
| Gly | Thr | Ile | Ser | Gln | Ala | Thr | Leu | Thr | Leu | Asp | Thr |
|     | 5915 |     |     |     | 5920 |     |     |     | 5925 |     |     |
| Ser | Ser | Thr | Ala | Ser | Trp | Glu | Gly | Thr | His | Ser | Pro |
|     | 5930 |     |     |     | 5935 |     |     |     | 5940 |     |     |
| Val | Thr | Gln | Arg | Phe | Pro | His | Ser | Glu | Glu | Thr | Thr |
|     | 5945 |     |     |     | 5950 |     |     |     | 5955 |     |     |
| Thr | Met | Ser | Arg | Ser | Thr | Lys | Gly | Val | Ser | Trp | Gln |
|     | 5960 |     |     |     | 5965 |     |     |     | 5970 |     |     |
| Ser | Pro | Pro | Ser | Val | Glu | Glu | Thr | Ser | Ser | Pro | Ser |
|     | 5975 |     |     |     | 5980 |     |     |     | 5985 |     |     |
| Ser | Pro | Val | Pro | Leu | Pro | Ala | Ile | Thr | Ser | His | Ser |
|     | 5990 |     |     |     | 5995 |     |     |     | 6000 |     |     |
| Ser | Leu | Tyr | Ser | Ala | Val | Ser | Gly | Ser | Ser | Pro | Thr |
|     | 6005 |     |     |     | 6010 |     |     |     | 6015 |     |     |
| Ser | Ala | Leu | Pro | Val | Thr | Ser | Leu | Leu | Thr | Ser | Gly |
|     | 6020 |     |     |     | 6025 |     |     |     | 6030 |     |     |
| Arg | Arg | Lys | Thr | Ile | Asp | Met | Leu | Asp | Thr | His | Ser |
|     | 6035 |     |     |     | 6040 |     |     |     | 6045 |     |     |
| Glu | Leu | Val | Thr | Ser | Ser | Leu | Pro | Ser | Ala | Ser | Ser |
|     | 6050 |     |     |     | 6055 |     |     |     | 6060 |     |     |
| Phe | Ser | Gly | Glu | Ile | Leu | Thr | Ser | Glu | Ala | Ser | Thr |
|     | 6065 |     |     |     | 6070 |     |     |     | 6075 |     |     |
| Asn | Thr | Glu | Thr | Ile | His | Phe | Ser | Glu | Asn | Thr | Ala |

-continued

Lys Glu Asp Ser Thr Ala Leu Val Met Asn Ser Thr Thr Glu Ser
        6080             6085             6090

Asn Thr Val Phe Ser Ser Val Ser Leu Asp Ala Ala Thr Glu Val
        6095             6100             6105

Ser Arg Ala Glu Val Thr Tyr Tyr Asp Pro Thr Phe Met Pro Ala
        6110             6115             6120

Ser Ala Gln Ser Thr Lys Ser Pro Asp Ile Ser Pro Glu Ala Ser
        6125             6130             6135

Ser Ser His Ser Asn Ser Pro Pro Leu Thr Ile Ser Thr His Lys
        6140             6145             6150

Thr Ile Ala Thr Gln Thr Gly Pro Ser Gly Val Thr Ser Leu Gly
        6155             6160             6165

Gln Leu Thr Leu Asp Thr Ser Thr Ile Ala Thr Ser Ala Gly Thr
        6170             6175             6180

Pro Ser Ala Arg Thr Gln Asp Phe Val Asp Ser Glu Thr Thr Ser
        6185             6190             6195

Val Met Asn Asn Asp Leu Asn Asp Val Leu Lys Thr Ser Pro Phe
        6200             6205             6210

Ser Ala Glu Glu Ala Asn Ser Leu Ser Ser Gln Ala Pro Leu Leu
        6215             6220             6225

Val Thr Thr Ser Pro Ser Pro Val Thr Ser Thr Leu Gln Glu His
        6230             6235             6240

Ser Thr Ser Ser Leu Val Ser Val Thr Ser Val Pro Thr Pro Thr
        6245             6250             6255

Leu Ala Lys Ile Thr Asp Met Asp Thr Asn Leu Glu Pro Val Thr
        6260             6265             6270

Arg Ser Pro Gln Asn Leu Arg Asn Thr Leu Ala Thr Ser Glu Ala
        6275             6280             6285

Thr Thr Asp Thr His Thr Met His Pro Ser Ile Asn Thr Ala Val
        6290             6295             6300

Ala Asn Val Gly Thr Thr Ser Ser Pro Asn Glu Phe Tyr Phe Thr
        6305             6310             6315

Val Ser Pro Asp Ser Asp Pro Tyr Lys Ala Thr Ser Ala Val Val
        6320             6325             6330

Ile Thr Ser Thr Ser Gly Asp Ser Ile Val Ser Thr Ser Met Pro
        6335             6340             6345

Arg Ser Ser Ala Met Lys Lys Ile Glu Ser Glu Thr Thr Phe Ser
        6350             6355             6360

Leu Ile Phe Arg Leu Arg Glu Thr Ser Thr Ser Gln Lys Ile Gly
        6365             6370             6375

Ser Ser Ser Asp Thr Ser Thr Val Phe Asp Lys Ala Phe Thr Ala
        6380             6385             6390

Ala Thr Thr Glu Val Ser Arg Thr Glu Leu Thr Ser Ser Ser Arg
        6395             6400             6405

Thr Ser Ile Gln Gly Thr Glu Lys Pro Thr Met Ser Pro Asp Thr
        6410             6415             6420

Ser Thr Arg Ser Val Thr Met Leu Ser Thr Phe Ala Gly Leu Thr
        6425             6430             6435

Lys Ser Glu Glu Arg Thr Ile Ala Thr Gln Thr Gly Pro His Arg
        6440             6445             6450

Ala Thr Ser Gln Gly Thr Leu Thr Trp Asp Thr Ser Ile Thr Thr
        6455             6460             6465

```
Ser Gln Ala Gly Thr His Ser Ala Met Thr His Gly Phe Ser Gln
6470                    6475                6480

Leu Asp Leu Ser Thr Leu Thr Ser Arg Val Pro Glu Tyr Ile Ser
6485                    6490                6495

Gly Thr Ser Pro Pro Ser Val Glu Lys Thr Ser Ser Ser Ser Ser
6500                    6505                6510

Leu Leu Ser Leu Pro Ala Ile Thr Ser Pro Ser Val Pro Thr
6515                    6520                6525

Thr Leu Pro Glu Ser Arg Pro Ser Ser Pro Val His Leu Thr Ser
6530                    6535                6540

Leu Pro Thr Ser Gly Leu Val Lys Thr Thr Asp Met Leu Ala Ser
6545                    6550                6555

Val Ala Ser Leu Pro Pro Asn Leu Gly Ser Thr Ser His Lys Ile
6560                    6565                6570

Pro Thr Thr Ser Glu Asp Ile Lys Asp Thr Glu Lys Met Tyr Pro
6575                    6580                6585

Ser Thr Asn Ile Ala Val Thr Asn Val Gly Thr Thr Ser Glu
6590                    6595                6600

Lys Glu Ser Tyr Ser Ser Val Pro Ala Tyr Ser Glu Pro Pro Lys
6605                    6610                6615

Val Thr Ser Pro Met Val Thr Ser Phe Asn Ile Arg Asp Thr Ile
6620                    6625                6630

Val Ser Thr Ser Met Pro Gly Ser Ser Glu Ile Thr Arg Ile Glu
6635                    6640                6645

Met Glu Ser Thr Phe Ser Leu Ala His Gly Leu Lys Gly Thr Ser
6650                    6655                6660

Thr Ser Gln Asp Pro Ile Val Ser Thr Glu Lys Ser Ala Val Leu
6665                    6670                6675

His Lys Leu Thr Thr Gly Ala Thr Glu Thr Ser Arg Thr Glu Val
6680                    6685                6690

Ala Ser Ser Arg Arg Thr Ser Ile Pro Gly Pro Asp His Ser Thr
6695                    6700                6705

Glu Ser Pro Asp Ile Ser Thr Glu Val Ile Pro Ser Leu Pro Ile
6710                    6715                6720

Ser Leu Gly Ile Thr Glu Ser Ser Asn Met Thr Ile Ile Thr Arg
6725                    6730                6735

Thr Gly Pro Pro Leu Gly Ser Thr Ser Gln Gly Thr Phe Thr Leu
6740                    6745                6750

Asp Thr Pro Thr Thr Ser Ser Arg Ala Gly Thr His Ser Met Ala
6755                    6760                6765

Thr Gln Glu Phe Pro His Ser Glu Met Thr Thr Val Met Asn Lys
6770                    6775                6780

Asp Pro Glu Ile Leu Ser Trp Thr Ile Pro Pro Ser Ile Glu Lys
6785                    6790                6795

Thr Ser Phe Ser Ser Ser Leu Met Pro Ser Pro Ala Met Thr Ser
6800                    6805                6810

Pro Pro Val Ser Ser Thr Leu Pro Lys Thr Ile His Thr Thr Pro
6815                    6820                6825

Ser Pro Met Thr Ser Leu Leu Thr Pro Ser Leu Val Met Thr Thr
6830                    6835                6840

Asp Thr Leu Gly Thr Ser Pro Glu Pro Thr Thr Ser Ser Pro Pro
6845                    6850                6855

Asn Leu Ser Ser Thr Ser His Glu Ile Leu Thr Thr Asp Glu Asp
```

-continued

```
                  6860            6865             6870

Thr  Thr  Ala  Ile  Glu  Ala  Met  His  Pro  Ser  Thr  Ser  Thr  Ala  Ala
     6875                 6880                 6885

Thr  Asn  Val  Glu  Thr  Thr  Ser  Ser  Gly  His  Gly  Ser  Gln  Ser  Ser
     6890                 6895                 6900

Val  Leu  Ala  Asp  Ser  Glu  Lys  Thr  Lys  Ala  Thr  Ala  Pro  Met  Asp
     6905                 6910                 6915

Thr  Thr  Ser  Thr  Met  Gly  His  Thr  Thr  Val  Ser  Thr  Ser  Met  Ser
     6920                 6925                 6930

Val  Ser  Ser  Glu  Thr  Thr  Lys  Ile  Lys  Arg  Glu  Ser  Thr  Tyr  Ser
     6935                 6940                 6945

Leu  Thr  Pro  Gly  Leu  Arg  Glu  Thr  Ser  Ile  Ser  Gln  Asn  Ala  Ser
     6950                 6955                 6960

Phe  Ser  Thr  Asp  Thr  Ser  Ile  Val  Leu  Ser  Glu  Val  Pro  Thr  Gly
     6965                 6970                 6975

Thr  Thr  Ala  Glu  Val  Ser  Arg  Thr  Glu  Val  Thr  Ser  Ser  Gly  Arg
     6980                 6985                 6990

Thr  Ser  Ile  Pro  Gly  Pro  Ser  Gln  Ser  Thr  Val  Leu  Pro  Glu  Ile
     6995                 7000                 7005

Ser  Thr  Arg  Thr  Met  Thr  Arg  Leu  Phe  Ala  Ser  Pro  Thr  Met  Thr
     7010                 7015                 7020

Glu  Ser  Ala  Glu  Met  Thr  Ile  Pro  Thr  Gln  Thr  Gly  Pro  Ser  Gly
     7025                 7030                 7035

Ser  Thr  Ser  Gln  Asp  Thr  Leu  Thr  Leu  Asp  Thr  Ser  Thr  Thr  Lys
     7040                 7045                 7050

Ser  Gln  Ala  Lys  Thr  His  Ser  Thr  Leu  Thr  Gln  Arg  Phe  Pro  His
     7055                 7060                 7065

Ser  Glu  Met  Thr  Thr  Leu  Met  Ser  Arg  Gly  Pro  Gly  Asp  Met  Ser
     7070                 7075                 7080

Trp  Gln  Ser  Ser  Pro  Ser  Leu  Glu  Asn  Pro  Ser  Ser  Leu  Pro  Ser
     7085                 7090                 7095

Leu  Leu  Ser  Leu  Pro  Ala  Thr  Thr  Ser  Pro  Pro  Ile  Ser  Ser
     7100                 7105                 7110

Thr  Leu  Pro  Val  Thr  Ile  Ser  Ser  Ser  Pro  Leu  Pro  Val  Thr  Ser
     7115                 7120                 7125

Leu  Leu  Thr  Ser  Ser  Pro  Val  Thr  Thr  Asp  Met  Leu  His  Thr
     7130                 7135                 7140

Ser  Pro  Glu  Leu  Val  Thr  Ser  Ser  Pro  Pro  Lys  Leu  Ser  His  Thr
     7145                 7150                 7155

Ser  Asp  Glu  Arg  Leu  Thr  Thr  Gly  Lys  Asp  Thr  Thr  Asn  Thr  Glu
     7160                 7165                 7170

Ala  Val  His  Pro  Ser  Thr  Asn  Thr  Ala  Ala  Ser  Asn  Val  Glu  Ile
     7175                 7180                 7185

Pro  Ser  Ser  Gly  His  Glu  Ser  Pro  Ser  Ser  Ala  Leu  Ala  Asp  Ser
     7190                 7195                 7200

Glu  Thr  Ser  Lys  Ala  Thr  Ser  Pro  Met  Phe  Ile  Thr  Ser  Thr  Gln
     7205                 7210                 7215

Glu  Asp  Thr  Thr  Val  Ala  Ile  Ser  Thr  Pro  His  Phe  Leu  Glu  Thr
     7220                 7225                 7230

Ser  Arg  Ile  Gln  Lys  Glu  Ser  Ile  Ser  Ser  Leu  Ser  Pro  Lys  Leu
     7235                 7240                 7245

Arg  Glu  Thr  Gly  Ser  Ser  Val  Glu  Thr  Ser  Ser  Ala  Ile  Glu  Thr
     7250                 7255                 7260
```

```
Ser Ala Val Leu Ser Glu Val Ser Ile Gly Ala Thr Thr Glu Ile
    7265            7270                 7275

Ser Arg Thr Glu Val Thr Ser Ser Arg Thr Ser Ile Ser Gly
    7280            7285                 7290

Ser Ala Glu Ser Thr Met Leu Pro Glu Ile Ser Thr Thr Arg Lys
    7295            7300                 7305

Ile Ile Lys Phe Pro Thr Ser Pro Ile Leu Ala Glu Ser Ser Glu
    7310            7315                 7320

Met Thr Ile Lys Thr Gln Thr Ser Pro Pro Gly Ser Thr Ser Glu
    7325            7330                 7335

Ser Thr Phe Thr Leu Asp Thr Ser Thr Thr Pro Ser Leu Val Ile
    7340            7345                 7350

Thr His Ser Thr Met Thr Gln Arg Leu Pro His Ser Glu Ile Thr
    7355            7360                 7365

Thr Leu Val Ser Arg Gly Ala Gly Asp Val Pro Arg Pro Ser Ser
    7370            7375                 7380

Leu Pro Val Glu Glu Thr Ser Pro Pro Ser Ser Gln Leu Ser Leu
    7385            7390                 7395

Ser Ala Met Ile Ser Pro Ser Pro Val Ser Ser Thr Leu Pro Ala
    7400            7405                 7410

Ser Ser His Ser Ser Ser Ala Ser Val Thr Ser Leu Leu Thr Pro
    7415            7420                 7425

Gly Gln Val Lys Thr Thr Glu Val Leu Asp Ala Ser Ala Glu Pro
    7430            7435                 7440

Glu Thr Ser Ser Pro Pro Ser Leu Ser Ser Thr Ser Val Glu Ile
    7445            7450                 7455

Leu Ala Thr Ser Glu Val Thr Thr Asp Thr Glu Lys Ile His Pro
    7460            7465                 7470

Phe Ser Asn Thr Ala Val Thr Lys Val Gly Thr Ser Ser Ser Gly
    7475            7480                 7485

His Glu Ser Pro Ser Ser Val Leu Pro Asp Ser Glu Thr Thr Lys
    7490            7495                 7500

Ala Thr Ser Ala Met Gly Thr Ile Ser Ile Met Gly Asp Thr Ser
    7505            7510                 7515

Val Ser Thr Leu Thr Pro Ala Leu Ser Asn Thr Arg Lys Ile Gln
    7520            7525                 7530

Ser Glu Pro Ala Ser Ser Leu Thr Thr Arg Leu Arg Glu Thr Ser
    7535            7540                 7545

Thr Ser Glu Glu Thr Ser Leu Ala Thr Glu Ala Asn Thr Val Leu
    7550            7555                 7560

Ser Lys Val Ser Thr Gly Ala Thr Thr Glu Val Ser Arg Thr Glu
    7565            7570                 7575

Ala Ile Ser Phe Ser Arg Thr Ser Met Ser Gly Pro Glu Gln Ser
    7580            7585                 7590

Thr Met Ser Gln Asp Ile Ser Ile Gly Thr Ile Pro Arg Ile Ser
    7595            7600                 7605

Ala Ser Ser Val Leu Thr Glu Ser Ala Lys Met Thr Ile Thr Thr
    7610            7615                 7620

Gln Thr Gly Pro Ser Glu Ser Thr Leu Glu Ser Thr Leu Asn Leu
    7625            7630                 7635

Asn Thr Ala Thr Thr Pro Ser Trp Val Glu Thr His Ser Ile Val
    7640            7645                 7650
```

```
Ile Gln Gly Phe Pro His Pro Glu Met Thr Thr Ser Met Gly Arg
7655                 7660                 7665

Gly Pro Gly Gly Val Ser Trp Pro Ser Pro Phe Val Lys Glu
7670                 7675                 7680

Thr Ser Pro Pro Ser Ser Pro Leu Ser Leu Pro Ala Val Thr Ser
7685                 7690                 7695

Pro His Pro Val Ser Thr Thr Phe Leu Ala His Ile Pro Pro Ser
7700                 7705                 7710

Pro Leu Pro Val Thr Ser Leu Leu Thr Ser Gly Pro Ala Thr Thr
7715                 7720                 7725

Thr Asp Ile Leu Gly Thr Ser Thr Glu Pro Gly Thr Ser Ser Ser
7730                 7735                 7740

Ser Ser Leu Ser Thr Thr Ser His Glu Arg Leu Thr Thr Tyr Lys
7745                 7750                 7755

Asp Thr Ala His Thr Glu Ala Val His Pro Ser Thr Asn Thr Gly
7760                 7765                 7770

Gly Thr Asn Val Ala Thr Thr Ser Ser Gly Tyr Lys Ser Gln Ser
7775                 7780                 7785

Ser Val Leu Ala Asp Ser Ser Pro Met Cys Thr Thr Ser Thr Met
7790                 7795                 7800

Gly Asp Thr Ser Val Leu Thr Ser Thr Pro Ala Phe Leu Glu Thr
7805                 7810                 7815

Arg Arg Ile Gln Thr Glu Leu Ala Ser Ser Leu Thr Pro Gly Leu
7820                 7825                 7830

Arg Glu Ser Ser Gly Ser Glu Gly Thr Ser Ser Gly Thr Lys Met
7835                 7840                 7845

Ser Thr Val Leu Ser Lys Val Pro Thr Gly Ala Thr Thr Glu Ile
7850                 7855                 7860

Ser Lys Glu Asp Val Thr Ser Ile Pro Gly Pro Ala Gln Ser Thr
7865                 7870                 7875

Ile Ser Pro Asp Ile Ser Thr Arg Thr Val Ser Trp Phe Ser Thr
7880                 7885                 7890

Ser Pro Val Met Thr Glu Ser Ala Glu Ile Thr Met Asn Thr His
7895                 7900                 7905

Thr Ser Pro Leu Gly Ala Thr Thr Gln Gly Thr Ser Thr Leu Asp
7910                 7915                 7920

Thr Ser Ser Thr Thr Ser Leu Thr Met Thr His Ser Thr Ile Ser
7925                 7930                 7935

Gln Gly Phe Ser His Ser Gln Met Ser Thr Leu Met Arg Arg Gly
7940                 7945                 7950

Pro Glu Asp Val Ser Trp Met Ser Pro Pro Leu Leu Glu Lys Thr
7955                 7960                 7965

Arg Pro Ser Phe Ser Leu Met Ser Ser Pro Ala Thr Thr Ser Pro
7970                 7975                 7980

Ser Pro Val Ser Ser Thr Leu Pro Glu Ser Ile Ser Ser Ser Pro
7985                 7990                 7995

Leu Pro Val Thr Ser Leu Leu Thr Ser Gly Leu Ala Lys Thr Thr
8000                 8005                 8010

Asp Met Leu His Lys Ser Ser Glu Pro Val Thr Asn Ser Pro Ala
8015                 8020                 8025

Asn Leu Ser Ser Thr Ser Val Glu Ile Leu Ala Thr Ser Glu Val
8030                 8035                 8040

Thr Thr Asp Thr Glu Lys Thr His Pro Ser Ser Asn Arg Thr Val
```

-continued

```
            8045                8050                8055
Thr Asp Val Gly Thr Ser Ser Gly His Glu Ser Thr Ser Phe
            8060                8065                8070
Val Leu Ala Asp Ser Gln Thr Ser Lys Val Thr Ser Pro Met Val
            8075                8080                8085
Ile Thr Ser Thr Met Glu Asp Thr Ser Val Ser Thr Ser Thr Pro
            8090                8095                8100
Gly Phe Phe Glu Thr Ser Arg Ile Gln Thr Glu Pro Thr Ser Ser
            8105                8110                8115
Leu Thr Leu Gly Leu Arg Lys Thr Ser Ser Glu Gly Thr Ser
            8120                8125                8130
Leu Ala Thr Glu Met Ser Thr Val Leu Ser Gly Val Pro Thr Gly
            8135                8140                8145
Ala Thr Ala Glu Val Ser Arg Thr Glu Val Thr Ser Ser Ser Arg
            8150                8155                8160
Thr Ser Ile Ser Gly Phe Ala Gln Leu Thr Val Ser Pro Glu Thr
            8165                8170                8175
Ser Thr Glu Thr Ile Thr Arg Leu Pro Thr Ser Ser Ile Met Thr
            8180                8185                8190
Glu Ser Ala Glu Met Met Ile Lys Thr Gln Thr Asp Pro Pro Gly
            8195                8200                8205
Ser Thr Pro Glu Ser Thr His Thr Val Asp Ile Ser Thr Thr Pro
            8210                8215                8220
Asn Trp Val Glu Thr His Ser Thr Val Thr Gln Arg Phe Ser His
            8225                8230                8235
Ser Glu Met Thr Thr Leu Val Ser Arg Ser Pro Gly Asp Met Leu
            8240                8245                8250
Trp Pro Ser Gln Ser Ser Val Glu Glu Thr Ser Ser Ala Ser Ser
            8255                8260                8265
Leu Leu Ser Leu Pro Ala Thr Thr Ser Pro Ser Pro Val Ser Ser
            8270                8275                8280
Thr Leu Val Glu Asp Phe Pro Ser Ala Ser Leu Pro Val Thr Ser
            8285                8290                8295
Leu Leu Asn Pro Gly Leu Val Ile Thr Thr Asp Arg Met Gly Ile
            8300                8305                8310
Ser Arg Glu Pro Gly Thr Ser Ser Thr Ser Asn Leu Ser Ser Thr
            8315                8320                8325
Ser His Glu Arg Leu Thr Thr Leu Glu Asp Thr Val Asp Thr Glu
            8330                8335                8340
Asp Met Gln Pro Ser Thr His Thr Ala Val Thr Asn Val Arg Thr
            8345                8350                8355
Ser Ile Ser Gly His Glu Ser Gln Ser Ser Val Leu Ser Asp Ser
            8360                8365                8370
Glu Thr Pro Lys Ala Thr Ser Pro Met Gly Thr Thr Tyr Thr Met
            8375                8380                8385
Gly Glu Thr Ser Val Ser Ile Ser Thr Ser Asp Phe Phe Glu Thr
            8390                8395                8400
Ser Arg Ile Gln Ile Glu Pro Thr Ser Ser Leu Thr Ser Gly Leu
            8405                8410                8415
Arg Glu Thr Ser Ser Ser Glu Arg Ile Ser Ser Ala Thr Glu Gly
            8420                8425                8430
Ser Thr Val Leu Ser Glu Val Pro Ser Gly Ala Thr Thr Glu Val
            8435                8440                8445
```

-continued

```
Ser Arg Thr Glu Val Ile Ser Ser Arg Gly Thr Ser Met Ser Gly
    8450                8455                8460

Pro Asp Gln Phe Thr Ile Ser Pro Asp Ile Ser Thr Glu Ala Ile
    8465                8470                8475

Thr Arg Leu Ser Thr Ser Pro Ile Met Thr Glu Ser Ala Glu Ser
    8480                8485                8490

Ala Ile Thr Ile Glu Thr Gly Ser Pro Gly Ala Thr Ser Glu Gly
    8495                8500                8505

Thr Leu Thr Leu Asp Thr Ser Thr Thr Thr Phe Trp Ser Gly Thr
    8510                8515                8520

His Ser Thr Ala Ser Pro Gly Phe Ser His Ser Glu Met Thr Thr
    8525                8530                8535

Leu Met Ser Arg Thr Pro Gly Asp Val Pro Trp Pro Ser Leu Pro
    8540                8545                8550

Ser Val Glu Glu Ala Ser Ser Val Ser Ser Ser Leu Ser Ser Pro
    8555                8560                8565

Ala Met Thr Ser Thr Ser Phe Phe Ser Thr Leu Pro Glu Ser Ile
    8570                8575                8580

Ser Ser Ser Pro His Pro Val Thr Ala Leu Leu Thr Leu Gly Pro
    8585                8590                8595

Val Lys Thr Thr Asp Met Leu Arg Thr Ser Ser Glu Pro Glu Thr
    8600                8605                8610

Ser Ser Pro Pro Asn Leu Ser Ser Thr Ser Ala Glu Ile Leu Ala
    8615                8620                8625

Thr Ser Glu Val Thr Lys Asp Arg Glu Lys Ile His Pro Ser Ser
    8630                8635                8640

Asn Thr Pro Val Val Asn Val Gly Thr Val Ile Tyr Lys His Leu
    8645                8650                8655

Ser Pro Ser Ser Val Leu Ala Asp Leu Val Thr Thr Lys Pro Thr
    8660                8665                8670

Ser Pro Met Ala Thr Thr Ser Thr Leu Gly Asn Thr Ser Val Ser
    8675                8680                8685

Thr Ser Thr Pro Ala Phe Pro Glu Thr Met Met Thr Gln Pro Thr
    8690                8695                8700

Ser Ser Leu Thr Ser Gly Leu Arg Glu Ile Ser Thr Ser Gln Glu
    8705                8710                8715

Thr Ser Ser Ala Thr Glu Arg Ser Ala Ser Leu Ser Gly Met Pro
    8720                8725                8730

Thr Gly Ala Thr Thr Lys Val Ser Arg Thr Glu Ala Leu Ser Leu
    8735                8740                8745

Gly Arg Thr Ser Thr Pro Gly Pro Ala Gln Ser Thr Ile Ser Pro
    8750                8755                8760

Glu Ile Ser Thr Glu Thr Ile Thr Arg Ile Ser Thr Pro Leu Thr
    8765                8770                8775

Thr Thr Gly Ser Ala Glu Met Thr Ile Thr Pro Lys Thr Gly His
    8780                8785                8790

Ser Gly Ala Ser Ser Gln Gly Thr Phe Thr Leu Asp Thr Ser Ser
    8795                8800                8805

Arg Ala Ser Trp Pro Gly Thr His Ser Ala Ala Thr His Arg Ser
    8810                8815                8820

Pro His Ser Gly Met Thr Thr Pro Met Ser Arg Gly Pro Glu Asp
    8825                8830                8835
```

```
Val Ser Trp Pro Ser Arg Pro Ser Val Glu Lys Thr Ser Pro Pro
8840            8845            8850

Ser Ser Leu Val Ser Leu Ser Ala Val Thr Ser Ser Pro Leu
8855            8860            8865

Tyr Ser Thr Pro Ser Glu Ser Ser His Ser Ser Pro Leu Arg Val
8870            8875            8880

Thr Ser Leu Phe Thr Pro Val Met Met Lys Thr Thr Asp Met Leu
8885            8890            8895

Asp Thr Ser Leu Glu Pro Val Thr Thr Ser Pro Pro Ser Met Asn
8900            8905            8910

Ile Thr Ser Asp Glu Ser Leu Ala Thr Ser Lys Ala Thr Met Glu
8915            8920            8925

Thr Glu Ala Ile Gln Leu Ser Glu Asn Thr Ala Val Thr Gln Met
8930            8935            8940

Gly Thr Ile Ser Ala Arg Gln Glu Phe Tyr Ser Ser Tyr Pro Gly
8945            8950            8955

Leu Pro Glu Pro Ser Lys Val Thr Ser Pro Val Val Thr Ser Ser
8960            8965            8970

Thr Ile Lys Asp Ile Val Ser Thr Thr Ile Pro Ala Ser Ser Glu
8975            8980            8985

Ile Thr Arg Ile Glu Met Glu Ser Thr Ser Thr Leu Thr Pro Thr
8990            8995            9000

Pro Arg Glu Thr Ser Thr Ser Gln Glu Ile His Ser Ala Thr Lys
9005            9010            9015

Pro Ser Thr Val Pro Tyr Lys Ala Leu Thr Ser Ala Thr Ile Glu
9020            9025            9030

Asp Ser Met Thr Gln Val Met Ser Ser Ser Arg Gly Pro Ser Pro
9035            9040            9045

Asp Gln Ser Thr Met Ser Gln Asp Ile Ser Thr Glu Val Ile Thr
9050            9055            9060

Arg Leu Ser Thr Ser Pro Ile Lys Thr Glu Ser Thr Glu Met Thr
9065            9070            9075

Ile Thr Thr Gln Thr Gly Ser Pro Gly Ala Thr Ser Arg Gly Thr
9080            9085            9090

Leu Thr Leu Asp Thr Ser Thr Thr Phe Met Ser Gly Thr His Ser
9095            9100            9105

Thr Ala Ser Gln Gly Phe Ser His Ser Gln Met Thr Ala Leu Met
9110            9115            9120

Ser Arg Thr Pro Gly Asp Val Pro Trp Leu Ser His Pro Ser Val
9125            9130            9135

Glu Glu Ala Ser Ser Ala Ser Phe Ser Leu Ser Ser Pro Val Met
9140            9145            9150

Thr Ser Ser Ser Pro Val Ser Ser Thr Leu Pro Asp Ser Ile His
9155            9160            9165

Ser Ser Ser Leu Pro Val Thr Ser Leu Leu Thr Ser Gly Leu Val
9170            9175            9180

Lys Thr Thr Glu Leu Leu Gly Thr Ser Ser Glu Pro Glu Thr Ser
9185            9190            9195

Ser Pro Pro Asn Leu Ser Ser Thr Ser Ala Glu Ile Leu Ala Ile
9200            9205            9210

Thr Glu Val Thr Thr Asp Thr Glu Lys Leu Glu Met Thr Asn Val
9215            9220            9225

Val Thr Ser Gly Tyr Thr His Glu Ser Pro Ser Ser Val Leu Ala
```

-continued

```
            9230                9235                9240

Asp Ser Val Thr Thr Lys Ala Thr Ser Ser Met Gly Ile Thr Tyr
    9245                9250                9255

Pro Thr Gly Asp Thr Asn Val Leu Thr Ser Thr Pro Ala Phe Ser
    9260                9265                9270

Asp Thr Ser Arg Ile Gln Thr Lys Ser Lys Leu Ser Leu Thr Pro
    9275                9280                9285

Gly Leu Met Glu Thr Ser Ile Ser Glu Glu Thr Ser Ser Ala Thr
    9290                9295                9300

Glu Lys Ser Thr Val Leu Ser Ser Val Pro Thr Gly Ala Thr Thr
    9305                9310                9315

Glu Val Ser Arg Thr Glu Ala Ile Ser Ser Ser Arg Thr Ser Ile
    9320                9325                9330

Pro Gly Pro Ala Gln Ser Thr Met Ser Ser Asp Thr Ser Met Glu
    9335                9340                9345

Thr Ile Thr Arg Ile Ser Thr Pro Leu Thr Arg Lys Glu Ser Thr
    9350                9355                9360

Asp Met Ala Ile Thr Pro Lys Thr Gly Pro Ser Gly Ala Thr Ser
    9365                9370                9375

Gln Gly Thr Phe Thr Leu Asp Ser Ser Ser Thr Ala Ser Trp Pro
    9380                9385                9390

Gly Thr His Ser Ala Thr Thr Gln Arg Phe Pro Gln Ser Val Val
    9395                9400                9405

Thr Thr Pro Met Ser Arg Gly Pro Glu Asp Val Ser Trp Pro Ser
    9410                9415                9420

Pro Leu Ser Val Glu Lys Asn Ser Pro Ser Ser Leu Val Ser
    9425                9430                9435

Ser Ser Ser Val Thr Ser Pro Ser Pro Leu Tyr Ser Thr Pro Ser
    9440                9445                9450

Gly Ser Ser His Ser Ser Pro Val Pro Val Thr Ser Leu Phe Thr
    9455                9460                9465

Ser Ile Met Met Lys Ala Thr Asp Met Leu Asp Ala Ser Leu Glu
    9470                9475                9480

Pro Glu Thr Thr Ser Ala Pro Asn Met Asn Ile Thr Ser Asp Glu
    9485                9490                9495

Ser Leu Ala Ala Ser Lys Ala Thr Thr Glu Thr Glu Ala Ile His
    9500                9505                9510

Val Phe Glu Asn Thr Ala Ala Ser His Val Glu Thr Thr Ser Ala
    9515                9520                9525

Thr Glu Glu Leu Tyr Ser Ser Pro Gly Phe Ser Glu Pro Thr
    9530                9535                9540

Lys Val Ile Ser Pro Val Val Thr Ser Ser Ser Ile Arg Asp Asn
    9545                9550                9555

Met Val Ser Thr Thr Met Pro Gly Ser Ser Gly Ile Thr Arg Ile
    9560                9565                9570

Glu Ile Glu Ser Met Ser Ser Leu Thr Pro Gly Leu Arg Glu Thr
    9575                9580                9585

Arg Thr Ser Gln Asp Ile Thr Ser Ser Thr Glu Thr Ser Thr Val
    9590                9595                9600

Leu Tyr Lys Met Pro Ser Gly Ala Thr Pro Glu Val Ser Arg Thr
    9605                9610                9615

Glu Val Met Pro Ser Ser Arg Thr Ser Ile Pro Gly Pro Ala Gln
    9620                9625                9630
```

```
Ser Thr Met Ser Leu Asp Ile Ser Asp Glu Val Val Thr Arg Leu
    9635                9640            9645
Ser Thr Ser Pro Ile Met Thr Glu Ser Ala Glu Ile Thr Ile Thr
    9650                9655            9660
Thr Gln Thr Gly Tyr Ser Leu Ala Thr Ser Gln Val Thr Leu Pro
    9665                9670            9675
Leu Gly Thr Ser Met Thr Phe Leu Ser Gly Thr His Ser Thr Met
    9680                9685            9690
Ser Gln Gly Leu Ser His Ser Glu Met Thr Asn Leu Met Ser Arg
    9695                9700            9705
Gly Pro Glu Ser Leu Ser Trp Thr Ser Pro Arg Phe Val Glu Thr
    9710                9715            9720
Thr Arg Ser Ser Ser Ser Leu Thr Ser Leu Pro Leu Thr Thr Ser
    9725                9730            9735
Leu Ser Pro Val Ser Ser Thr Leu Leu Asp Ser Ser Pro Ser Ser
    9740                9745            9750
Pro Leu Pro Val Thr Ser Leu Ile Leu Pro Gly Leu Val Lys Thr
    9755                9760            9765
Thr Glu Val Leu Asp Thr Ser Ser Glu Pro Lys Thr Ser Ser Ser
    9770                9775            9780
Pro Asn Leu Ser Ser Thr Ser Val Glu Ile Pro Ala Thr Ser Glu
    9785                9790            9795
Ile Met Thr Asp Thr Glu Lys Ile His Pro Ser Ser Asn Thr Ala
    9800                9805            9810
Val Ala Lys Val Arg Thr Ser Ser Ser Val His Glu Ser His Ser
    9815                9820            9825
Ser Val Leu Ala Asp Ser Glu Thr Thr Ile Thr Ile Pro Ser Met
    9830                9835            9840
Gly Ile Thr Ser Ala Val Asp Asp Thr Thr Val Phe Thr Ser Asn
    9845                9850            9855
Pro Ala Phe Ser Glu Thr Arg Arg Ile Pro Thr Glu Pro Thr Phe
    9860                9865            9870
Ser Leu Thr Pro Gly Phe Arg Glu Thr Ser Thr Ser Glu Glu Thr
    9875                9880            9885
Thr Ser Ile Thr Glu Thr Ser Ala Val Leu Tyr Gly Val Pro Thr
    9890                9895            9900
Ser Ala Thr Thr Glu Val Ser Met Thr Glu Ile Met Ser Ser Asn
    9905                9910            9915
Arg Ile His Ile Pro Asp Ser Asp Gln Ser Thr Met Ser Pro Asp
    9920                9925            9930
Ile Ile Thr Glu Val Ile Thr Arg Leu Ser Ser Ser Ser Met Met
    9935                9940            9945
Ser Glu Ser Thr Gln Met Thr Ile Thr Thr Gln Lys Ser Ser Pro
    9950                9955            9960
Gly Ala Thr Ala Gln Ser Thr Leu Thr Leu Ala Thr Thr Thr Ala
    9965                9970            9975
Pro Leu Ala Arg Thr His Ser Thr Val Pro Pro Arg Phe Leu His
    9980                9985            9990
Ser Glu Met Thr Thr Leu Met Ser Arg Ser Pro Glu Asn Pro Ser
    9995               10000              10005
Trp Lys Ser Ser Leu Phe Val Glu Lys Thr Ser Ser Ser Ser Ser
   10010               10015              10020
```

-continued

| | | | | | | | | | |
|---|---|---|---|---|---|---|---|---|---|
| Leu | Leu | Ser | Leu | Pro | Val | Thr | Thr | Ser | Pro | Ser | Val | Ser | Ser | Thr |
| 10025 | | | | | 10030 | | | | 10035 | | | |

Leu Leu Ser Leu Pro Val Thr Thr Ser Pro Ser Val Ser Ser Thr
    10025                10030              10035

Leu Pro Gln Ser Ile Pro Ser Ser Ser Phe Ser Val Thr Ser Leu
    10040                10045              10050

Leu Thr Pro Gly Met Val Lys Thr Thr Asp Thr Ser Thr Glu Pro
    10055                10060              10065

Gly Thr Ser Leu Ser Pro Asn Leu Ser Gly Thr Ser Val Glu Ile
    10070                10075              10080

Leu Ala Ala Ser Glu Val Thr Thr Asp Thr Glu Lys Ile His Pro
    10085                10090              10095

Ser Ser Ser Met Ala Val Thr Asn Val Gly Thr Thr Ser Ser Gly
    10100                10105              10110

His Glu Leu Tyr Ser Ser Val Ser Ile His Ser Glu Pro Ser Lys
    10115                10120              10125

Ala Thr Tyr Pro Val Gly Thr Pro Ser Ser Met Ala Glu Thr Ser
    10130                10135              10140

Ile Ser Thr Ser Met Pro Ala Asn Phe Glu Thr Thr Gly Phe Glu
    10145                10150              10155

Ala Glu Pro Phe Ser His Leu Thr Ser Gly Phe Arg Lys Thr Asn
    10160                10165              10170

Met Ser Leu Asp Thr Ser Ser Val Thr Pro Thr Asn Thr Pro Ser
    10175                10180              10185

Ser Pro Gly Ser Thr His Leu Leu Gln Ser Ser Lys Thr Asp Phe
    10190                10195              10200

Thr Ser Ser Ala Lys Thr Ser Ser Pro Asp Trp Pro Pro Ala Ser
    10205                10210              10215

Gln Tyr Thr Glu Ile Pro Val Asp Ile Ile Thr Pro Phe Asn Ala
    10220                10225              10230

Ser Pro Ser Ile Thr Glu Ser Thr Gly Ile Thr Ser Phe Pro Glu
    10235                10240              10245

Ser Arg Phe Thr Met Ser Val Thr Glu Ser Thr His His Leu Ser
    10250                10255              10260

Thr Asp Leu Leu Pro Ser Ala Glu Thr Ile Ser Thr Gly Thr Val
    10265                10270              10275

Met Pro Ser Leu Ser Glu Ala Met Thr Ser Phe Ala Thr Thr Gly
    10280                10285              10290

Val Pro Arg Ala Ile Ser Gly Ser Gly Ser Pro Phe Ser Arg Thr
    10295                10300              10305

Glu Ser Gly Pro Gly Asp Ala Thr Leu Ser Thr Ile Ala Glu Ser
    10310                10315              10320

Leu Pro Ser Ser Thr Pro Val Pro Phe Ser Ser Ser Thr Phe Thr
    10325                10330              10335

Thr Thr Asp Ser Ser Thr Ile Pro Ala Leu His Glu Ile Thr Ser
    10340                10345              10350

Ser Ser Ala Thr Pro Tyr Arg Val Asp Thr Ser Leu Gly Thr Glu
    10355                10360              10365

Ser Ser Thr Thr Glu Gly Arg Leu Val Met Val Ser Thr Leu Asp
    10370                10375              10380

Thr Ser Ser Gln Pro Gly Arg Thr Ser Ser Ser Pro Ile Leu Asp
    10385                10390              10395

Thr Arg Met Thr Glu Ser Val Glu Leu Gly Thr Val Thr Ser Ala
    10400                10405              10410

Tyr Gln Val Pro Ser Leu Ser Thr Arg Leu Thr Arg Thr Asp Gly

```
        10415               10420               10425
Ile Met Glu His Ile Thr Lys Ile Pro Asn Glu Ala Ala His Arg
    10430               10435               10440
Gly Thr Ile Arg Pro Val Lys Gly Pro Gln Thr Ser Thr Ser Pro
    10445               10450               10455
Ala Ser Pro Lys Gly Leu His Thr Gly Gly Thr Lys Arg Met Glu
    10460               10465               10470
Thr Thr Thr Thr Ala Leu Lys Thr Thr Thr Thr Ala Leu Lys Thr
    10475               10480               10485
Thr Ser Arg Ala Thr Leu Thr Thr Ser Val Tyr Thr Pro Thr Leu
    10490               10495               10500
Gly Thr Leu Thr Pro Leu Asn Ala Ser Met Gln Met Ala Ser Thr
    10505               10510               10515
Ile Pro Thr Glu Met Met Ile Thr Thr Pro Tyr Val Phe Pro Asp
    10520               10525               10530
Val Pro Glu Thr Thr Ser Ser Leu Ala Thr Ser Leu Gly Ala Glu
    10535               10540               10545
Thr Ser Thr Ala Leu Pro Arg Thr Thr Pro Ser Val Phe Asn Arg
    10550               10555               10560
Glu Ser Glu Thr Thr Ala Ser Leu Val Ser Arg Ser Gly Ala Glu
    10565               10570               10575
Arg Ser Pro Val Ile Gln Thr Leu Asp Val Ser Ser Ser Glu Pro
    10580               10585               10590
Asp Thr Thr Ala Ser Trp Val Ile His Pro Ala Glu Thr Ile Pro
    10595               10600               10605
Thr Val Ser Lys Thr Thr Pro Asn Phe Phe His Ser Glu Leu Asp
    10610               10615               10620
Thr Val Ser Ser Thr Ala Thr Ser His Gly Ala Asp Val Ser Ser
    10625               10630               10635
Ala Ile Pro Thr Asn Ile Ser Pro Ser Glu Leu Asp Ala Leu Thr
    10640               10645               10650
Pro Leu Val Thr Ile Ser Gly Thr Asp Thr Ser Thr Thr Phe Pro
    10655               10660               10665
Thr Leu Thr Lys Ser Pro His Glu Thr Glu Thr Arg Thr Thr Trp
    10670               10675               10680
Leu Thr His Pro Ala Glu Thr Ser Ser Thr Ile Pro Arg Thr Ile
    10685               10690               10695
Pro Asn Phe Ser His His Glu Ser Asp Ala Thr Pro Ser Ile Ala
    10700               10705               10710
Thr Ser Pro Gly Ala Glu Thr Ser Ser Ala Ile Pro Ile Met Thr
    10715               10720               10725
Val Ser Pro Gly Ala Glu Asp Leu Val Thr Ser Gln Val Thr Ser
    10730               10735               10740
Ser Gly Thr Asp Arg Asn Met Thr Ile Pro Thr Leu Thr Leu Ser
    10745               10750               10755
Pro Gly Glu Pro Lys Thr Ile Ala Ser Leu Val Thr His Pro Glu
    10760               10765               10770
Ala Gln Thr Ser Ser Ala Ile Pro Thr Ser Thr Ile Ser Pro Ala
    10775               10780               10785
Val Ser Arg Leu Val Thr Ser Met Val Thr Ser Leu Ala Ala Lys
    10790               10795               10800
Thr Ser Thr Thr Asn Arg Ala Leu Thr Asn Ser Pro Gly Glu Pro
    10805               10810               10815
```

```
Ala Thr Thr Val Ser Leu Val Thr His Pro Ala Gln Thr Ser Pro
10820              10825             10830

Thr Val Pro Trp Thr Thr Ser Ile Phe Phe His Ser Lys Ser Asp
10835              10840             10845

Thr Thr Pro Ser Met Thr Thr Ser His Gly Ala Glu Ser Ser Ser
10850              10855             10860

Ala Val Pro Thr Pro Thr Val Ser Thr Glu Val Pro Gly Val Val
10865              10870             10875

Thr Pro Leu Val Thr Ser Ser Arg Ala Val Ile Ser Thr Thr Ile
10880              10885             10890

Pro Ile Leu Thr Leu Ser Pro Gly Glu Pro Glu Thr Thr Pro Ser
10895              10900             10905

Met Ala Thr Ser His Gly Glu Glu Ala Ser Ser Ala Ile Pro Thr
10910              10915             10920

Pro Thr Val Ser Pro Gly Val Pro Gly Val Val Thr Ser Leu Val
10925              10930             10935

Thr Ser Ser Arg Ala Val Thr Ser Thr Thr Ile Pro Ile Leu Thr
10940              10945             10950

Phe Ser Leu Gly Glu Pro Glu Thr Thr Pro Ser Met Ala Thr Ser
10955              10960             10965

His Gly Thr Glu Ala Gly Ser Ala Val Pro Thr Val Leu Pro Glu
10970              10975             10980

Val Pro Gly Met Val Thr Ser Leu Val Ala Ser Ser Arg Ala Val
10985              10990             10995

Thr Ser Thr Thr Leu Pro Thr Leu Thr Leu Ser Pro Gly Glu Pro
11000              11005             11010

Glu Thr Thr Pro Ser Met Ala Thr Ser His Gly Ala Glu Ala Ser
11015              11020             11025

Ser Thr Val Pro Thr Val Ser Pro Glu Val Pro Gly Val Val Thr
11030              11035             11040

Ser Leu Val Thr Ser Ser Ser Gly Val Asn Ser Thr Ser Ile Pro
11045              11050             11055

Thr Leu Ile Leu Ser Pro Gly Glu Leu Glu Thr Thr Pro Ser Met
11060              11065             11070

Ala Thr Ser His Gly Ala Glu Ala Ser Ser Ala Val Pro Thr Pro
11075              11080             11085

Thr Val Ser Pro Gly Val Ser Gly Val Val Thr Pro Leu Val Thr
11090              11095             11100

Ser Ser Arg Ala Val Thr Ser Thr Thr Ile Pro Ile Leu Thr Leu
11105              11110             11115

Ser Ser Ser Glu Pro Glu Thr Thr Pro Ser Met Ala Thr Ser His
11120              11125             11130

Gly Val Glu Ala Ser Ser Ala Val Leu Thr Val Ser Pro Glu Val
11135              11140             11145

Pro Gly Met Val Thr Ser Leu Val Thr Ser Ser Arg Ala Val Thr
11150              11155             11160

Ser Thr Thr Ile Pro Thr Leu Thr Ile Ser Ser Asp Glu Pro Glu
11165              11170             11175

Thr Thr Thr Ser Leu Val Thr His Ser Glu Ala Lys Met Ile Ser
11180              11185             11190

Ala Ile Pro Thr Leu Ala Val Ser Pro Thr Val Gln Gly Leu Val
11195              11200             11205
```

```
Thr Ser   Leu Val Thr Ser Ser   Gly Ser Glu Thr Ser   Ala Phe Ser
    11210             11215                 11220

Asn Leu   Thr Val Ala Ser Ser   Gln Pro Glu Thr Ile   Asp Ser Trp
    11225             11230                 11235

Val Ala   His Pro Gly Thr Glu   Ala Ser Ser Val Val   Pro Thr Leu
    11240             11245                 11250

Thr Val   Ser Thr Gly Glu Pro   Phe Thr Asn Ile Ser   Leu Val Thr
    11255             11260                 11265

His Pro   Ala Glu Ser Ser Ser   Thr Leu Pro Arg Thr   Thr Ser Arg
    11270             11275                 11280

Phe Ser   His Ser Glu Leu Asp   Thr Met Pro Ser Thr   Val Thr Ser
    11285             11290                 11295

Pro Glu   Ala Glu Ser Ser Ser   Ala Ile Ser Thr Thr   Ile Ser Pro
    11300             11305                 11310

Gly Ile   Pro Gly Val Leu Thr   Ser Leu Val Thr Ser   Ser Gly Arg
    11315             11320                 11325

Asp Ile   Ser Ala Thr Phe Pro   Thr Val Pro Glu Ser   Pro His Glu
    11330             11335                 11340

Ser Glu   Ala Thr Ala Ser Trp   Val Thr His Pro Ala   Val Thr Ser
    11345             11350                 11355

Thr Thr   Val Pro Arg Thr Thr   Pro Asn Tyr Ser His   Ser Glu Pro
    11360             11365                 11370

Asp Thr   Thr Pro Ser Ile Ala   Thr Ser Pro Gly Ala   Glu Ala Thr
    11375             11380                 11385

Ser Asp   Phe Pro Thr Ile Thr   Val Ser Pro Asp Val   Pro Asp Met
    11390             11395                 11400

Val Thr   Ser Gln Val Thr Ser   Ser Gly Thr Asp Thr   Ser Ile Thr
    11405             11410                 11415

Ile Pro   Thr Leu Thr Leu Ser   Ser Gly Glu Pro Glu   Thr Thr Thr
    11420             11425                 11430

Ser Phe   Ile Thr Tyr Ser Glu   Thr His Thr Ser Ser   Ala Ile Pro
    11435             11440                 11445

Thr Leu   Pro Val Ser Pro Gly   Ala Ser Lys Met Leu   Thr Ser Leu
    11450             11455                 11460

Val Ile   Ser Ser Gly Thr Asp   Ser Thr Thr Thr Phe   Pro Thr Leu
    11465             11470                 11475

Thr Glu   Thr Pro Tyr Glu Pro   Glu Thr Thr Ala Ile   Gln Leu Ile
    11480             11485                 11490

His Pro   Ala Glu Thr Asn Thr   Met Val Pro Arg Thr   Thr Pro Lys
    11495             11500                 11505

Phe Ser   His Ser Lys Ser Asp   Thr Thr Leu Pro Val   Ala Ile Thr
    11510             11515                 11520

Ser Pro   Gly Pro Glu Ala Ser   Ser Ala Val Ser Thr   Thr Thr Ile
    11525             11530                 11535

Ser Pro   Asp Met Ser Asp Leu   Val Thr Ser Leu Val   Pro Ser Ser
    11540             11545                 11550

Gly Thr   Asp Thr Ser Thr Thr   Phe Pro Thr Leu Ser   Glu Thr Pro
    11555             11560                 11565

Tyr Glu   Pro Glu Thr Thr Ala   Thr Trp Leu Thr His   Pro Ala Glu
    11570             11575                 11580

Thr Ser   Thr Thr Val Ser Gly   Thr Ile Pro Asn Phe   Ser His Arg
    11585             11590                 11595

Gly Ser   Asp Thr Ala Pro Ser   Met Val Thr Ser Pro   Gly Val Asp
```

-continued

```
                11600               11605               11610

Thr Arg     Ser Gly Val Pro Thr     Thr Thr Ile Pro Pro     Ser Ile Pro
   11615               11620                   11625

Gly Val     Val Thr Ser Gln Val     Thr Ser Ser Ala Thr     Asp Thr Ser
   11630               11635                   11640

Thr Ala     Ile Pro Thr Leu Thr     Pro Ser Pro Gly Glu     Pro Glu Thr
   11645               11650                   11655

Thr Ala     Ser Ser Ala Thr His     Pro Gly Thr Gln Thr     Gly Phe Thr
   11660               11665                   11670

Val Pro     Ile Arg Thr Val Pro     Ser Ser Glu Pro Asp     Thr Met Ala
   11675               11680                   11685

Ser Trp     Val Thr His Pro Pro     Gln Thr Ser Thr Pro     Val Ser Arg
   11690               11695                   11700

Thr Thr     Ser Ser Phe Ser His     Ser Ser Pro Asp Ala     Thr Pro Val
   11705               11710                   11715

Met Ala     Thr Ser Pro Arg Thr     Glu Ala Ser Ser Ala     Val Leu Thr
   11720               11725                   11730

Thr Ile     Ser Pro Gly Ala Pro     Glu Met Val Thr Ser     Gln Ile Thr
   11735               11740                   11745

Ser Ser     Gly Ala Ala Thr Ser     Thr Thr Val Pro Thr     Leu Thr His
   11750               11755                   11760

Ser Pro     Gly Met Pro Glu Thr     Thr Ala Leu Leu Ser     Thr His Pro
   11765               11770                   11775

Arg Thr     Glu Thr Ser Lys Thr     Phe Pro Ala Ser Thr     Val Phe Pro
   11780               11785                   11790

Gln Val     Ser Glu Thr Thr Ala     Ser Leu Thr Ile Arg     Pro Gly Ala
   11795               11800                   11805

Glu Thr     Ser Thr Ala Leu Pro     Thr Gln Thr Thr Ser     Ser Leu Phe
   11810               11815                   11820

Thr Leu     Leu Val Thr Gly Thr     Ser Arg Val Asp Leu     Ser Pro Thr
   11825               11830                   11835

Ala Ser     Pro Gly Val Ser Ala     Lys Thr Ala Pro Leu     Ser Thr His
   11840               11845                   11850

Pro Gly     Thr Glu Thr Ser Thr     Met Ile Pro Thr Ser     Thr Leu Ser
   11855               11860                   11865

Leu Gly     Leu Leu Glu Thr Thr     Gly Leu Leu Ala Thr     Ser Ser Ser
   11870               11875                   11880

Ala Glu     Thr Ser Thr Ser Thr     Leu Thr Leu Thr Val     Ser Pro Ala
   11885               11890                   11895

Val Ser     Gly Leu Ser Ser Ala     Ser Ile Thr Thr Asp     Lys Pro Gln
   11900               11905                   11910

Thr Val     Thr Ser Trp Asn Thr     Glu Thr Ser Pro Ser     Val Thr Ser
   11915               11920                   11925

Val Gly     Pro Pro Glu Phe Ser     Arg Thr Val Thr Gly     Thr Thr Met
   11930               11935                   11940

Thr Leu     Ile Pro Ser Glu Met     Pro Thr Pro Pro Lys     Thr Ser His
   11945               11950                   11955

Gly Glu     Gly Val Ser Pro Thr     Thr Ile Leu Arg Thr     Thr Met Val
   11960               11965                   11970

Glu Ala     Thr Asn Leu Ala Thr     Thr Gly Ser Ser Pro     Thr Val Ala
   11975               11980                   11985

Lys Thr     Thr Thr Thr Phe Asn     Thr Leu Ala Gly Ser     Leu Phe Thr
   11990               11995                   12000
```

```
Pro Leu Thr Thr Pro Gly Met Ser Thr Leu Ala Ser   Glu Ser Val
    12005           12010               12015

Thr Ser Arg Thr Ser Tyr Asn His Arg Ser Trp Ile   Ser Thr Thr
    12020           12025               12030

Ser Ser Tyr Asn Arg Arg Tyr Trp Thr Pro Ala Thr   Ser Thr Pro
    12035           12040               12045

Val Thr Ser Thr Phe Ser Pro Gly Ile Ser Thr Ser   Ser Ile Pro
    12050           12055               12060

Ser Ser Thr Ala Ala Thr Val Pro Phe Met Val Pro   Phe Thr Leu
    12065           12070               12075

Asn Phe Thr Ile Thr Asn Leu Gln Tyr Glu Glu Asp   Met Arg His
    12080           12085               12090

Pro Gly Ser Arg Lys Phe Asn Ala Thr Glu Arg Glu   Leu Gln Gly
    12095           12100               12105

Leu Leu Lys Pro Leu Phe Arg Asn Ser Ser Leu Glu   Tyr Leu Tyr
    12110           12115               12120

Ser Gly Cys Arg Leu Ala Ser Leu Arg Pro Glu Lys   Asp Ser Ser
    12125           12130               12135

Ala Thr Ala Val Asp Ala Ile Cys Thr His Arg Pro   Asp Pro Glu
    12140           12145               12150

Asp Leu Gly Leu Asp Arg Glu Arg Leu Tyr Trp Glu   Leu Ser Asn
    12155           12160               12165

Leu Thr Asn Gly Ile Gln Glu Leu Gly Pro Tyr Thr   Leu Asp Arg
    12170           12175               12180

Asn Ser Leu Tyr Val Asn Gly Phe Thr His Arg Ser   Ser Met Pro
    12185           12190               12195

Thr Thr Ser Thr Pro Gly Thr Ser Thr Val Asp Val   Gly Thr Ser
    12200           12205               12210

Gly Thr Pro Ser Ser Ser Pro Ser Pro Thr Thr Ala   Gly Pro Leu
    12215           12220               12225

Leu Met Pro Phe Thr Leu Asn Phe Thr Ile Thr Asn   Leu Gln Tyr
    12230           12235               12240

Glu Glu Asp Met Arg Arg Thr Gly Ser Arg Lys Phe   Asn Thr Met
    12245           12250               12255

Glu Ser Val Leu Gln Gly Leu Leu Lys Pro Leu Phe   Lys Asn Thr
    12260           12265               12270

Ser Val Gly Pro Leu Tyr Ser Gly Cys Arg Leu Thr   Leu Leu Arg
    12275           12280               12285

Pro Glu Lys Asp Gly Ala Ala Thr Gly Val Asp Ala   Ile Cys Thr
    12290           12295               12300

His Arg Leu Asp Pro Lys Ser Pro Gly Leu Asn Arg   Glu Gln Leu
    12305           12310               12315

Tyr Trp Glu Leu Ser Lys Leu Thr Asn Asp Ile Glu   Glu Leu Gly
    12320           12325               12330

Pro Tyr Thr Leu Asp Arg Asn Ser Leu Tyr Val Asn   Gly Phe Thr
    12335           12340               12345

His Gln Ser Ser Val Ser Thr Thr Ser Thr Pro Gly   Thr Ser Thr
    12350           12355               12360

Val Asp Leu Arg Thr Ser Gly Thr Pro Ser Ser Leu   Ser Ser Pro
    12365           12370               12375

Thr Ile Met Ala Ala Gly Pro Leu Leu Val Pro Phe   Thr Leu Asn
    12380           12385               12390
```

```
Phe Thr Ile Thr Asn Leu Gln   Tyr Gly Glu Asp Met   Gly His Pro
    12395           12400               12405

Gly Ser Arg Lys Phe Asn Thr   Thr Glu Arg Val Leu   Gln Gly Leu
    12410           12415               12420

Leu Gly Pro Ile Phe Lys Asn   Thr Ser Val Gly Pro   Leu Tyr Ser
    12425           12430               12435

Gly Cys Arg Leu Thr Ser Leu   Arg Ser Glu Lys Asp   Gly Ala Ala
    12440           12445               12450

Thr Gly Val Asp Ala Ile Cys   Ile His His Leu Asp   Pro Lys Ser
    12455           12460               12465

Pro Gly Leu Asn Arg Glu Arg   Leu Tyr Trp Glu Leu   Ser Gln Leu
    12470           12475               12480

Thr Asn Gly Ile Lys Glu Leu   Gly Pro Tyr Thr Leu   Asp Arg Asn
    12485           12490               12495

Ser Leu Tyr Val Asn Gly Phe   Thr His Arg Thr Ser   Val Pro Thr
    12500           12505               12510

Ser Ser Thr Pro Gly Thr Ser   Thr Val Asp Leu Gly   Thr Ser Gly
    12515           12520               12525

Thr Pro Phe Ser Leu Pro Ser   Pro Ala Thr Ala Gly   Pro Leu Leu
    12530           12535               12540

Val Leu Phe Thr Leu Asn Phe   Thr Ile Thr Asn Leu   Lys Tyr Glu
    12545           12550               12555

Glu Asp Met His Arg Pro Gly   Ser Arg Lys Phe Asn   Thr Thr Glu
    12560           12565               12570

Arg Val Leu Gln Thr Leu Leu   Gly Pro Met Phe Lys   Asn Thr Ser
    12575           12580               12585

Val Gly Leu Leu Tyr Ser Gly   Cys Arg Leu Thr Leu   Leu Arg Ser
    12590           12595               12600

Glu Lys Asp Gly Ala Ala Thr   Gly Val Asp Ala Ile   Cys Thr His
    12605           12610               12615

Arg Leu Asp Pro Lys Ser Pro   Gly Val Asp Arg Glu   Gln Leu Tyr
    12620           12625               12630

Trp Glu Leu Ser Gln Leu Thr   Asn Gly Ile Lys Glu   Leu Gly Pro
    12635           12640               12645

Tyr Thr Leu Asp Arg Asn Ser   Leu Tyr Val Asn Gly   Phe Thr His
    12650           12655               12660

Trp Ile Pro Val Pro Thr Ser   Ser Thr Pro Gly Thr   Ser Thr Val
    12665           12670               12675

Asp Leu Gly Ser Gly Thr Pro   Ser Ser Leu Pro Ser   Pro Thr Thr
    12680           12685               12690

Ala Gly Pro Leu Leu Val Pro   Phe Thr Leu Asn Phe   Thr Ile Thr
    12695           12700               12705

Asn Leu Lys Tyr Glu Glu Asp   Met His Cys Pro Gly   Ser Arg Lys
    12710           12715               12720

Phe Asn Thr Thr Glu Arg Val   Leu Gln Ser Leu Leu   Gly Pro Met
    12725           12730               12735

Phe Lys Asn Thr Ser Val Gly   Pro Leu Tyr Ser Gly   Cys Arg Leu
    12740           12745               12750

Thr Leu Leu Arg Ser Glu Lys   Asp Gly Ala Ala Thr   Gly Val Asp
    12755           12760               12765

Ala Ile Cys Thr His Arg Leu   Asp Pro Lys Ser Pro   Gly Val Asp
    12770           12775               12780

Arg Glu Gln Leu Tyr Trp Glu   Leu Ser Gln Leu Thr   Asn Gly Ile
```

```
              12785               12790               12795

Lys Glu   Leu Gly Pro Tyr Thr   Leu Asp Arg Asn Ser   Leu Tyr Val
    12800               12805               12810

Asn Gly   Phe Thr His Gln Thr   Ser Ala Pro Asn Thr   Ser Thr Pro
    12815               12820               12825

Gly Thr   Ser Thr Val Asp Leu   Gly Thr Ser Gly Thr   Pro Ser Ser
    12830               12835               12840

Leu Pro   Ser Pro Thr Ser Ala   Gly Pro Leu Leu Val   Pro Phe Thr
    12845               12850               12855

Leu Asn   Phe Thr Ile Thr Asn   Leu Gln Tyr Glu Glu   Asp Met His
    12860               12865               12870

His Pro   Gly Ser Arg Lys Phe   Asn Thr Thr Glu Arg   Val Leu Gln
    12875               12880               12885

Gly Leu   Leu Gly Pro Met Phe   Lys Asn Thr Ser Val   Gly Leu Leu
    12890               12895               12900

Tyr Ser   Gly Cys Arg Leu Thr   Leu Leu Arg Pro Glu   Lys Asn Gly
    12905               12910               12915

Ala Ala   Thr Gly Met Asp Ala   Ile Cys Ser His Arg   Leu Asp Pro
    12920               12925               12930

Lys Ser   Pro Gly Leu Asn Arg   Glu Gln Leu Tyr Trp   Glu Leu Ser
    12935               12940               12945

Gln Leu   Thr His Gly Ile Lys   Glu Leu Gly Pro Tyr   Thr Leu Asp
    12950               12955               12960

Arg Asn   Ser Leu Tyr Val Asn   Gly Phe Thr His Arg   Ser Ser Val
    12965               12970               12975

Ala Pro   Thr Ser Thr Pro Gly   Thr Ser Thr Val Asp   Leu Gly Thr
    12980               12985               12990

Ser Gly   Thr Pro Ser Ser Leu   Pro Ser Pro Thr Thr   Ala Val Pro
    12995               13000               13005

Leu Leu   Val Pro Phe Thr Leu   Asn Phe Thr Ile Thr   Asn Leu Gln
    13010               13015               13020

Tyr Gly   Glu Asp Met Arg His   Pro Gly Ser Arg Lys   Phe Asn Thr
    13025               13030               13035

Thr Glu   Arg Val Leu Gln Gly   Leu Leu Gly Pro Leu   Phe Lys Asn
    13040               13045               13050

Ser Ser   Val Gly Pro Leu Tyr   Ser Gly Cys Arg Leu   Ile Ser Leu
    13055               13060               13065

Arg Ser   Glu Lys Asp Gly Ala   Ala Thr Gly Val Asp   Ala Ile Cys
    13070               13075               13080

Thr His   His Leu Asn Pro Gln   Ser Pro Gly Leu Asp   Arg Glu Gln
    13085               13090               13095

Leu Tyr   Trp Gln Leu Ser Gln   Met Thr Asn Gly Ile   Lys Glu Leu
    13100               13105               13110

Gly Pro   Tyr Thr Leu Asp Arg   Asn Ser Leu Tyr Val   Asn Gly Phe
    13115               13120               13125

Thr His   Arg Ser Ser Gly Leu   Thr Thr Ser Thr Pro   Trp Thr Ser
    13130               13135               13140

Thr Val   Asp Leu Gly Thr Ser   Gly Thr Pro Ser Pro   Val Pro Ser
    13145               13150               13155

Pro Thr   Thr Thr Gly Pro Leu   Leu Val Pro Phe Thr   Leu Asn Phe
    13160               13165               13170

Thr Ile   Thr Asn Leu Gln Tyr   Glu Glu Asn Met Gly   His Pro Gly
    13175               13180               13185
```

-continued

| | | | | | | | | | | | |
|---|---|---|---|---|---|---|---|---|---|---|---|
| Ser | Arg | Lys | Phe | Asn | Ile | Thr | Glu | Ser | Val | Leu | Gln | Gly | Leu | Leu |
| 13190 | | | | | 13195 | | | | | 13200 | | | | |
| Lys | Pro | Leu | Phe | Lys | Ser | Thr | Ser | Val | Gly | Pro | Leu | Tyr | Ser | Gly |
| 13205 | | | | | 13210 | | | | | 13215 | | | | |
| Cys | Arg | Leu | Thr | Leu | Leu | Arg | Pro | Glu | Lys | Asp | Gly | Val | Ala | Thr |
| 13220 | | | | | 13225 | | | | | 13230 | | | | |
| Arg | Val | Asp | Ala | Ile | Cys | Thr | His | Arg | Pro | Asp | Pro | Lys | Ile | Pro |
| 13235 | | | | | 13240 | | | | | 13245 | | | | |
| Gly | Leu | Asp | Arg | Gln | Gln | Leu | Tyr | Trp | Glu | Leu | Ser | Gln | Leu | Thr |
| 13250 | | | | | 13255 | | | | | 13260 | | | | |
| His | Ser | Ile | Thr | Glu | Leu | Gly | Pro | Tyr | Thr | Leu | Asp | Arg | Asp | Ser |
| 13265 | | | | | 13270 | | | | | 13275 | | | | |
| Leu | Tyr | Val | Asn | Gly | Phe | Thr | Gln | Arg | Ser | Ser | Val | Pro | Thr | Thr |
| 13280 | | | | | 13285 | | | | | 13290 | | | | |
| Ser | Thr | Pro | Gly | Thr | Phe | Thr | Val | Gln | Pro | Glu | Thr | Ser | Glu | Thr |
| 13295 | | | | | 13300 | | | | | 13305 | | | | |
| Pro | Ser | Ser | Leu | Pro | Gly | Pro | Thr | Ala | Thr | Gly | Pro | Val | Leu | Leu |
| 13310 | | | | | 13315 | | | | | 13320 | | | | |
| Pro | Phe | Thr | Leu | Asn | Phe | Thr | Ile | Thr | Asn | Leu | Gln | Tyr | Glu | Glu |
| 13325 | | | | | 13330 | | | | | 13335 | | | | |
| Asp | Met | Arg | Arg | Pro | Gly | Ser | Arg | Lys | Phe | Asn | Thr | Thr | Glu | Arg |
| 13340 | | | | | 13345 | | | | | 13350 | | | | |
| Val | Leu | Gln | Gly | Leu | Leu | Met | Pro | Leu | Phe | Lys | Asn | Thr | Ser | Val |
| 13355 | | | | | 13360 | | | | | 13365 | | | | |
| Ser | Ser | Leu | Tyr | Ser | Gly | Cys | Arg | Leu | Thr | Leu | Leu | Arg | Pro | Glu |
| 13370 | | | | | 13375 | | | | | 13380 | | | | |
| Lys | Asp | Gly | Ala | Ala | Thr | Arg | Val | Asp | Ala | Val | Cys | Thr | His | Arg |
| 13385 | | | | | 13390 | | | | | 13395 | | | | |
| Pro | Asp | Pro | Lys | Ser | Pro | Gly | Leu | Asp | Arg | Glu | Arg | Leu | Tyr | Trp |
| 13400 | | | | | 13405 | | | | | 13410 | | | | |
| Lys | Leu | Ser | Gln | Leu | Thr | His | Gly | Ile | Thr | Glu | Leu | Gly | Pro | Tyr |
| 13415 | | | | | 13420 | | | | | 13425 | | | | |
| Thr | Leu | Asp | Arg | His | Ser | Leu | Tyr | Val | Asn | Gly | Phe | Thr | His | Gln |
| 13430 | | | | | 13435 | | | | | 13440 | | | | |
| Ser | Ser | Met | Thr | Thr | Thr | Arg | Thr | Pro | Asp | Thr | Ser | Thr | Met | His |
| 13445 | | | | | 13450 | | | | | 13455 | | | | |
| Leu | Ala | Thr | Ser | Arg | Thr | Pro | Ala | Ser | Leu | Ser | Gly | Pro | Met | Thr |
| 13460 | | | | | 13465 | | | | | 13470 | | | | |
| Ala | Ser | Pro | Leu | Leu | Val | Leu | Phe | Thr | Ile | Asn | Phe | Thr | Ile | Thr |
| 13475 | | | | | 13480 | | | | | 13485 | | | | |
| Asn | Leu | Arg | Tyr | Glu | Glu | Asn | Met | His | His | Pro | Gly | Ser | Arg | Lys |
| 13490 | | | | | 13495 | | | | | 13500 | | | | |
| Phe | Asn | Thr | Thr | Glu | Arg | Val | Leu | Gln | Gly | Leu | Leu | Arg | Pro | Val |
| 13505 | | | | | 13510 | | | | | 13515 | | | | |
| Phe | Lys | Asn | Thr | Ser | Val | Gly | Pro | Leu | Tyr | Ser | Gly | Cys | Arg | Leu |
| 13520 | | | | | 13525 | | | | | 13530 | | | | |
| Thr | Leu | Leu | Arg | Pro | Lys | Lys | Asp | Gly | Ala | Ala | Thr | Lys | Val | Asp |
| 13535 | | | | | 13540 | | | | | 13545 | | | | |
| Ala | Ile | Cys | Thr | Tyr | Arg | Pro | Asp | Pro | Lys | Ser | Pro | Gly | Leu | Asp |
| 13550 | | | | | 13555 | | | | | 13560 | | | | |
| Arg | Glu | Gln | Leu | Tyr | Trp | Glu | Leu | Ser | Gln | Leu | Thr | His | Ser | Ile |
| 13565 | | | | | 13570 | | | | | 13575 | | | | |

```
Thr Glu Leu Gly Pro Tyr Thr Leu Asp Arg Asp Ser Leu Tyr Val
    13580               13585               13590

Asn Gly Phe Thr Gln Arg Ser Ser Val Pro Thr Thr Ser Ile Pro
    13595               13600               13605

Gly Thr Pro Thr Val Asp Leu Gly Thr Ser Gly Thr Pro Val Ser
    13610               13615               13620

Lys Pro Gly Pro Ser Ala Ala Ser Pro Leu Leu Val Leu Phe Thr
    13625               13630               13635

Leu Asn Phe Thr Ile Thr Asn Leu Arg Tyr Glu Glu Asn Met Gln
    13640               13645               13650

His Pro Gly Ser Arg Lys Phe Asn Thr Thr Glu Arg Val Leu Gln
    13655               13660               13665

Gly Leu Leu Arg Ser Leu Phe Lys Ser Thr Ser Val Gly Pro Leu
    13670               13675               13680

Tyr Ser Gly Cys Arg Leu Thr Leu Leu Arg Pro Glu Lys Asp Gly
    13685               13690               13695

Thr Ala Thr Gly Val Asp Ala Ile Cys Thr His His Pro Asp Pro
    13700               13705               13710

Lys Ser Pro Arg Leu Asp Arg Glu Gln Leu Tyr Trp Glu Leu Ser
    13715               13720               13725

Gln Leu Thr His Asn Ile Thr Glu Leu Gly Pro Tyr Ala Leu Asp
    13730               13735               13740

Asn Asp Ser Leu Phe Val Asn Gly Phe Thr His Arg Ser Ser Val
    13745               13750               13755

Ser Thr Thr Ser Thr Pro Gly Thr Pro Thr Val Tyr Leu Gly Ala
    13760               13765               13770

Ser Lys Thr Pro Ala Ser Ile Phe Gly Pro Ser Ala Ala Ser His
    13775               13780               13785

Leu Leu Ile Leu Phe Thr Leu Asn Phe Thr Ile Thr Asn Leu Arg
    13790               13795               13800

Tyr Glu Glu Asn Met Trp Pro Gly Ser Arg Lys Phe Asn Thr Thr
    13805               13810               13815

Glu Arg Val Leu Gln Gly Leu Leu Arg Pro Leu Phe Lys Asn Thr
    13820               13825               13830

Ser Val Gly Pro Leu Tyr Ser Gly Cys Arg Leu Thr Leu Leu Arg
    13835               13840               13845

Pro Glu Lys Asp Gly Glu Ala Thr Gly Val Asp Ala Ile Cys Thr
    13850               13855               13860

His Arg Pro Asp Pro Thr Gly Pro Gly Leu Asp Arg Glu Gln Leu
    13865               13870               13875

Tyr Leu Glu Leu Ser Gln Leu Thr His Ser Ile Thr Glu Leu Gly
    13880               13885               13890

Pro Tyr Thr Leu Asp Arg Asp Ser Leu Tyr Val Asn Gly Phe Thr
    13895               13900               13905

His Arg Ser Ser Val Pro Thr Thr Ser Thr Gly Val Val Ser Glu
    13910               13915               13920

Glu Pro Phe Thr Leu Asn Phe Thr Ile Asn Asn Leu Arg Tyr Met
    13925               13930               13935

Ala Asp Met Gly Gln Pro Gly Ser Leu Lys Phe Asn Ile Thr Asp
    13940               13945               13950

Asn Val Met Gln His Leu Leu Ser Pro Leu Phe Gln Arg Ser Ser
    13955               13960               13965

Leu Gly Ala Arg Tyr Thr Gly Cys Arg Val Ile Ala Leu Arg Ser
```

```
            13970           13975           13980

Val Lys  Asn Gly Ala Glu Thr  Arg Val Asp Leu Leu  Cys Thr Tyr
         13985             13990             13995

Leu Gln  Pro Leu Ser Gly Pro  Gly Leu Pro Ile Lys  Gln Val Phe
         14000             14005             14010

His Glu  Leu Ser Gln Gln Thr  His Gly Ile Thr Arg  Leu Gly Pro
         14015             14020             14025

Tyr Ser  Leu Asp Lys Asp Ser  Leu Tyr Leu Asn Gly  Tyr Asn Glu
         14030             14035             14040

Pro Gly  Pro Asp Glu Pro Pro  Thr Thr Pro Lys Pro  Ala Thr Thr
         14045             14050             14055

Phe Leu  Pro Pro Leu Ser Glu  Ala Thr Thr Ala Met  Gly Tyr His
         14060             14065             14070

Leu Lys  Thr Leu Thr Leu Asn  Phe Thr Ile Ser Asn  Leu Gln Tyr
         14075             14080             14085

Ser Pro  Asp Met Gly Lys Gly  Ser Ala Thr Phe Asn  Ser Thr Glu
         14090             14095             14100

Gly Val  Leu Gln His Leu Leu  Arg Pro Leu Phe Gln  Lys Ser Ser
         14105             14110             14115

Met Gly  Pro Phe Tyr Leu Gly  Cys Gln Leu Ile Ser  Leu Arg Pro
         14120             14125             14130

Glu Lys  Asp Gly Ala Ala Thr  Gly Val Asp Thr Thr  Cys Thr Tyr
         14135             14140             14145

His Pro  Asp Pro Val Gly Pro  Gly Leu Asp Ile Gln  Gln Leu Tyr
         14150             14155             14160

Trp Glu  Leu Ser Gln Leu Thr  His Gly Val Thr Gln  Leu Gly Phe
         14165             14170             14175

Tyr Val  Leu Asp Arg Asp Ser  Leu Phe Ile Asn Gly  Tyr Ala Pro
         14180             14185             14190

Gln Asn  Leu Ser Ile Arg Gly  Glu Tyr Gln Ile Asn  Phe His Ile
         14195             14200             14205

Val Asn  Trp Asn Leu Ser Asn  Pro Asp Pro Thr Ser  Ser Glu Tyr
         14210             14215             14220

Ile Thr  Leu Leu Arg Asp Ile  Gln Asp Lys Val Thr  Thr Leu Tyr
         14225             14230             14235

Lys Gly  Ser Gln Leu His Asp  Thr Phe Arg Phe Cys  Leu Val Thr
         14240             14245             14250

Asn Leu  Thr Met Asp Ser Val  Leu Val Thr Val Lys  Ala Leu Phe
         14255             14260             14265

Ser Ser  Asn Leu Asp Pro Ser  Leu Val Glu Gln Val  Phe Leu Asp
         14270             14275             14280

Lys Thr  Leu Asn Ala Ser Phe  His Trp Leu Gly Ser  Thr Tyr Gln
         14285             14290             14295

Leu Val  Asp Ile His Val Thr  Glu Met Glu Ser Ser  Val Tyr Gln
         14300             14305             14310

Pro Thr  Ser Ser Ser Ser Thr  Gln His Phe Tyr Leu  Asn Phe Thr
         14315             14320             14325

Ile Thr  Asn Leu Pro Tyr Ser  Gln Asp Lys Ala Gln  Pro Gly Thr
         14330             14335             14340

Thr Asn  Tyr Gln Arg Asn Lys  Arg Asn Ile Glu Asp  Ala Leu Asn
         14345             14350             14355

Gln Leu  Phe Arg Asn Ser Ser  Ile Lys Ser Tyr Phe  Ser Asp Cys
         14360             14365             14370
```

```
Gln Val Ser Thr Phe Arg Ser     Val Pro Asn Arg His     His Thr Gly
    14375           14380                   14385

Val Asp Ser Leu Cys Asn Phe     Ser Pro Leu Ala Arg     Arg Val Asp
    14390           14395                   14400

Arg Val Ala Ile Tyr Glu Glu     Phe Leu Arg Met Thr     Arg Asn Gly
    14405           14410                   14415

Thr Gln Leu Gln Asn Phe Thr     Leu Asp Arg Ser Ser     Val Leu Val
    14420           14425                   14430

Asp Gly Tyr Ser Pro Asn Arg     Asn Glu Pro Leu Thr     Gly Asn Ser
    14435           14440                   14445

Asp Leu Pro Phe Trp Ala Val     Ile Leu Ile Gly Leu     Ala Gly Leu
    14450           14455                   14460

Leu Gly Val Ile Thr Cys Leu     Ile Cys Gly Val Leu     Val Thr Thr
    14465           14470                   14475

Arg Arg Arg Lys Lys Glu Gly     Glu Tyr Asn Val Gln     Gln Gln Cys
    14480           14485                   14490

Pro Gly Tyr Tyr Gln Ser His     Leu Asp Leu Glu Asp     Leu Gln
    14495           14500                   14505

<210> SEQ ID NO 68
<211> LENGTH: 906
<212> TYPE: PRT
<213> ORGANISM: Homo sapiens

<400> SEQUENCE: 68

Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
                20                  25                  30

Lys Thr Gly Phe Pro Glu Asp Val Tyr Ser Ala Val Leu Ser Lys Asp
            35                  40                  45

Val His Glu Gly Gln Pro Leu Leu Asn Val Lys Phe Ser Asn Cys Asn
        50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
                100                 105                 110

Glu Lys Trp Gln Val Ala Val Lys Leu Ser Leu Lys Pro Thr Leu Thr
            115                 120                 125

Glu Glu Ser Val Lys Glu Ser Ala Glu Val Glu Glu Ile Val Phe Pro
        130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
                180                 185                 190

Leu Arg Tyr Ser Val Thr Gly Pro Gly Ala Asp Gln Pro Pro Thr Gly
            195                 200                 205

Ile Phe Ile Ile Asn Pro Ile Ser Gly Gln Leu Ser Val Thr Lys Pro
        210                 215                 220

Leu Asp Arg Glu Gln Ile Ala Arg Phe His Leu Arg Ala His Ala Val
```

```
              225                 230                 235                 240
Asp Ile Asn Gly Asn Gln Val Glu Asn Pro Ile Asp Ile Val Ile Asn
                245                 250                 255
Val Ile Asp Met Asn Asp Asn Arg Pro Glu Phe Leu His Gln Val Trp
            260                 265                 270
Asn Gly Thr Val Pro Glu Gly Ser Lys Pro Gly Thr Tyr Val Met Thr
        275                 280                 285
Val Thr Ala Ile Asp Ala Asp Pro Asn Ala Leu Asn Gly Met Leu
    290                 295                 300
Arg Tyr Arg Ile Val Ser Gln Ala Pro Ser Thr Pro Ser Pro Asn Met
305                 310                 315                 320
Phe Thr Ile Asn Asn Glu Thr Gly Asp Ile Ile Thr Val Ala Ala Gly
                325                 330                 335
Leu Asp Arg Glu Lys Val Gln Gln Tyr Thr Leu Ile Ile Gln Ala Thr
            340                 345                 350
Asp Met Glu Gly Asn Pro Thr Tyr Gly Leu Ser Asn Thr Ala Thr Ala
        355                 360                 365
Val Ile Thr Val Thr Asp Val Asn Asp Asn Pro Pro Glu Phe Thr Ala
    370                 375                 380
Met Thr Phe Tyr Gly Glu Val Pro Glu Asn Arg Val Asp Ile Ile Val
385                 390                 395                 400
Ala Asn Leu Thr Val Thr Asp Lys Asp Gln Pro His Thr Pro Ala Trp
                405                 410                 415
Asn Ala Val Tyr Arg Ile Ser Gly Gly Asp Pro Thr Gly Arg Phe Ala
            420                 425                 430
Ile Gln Thr Asp Pro Asn Ser Asn Asp Gly Leu Val Thr Val Val Lys
        435                 440                 445
Pro Ile Asp Phe Glu Thr Asn Arg Met Phe Val Leu Thr Val Ala Ala
    450                 455                 460
Glu Asn Gln Val Pro Leu Ala Lys Gly Ile Gln His Pro Pro Gln Ser
465                 470                 475                 480
Thr Ala Thr Val Ser Val Thr Val Ile Asp Val Asn Glu Asn Pro Tyr
                485                 490                 495
Phe Ala Pro Asn Pro Lys Ile Ile Arg Gln Glu Glu Gly Leu His Ala
            500                 505                 510
Gly Thr Met Leu Thr Thr Phe Thr Ala Gln Asp Pro Asp Arg Tyr Met
        515                 520                 525
Gln Gln Asn Ile Arg Tyr Thr Lys Leu Ser Asp Pro Ala Asn Trp Leu
    530                 535                 540
Lys Ile Asp Pro Val Asn Gly Gln Ile Thr Thr Ile Ala Val Leu Asp
545                 550                 555                 560
Arg Glu Ser Pro Asn Val Lys Asn Asn Ile Tyr Asn Ala Thr Phe Leu
                565                 570                 575
Ala Ser Asp Asn Gly Ile Pro Pro Met Ser Gly Thr Gly Thr Leu Gln
            580                 585                 590
Ile Tyr Leu Leu Asp Ile Asn Asp Asn Ala Pro Gln Val Leu Pro Gln
        595                 600                 605
Glu Ala Glu Thr Cys Glu Thr Pro Asp Pro Asn Ser Ile Asn Ile Thr
    610                 615                 620
Ala Leu Asp Tyr Asp Ile Asp Pro Asn Ala Gly Pro Phe Ala Phe Asp
625                 630                 635                 640
Leu Pro Leu Ser Pro Val Thr Ile Lys Arg Asn Trp Thr Ile Thr Arg
                645                 650                 655
```

-continued

Leu Asn Gly Asp Phe Ala Gln Leu Asn Leu Lys Ile Lys Phe Leu Glu
                660                 665                 670

Ala Gly Ile Tyr Glu Val Pro Ile Ile Thr Asp Ser Gly Asn Pro
            675                 680                 685

Pro Lys Ser Asn Ile Ser Ile Leu Arg Val Lys Val Cys Gln Cys Asp
        690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
                725                 730                 735

Ile Leu Val Leu Met Phe Val Val Trp Met Lys Arg Asp Lys Glu
            740                 745                 750

Arg Gln Ala Lys Gln Leu Leu Ile Asp Pro Glu Asp Val Arg Asp
        755                 760                 765

Asn Ile Leu Lys Tyr Asp Glu Glu Gly Gly Glu Glu Asp Gln Asp
    770                 775                 780

Tyr Asp Leu Ser Gln Leu Gln Gln Pro Asp Thr Val Glu Pro Asp Ala
785                 790                 795                 800

Ile Lys Pro Val Gly Ile Arg Arg Met Asp Glu Arg Pro Ile His Ala
                805                 810                 815

Glu Pro Gln Tyr Pro Val Arg Ser Ala Ala Pro His Pro Gly Asp Ile
            820                 825                 830

Gly Asp Phe Ile Asn Glu Gly Leu Lys Ala Ala Asp Asn Asp Pro Thr
        835                 840                 845

Ala Pro Pro Tyr Asp Ser Leu Leu Val Phe Asp Tyr Glu Gly Ser Gly
    850                 855                 860

Ser Thr Ala Gly Ser Leu Ser Ser Leu Asn Ser Ser Ser Ser Gly Gly
865                 870                 875                 880

Glu Gln Asp Tyr Asp Tyr Leu Asn Asp Trp Gly Pro Arg Phe Lys Lys
                885                 890                 895

Leu Ala Asp Met Tyr Gly Gly Gly Asp Asp
            900                 905

<210> SEQ ID NO 69
<211> LENGTH: 294
<212> TYPE: PRT
<213> ORGANISM: Homo sapiens

<400> SEQUENCE: 69

Met Glu Asp Ser Met Asp Met Ser Pro Leu Arg Pro Gln Asn
1               5                   10                  15

Tyr Leu Phe Gly Cys Glu Leu Lys Ala Asp Lys Asp Tyr His Phe Lys
                20                  25                  30

Val Asp Asn Asp Glu Asn Glu His Gln Leu Ser Leu Arg Thr Val Ser
            35                  40                  45

Leu Gly Ala Gly Ala Lys Asp Glu Leu His Ile Val Glu Ala Glu Ala
        50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu

```
                115                 120                 125
Glu Glu Glu Asp Val Lys Leu Leu Ser Ile Ser Gly Lys Arg Ser Ala
    130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Asp Asp Glu Asp
                165                 170                 175

Asp Asp Asp Asp Phe Asp Asp Glu Glu Ala Glu Glu Lys Ala Pro Val
            180                 185                 190

Lys Lys Ser Ile Arg Asp Thr Pro Ala Lys Asn Ala Gln Lys Ser Asn
                195                 200                 205

Gln Asn Gly Lys Asp Ser Lys Pro Ser Ser Thr Pro Arg Ser Lys Gly
    210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Gly Gly Ser Leu Pro Lys Val Glu Ala Lys Phe Ile Asn Tyr Val
            260                 265                 270

Lys Asn Cys Phe Arg Met Thr Asp Gln Glu Ala Ile Gln Asp Leu Trp
                275                 280                 285

Gln Trp Arg Lys Ser Leu
    290

<210> SEQ ID NO 70
<211> LENGTH: 180
<212> TYPE: PRT
<213> ORGANISM: Homo sapiens

<400> SEQUENCE: 70

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180
```

<210> SEQ ID NO 71
<211> LENGTH: 314
<212> TYPE: PRT
<213> ORGANISM: Homo sapiens

<400> SEQUENCE: 71

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
                180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
                260                 265                 270

Phe His Ser His Glu Phe His Ser His Glu Asp Met Leu Val Val Asp
            275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 72
<211> LENGTH: 393
<212> TYPE: PRT
<213> ORGANISM: Homo sapiens

<400> SEQUENCE: 72

Met Glu Glu Pro Gln Ser Asp Pro Ser Val Glu Pro Pro Leu Ser Gln
1               5                   10                  15

```
Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 73
<211> LENGTH: 636
<212> TYPE: PRT
<213> ORGANISM: Homo sapiens

<400> SEQUENCE: 73
```

```
Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
                180                 185                 190

Arg Cys Pro Asn His Glu Leu Gly Arg Asp Phe Asn Glu Gly Gln Ser
                195                 200                 205

Ala Pro Ala Ser His Leu Ile Arg Val Glu Gly Asn Asn Leu Ser Gln
            210                 215                 220

Tyr Val Asp Asp Pro Val Thr Gly Arg Gln Ser Val Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Met Arg Asp Gly Gln Val Leu Gly Arg Arg
            275                 280                 285

Ser Phe Glu Gly Arg Ile Cys Ala Cys Pro Gly Arg Asp Arg Lys Ala
        290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415
```

-continued

```
Val His Gly Gly Met Asn Lys Leu Pro Ser Val Asn Gln Leu Val Gly
            420                 425                 430

Gln Pro Pro His Ser Ser Ala Ala Thr Pro Asn Leu Gly Pro Val
        435                 440                 445

Gly Pro Gly Met Leu Asn Asn His Gly His Ala Val Pro Ala Asn Gly
450                 455                 460

Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Ser Phe
                485                 490                 495

Leu Thr Gly Leu Gly Cys Pro Asn Cys Ile Glu Tyr Phe Thr Ser Gln
            500                 505                 510

Gly Leu Gln Ser Ile Tyr His Leu Gln Asn Leu Thr Ile Glu Asp Leu
        515                 520                 525

Gly Ala Leu Lys Ile Pro Glu Gln Tyr Arg Met Thr Ile Trp Arg Gly
530                 535                 540

Leu Gln Asp Leu Lys Gln Gly His Asp Tyr Ser Thr Ala Gln Gln Leu
545                 550                 555                 560

Leu Arg Ser Ser Asn Ala Ala Thr Ile Ser Ile Gly Gly Ser Gly Glu
                565                 570                 575

Leu Gln Arg Gln Arg Val Met Glu Ala Val His Phe Arg Val Arg His
            580                 585                 590

Thr Ile Thr Ile Pro Asn Arg Gly Gly Pro Gly Gly Pro Asp Glu
        595                 600                 605

Trp Ala Asp Phe Gly Phe Asp Leu Pro Asp Cys Lys Ala Arg Lys Gln
610                 615                 620

Pro Ile Lys Glu Glu Phe Thr Glu Ala Glu Ile His
625                 630                 635

<210> SEQ ID NO 74
<211> LENGTH: 450
<212> TYPE: PRT
<213> ORGANISM: Homo sapiens

<400> SEQUENCE: 74

Met Pro His Asn Ser Ile Arg Ser Gly His Gly Gly Leu Asn Gln Leu
1               5                   10                  15

Gly Gly Ala Phe Val Asn Gly Arg Pro Leu Pro Glu Val Val Arg Gln
            20                  25                  30

Arg Ile Val Asp Leu Ala His Gln Gly Val Arg Pro Cys Asp Ile Ser
        35                  40                  45

Arg Gln Leu Arg Val Ser His Gly Cys Val Ser Lys Ile Leu Gly Arg
    50                  55                  60

Tyr Tyr Glu Thr Gly Ser Ile Arg Pro Gly Val Ile Gly Gly Ser Lys
65                  70                  75                  80

Pro Lys Val Ala Thr Pro Lys Val Val Glu Lys Ile Gly Asp Tyr Lys
                85                  90                  95

Arg Gln Asn Pro Thr Met Phe Ala Trp Glu Ile Arg Asp Arg Leu Leu
            100                 105                 110

Ala Glu Gly Val Cys Asp Asn Asp Thr Val Pro Ser Val Ser Ser Ile
        115                 120                 125

Asn Arg Ile Ile Arg Thr Lys Val Gln Gln Pro Phe Asn Leu Pro Met
    130                 135                 140

Asp Ser Cys Val Ala Thr Lys Ser Leu Ser Pro Gly His Thr Leu Ile
145                 150                 155                 160
```

```
Pro Ser Ser Ala Val Thr Pro Pro Glu Ser Pro Gln Ser Asp Ser Leu
                165                 170                 175

Gly Ser Thr Tyr Ser Ile Asn Gly Leu Leu Gly Ile Ala Gln Pro Gly
            180                 185                 190

Ser Asp Lys Arg Lys Met Asp Asp Ser Asp Gln Asp Ser Cys Arg Leu
        195                 200                 205

Ser Ile Asp Ser Gln Ser Ser Ser Gly Pro Arg Lys His Leu Arg
    210                 215                 220

Thr Asp Ala Phe Ser Gln His His Leu Glu Pro Leu Glu Cys Pro Phe
225                 230                 235                 240

Glu Arg Gln His Tyr Pro Glu Ala Tyr Ala Ser Pro Ser His Thr Lys
                245                 250                 255

Gly Glu Gln Gly Leu Tyr Pro Leu Pro Leu Leu Asn Ser Thr Leu Asp
            260                 265                 270

Asp Gly Lys Ala Thr Leu Thr Pro Ser Asn Thr Pro Leu Gly Arg Asn
        275                 280                 285

Leu Ser Thr His Gln Thr Tyr Pro Val Val Ala Asp Pro His Ser Pro
    290                 295                 300

Phe Ala Ile Lys Gln Glu Thr Pro Glu Val Ser Ser Ser Ser Ser Thr
305                 310                 315                 320

Pro Ser Ser Leu Ser Ser Ala Phe Leu Asp Leu Gln Gln Val Gly
                325                 330                 335

Ser Gly Val Pro Pro Phe Asn Ala Phe Pro His Ala Ala Ser Val Tyr
            340                 345                 350

Gly Gln Phe Thr Gly Gln Ala Leu Leu Ser Gly Arg Glu Met Val Gly
        355                 360                 365

Pro Thr Leu Pro Gly Tyr Pro Pro His Ile Pro Thr Ser Gly Gln Gly
    370                 375                 380

Ser Tyr Ala Ser Ser Ala Ile Ala Gly Met Val Ala Gly Ser Glu Tyr
385                 390                 395                 400

Ser Gly Asn Ala Tyr Gly His Thr Pro Tyr Ser Ser Tyr Ser Glu Ala
                405                 410                 415

Trp Arg Phe Pro Asn Ser Ser Leu Leu Ser Ser Pro Tyr Tyr Tyr Ser
            420                 425                 430

Ser Thr Ser Arg Pro Ser Ala Pro Pro Thr Thr Ala Thr Ala Phe Asp
        435                 440                 445

His Leu
    450

<210> SEQ ID NO 75
<211> LENGTH: 290
<212> TYPE: PRT
<213> ORGANISM: Homo sapiens

<400> SEQUENCE: 75

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
```

```
                 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 76
<211> LENGTH: 535
<212> TYPE: PRT
<213> ORGANISM: Homo sapiens

<400> SEQUENCE: 76

Met Leu Gly Pro Cys Met Leu Leu Leu Leu Leu Leu Leu Gly Leu Arg
1               5                  10                  15

Leu Gln Leu Ser Leu Gly Ile Ile Pro Val Glu Glu Glu Asn Pro Asp
                20                  25                  30

Phe Trp Asn Arg Glu Ala Ala Glu Ala Leu Gly Ala Ala Lys Lys Leu
            35                  40                  45

Gln Pro Ala Gln Thr Ala Ala Lys Asn Leu Ile Ile Phe Leu Gly Asp
        50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
                100                 105                 110

Asp Ser Gly Ala Thr Ala Thr Ala Tyr Leu Cys Gly Val Lys Gly Asn
            115                 120                 125

Phe Gln Thr Ile Gly Leu Ser Ala Ala Ala Arg Phe Asn Gln Cys Asn
        130                 135                 140
```

```
Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
            165                 170                 175

Ser Pro Ala Gly Thr Tyr Ala His Thr Val Asn Arg Asn Trp Tyr Ser
            180                 185                 190

Asp Ala Asp Val Pro Ala Ser Ala Arg Gln Glu Gly Cys Gln Asp Ile
            195                 200                 205

Ala Thr Gln Leu Ile Ser Asn Met Asp Ile Asp Val Ile Leu Gly Gly
210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
            245                 250                 255

Gln Glu Trp Leu Ala Lys Arg Gln Gly Ala Arg Tyr Val Trp Asn Arg
            260                 265                 270

Thr Glu Leu Met Gln Ala Ser Leu Asp Pro Ser Val Thr His Leu Met
            275                 280                 285

Gly Leu Phe Glu Pro Gly Asp Met Lys Tyr Glu Ile His Arg Asp Ser
290                 295                 300

Thr Leu Asp Pro Ser Leu Met Glu Met Thr Glu Ala Ala Leu Arg Leu
305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
            340                 345                 350

Thr Ile Met Phe Asp Asp Ala Ile Glu Arg Ala Gly Gln Leu Thr Ser
            355                 360                 365

Glu Glu Asp Thr Leu Ser Leu Val Thr Ala Asp His Ser His Val Phe
370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
            405                 410                 415

Asn Gly Pro Gly Tyr Val Leu Lys Asp Gly Ala Arg Pro Asp Val Thr
            420                 425                 430

Glu Ser Glu Ser Gly Ser Pro Glu Tyr Arg Gln Gln Ser Ala Val Pro
            435                 440                 445

Leu Asp Glu Glu Thr His Ala Gly Glu Asp Val Ala Val Phe Ala Arg
450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
            485                 490                 495

Asp Leu Ala Pro Pro Ala Gly Thr Thr Asp Ala Ala His Pro Gly Arg
            500                 505                 510

Ser Val Val Pro Ala Leu Leu Pro Leu Leu Ala Gly Thr Leu Leu Leu
            515                 520                 525

Leu Glu Thr Ala Thr Ala Pro
530                 535

<210> SEQ ID NO 77
<211> LENGTH: 375
<212> TYPE: PRT
```

<213> ORGANISM: Homo sapiens

<400> SEQUENCE: 77

```
Met Leu Leu Phe Leu Leu Ser Ala Leu Val Leu Leu Thr Gln Pro Leu
1               5                   10                  15
Gly Tyr Leu Glu Ala Glu Met Lys Thr Tyr Ser His Arg Thr Met Pro
            20                  25                  30
Ser Ala Cys Thr Leu Val Met Cys Ser Ser Val Glu Ser Gly Leu Pro
        35                  40                  45
Gly Arg Asp Gly Arg Asp Gly Arg Glu Gly Pro Arg Gly Glu Lys Gly
    50                  55                  60
Asp Pro Gly Leu Pro Gly Ala Ala Gly Gln Ala Gly Met Pro Gly Gln
65                  70                  75                  80
Ala Gly Pro Val Gly Pro Lys Gly Asp Asn Gly Ser Val Gly Glu Pro
                85                  90                  95
Gly Pro Lys Gly Asp Thr Gly Pro Ser Gly Pro Pro Gly Pro Pro Gly
            100                 105                 110
Val Pro Gly Pro Ala Gly Arg Glu Gly Pro Leu Gly Lys Gln Gly Asn
            115                 120                 125
Ile Gly Pro Gln Gly Lys Pro Gly Pro Lys Gly Glu Ala Gly Pro Lys
    130                 135                 140
Gly Glu Val Gly Ala Pro Gly Met Gln Gly Ser Ala Gly Ala Arg Gly
145                 150                 155                 160
Leu Ala Gly Pro Lys Gly Glu Arg Gly Val Pro Gly Glu Arg Gly Val
                165                 170                 175
Pro Gly Asn Thr Gly Ala Ala Gly Ser Ala Gly Ala Met Gly Pro Gln
            180                 185                 190
Gly Ser Pro Gly Ala Arg Gly Pro Pro Gly Leu Lys Gly Asp Lys Gly
            195                 200                 205
Ile Pro Gly Asp Lys Gly Ala Lys Gly Glu Ser Gly Leu Pro Asp Val
    210                 215                 220
Ala Ser Leu Arg Gln Gln Val Glu Ala Leu Gln Gly Gln Val Gln His
225                 230                 235                 240
Leu Gln Ala Ala Phe Ser Gln Tyr Lys Lys Val Glu Leu Phe Pro Asn
                245                 250                 255
Gly Gln Ser Val Gly Glu Lys Ile Phe Lys Thr Ala Gly Phe Val Lys
            260                 265                 270
Pro Phe Thr Glu Ala Gln Leu Leu Cys Thr Gln Ala Gly Gly Gln Leu
            275                 280                 285
Ala Ser Pro Arg Ser Ala Ala Glu Asn Ala Ala Leu Gln Gln Leu Val
    290                 295                 300
Val Ala Lys Asn Glu Ala Ala Phe Leu Ser Met Thr Asp Ser Lys Thr
305                 310                 315                 320
Glu Gly Lys Phe Thr Tyr Pro Thr Gly Glu Ser Leu Val Tyr Ser Asn
                325                 330                 335
Trp Ala Pro Gly Glu Pro Asn Asp Asp Gly Gly Ser Glu Asp Cys Val
            340                 345                 350
Glu Ile Phe Thr Asn Gly Lys Trp Asn Asp Arg Ala Cys Gly Glu Lys
            355                 360                 365
Arg Leu Val Val Cys Glu Phe
    370                 375
```

<210> SEQ ID NO 78
<211> LENGTH: 248

```
<212> TYPE: PRT
<213> ORGANISM: Homo sapiens

<400> SEQUENCE: 78

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Leu Lys Gly Asp Pro Gly Pro Gly Pro Met Gly Pro Pro Gly
    50                  55                  60

Glu Met Pro Cys Pro Pro Gly Asn Asp Gly Leu Pro Gly Ala Pro Gly
65                  70                  75                  80

Ile Pro Gly Glu Cys Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 79
<211> LENGTH: 904
<212> TYPE: PRT
<213> ORGANISM: Homo sapiens

<400> SEQUENCE: 79

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95
```

```
Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
    450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
```

```
              515                 520                 525
Leu Glu Lys Leu Glu Ile Leu Asp Leu Gln His Asn Asn Leu Ala Arg
        530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
                580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
        610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
        690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
        770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
                820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
        850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 80
<211> LENGTH: 455
<212> TYPE: PRT
<213> ORGANISM: Homo sapiens
```

<400> SEQUENCE: 80

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65              70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala

```
                405                 410                 415
Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
            450                 455

<210> SEQ ID NO 81
<211> LENGTH: 390
<212> TYPE: PRT
<213> ORGANISM: Homo sapiens

<400> SEQUENCE: 81

Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
            20                  25                  30

Lys Asp Leu Lys Pro Val Leu Asp Ser Tyr Val Phe Asn Asp Gly Ser
        35                  40                  45

Ser Arg Glu Leu Met Asn Leu Thr Gly Thr Ile Pro Val Pro Tyr Arg
    50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
    130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320
```

-continued

Thr Ala Pro Leu Tyr Lys Gln Ile Leu Asn Leu Tyr Ala Glu Glu Asn
                    325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
            355                 360                 365

Lys Gln Phe Gln Leu Arg Ala Leu Met Gln Lys Ala Arg Lys Thr Ala
370                 375                 380

Gly Leu Ser Asp Leu Tyr
385                 390

<210> SEQ ID NO 82
<211> LENGTH: 237
<212> TYPE: PRT
<213> ORGANISM: Homo sapiens

<400> SEQUENCE: 82

Met Ala Gly Val Ser Ala Cys Ile Lys Tyr Ser Met Phe Thr Phe Asn
1               5                   10                  15

Phe Leu Phe Trp Leu Cys Gly Ile Leu Ile Leu Ala Leu Ala Ile Trp
                20                  25                  30

Val Arg Val Ser Asn Asp Ser Gln Ala Ile Phe Gly Ser Glu Asp Val
            35                  40                  45

Gly Ser Ser Tyr Val Ala Val Asp Ile Leu Ile Ala Val Gly Ala
        50                  55                  60

Ile Ile Met Ile Leu Gly Phe Leu Gly Cys Cys Gly Ala Ile Lys Glu
65                  70                  75                  80

Ser Arg Cys Met Leu Leu Leu Phe Phe Ile Gly Leu Leu Ile Leu
                85                  90                  95

Leu Leu Gln Val Ala Thr Gly Ile Leu Gly Ala Val Phe Lys Ser Lys
                100                 105                 110

Ser Asp Arg Ile Val Asn Glu Thr Leu Tyr Glu Asn Thr Lys Leu Leu
            115                 120                 125

Ser Ala Thr Gly Glu Ser Glu Lys Gln Phe Gln Glu Ala Ile Ile Val
        130                 135                 140

Phe Gln Glu Glu Phe Lys Cys Cys Gly Leu Val Asn Gly Ala Ala Asp
145                 150                 155                 160

Trp Gly Asn Asn Phe Gln His Tyr Pro Glu Leu Cys Ala Cys Leu Asp
                165                 170                 175

Lys Gln Arg Pro Cys Gln Ser Tyr Asn Gly Lys Gln Val Tyr Lys Glu
            180                 185                 190

Thr Cys Ile Ser Phe Ile Lys Asp Phe Leu Ala Lys Asn Leu Ile Ile
        195                 200                 205

Val Ile Gly Ile Ser Phe Gly Leu Ala Val Ile Glu Ile Leu Gly Leu
210                 215                 220

Val Phe Ser Met Val Leu Tyr Cys Gln Ile Gly Asn Lys
225                 230                 235

<210> SEQ ID NO 83
<211> LENGTH: 1356
<212> TYPE: PRT
<213> ORGANISM: Homo sapiens

<400> SEQUENCE: 83

Met Gln Ser Lys Val Leu Leu Ala Val Ala Leu Trp Leu Cys Val Glu
1               5                   10                  15

```
Thr Arg Ala Ala Ser Val Gly Leu Pro Ser Val Ser Leu Asp Leu Pro
             20                  25                  30

Arg Leu Ser Ile Gln Lys Asp Ile Leu Thr Ile Lys Ala Asn Thr Thr
         35                  40                  45

Leu Gln Ile Thr Cys Arg Gly Gln Arg Asp Leu Asp Trp Leu Trp Pro
 50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
             85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
```

-continued

```
            435                 440                 445
Ala Ile Pro Pro His His Ile His Trp Tyr Trp Gln Leu Glu Glu
450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
                500                 505                 510
Thr Val Ser Thr Leu Val Ile Gln Ala Asn Val Ser Ala Leu Tyr
            515                 520                 525
Lys Cys Glu Ala Val Asn Lys Val Gly Arg Gly Glu Arg Val Ile Ser
530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
            595                 600                 605
Leu Trp Lys Leu Asn Ala Thr Met Phe Ser Asn Ser Thr Asn Asp Ile
            610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
            675                 680                 685
Thr Ala Ser Gly Asn Pro Pro Pro Gln Ile Met Trp Phe Lys Asp Asn
            690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu Ile Ile Ile Leu
            755                 760                 765
Val Gly Thr Ala Val Ile Ala Met Phe Phe Trp Leu Leu Leu Val Ile
            770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
                820                 825                 830
Arg Leu Lys Leu Gly Lys Pro Leu Gly Arg Gly Ala Phe Gly Gln Val
            835                 840                 845
Ile Glu Ala Asp Ala Phe Gly Ile Asp Lys Thr Ala Thr Cys Arg Thr
850                 855                 860
```

-continued

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Ala Pro
                980                 985                 990

Glu Asp Leu Tyr Lys Asp Phe Leu Thr Leu Glu His Leu Ile Cys Tyr
                995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

```
Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 84
<211> LENGTH: 459
<212> TYPE: PRT
<213> ORGANISM: Homo sapiens

<400> SEQUENCE: 84

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
            35                  40                  45

Leu Gly Gly Gly Ser Ser Gly Glu Asp Asp Pro Leu Gly Glu Glu Asp
50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Glu Gly Ser Leu Lys Leu Glu Asp
            100                 105                 110

Leu Pro Thr Val Glu Ala Pro Gly Asp Pro Gln Glu Pro Gln Asn Asn
            115                 120                 125

Ala His Arg Asp Lys Glu Gly Asp Asp Gln Ser His Trp Arg Tyr Gly
        130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
            195                 200                 205

Gly Leu Glu Met Ala Leu Gly Pro Gly Arg Glu Tyr Arg Ala Leu Gln
        210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270
```

-continued

```
Ala Val Leu Ala Ala Phe Leu Glu Glu Gly Pro Glu Asn Ser Ala
            275                 280                 285

Tyr Glu Gln Leu Leu Ser Arg Leu Glu Glu Ile Ala Glu Glu Gly Ser
290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
                340                 345                 350

Ala Lys Gln Leu His Thr Leu Ser Asp Thr Leu Trp Gly Pro Gly Asp
                355                 360                 365

Ser Arg Leu Gln Leu Asn Phe Arg Ala Thr Gln Pro Leu Asn Gly Arg
370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
                420                 425                 430

Val Gln Met Arg Arg Gln His Arg Arg Gly Thr Lys Gly Gly Val Ser
                435                 440                 445

Tyr Arg Pro Ala Glu Val Ala Glu Thr Gly Ala
450                 455

<210> SEQ ID NO 85
<211> LENGTH: 385
<212> TYPE: PRT
<213> ORGANISM: Homo sapiens

<400> SEQUENCE: 85

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
                100                 105                 110

Asp Pro Asp Arg Asn His Leu Thr Arg Ala Pro Arg Val Lys Trp Val
            115                 120                 125

Arg Ala Gln Ala Val Val Leu Val Leu Glu Pro Gly Thr Val Phe Thr
130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
```

-continued

```
                180                 185                 190
Asp Ser Asp Asp Gln Trp Gly Glu Tyr Ser Cys Val Phe Leu Pro Glu
            195                 200                 205
Pro Met Gly Thr Ala Asn Ile Gln Leu His Gly Pro Pro Arg Val Lys
        210                 215                 220
Ala Val Lys Ser Ser Glu His Ile Asn Glu Gly Thr Ala Met Leu
225                 230                 235                 240
Val Cys Lys Ser Glu Ser Val Pro Pro Val Thr Asp Trp Ala Trp Tyr
            245                 250                 255
Lys Ile Thr Asp Ser Glu Asp Lys Ala Leu Met Asn Gly Ser Glu Ser
        260                 265                 270
Arg Phe Phe Val Ser Ser Ser Gln Gly Arg Ser Glu Leu His Ile Glu
    275                 280                 285
Asn Leu Asn Met Glu Ala Asp Pro Gly Gln Tyr Arg Cys Asn Gly Thr
        290                 295                 300
Ser Ser Lys Gly Ser Asp Gln Ala Ile Ile Thr Leu Arg Val Arg Ser
305                 310                 315                 320
His Leu Ala Ala Leu Trp Pro Phe Leu Gly Ile Val Ala Glu Val Leu
            325                 330                 335
Val Leu Val Thr Ile Ile Phe Ile Tyr Glu Lys Arg Arg Lys Pro Glu
        340                 345                 350
Asp Val Leu Asp Asp Asp Ala Gly Ser Ala Pro Leu Lys Ser Ser
        355                 360                 365
Gly Gln His Gln Asn Asp Lys Gly Lys Asn Val Arg Gln Arg Asn Ser
    370                 375                 380
Ser
385

<210> SEQ ID NO 86
<211> LENGTH: 211
<212> TYPE: PRT
<213> ORGANISM: Homo sapiens

<400> SEQUENCE: 86

Met Ala Asn Ala Gly Leu Gln Leu Leu Gly Phe Ile Leu Ala Phe Leu
1               5                   10                  15
Gly Trp Ile Gly Ala Ile Val Ser Thr Ala Leu Pro Gln Trp Arg Ile
            20                  25                  30
Tyr Ser Tyr Ala Gly Asp Asn Ile Val Thr Ala Gln Ala Met Tyr Glu
        35                  40                  45
Gly Leu Trp Met Ser Cys Val Ser Gln Ser Thr Gly Gln Ile Gln Cys
    50                  55                  60
Lys Val Phe Asp Ser Leu Leu Asn Leu Ser Ser Thr Leu Gln Ala Thr
65                  70                  75                  80
Arg Ala Leu Met Val Val Gly Ile Leu Leu Gly Val Ile Ala Ile Phe
            85                  90                  95
Val Ala Thr Val Gly Met Lys Cys Met Lys Cys Leu Glu Asp Asp Glu
        100                 105                 110
Val Gln Lys Met Arg Met Ala Val Ile Gly Gly Ala Ile Phe Leu Leu
    115                 120                 125
Ala Gly Leu Ala Ile Leu Val Ala Thr Ala Trp Tyr Gly Asn Arg Ile
130                 135                 140
Val Gln Glu Phe Tyr Asp Pro Met Thr Pro Val Asn Ala Arg Tyr Glu
145                 150                 155                 160
```

```
Phe Gly Gln Ala Leu Phe Thr Gly Trp Ala Ala Ser Leu Cys Leu
                165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
        195                 200                 205

Asp Tyr Val
    210

<210> SEQ ID NO 87
<211> LENGTH: 4544
<212> TYPE: PRT
<213> ORGANISM: Homo sapiens

<400> SEQUENCE: 87

Met Leu Thr Pro Pro Leu Leu Leu Leu Pro Leu Leu Ser Ala Leu
1               5                   10                  15

Val Ala Ala Ala Ile Asp Ala Pro Lys Thr Cys Ser Pro Lys Gln Phe
                20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
        50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Asp Arg Ile
290                 295                 300

Phe Val Cys Asn Arg Asn Gly Asp Thr Cys Val Thr Leu Leu Asp Leu
305                 310                 315                 320
```

```
Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735
```

```
Tyr Glu Gly Pro Glu Leu Asn His Ala Phe Gly Leu Cys His His Gly
             740                 745                 750

Asn Tyr Leu Phe Trp Thr Glu Tyr Arg Ser Gly Ser Val Tyr Arg Leu
         755                 760                 765

Glu Arg Gly Val Gly Gly Ala Pro Pro Thr Val Thr Leu Leu Arg Ser
     770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                 805                 810                 815

Leu Cys Leu Ala Thr Pro Gly Ser Arg Gln Cys Ala Cys Ala Glu Asp
         820                 825                 830

Gln Val Leu Asp Ala Asp Gly Val Thr Cys Leu Ala Asn Pro Ser Tyr
     835                 840                 845

Val Pro Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                 885                 890                 895

Ser Asp Arg Phe Lys Cys Glu Asn Asn Arg Cys Ile Pro Asn Arg Trp
         900                 905                 910

Leu Cys Asp Gly Asp Asn Asp Cys Gly Asn Ser Glu Asp Glu Ser Asn
     915                 920                 925

Ala Thr Cys Ser Ala Arg Thr Cys Pro Pro Asn Gln Phe Ser Cys Ala
     930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                 965                 970                 975

Phe Pro Leu Thr Gln Phe Thr Cys Asn Asn Gly Arg Cys Ile Asn Ile
         980                 985                 990

Asn Trp Arg Cys Asp Asn Asp Asn Asp Cys Gly Asp Asn Ser Asp Glu
     995                 1000                1005

Ala Gly Cys Ser His Ser Cys Ser Ser Thr Gln Phe Lys Cys Asn
     1010                1015                1020

Ser Gly Arg Cys Ile Pro Glu His Trp Thr Cys Asp Gly Asp Asn
     1025                1030                1035

Asp Cys Gly Asp Tyr Ser Asp Glu Thr His Ala Asn Cys Thr Asn
     1040                1045                1050

Gln Ala Thr Arg Pro Pro Gly Gly Cys His Thr Asp Glu Phe Gln
     1055                1060                1065

Cys Arg Leu Asp Gly Leu Cys Ile Pro Leu Arg Trp Arg Cys Asp
     1070                1075                1080

Gly Asp Thr Asp Cys Met Asp Ser Ser Asp Glu Lys Ser Cys Glu
     1085                1090                1095

Gly Val Thr His Val Cys Asp Pro Ser Val Lys Phe Gly Cys Lys
     1100                1105                1110

Asp Ser Ala Arg Cys Ile Ser Lys Ala Trp Val Cys Asp Gly Asp
     1115                1120                1125

Asn Asp Cys Glu Asp Asn Ser Asp Glu Glu Asn Cys Glu Ser Leu
     1130                1135                1140

Ala Cys Arg Pro Pro Ser His Pro Cys Ala Asn Asn Thr Ser Val
```

-continued

```
            1145                1150                1155

Cys Leu Pro Pro Asp Lys Leu Cys Asp Gly Asn Asp Asp Cys Gly
        1160                1165                1170

Asp Gly Ser Asp Glu Gly Glu Leu Cys Asp Gln Cys Ser Leu Asn
        1175                1180                1185

Asn Gly Gly Cys Ser His Asn Cys Ser Val Ala Pro Gly Glu Gly
        1190                1195                1200

Ile Val Cys Ser Cys Pro Leu Gly Met Glu Leu Gly Pro Asp Asn
        1205                1210                1215

His Thr Cys Gln Ile Gln Ser Tyr Cys Ala Lys His Leu Lys Cys
        1220                1225                1230

Ser Gln Lys Cys Asp Gln Asn Lys Phe Ser Val Lys Cys Ser Cys
        1235                1240                1245

Tyr Glu Gly Trp Val Leu Glu Pro Asp Gly Glu Ser Cys Arg Ser
        1250                1255                1260

Leu Asp Pro Phe Lys Pro Phe Ile Ile Phe Ser Asn Arg His Glu
        1265                1270                1275

Ile Arg Arg Ile Asp Leu His Lys Gly Asp Tyr Ser Val Leu Val
        1280                1285                1290

Pro Gly Leu Arg Asn Thr Ile Ala Leu Asp Phe His Leu Ser Gln
        1295                1300                1305

Ser Ala Leu Tyr Trp Thr Asp Val Val Glu Asp Lys Ile Tyr Arg
        1310                1315                1320

Gly Lys Leu Leu Asp Asn Gly Ala Leu Thr Ser Phe Glu Val Val
        1325                1330                1335

Ile Gln Tyr Gly Leu Ala Thr Pro Glu Gly Leu Ala Val Asp Trp
        1340                1345                1350

Ile Ala Gly Asn Ile Tyr Trp Val Glu Ser Asn Leu Asp Gln Ile
        1355                1360                1365

Glu Val Ala Lys Leu Asp Gly Thr Leu Arg Thr Thr Leu Leu Ala
        1370                1375                1380

Gly Asp Ile Glu His Pro Arg Ala Ile Ala Leu Asp Pro Arg Asp
        1385                1390                1395

Gly Ile Leu Phe Trp Thr Asp Trp Asp Ala Ser Leu Pro Arg Ile
        1400                1405                1410

Glu Ala Ala Ser Met Ser Gly Ala Gly Arg Arg Thr Val His Arg
        1415                1420                1425

Glu Thr Gly Ser Gly Gly Trp Pro Asn Gly Leu Thr Val Asp Tyr
        1430                1435                1440

Leu Glu Lys Arg Ile Leu Trp Ile Asp Ala Arg Ser Asp Ala Ile
        1445                1450                1455

Tyr Ser Ala Arg Tyr Asp Gly Ser Gly His Met Glu Val Leu Arg
        1460                1465                1470

Gly His Glu Phe Leu Ser His Pro Phe Ala Val Thr Leu Tyr Gly
        1475                1480                1485

Gly Glu Val Tyr Trp Thr Asp Trp Arg Thr Asn Thr Leu Ala Lys
        1490                1495                1500

Ala Asn Lys Trp Thr Gly His Asn Val Thr Val Val Gln Arg Thr
        1505                1510                1515

Asn Thr Gln Pro Phe Asp Leu Gln Val Tyr His Pro Ser Arg Gln
        1520                1525                1530

Pro Met Ala Pro Asn Pro Cys Glu Ala Asn Gly Gly Gln Gly Pro
        1535                1540                1545
```

-continued

```
Cys Ser His Leu Cys Leu Ile Asn Tyr Asn Arg Thr Val Ser Cys
1550                1555                1560

Ala Cys Pro His Leu Met Lys Leu His Lys Asp Asn Thr Thr Cys
1565                1570                1575

Tyr Glu Phe Lys Lys Phe Leu Leu Tyr Ala Arg Gln Met Glu Ile
1580                1585                1590

Arg Gly Val Asp Leu Asp Ala Pro Tyr Tyr Asn Tyr Ile Ile Ser
1595                1600                1605

Phe Thr Val Pro Asp Ile Asp Asn Val Thr Val Leu Asp Tyr Asp
1610                1615                1620

Ala Arg Glu Gln Arg Val Tyr Trp Ser Asp Val Arg Thr Gln Ala
1625                1630                1635

Ile Lys Arg Ala Phe Ile Asn Gly Thr Gly Val Glu Thr Val Val
1640                1645                1650

Ser Ala Asp Leu Pro Asn Ala His Gly Leu Ala Val Asp Trp Val
1655                1660                1665

Ser Arg Asn Leu Phe Trp Thr Ser Tyr Asp Thr Asn Lys Lys Gln
1670                1675                1680

Ile Asn Val Ala Arg Leu Asp Gly Ser Phe Lys Asn Ala Val Val
1685                1690                1695

Gln Gly Leu Glu Gln Pro His Gly Leu Val Val His Pro Leu Arg
1700                1705                1710

Gly Lys Leu Tyr Trp Thr Asp Gly Asp Asn Ile Ser Met Ala Asn
1715                1720                1725

Met Asp Gly Ser Asn Arg Thr Leu Leu Phe Ser Gly Gln Lys Gly
1730                1735                1740

Pro Val Gly Leu Ala Ile Asp Phe Pro Glu Ser Lys Leu Tyr Trp
1745                1750                1755

Ile Ser Ser Gly Asn His Thr Ile Asn Arg Cys Asn Leu Asp Gly
1760                1765                1770

Ser Gly Leu Glu Val Ile Asp Ala Met Arg Ser Gln Leu Gly Lys
1775                1780                1785

Ala Thr Ala Leu Ala Ile Met Gly Asp Lys Leu Trp Trp Ala Asp
1790                1795                1800

Gln Val Ser Glu Lys Met Gly Thr Cys Ser Lys Ala Asp Gly Ser
1805                1810                1815

Gly Ser Val Val Leu Arg Asn Ser Thr Thr Leu Val Met His Met
1820                1825                1830

Lys Val Tyr Asp Glu Ser Ile Gln Leu Asp His Lys Gly Thr Asn
1835                1840                1845

Pro Cys Ser Val Asn Asn Gly Asp Cys Ser Gln Leu Cys Leu Pro
1850                1855                1860

Thr Ser Glu Thr Thr Arg Ser Cys Met Cys Thr Ala Gly Tyr Ser
1865                1870                1875

Leu Arg Ser Gly Gln Gln Ala Cys Glu Gly Val Gly Ser Phe Leu
1880                1885                1890

Leu Tyr Ser Val His Glu Gly Ile Arg Gly Ile Pro Leu Asp Pro
1895                1900                1905

Asn Asp Lys Ser Asp Ala Leu Val Pro Val Ser Gly Thr Ser Leu
1910                1915                1920

Ala Val Gly Ile Asp Phe His Ala Glu Asn Asp Thr Ile Tyr Trp
1925                1930                1935
```

```
Val Asp Met Gly Leu Ser Thr Ile Ser Arg Ala Lys Arg Asp Gln
1940                1945                1950

Thr Trp Arg Glu Asp Val Val Thr Asn Gly Ile Gly Arg Val Glu
1955                1960                1965

Gly Ile Ala Val Asp Trp Ile Ala Gly Asn Ile Tyr Trp Thr Asp
1970                1975                1980

Gln Gly Phe Asp Val Ile Glu Val Ala Arg Leu Asn Gly Ser Phe
1985                1990                1995

Arg Tyr Val Val Ile Ser Gln Gly Leu Asp Lys Pro Arg Ala Ile
2000                2005                2010

Thr Val His Pro Glu Lys Gly Tyr Leu Phe Trp Thr Glu Trp Gly
2015                2020                2025

Gln Tyr Pro Arg Ile Glu Arg Ser Arg Leu Asp Gly Thr Glu Arg
2030                2035                2040

Val Val Leu Val Asn Val Ser Ile Ser Trp Pro Asn Gly Ile Ser
2045                2050                2055

Val Asp Tyr Gln Asp Gly Lys Leu Tyr Trp Cys Asp Ala Arg Thr
2060                2065                2070

Asp Lys Ile Glu Arg Ile Asp Leu Glu Thr Gly Glu Asn Arg Glu
2075                2080                2085

Val Val Leu Ser Ser Asn Asn Met Asp Met Phe Ser Val Ser Val
2090                2095                2100

Phe Glu Asp Phe Ile Tyr Trp Ser Asp Arg Thr His Ala Asn Gly
2105                2110                2115

Ser Ile Lys Arg Gly Ser Lys Asp Asn Ala Thr Asp Ser Val Pro
2120                2125                2130

Leu Arg Thr Gly Ile Gly Val Gln Leu Lys Asp Ile Lys Val Phe
2135                2140                2145

Asn Arg Asp Arg Gln Lys Gly Thr Asn Val Cys Ala Val Ala Asn
2150                2155                2160

Gly Gly Cys Gln Gln Leu Cys Leu Tyr Arg Gly Arg Gly Gln Arg
2165                2170                2175

Ala Cys Ala Cys Ala His Gly Met Leu Ala Glu Asp Gly Ala Ser
2180                2185                2190

Cys Arg Glu Tyr Ala Gly Tyr Leu Leu Tyr Ser Glu Arg Thr Ile
2195                2200                2205

Leu Lys Ser Ile His Leu Ser Asp Glu Arg Asn Leu Asn Ala Pro
2210                2215                2220

Val Gln Pro Phe Glu Asp Pro Glu His Met Lys Asn Val Ile Ala
2225                2230                2235

Leu Ala Phe Asp Tyr Arg Ala Gly Thr Ser Pro Gly Thr Pro Asn
2240                2245                2250

Arg Ile Phe Phe Ser Asp Ile His Phe Gly Asn Ile Gln Gln Ile
2255                2260                2265

Asn Asp Asp Gly Ser Arg Arg Ile Thr Ile Val Glu Asn Val Gly
2270                2275                2280

Ser Val Glu Gly Leu Ala Tyr His Arg Gly Trp Asp Thr Leu Tyr
2285                2290                2295

Trp Thr Ser Tyr Thr Thr Ser Thr Ile Thr Arg His Thr Val Asp
2300                2305                2310

Gln Thr Arg Pro Gly Ala Phe Glu Arg Glu Thr Val Ile Thr Met
2315                2320                2325

Ser Gly Asp Asp His Pro Arg Ala Phe Val Leu Asp Glu Cys Gln
```

-continued

```
            2330                2335                2340

Asn Leu Met Phe Trp Thr Asn Trp Asn Glu Gln His Pro Ser Ile
        2345                2350                2355

Met Arg Ala Ala Leu Ser Gly Ala Asn Val Leu Thr Leu Ile Glu
        2360                2365                2370

Lys Asp Ile Arg Thr Pro Asn Gly Leu Ala Ile Asp His Arg Ala
        2375                2380                2385

Glu Lys Leu Tyr Phe Ser Asp Ala Thr Leu Asp Lys Ile Glu Arg
        2390                2395                2400

Cys Glu Tyr Asp Gly Ser His Arg Tyr Val Ile Leu Lys Ser Glu
        2405                2410                2415

Pro Val His Pro Phe Gly Leu Ala Val Tyr Gly Glu His Ile Phe
        2420                2425                2430

Trp Thr Asp Trp Val Arg Arg Ala Val Gln Arg Ala Asn Lys His
        2435                2440                2445

Val Gly Ser Asn Met Lys Leu Leu Arg Val Asp Ile Pro Gln Gln
        2450                2455                2460

Pro Met Gly Ile Ile Ala Val Ala Asn Asp Thr Asn Ser Cys Glu
        2465                2470                2475

Leu Ser Pro Cys Arg Ile Asn Asn Gly Gly Cys Gln Asp Leu Cys
        2480                2485                2490

Leu Leu Thr His Gln Gly His Val Asn Cys Ser Cys Arg Gly Gly
        2495                2500                2505

Arg Ile Leu Gln Asp Asp Leu Thr Cys Arg Ala Val Asn Ser Ser
        2510                2515                2520

Cys Arg Ala Gln Asp Glu Phe Glu Cys Ala Asn Gly Glu Cys Ile
        2525                2530                2535

Asn Phe Ser Leu Thr Cys Asp Gly Val Pro His Cys Lys Asp Lys
        2540                2545                2550

Ser Asp Glu Lys Pro Ser Tyr Cys Asn Ser Arg Arg Cys Lys Lys
        2555                2560                2565

Thr Phe Arg Gln Cys Ser Asn Gly Arg Cys Val Ser Asn Met Leu
        2570                2575                2580

Trp Cys Asn Gly Ala Asp Asp Cys Gly Asp Gly Ser Asp Glu Ile
        2585                2590                2595

Pro Cys Asn Lys Thr Ala Cys Gly Val Gly Glu Phe Arg Cys Arg
        2600                2605                2610

Asp Gly Thr Cys Ile Gly Asn Ser Ser Arg Cys Asn Gln Phe Val
        2615                2620                2625

Asp Cys Glu Asp Ala Ser Asp Glu Met Asn Cys Ser Ala Thr Asp
        2630                2635                2640

Cys Ser Ser Tyr Phe Arg Leu Gly Val Lys Gly Val Leu Phe Gln
        2645                2650                2655

Pro Cys Glu Arg Thr Ser Leu Cys Tyr Ala Pro Ser Trp Val Cys
        2660                2665                2670

Asp Gly Ala Asn Asp Cys Gly Asp Tyr Ser Asp Glu Arg Asp Cys
        2675                2680                2685

Pro Gly Val Lys Arg Pro Arg Cys Pro Leu Asn Tyr Phe Ala Cys
        2690                2695                2700

Pro Ser Gly Arg Cys Ile Pro Met Ser Trp Thr Cys Asp Lys Glu
        2705                2710                2715

Asp Asp Cys Glu His Gly Glu Asp Glu Thr His Cys Asn Lys Phe
        2720                2725                2730
```

```
Cys Ser Glu Ala Gln Phe Glu Cys Gln Asn His Arg Cys Ile Ser
    2735            2740            2745

Lys Gln Trp Leu Cys Asp Gly Ser Asp Asp Cys Gly Asp Gly Ser
    2750            2755            2760

Asp Glu Ala Ala His Cys Glu Gly Lys Thr Cys Gly Pro Ser Ser
    2765            2770            2775

Phe Ser Cys Pro Gly Thr His Val Cys Val Pro Glu Arg Trp Leu
    2780            2785            2790

Cys Asp Gly Asp Lys Asp Cys Ala Asp Gly Ala Asp Glu Ser Ile
    2795            2800            2805

Ala Ala Gly Cys Leu Tyr Asn Ser Thr Cys Asp Asp Arg Glu Phe
    2810            2815            2820

Met Cys Gln Asn Arg Gln Cys Ile Pro Lys His Phe Val Cys Asp
    2825            2830            2835

His Asp Arg Asp Cys Ala Asp Gly Ser Asp Glu Ser Pro Glu Cys
    2840            2845            2850

Glu Tyr Pro Thr Cys Gly Pro Ser Glu Phe Arg Cys Ala Asn Gly
    2855            2860            2865

Arg Cys Leu Ser Ser Arg Gln Trp Glu Cys Asp Gly Glu Asn Asp
    2870            2875            2880

Cys His Asp Gln Ser Asp Glu Ala Pro Lys Asn Pro His Cys Thr
    2885            2890            2895

Ser Gln Glu His Lys Cys Asn Ala Ser Ser Gln Phe Leu Cys Ser
    2900            2905            2910

Ser Gly Arg Cys Val Ala Glu Ala Leu Leu Cys Asn Gly Gln Asp
    2915            2920            2925

Asp Cys Gly Asp Ser Ser Asp Glu Arg Gly Cys His Ile Asn Glu
    2930            2935            2940

Cys Leu Ser Arg Lys Leu Ser Gly Cys Ser Gln Asp Cys Glu Asp
    2945            2950            2955

Leu Lys Ile Gly Phe Lys Cys Arg Cys Arg Pro Gly Phe Arg Leu
    2960            2965            2970

Lys Asp Asp Gly Arg Thr Cys Ala Asp Val Asp Glu Cys Ser Thr
    2975            2980            2985

Thr Phe Pro Cys Ser Gln Arg Cys Ile Asn Thr His Gly Ser Tyr
    2990            2995            3000

Lys Cys Leu Cys Val Glu Gly Tyr Ala Pro Arg Gly Gly Asp Pro
    3005            3010            3015

His Ser Cys Lys Ala Val Thr Asp Glu Glu Pro Phe Leu Ile Phe
    3020            3025            3030

Ala Asn Arg Tyr Tyr Leu Arg Lys Leu Asn Leu Asp Gly Ser Asn
    3035            3040            3045

Tyr Thr Leu Leu Lys Gln Gly Leu Asn Asn Ala Val Ala Leu Asp
    3050            3055            3060

Phe Asp Tyr Arg Glu Gln Met Ile Tyr Trp Thr Asp Val Thr Thr
    3065            3070            3075

Gln Gly Ser Met Ile Arg Arg Met His Leu Asn Gly Ser Asn Val
    3080            3085            3090

Gln Val Leu His Arg Thr Gly Leu Ser Asn Pro Asp Gly Leu Ala
    3095            3100            3105

Val Asp Trp Val Gly Gly Asn Leu Tyr Trp Cys Asp Lys Gly Arg
    3110            3115            3120
```

-continued

```
Asp Thr Ile Glu Val Ser Lys Leu Asn Gly Ala Tyr Arg Thr Val
    3125                3130                3135

Leu Val Ser Ser Gly Leu Arg Glu Pro Arg Ala Leu Val Val Asp
    3140                3145                3150

Val Gln Asn Gly Tyr Leu Tyr Trp Thr Asp Trp Gly Asp His Ser
    3155                3160                3165

Leu Ile Gly Arg Ile Gly Met Asp Gly Ser Ser Arg Ser Val Ile
    3170                3175                3180

Val Asp Thr Lys Ile Thr Trp Pro Asn Gly Leu Thr Leu Asp Tyr
    3185                3190                3195

Val Thr Glu Arg Ile Tyr Trp Ala Asp Ala Arg Glu Asp Tyr Ile
    3200                3205                3210

Glu Phe Ala Ser Leu Asp Gly Ser Asn Arg His Val Val Leu Ser
    3215                3220                3225

Gln Asp Ile Pro His Ile Phe Ala Leu Thr Leu Phe Glu Asp Tyr
    3230                3235                3240

Val Tyr Trp Thr Asp Trp Glu Thr Lys Ser Ile Asn Arg Ala His
    3245                3250                3255

Lys Thr Thr Gly Thr Asn Lys Thr Leu Leu Ile Ser Thr Leu His
    3260                3265                3270

Arg Pro Met Asp Leu His Val Phe His Ala Leu Arg Gln Pro Asp
    3275                3280                3285

Val Pro Asn His Pro Cys Lys Val Asn Asn Gly Gly Cys Ser Asn
    3290                3295                3300

Leu Cys Leu Leu Ser Pro Gly Gly Gly His Lys Cys Ala Cys Pro
    3305                3310                3315

Thr Asn Phe Tyr Leu Gly Ser Asp Gly Arg Thr Cys Val Ser Asn
    3320                3325                3330

Cys Thr Ala Ser Gln Phe Val Cys Lys Asn Asp Lys Cys Ile Pro
    3335                3340                3345

Phe Trp Trp Lys Cys Asp Thr Glu Asp Cys Gly Asp His Ser
    3350                3355                3360

Asp Glu Pro Pro Asp Cys Pro Glu Phe Lys Cys Arg Pro Gly Gln
    3365                3370                3375

Phe Gln Cys Ser Thr Gly Ile Cys Thr Asn Pro Ala Phe Ile Cys
    3380                3385                3390

Asp Gly Asp Asn Asp Cys Gln Asp Asn Ser Asp Glu Ala Asn Cys
    3395                3400                3405

Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn
    3425                3430                3435

Cys Gly Asp Gly Glu Asp Glu Arg Asp Cys Pro Glu Val Thr Cys
    3440                3445                3450

Ala Pro Asn Gln Phe Gln Cys Ser Ile Thr Lys Arg Cys Ile Pro
    3455                3460                3465

Arg Val Trp Val Cys Asp Arg Asp Asn Asp Cys Val Asp Gly Ser
    3470                3475                3480

Asp Glu Pro Ala Asn Cys Thr Gln Met Thr Cys Gly Val Asp Glu
    3485                3490                3495

Phe Arg Cys Lys Asp Ser Gly Arg Cys Ile Pro Ala Arg Trp Lys
    3500                3505                3510

Cys Asp Gly Glu Asp Asp Cys Gly Asp Gly Ser Asp Glu Pro Lys
```

```
            3515                3520                3525
Glu Glu Cys Asp Glu Arg Thr Cys Glu Pro Tyr Gln Phe Arg Cys
    3530                3535                3540

Lys Asn Asn Arg Cys Val Pro Gly Arg Trp Gln Cys Asp Tyr Asp
    3545                3550                3555

Asn Asp Cys Gly Asp Asn Ser Asp Glu Glu Ser Cys Thr Pro Arg
    3560                3565                3570

Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
    3605                3610                3615

Gln Cys Lys Ser Gly His Cys Ile Pro Leu Arg Trp Arg Cys Asp
    3620                3625                3630

Ala Asp Ala Asp Cys Met Asp Gly Ser Asp Glu Glu Ala Cys Gly
    3635                3640                3645

Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp
    3665                3670                3675

Cys Gly Asp Asn Ser Asp Glu Asn Pro Glu Glu Cys Ala Arg Phe
    3680                3685                3690

Val Cys Pro Pro Asn Arg Pro Phe Arg Cys Lys Asn Asp Arg Val
    3695                3700                3705

Cys Leu Trp Ile Gly Arg Gln Cys Asp Gly Thr Asp Asn Cys Gly
    3710                3715                3720

Asp Gly Thr Asp Glu Glu Asp Cys Glu Pro Pro Thr Ala His Thr
    3725                3730                3735

Thr His Cys Lys Asp Lys Lys Glu Phe Leu Cys Arg Asn Gln Arg
    3740                3745                3750

Cys Leu Ser Ser Ser Leu Arg Cys Asn Met Phe Asp Asp Cys Gly
    3755                3760                3765

Asp Gly Ser Asp Glu Glu Asp Cys Ser Ile Asp Pro Lys Leu Thr
    3770                3775                3780

Ser Cys Ala Thr Asn Ala Ser Ile Cys Gly Asp Glu Ala Arg Cys
    3785                3790                3795

Val Arg Thr Glu Lys Ala Ala Tyr Cys Ala Cys Arg Ser Gly Phe
    3800                3805                3810

His Thr Val Pro Gly Gln Pro Gly Cys Gln Asp Ile Asn Glu Cys
    3815                3820                3825

Leu Arg Phe Gly Thr Cys Ser Gln Leu Cys Asn Asn Thr Lys Gly
    3830                3835                3840

Gly His Leu Cys Ser Cys Ala Arg Asn Phe Met Lys Thr His Asn
    3845                3850                3855

Thr Cys Lys Ala Glu Gly Ser Glu Tyr Gln Val Leu Tyr Ile Ala
    3860                3865                3870

Asp Asp Asn Glu Ile Arg Ser Leu Phe Pro Gly His Pro His Ser
    3875                3880                3885

Ala Tyr Glu Gln Ala Phe Gln Gly Asp Glu Ser Val Arg Ile Asp
    3890                3895                3900

Ala Met Asp Val His Val Lys Ala Gly Arg Val Tyr Trp Thr Asn
    3905                3910                3915
```

-continued

Trp His Thr Gly Thr Ile Ser Tyr Arg Ser Leu Pro Pro Ala Ala
3920                 3925                 3930

Pro Pro Thr Thr Ser Asn Arg His Arg Arg Gln Ile Asp Arg Gly
3935                 3940                 3945

Val Thr His Leu Asn Ile Ser Gly Leu Lys Met Pro Arg Gly Ile
3950                 3955                 3960

Ala Ile Asp Trp Val Ala Gly Asn Val Tyr Trp Thr Asp Ser Gly
3965                 3970                 3975

Arg Asp Val Ile Glu Val Ala Gln Met Lys Gly Glu Asn Arg Lys
3980                 3985                 3990

Thr Leu Ile Ser Gly Met Ile Asp Glu Pro His Ala Ile Val Val
3995                 4000                 4005

Asp Pro Leu Arg Gly Thr Met Tyr Trp Ser Asp Trp Gly Asn His
4010                 4015                 4020

Pro Lys Ile Glu Thr Ala Ala Met Asp Gly Thr Leu Arg Glu Thr
4025                 4030                 4035

Leu Val Gln Asp Asn Ile Gln Trp Pro Thr Gly Leu Ala Val Asp
4040                 4045                 4050

Tyr His Asn Glu Arg Leu Tyr Trp Ala Asp Ala Lys Leu Ser Val
4055                 4060                 4065

Ile Gly Ser Ile Arg Leu Asn Gly Thr Asp Pro Ile Val Ala Ala
4070                 4075                 4080

Asp Ser Lys Arg Gly Leu Ser His Pro Phe Ser Ile Asp Val Phe
4085                 4090                 4095

Glu Asp Tyr Ile Tyr Gly Val Thr Tyr Ile Asn Asn Arg Val Phe
4100                 4105                 4110

Lys Ile His Lys Phe Gly His Ser Pro Leu Val Asn Leu Thr Gly
4115                 4120                 4125

Gly Leu Ser His Ala Ser Asp Val Val Leu Tyr His Gln His Lys
4130                 4135                 4140

Gln Pro Glu Val Thr Asn Pro Cys Asp Arg Lys Lys Cys Glu Trp
4145                 4150                 4155

Leu Cys Leu Leu Ser Pro Ser Gly Pro Val Cys Thr Cys Pro Asn
4160                 4165                 4170

Gly Lys Arg Leu Asp Asn Gly Thr Cys Val Pro Val Pro Ser Pro
4175                 4180                 4185

Thr Pro Pro Pro Asp Ala Pro Arg Pro Gly Thr Cys Asn Leu Gln
4190                 4195                 4200

Cys Phe Asn Gly Gly Ser Cys Phe Leu Asn Ala Arg Arg Gln Pro
4205                 4210                 4215

Lys Cys Arg Cys Gln Pro Arg Tyr Thr Gly Asp Lys Cys Glu Leu
4220                 4225                 4230

Asp Gln Cys Trp Glu His Cys Arg Asn Gly Gly Thr Cys Ala Ala
4235                 4240                 4245

Ser Pro Ser Gly Met Pro Thr Cys Arg Cys Pro Thr Gly Phe Thr
4250                 4255                 4260

Gly Pro Lys Cys Thr Gln Gln Val Cys Ala Gly Tyr Cys Ala Asn
4265                 4270                 4275

Asn Ser Thr Cys Thr Val Asn Gln Gly Asn Gln Pro Gln Cys Arg
4280                 4285                 4290

Cys Leu Pro Gly Phe Leu Gly Asp Arg Cys Gln Tyr Arg Gln Cys
4295                 4300                 4305

-continued

```
Ser Gly Tyr Cys Glu Asn Phe Gly Thr Cys Gln Met Ala Ala Asp
    4310                4315             4320

Gly Ser Arg Gln Cys Arg Cys Thr Ala Tyr Phe Glu Gly Ser Arg
    4325                4330             4335

Cys Glu Val Asn Lys Cys Ser Arg Cys Leu Glu Gly Ala Cys Val
    4340                4345             4350

Val Asn Lys Gln Ser Gly Asp Val Thr Cys Asn Cys Thr Asp Gly
    4355                4360             4365

Arg Val Ala Pro Ser Cys Leu Thr Cys Val Gly His Cys Ser Asn
    4370                4375             4380

Gly Gly Ser Cys Thr Met Asn Ser Lys Met Met Pro Glu Cys Gln
    4385                4390             4395

Cys Pro Pro His Met Thr Gly Pro Arg Cys Glu Glu His Val Phe
    4400                4405             4410

Ser Gln Gln Gln Pro Gly His Ile Ala Ser Ile Leu Ile Pro Leu
    4415                4420             4425

Leu Leu Leu Leu Leu Leu Val Leu Val Ala Gly Val Val Phe Trp
    4430                4435             4440

Tyr Lys Arg Arg Val Gln Gly Ala Lys Gly Phe Gln His Gln Arg
    4445                4450             4455

Met Thr Asn Gly Ala Met Asn Val Glu Ile Gly Asn Pro Thr Tyr
    4460                4465             4470

Lys Met Tyr Glu Gly Gly Glu Pro Asp Asp Val Gly Gly Leu Leu
    4475                4480             4485

Asp Ala Asp Phe Ala Leu Asp Pro Asp Lys Pro Thr Asn Phe Thr
    4490                4495             4500

Asn Pro Val Tyr Ala Thr Leu Tyr Met Gly Gly His Gly Ser Arg
    4505                4510             4515

His Ser Leu Ala Ser Thr Asp Glu Lys Arg Glu Leu Leu Gly Arg
    4520                4525             4530

Gly Pro Glu Asp Glu Ile Gly Asp Pro Leu Ala
    4535                4540
```

EXTRACELLULAR VESICLES PURIFIED FROM DRIED BLOOD CARDS

CROSS-REFERENCE TO RELATED APPLICATIONS

The present application is a national phase entry of International Application No. PCT/EP2018/084789, filed Dec. 13, 2018, which claims the benefit of priority to EP application No. 17206867.8, filed Dec. 13, 2017, the entireties of which are incorporated by reference herein.

The present invention relates to purification and characterization of extracellular vesicles from dried body fluid cards.

BACKGROUND

Tumor cells and cells in general release membranous structures, which are termed extracellular vesicles (EVs) and include so-called microvesicles or exosomes depending on specific characteristics, including size and composition. Microvesicles and exosomes, in particular, have gained attention as "vehicles" for intercellular communication with extensive autocrine/paracrine functions. By exposing cell-type-specific adhesion receptors or ligands, EVs can interact with specific cells and deliver their "signals" including bioactive lipids, cytokines, growth factors, receptors and genetic material. Thus, the microvesicle/exosomal pathway is a potential mechanism for local and systemic intercellular transfer of information with a complexity superior to that of secreted soluble factors, but similar to that observed with direct cell-cell contact.

The direct use of circulating cell-derived vesicles for disease diagnosis has been limited by the current lack of methods to purify, measure and characterize these. The protein composition of the vesicles can be determined by flow cytometry and immunoblotting, as well as by array technologies using antigenic capturing of exosomes or other extracellular vesicles by protein microarrays, cf. Jørgensen et al, 2013, J Extracell Vesicles.

A standard protocol for obtaining exosomes from a cell solution, comprises that the solution is submitted to centrifugation of: 1000 g during 15 minutes to remove cells and huge debris; then continue at 4° C. at 18,000 g during 30 minutes to remove bigger subcell particles, apoptotic bodies and undesirable organelles; immediately, the supernatant of microvesicular fraction is sequentially filtered through nylon membranes of 1 µm, 500 nm and 220 nm, and then, centrifugated again at 4° C. at 100,000 g for 90 minutes in order to obtain the exosomes "pellet". Such pellet may be suspended again for its use.

Venous blood is a conventional source of circulating EVs, and this requires blood sampling by authorized personnel and immediate purification of the vesicles. The present inventors have found that intact EVs can in fact be obtained from dry blood card samples, which can be prepared by unauthorized personnel, or even at home by the user and shipped by regular mail. Intact extracellular vesicles can be detected in extracts from dry blood card samples even after prolonged storage.

SUMMARY

In one aspect, a method is provided, which comprises
a. providing a dried body fluid card sample,
b. extracting blood from said dried body fluid card sample, and
c. detecting at least one member of a plurality of genes or gene products associated with a population of extracellular vesicles (EVs).

In another aspect, a method is provided for diagnosing and/or prognosing a clinical condition, and/or evaluating and/or monitoring a treatment of clinical condition, said method comprising
a. providing a dried body fluid card sample,
b. extracting blood from said dried body fluid card sample, and
c. detecting at least one member of a plurality of genes or gene products associated with a population of extracellular vesicles, and
d. detecting at least one member of a plurality of genes or gene products associated with a clinical condition.

In a third aspect, a use is provided of at least one detection member for detecting in a liquid composition at least one member of a plurality of genes or gene products associated with a population of EVs and/or a physiological or clinical condition, wherein the liquid composition is extracted from a dried body fluid card sample.

DESCRIPTION OF DRAWINGS

FIG. 11. Comparison in three donors of the detected expression of CD235a.
FIG. 22. Time course experiment on the detection of HLA DR/DP/DQ and CD235a.

DETAILED DESCRIPTION

Figure 1:
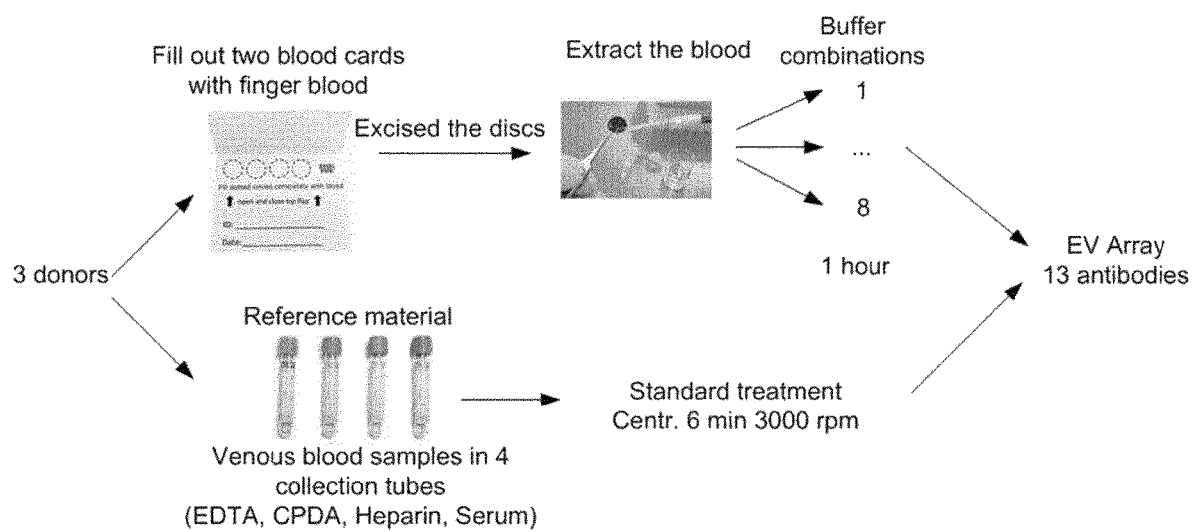
FIG. 1. Overview of experiment, example 2.

Methods are provided herein, which allows fast, easy, convenient and cheap extraction of extracellular vesicles from blood samples provided as a dry blood card sample. The method comprises steps of
 a. providing a dried body fluid card sample,
 b. extracting blood from said dried body fluid card sample, and
 c. detecting at least one member of a plurality of genes or gene products associated with a population of extracellular vesicles.

The term "gene", as used herein, is meant to comprise coding and non-coding regions, intronic and exonic regions, of a genetic locus, and also comprise upstream and downstream regulatory regions of the coding regions, such as upstream 5'-UTR, promoter regions, transcription initiation cis-acting elements, and downstream 3'-UTR, 3'-processing signals, polyadenylation signal, and transcriptional termination signals. Moreover, any mutation such as a polymorphism, deletion, substitution, or inversion in the gene is comprised in the term.

The term "gene product" as used herein is meant to include any transcriptional and translational products of a gene. "Transcriptional or translational products" is meant herein products of gene transcription, such as a RNA transcript, for example an unspliced RNA transcript, microRNA, a mRNA transcript and said mRNA transcript splicing products, and products of gene translation, such as polypeptide(s) translated from any of the gene mRNA transcripts and various products of post-translational processing of said polypeptides, such as the products of post-translational proteolytic processing of the polypeptide(s) or products of various post-translational modifications of said polypeptide(s). It is noted that a pre-messenger RNA molecule, pre-mRNA, contains the same sequence information (albeit that U nucleotides replace T nucleotides) as the gene, or mature messenger RNA molecule, mRNA, which was produced due to splicing of the pre-mRNA, and is a template for translation of genetic information of the gene into a protein.

The term "antibody" as used herein includes both polyclonal and monoclonal antibodies, as well as fragments thereof, such as, Fv, Fab and F(ab)2 fragments that are capable of binding antigen or hapten. It includes conventional animal monoclonal antibodies as well as human antibodies, and humanized forms of non-human antibodies, and it also includes 'antibodies' isolated from phage antibody libraries.

The antibodies of the present invention may be polyclonal or monoclonal and may be produced by in vivo or in vitro methods known in the art.

A monoclonal antibody is an antibody produced by a hybridoma cell. Methods of making monoclonal antibody-synthesizing hybridoma cells are well known to those skilled in the art, e.g, by the fusion of an antibody producing B lymphocyte with an immortalized B-lymphocyte cell line.

A polyclonal antibody is a mixture of antibody molecules (specific for a given antigen) that has been purified from an immunized (to that given antigen) animal's blood, where a non-limiting example is antibody molecules from rabbit. Such antibodies are polyclonal in that they are the products of many different populations of antibody-producing cells.

Mixtures of monoclonal and/or polyclonal antibodies can also be used; also a mixture of at least two monoclonal antibodies can be suitable.

The terms "polynucleotide" and "nucleic acid" are used interchangeably, and, when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "genetic marker" refers to a variable nucleotide sequence (polymorphism) of the DNA on the human chromosome. The variable nucleotide sequence can be identified by methods known to a person skilled in the art, as explained elsewhere herein, for example by using specific oligonucleotides in for example amplification methods and/or hybridization techniques and/or observation of a size difference. However, the variable nucleotide sequence may also be detected by sequencing or for example restriction fragment length polymorphism analysis. The variable nucleotide sequence may be represented by a deletion, an insertion, repeats, duplications, inversions, translocations and/or a point mutation. A genetic marker in the context of the present invention is a specific allele located at defined genetic locus, said locus comprising two or more polymorphic alleles. In fact, a genetic marker locus may comprise a variable number of polymorphic alleles.

The genetic markers may be any nucleic acid sequence, including conventional genetic markers such as microsatellites, minisatellites, Single Nucleotide Polymorphisms (SNPs), Restriction Fragment Length Polymorphisms (RFLPs), Amplified Fragment Length Polymorphisms (AFLPs), Random Amplification of Polymorfic DNA (RAPD), Variable Number of Tandem Repeats (VNTRs), Short Tandem Repeat (STRs), sequence characterised amplified regions (SCARs), or cleaved amplified polymorphic sequences (CAPSs).

One preferred type of genetic marker is a single nucleotide polymorphism (SNP) marker that is associated with human spinal dysmyelination. An SNP is a DNA sequence variation, wherein a single nucleotide—A, T, C, or G—differs between members of a species, or between paired chromosomes in an individual organism. For example, two DNA fragments, AAGCCTA to AAGCTTA, contain a difference in a single nucleotide. In this case, the SNP comprise two alleles: C and T. Single nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. SNPs located in non-coding regions may influence transcription factor binding, splicing or alter the sequence of non-coding RNA.

Another type of genetic marker is a microsatellite marker. Microsatellite markers refer to short sequences repeated after each other. In short, sequences are for example one nucleotide, such as two nucleotides, for example three nucleotides, such as four nucleotides, for example five nucleotides, such as six nucleotides, for example seven nucleotides, such as eight nucleotides, for example nine nucleotides, such as ten nucleotides. However, changes sometimes occur and the number of repeats may increase or decrease.

A "mutation" refers to a change in a nucleotide sequence of a nucleic acid compared with the wild type sequence as observed among other human subjects. Mutations may be used as genetic markers. Mutations arise from point mutations, deletions, insertions, duplications, inversions, and translocations. In general, mutations may occur within the coding region of a gene, within intronic sequences, or in regulatory regions, such as promoters, enhancers and 3'-processing signals. However, differences in nucleotide sequences found in other genomic sequences are also referred to as mutations.

Dried Body Fluid Card Sample

The methods and uses provided herein are applied to immobilized samples of body fluid in a solid support material, often an absorbent filter paper material.

The body fluid may be any type of body fluid, which houses EVs. For example, the body fluid can be selected from the group consisting of blood, sputum, sweat, urine, semen and expiration air.

In a preferred embodiment, the body fluid is blood and the body fluid may also be blood plasma or serum.

When the sample is blood, the dried body fluid card sample is referred to herein as a dry blood card sample. A dry blood card sample is also known as a dry blood spot (DBS) sample and is a well-known and widely used form of biosampling where blood samples are blotted and dried on filter paper. Dried blood spot testing has for example been widely used in neonatal screening, e.g. the neonatal heel prick or Guthrie test, a screening test done on new-borns consisting of making a pinprick puncture in one heel of the new-born and soaking the blood into pre-printed collection cards known as Guthrie cards. The blood samples can be used for a variety of metabolic test to detect genetic conditions.

The body fluid is generally applied to the card material by collecting a few drops, which are put directly on a designated area on the card material, which can be indicated as a printed circle. Dry blood card specimens can be collected by applying a few drops of blood, e.g. drawn by lancet from the finger, heel or toe, onto absorbent filter paper. The blood should be allowed to thoroughly saturate the paper and is allowed to dry, usually air dried. Dried body fluid card specimens are preferably stored in low gas-permeability plastic bags with desiccant added to reduce humidity, and can be kept at ambient temperature, even in tropical climates.

The card material is a material, which is capable of absorbing a sufficient amount of fluid. The material may for example be absorbent filter paper, nitrocellulose membrane or polyvinylidene difluoride (PVDF). However, any type of paper used in the art may be applicable.

Dried body fluid card samples are generally prepared by collecting the sample by those methods generally available in the art for the specific body fluid sample, optionally processing the body fluid sample, for example purifying or isolating a specific phase of the sample or adding one or more helper agents (e.g. anti-coagulation agents), and then placing one or more drops on the card material and drying the material.

Blood cards are generally prepared by a method comprising the steps of:
1) cleaning the area, wherefrom the blood is to be collected, with a disinfectant,
2) using a lancet device to prick a hole in the skin, preferably in the fingertip,
3) massaging the tissue around the hole until a blood drop appear,
4) placing the blood drop on the blood card,
5) optionally continuing the procedure in order to collect more blood drop samples, and
6) drying the blood card.

In one embodiment, the blood cards are prepared by
1) cleaning the hands and disinfecting a designated finger by swiping with alcohol.
2) using a lancet device to prick a hole in the fingertip,
3) massaging the fingertip until blood drops appear,
4) placing the blood drop on the blood card on an indicated circle on the blood card
5) optionally continuing the procedure in order to collect more blood drop samples, which are placed on other indicated circles of the same or other blood cards, 6) drying the blood card at room temperature at least one hour.

The dried samples can easily be shipped to an analytical laboratory and analysed. Once in the laboratory, technicians can separate a small disc of the saturated paper from the sheet using a hole punch, and placing it in an appropriate container, usually a microtiter plate comprising an elution buffer, where the blood is eluted by incubation, usually at 4° C. overnight. An alternative to punching out a paper disc is automated extraction by flushing an eluent through the filter without punching it out.

The eluate can then be used for analysis using various methods such as DNA amplification, antibody based assays, such as ELISA assays, HPLC, Nanotracking Analysis (NTA), scanning Ion Occlusion Sensing (qNano), dynamic light scattering/zeta potential (Zetasizer) or Flowcytometry.

Extraction of Extracellular Vesicles From Dried Body Fluid Sample Cards

The present inventors have surprisingly found that dry blood card samples can be used as a source of circulating extracellular vesicles, which hold great potential for use of extracellular vesicles in body fluids in diagnostic and prognostic assays as well as for evaluation and monitoring of different physiological conditions and their treatments.

The methods disclosed herein generally comprise the steps of
a. providing a dried body fluid card sample,
b. extracting the body fluid components from said dried body fluid card sample, and
c. detecting at least one member of a plurality of genes or gene products associated with a population of extracellular vesicles.

Methods are also provided for diagnosing and/or prognosing a clinical condition, and/or evaluating and/or monitoring a treatment of clinical condition, said method comprising
a. providing a dried body fluid card sample,
b. extracting the body fluid components from said dried body fluid card sample, and
c. detecting at least one member of a plurality of genes or gene products associated with a population of extracellular vesicles.

The methods are preferably applied to dry blood card samples, and therefore, the methods disclosed herein generally comprise the steps of
a. providing a dry blood card sample,
b. extracting blood from said dry blood card sample, and
c. detecting at least one member of a plurality of genes or gene products associated with a population of extracellular vesicles.

Further, methods are also provided for diagnosing and/or prognosing a clinical condition, and/or evaluating and/or monitoring a treatment of clinical condition, said method comprising
a. providing a dry blood card sample,
b. extracting blood from said dry blood card sample, and
c. detecting at least one member of a plurality of genes or gene products associated with a population of extracellular vesicles.

The dried body fluid sample, such as dry blood card sample, can in separate steps be provided as described above. The dried body fluid sample, such as dry blood card sample, is preferably applied to the card within 21 days of the collection/extraction, and preferably within 14 days. However, even after 21 days, extracellular vesicles are detectable and no upper limit for the storage of the dry blood card samples is anticipated.

Extraction of the dried body fluid sample, such as blood sample, from the dried body fluid card sample specifically involves eluting the sample using an elution buffer, which supports extraction of intact and detectable extracellular vesicles. The inventors have found that wetting or soaking the dried body fluid card sample in an optimized elution buffer leads to extraction of intact, detectable extracellular vesicles. The wetted dried body fluid card should be incubated for a sufficient time to allow extraction of the body fluid components into the elution buffer. This usually requires at least 10 minutes incubation, more preferred at least 1 hour, preferably at room temperature (approximately 18-25° C.). However, extraction may also be performed by overnight incubation, in which case it should in the cold, for example by placing the sample at 4° C.

The elution buffer is then allowed to elute from the dried body fluid card, either by gravitational force, by vacuum or by centrifugation. The elution buffer is for example conveniently extracted from the dried body fluid card sample, such as dry blood card sample, by centrifugation in a spin column, which retains the sample card in the spin column and collects the sample buffer in a reaction tube. Elution could also be performed directly into a size exclusion column (SEC), density gradient centrifugation, affinity capturing or other membrane filtration systems.

The eluted sample should be cleared of cells and cellular debris, which can be done by centrifugation at an appropriate force to leave extracellular vesicles in the supernatant, while pelleting the cells and cellular debris. This can be obtained by spinning 20.000×g for 5 min.

The extract be used immediately for detection and characterization of extracellular vesicles, or it can be stored and analyzed later. For prolonged storage, the sample should be frozen. The extracellular vesicles could also be pelleted by ultracentrifugation and stored as such in a freezer.

In one embodiment, the extract is transferred to an appropriate reaction buffer suitable for the further analysis of the vesicles.

In one embodiment, extraction of components from the dried body fluid card sample involves one or more of the steps of
1) excising a circle from the sample card (12.5 mm diameter) using a disc punch designed for the purpose,
2) wetting the excised circle with 60 μL of Elution Buffer,
3) placing the wetted circle in a spin column, which is placed in a collection tube containing 60 μL Reaction Buffer,
4) closing the spin column and incubating the assembly for 1 hour at room temperature,
5) centrifuging the spin column assembly is at 20.000×g for 5 min,
6) discarding the spin column and excised circle, and transferring from the top 60 μL sample comprising extracellular vesicles to a new sample tube.

In a preferred embodiment, the sample is a blood sample, and then extraction of blood from the dry blood card sample preferably involves one or more of the steps of
1) excising a circle from the blood card (12.5 mm diameter) using a disc punch designed for the purpose,
2) wetting the excised blood circle with 60 μL of Elution Buffer,
3) placing the wetted blood circle in a spin column, which is placed in a collection tube containing 60 μL Reaction Buffer, 4) closing the spin column and incubating the assembly for 1 hour at room temperature,
5) centrifuging the spin column assembly is at 20.000×g for 5 min,
6) discarding the spin column and excised circle, and transferring from the top 60 μL sample comprising extracellular vesicles to a new sample tube.

The sample can then be subjected to analysis directly, or it can be frozen and analysed later.

Thus, extracellular vesicles are in one embodiment extracted from the dried body fluid card sample, such as from the dry blood card sample, using an elution buffer, where the sample is eluted directly into an appropriate reaction buffer. The choice of reaction buffer depends on the analysis that the extracellular vesicles are to be subjected to.

The body fluid/components of the body fluid are extracting from the dried body fluid card sample using an elution buffer, which supports elution of and protects intact and/or detectable extracellular vesicles. A person of skill in the art may be able to determine the features of such a composition. In one preferred embodiment, the body fluid/components of the body/blood is extracted using a pH-buffered solution, such as a phosphate buffered saline (PBS). In a preferred embodiment, the elution buffer is phosphate buffered saline (PBS) comprising 137 mmol NaCl, 2.7 mmol KCl, 10 mmol $NA_2HPO_4$ and 1.8 mmol $KH_2PO_4$.

The elution buffer may also comprise one or more detergents, such as Tween20® (polysorbate 20), or Sodium dodecyl sulfate (SDS). Usually between 0.01% and 1% is preferred, such as 0.01, 0.02, 0.03, 0.04, 0.05, 0.06, 0.07, 0.08, 0.09 or 0.1, 0.2, 0.3, 0.4, 0.5, 0.6, 0.7, 0.8, 0.9, or 1% Tween20® (polysorbate 20) or SDS. For example between 0.05 and 0.2% Tween20® (polysorbate 20) or SDS.

The elution buffer may also comprise other components, such as salts and further buffers. The elution buffer may for example comprise sodium azide ($NaN_3$); sodium chloride (NaCl); potassium chloride (KCl), sodium phosphate ($NA_2HPO_4$) and/or potassium phosphate ($KH_2PO_4$).

In one embodiment, the elution buffer comprises approximately 0.005% sodium azide.

In a preferred embodiment, the elution buffer is phosphate buffered saline (PBS) approximately comprising 137 mmol NaCl, 2.7 mmol KCl, 10 mmol $NA_2HPO_4$ and 1.8 mmol $KH_2PO_4$.

Other buffer components could be detergents as for example CHAPS, N-ocytlglucoside, Triton X100 (octyl phenol ethoxylate); salts and metals as combinations of sodium, potassium, calcium, chloride, and phosphate together with other components such as EDTA, Tris, MES, HEPES, MOPS, Tris-base, azide. Components to add viscosity such as Ficoll (polysaccharide), glucose, sucrose, Lymphoprep (sodium diatrizoate and polysaccharides), OptiPrep (iodixanol).

Extracellular Vesicles

Extracellular vesicles are a heterogeneous population of membrane-enclosed vesicles that can be divided into a number of subpopulations based on specific characteristics such as size, biogenesis, cellular origin, protein composition, and biological function. The two major subtypes of EVs are exosomes and microvesicles.

Extracellular vesicles range in size from about 30 nm to 1000 nm. Extracellular vesicles are shed from almost all cell types and can be found in virtually all biological fluids, including blood, sputum, sweat, urine, semen and expiration air, and also in cultured medium of cell cultures. Extracellular vesicles include microvesicles and exosomes. Microvesicles, also called circulating microvesicles or microparticles range from 100 to 1000 nm while exosomes are generally smaller.

The extracellular vesicles referred to in the present disclosure are preferably exosomes. Exosomes have specialized functions and play key roles in many different physiological processes including coagulation, intercellular signalling and waste management. In addition, exosomes are recognized as potential markers for prognosis and therapy, and for use as biomarkers for human health and disease.

In the context of the present disclosure, exosomes can be defined based on size ranging from 30-100 nm, density ranging from 1.12-1.19 g/ml and expression of specific biomarkers, as mentioned herein below.

Characterization of Extracellular Vesicles

To identify circulating as well as cell culture-derived vesicles, the current standard is immunoblotting or a flow cytometrical analysis for specific proteins, both of which requires large amounts of purified vesicles. The methods of the present invention provide sufficient amounts of circulating extracellular vesicles, such as exosomes, extracted from dried body fluid card samples, such as in a preferred embodiment dry blood card samples. The extracellular vesicles/exosomes are provided in an eluate, which is subject to analysis for detection of the vesicles/exosomes. The vesicles/exosomes are determined and characterized by detecting at least one member of a plurality of genes or gene products associated with a population of extracellular vesicles. The term "gene products associated with a population of extracellular vesicles" is meant to include both surface bound and intravesicular products, i.e. gene products, such as polypeptides, which are present in the lumen of the extracellular vesicles or present on the surface of the vesicles.

In methods for diagnosing and/or prognosing a physiological or clinical condition, and/or evaluating and/or monitoring a treatment of clinical condition, the vesicles/exosomes are determined and characterized by detecting at least one member of a plurality of genes or gene products associated with a physiological or clinical condition.

The presence of genes and transcriptional gene products, such as RNA species, can be detected using well-known techniques for polynucleotide detection, including PCR-base methods, southern blotting and oligonucleotide probes.

The presence of translational gene products, in particular cell surface markers, and cell surface structures, can be detected using well-known techniques in the art, in particular by antibody-based assays. Translational gene products may for example be detected by Nanotracking analysis (NTA), SIOS (qNano), Dynamic light Scattering (Zetasizer), Flowcytometry and ELISA.

Translational gene product detection can thus be performed using ligands, in particular antibodies or functional fragments thereof. In a preferred embodiment, the at least one member of a plurality of genes or gene products associated with a population of extracellular vesicles and/or at least one member of a plurality of genes or gene products associated with a clinical condition is detected by an antibody. Both genes and transcriptional and translational products thereof can be detected by microarray technologies, and such approaches are also preferred for use in the presented methods. Thus, in a particularly preferred embodiment, translational gene products associated with a population of extracellular vesicles and/or a clinical or physiological condition is detected using a microarray approach.

Specific arrays for detection of extracellular vesicles are available, which allow high-throughput multiplexed phenotyping of extracellular vesicles. Highly sensitive extracellular vesicle arrays exist, which are capable of detecting and phenotyping exosomes and other extracellular vesicles in a high-throughput manner.

The methods provided herein, involves detecting at least one member of a plurality of genes or gene products associated with a population of extracellular vesicles. In a preferred embodiment, at least one member of the plurality of gene or gene products is associated with an EV population, and it is most preferred that the at least one member of the plurality of gene or gene products is associated with an EV population. As a number of genes and gene products are known to be expressed in EVs, the at least one member of the plurality of gene or gene products is an EV-specific gene or gene product. Examples of such gene products are provided in table 1 below and in one embodiment, the extracellular vesicles express one or more gene products of a gene selected from the group set out in table 1.

TABLE 1

List of antibodies for use in characterization of extracellular vesicles

| UniProt ID | Antibody target | Antibody Producer | Catalog # | Clone | Alternative names |
|---|---|---|---|---|---|
| P68133 | Actin Ab5 | BD Biosciences | 612656 | C4 | ACTS, alpha skeletal muscle, ACTA1 |
| O75969 | AKAP3 | Santa Cruz Bio | Sc-47788 | C-20 | A-kinase anchor protein 3 |
| Q8WUM4 | Alix | Biolegend | 634501 | 3A9 | PDC6I, Programmed cell death 6-interacting protein |
| P08758 | Annexin V | R & D Systems | AF399 | — | Annexin A5, ANXA5 |
| P15514 | AREG | Santa Cruz Bio | sc-27156 | S-13 | Amphiregulin |
| P60709 | Beta actin | Sigma | A5441 | — | Actin, cytoplasmic 1, ACTB |
| P21217 | CA19-9 | LS Bio | LS-B5680 | — | FUT3, Galactoside 3(4)-L-fucosyltransferase |
| O43570 | CAXII | R & D Systems | MAB2190 | 315602 | Carbonic anhydrase 12 |
| P17813 | CD105 | LS Bio | LS-C149182 | — | Endoglin |
| P19320 | CD106 | R & D Systems | MAB809 | HAE-2Z | VCAM1, Vascular cell adhesion protein 1 |
| P15144 | CD13 | R & D Systems | MAB3815 | 498001 | Aminopeptidase N |
| P18827 | CD138 | R & D Systems | AF2780 | — | Syndecan-1 |
| P08571 | CD14 | BD Biosciences | 555396 | M5E2 | Monocyte differentiation antigen |
| P08571 | CD14 | R & D Systems | MAB3833 | 50040 | Monocyte differentiation antigen |
| P07204 | CD141 | R & D Systems | MAB3947 | 501733 | Thrombomodulin, TM, Fetomodulin |
| P13726 | CD142 | R & D Systems | MAB2339 | 323514 | Tissue Factor |
| P43121 | CD146 | Abcam | ab24577 | P1H12 | MUC18, MCAM |
| P48509 | CD151 | R & D Systems | MAB1884 | 210127 | Tspan24, PETA-3, Platelet-endothelial tetraspan antigen 3, |
| P08637 and O75015 | CD16 | BD Biosciences | 555404 | 3G8 | FCG3A and B Low affinity immunoglobulin gamma Fc region receptor III-A and B |
| Q14242 | CD162 | R & D Systems | AF3345 | AF3345 | P-selectin glycoprotein ligand 1, PSGL-1 |

TABLE 1-continued

List of antibodies for use in characterization of extracellular vesicles

| UniProt ID | Antibody target | Antibody Producer | Catalog # | Clone | Alternative names |
|---|---|---|---|---|---|
| Q86VB7 | CD163 | Trillium Diagnostics | clone Mac2-158 | Mac2-158 | Scavenger receptor cysteine-rich type 1 protein M130 |
| P32004 | CD171 | Sigma | HPA005830 | — | L1CAM Neural cell adhesion molecule L1 |
| P15391 | CD19 | R & D Systems | MAB4867 | 4G7-2E3 | B-lymphocyte antigen |
| P22897 | CD206 | R&D Systems | AF2534 | — | MRC1 Macrophage mannose receptor 1 |
| P02724 | CD235a | R & D Systems | MAB1228 | | Glycophorin A, MN sialoglycoprotein, PAS-2 |
| Q5ZPR3 | CD276 (B7-H3) | Sdix | 2622.00.02 | — | B7-H3 |
| P10747 | CD28 | BD Biosciences | 340975 | L293 | T-cell-specific surface glycoprotein |
| P07766 | CD3 | BD Biosciences | 555337 | Hit3a | T-cell surface glycoprotein |
| P11049 | CD37 | R & D Systems | MAB4625 | 424925 | Leukocyte antigen, Tspan26 |
| P01730 | CD4 | R & D Systems | MAB379 | 34930 | T-cell surface glycoprotein, T-cell surface antigen T4/Leu-3 |
| P08514 | CD41 | Biolegend | 303702 | HIP8 | Integrin alpha-IIb, ITA2B |
| P14770 | CD42a | LS Bio | LS-C45240 | — | GPIX, platelet glycoprotein IX |
| P08575 | CD45 | R & D Systems | MAB1430 | 2D1 | GPIX, Receptor-type tyrosine-protein phosphatase C |
| P13612 | CD49d | BD Biosciences | 340976 | L25 | Integrin alpha-4, ITA4 |
| P13591 | CD56 | BD Biosciences | 559043 | 3G8 | NCAM1, Neural cell adhesion molecule 1 |
| P16581 | CD62 E | Thermo Scientific | MA1-22165 | — | E-selectin |
| P16109 | CD62 E/P | R & D Systems | BBA1 | BBIG-E(13D5) | P-selectin |
| P08962 | CD63 | AbD serotec | MCA2142 | — | Tspan30, LAMP-3, lysosomal-associated membrane protein3, OMA81H, MLA1 |
| P33681 | CD80 | R & D Systems | MAB140 | 37711 | T-lymphocyte activation antigen, Activation B7-1 antigen, BB1, CTLA-4 counter receptor B7.1, CD28LG |
| P60033 | CD81 | Ancell | 302-020 | — | 26 kDa cell surface protein TAPA-1, Tspan28 |
| P27701 | CD82 | R & D Systems | MAB4616 | 423524 | C33 antigen, IA4, Inducible membrane protein R2, metastasis suppressor Kangai-1, Tspan27 |

TABLE 1-continued

List of antibodies for use in characterization of extracellular vesicles

| UniProt ID | Antibody target | Antibody Producer | Catalog # | Clone | Alternative names |
|---|---|---|---|---|---|
| Q01151 | CD83 | R & D Systems | MAB1774 | H15e | B-cell activation proein, cell surface protein HB15 |
| P01732 | CD8α | R & D Systems | MAB1509 | 37006 | T-lymphocyte differentiation antigen T8/Leu-2, T-cell surface glycoprotein CD8 |
| P21926 | CD9 | Ancell | 156-020 | — | 5H9 antigen, cell growth-inhibiting gene 2 protein, leukocyte antigen MIC3, motility-related protein, MRP-1, Tspan29 |
| P06731 | CEA | R & D Systems | MAB41281 | 487609 | Carcinoembryonic antigen-related cell adhesion molecule 5, CD66e, meconium antigen 100 |
| P08581 | c-MET | Sino Biological | 10692-R016-100 | O16 | Hepatocyte growth factor receptor, HGR receptor, HGF/SF receptor, scatter factor receptor, tyrosin-protein kinase Met |
| P38432 | Coilin | Santa Cruz Bio | Sc-55594 | F-7 | COIL, p80-coilin |
| P16410 | CTLA4 | LS Bio | LC-C134750 | ANC152.2/8H5 | Cytotoxic T-lymphocyte protein 4, CD152 |
| P00533 | EGFR | Ab Online | ABIN191750 | — | Epidermal growth factor receptor, c-ErbB-1, receptor tyrosin-protein kinase erbB1, HER1 |
|  | EGFRvIII | Ab Online | ABIN742035 | — |  |
| P16422 | EpCam | Santa Cruz Bio | Sc-59782 | 0.N.277 | Epithelial cell adhesion molecule, adenocarcinoma-associated antigen, cell surface glycoprotein Trop-1, EGP, Epithelial glycoprotein 314, hEGP314, KS 1/4 antigen, major gastrointestinal tumor-associated protein GA733-2, tumor-associated calcium signal transducer 1, CD326 |
| P48023 | Fas Ligand (CD178) | AbD serotec | MCA2408GA | 10F2 | Tumor necrosis factor ligand superfamily member 6, apoptosis antigen ligand, APTL, CD95L, CD178 |
| O75955 | Flotillin-1 | Abcam | ab41927 | — | FLOT-1 |
| P11021 | GRP78 | Santa Cruz Bio | Sc-1050 | N-20 | 78 kDa glucose-regulated protein, endoplasmic reticulum lumental ca(2+) binding protein |

TABLE 1-continued

List of antibodies for use in characterization of extracellular vesicles

| UniProt ID | Antibody target | Antibody Producer | Catalog # | Clone | Alternative names |
|---|---|---|---|---|---|
| | | | | | grp78, heat shock 70 kda protein 5, Immunoglobulin heavy chain-binding protein, BiP |
| Q99075 | HB EGF | Abcam | ab66792 | 4G10 | Proheparin-binding EGF-like growth factor, diphteria toxin receptor, DT-R |
| P04626 | HER2 | Cell Signalling | 2165S | 29D8 | Receptor tyrosine-protein kinase erbB-2, metastatic lymph node gene 19 protein, MLN19, proto-oncogene Neu, c-ErbB-2, tyrosine kinase-type cell surface receptor HER2, p185erbB2, CD340 |
| P21860 | HER3 | Abcam | ab91084 | 2F9 | Receptor tyrosine-protein kinase erbB-3, proto-oncogene-like protein, c-ErbB-3, tyrosine kinase-type cell surface receptor HER3 |
| | HER4 | Abcam | ab3104 | H4.77.16 | Receptor tyrosine-protein kinase erbB-4, proto-oncogene-like protein, c-ErbB-4, tyrosine kinase-type cell surface receptor HER4, p180erbB4 |
| Tissue-specific | HLA ABC | Biolegend | 311402 | W6/32 | |
| Tissue-specific | HLA DR | Biolegend | 307602 | L243 | |
| Tissue-specific | HLA DR | Abcam | ab8085 | HL-40 | |
| Tissue-specific | HLA DR/DP/DQ | Loke Diagnostic | xxx | HB-145 | |
| P31268 | HoxA7 | Santa Cruz Bio | Sc-81290 | 743C1A | Homeobox protein Hox-A7, Hox 1.1, Hox-A1 |
| P08238 | Hsp90 | Abcam | ab13494 | IGF1 | Heat shock protein HSP 90-beta, heat shock 84 kDa, hsp84 |
| P05362 | ICAM-1 | eBioscience | BMS1011 | R6.5 | Intercellular adhesion molecule 1, major group rhinovirus receptor, CD54 |
| Q08431 | Lactadhedrin | Haematologic Technologies Inc. | BLAC-1200 | — | Breast epithelial antigen BA46, HMFG, MFGM, Milk fat globule-EGF factor 8 |
| P13473 | LAMP2 | R & D Systems | MAB6228 | H4A3 | Lysosome-associated membrane glycoprotein 2, CD107 antigen-like family member B, CD107b, LGP-96 |

TABLE 1-continued

List of antibodies for use in characterization of extracellular vesicles

| UniProt ID | Antibody target | Antibody Producer | Catalog # | Clone | Alternative names |
|---|---|---|---|---|---|
| P20701 | LFA1 (CD11a) | Ab biotec | 250944 | HI111 | Integrin alpha-L, CD11 antigen-like family member A, leukocyte adhesion glycoprotein LFA-1 alpha chain, LFA-1A, CD11a |
| Q29983 and Q29980 | MIC A/B | R & D Systems | MAB13001 | 159207 | MHC class I polypeptide-related sequence A and B |
| P15941 | MUC1 | R & D Systems | MAB6298 | 604804 | Mucin-1, breast carcinoma-associated antigen DF3, cancer antigen 15-3, CA15-3, Episialin, H23AG, Krebs von den Lungen-6, KL-6, peanut-reactive urinary mucin, PUM, CD227 |
| Q8WXI7 | Mucin16 | Santa Cruz Bio | Sc-52095 | X306 | Mucin-16, MUC16, ovarian cancer-related tumor marker CA125 |
| P19022 | N-Cadherin | Abcam | ab19348 | 8C11 | Cadherin-2, CDw325, neural cadherin, CD325, CDH2 |
| P06748 | Nucleophosmin | Abcam | ab10530 | FC82291 | NPM, nucleolar phosphoprotein B23, Nucleolar protein N038, Numatrin |
| P78358 | NY-ESO-1 | Santa Cruz Bio | Sc-53869 | E978 | Cancer/testis antigen 1, CTAG1A, Autoimmunogenic cancer/testis antigen 6.1, CT6.1, L antigen family member 2, LAGE-2B |
| P10451 | Osteopontin | Acris | AP08377PU-N | — | Bone sialoprotein 1, nephropontin, secreted phosphoprotein 1, SPP-1, urinary stone protein, uropontin |
| P04637 | p53 | Abcam | ab26-100 | pAb240 | Cellular tumor antigen p53, antigen NY-CO-13, phosphoprotein p53, tumor suppressor p53 |
| O15350 | p73 alpha | Leica | NCL-p73 | 24 | Tumor protein p73, p53-like trascription factor, p53-related protein |
| Q06710 | PAX-8 | Cell Marque | 363A-15 | — | Paired box protein Pax-8 |
| Q9N2Q7 | PD-L1 | Sino Biological | 10084-R001-50 | — | Programmed cell death 1 ligand 1, CD274, PDCD1 ligand 1, B7 homolog 1, B7-H1 |
| P05187 | PLAP | Santa Cruz Bio | Sc-47691 | 8B6 | Alkaline phosphatase, placental type, |

TABLE 1-continued

List of antibodies for use in characterization of extracellular vesicles

| UniProt ID | Antibody target | Antibody Producer | Catalog # | Clone | Alternative names |
|---|---|---|---|---|---|
| | | | | | alkaline phosphatase Regan isozyme, PLAP-1, ALPP |
| P35247 | SFTPD | Acris | BM4005 | VIF11 | Pulmonary surfactant-associated protein D, SP-D, Collectin-7, Lung surfacantant protein D |
| Q8IWL2 | SP-A | Novus | NBP1-05152 | 6F10 | Pulmonary surfactant-associated protein A1, PSP-A, 35 kDa pulmonary surfactant-associated protein, Alveolar proteinosis protein, Collectin-4 |
| Glycan | sTn | Abcam | ab76754 | 219 | |
| | TAG72 | Abcam | ab17361 | 0.N.561 | Tumor-associated glycoprotein 72 |
| O15455 | TLR3 | Santa Cruz Bio | Sc-32232 | TLR3.7 | Toll-like receptor 3, CD283 |
| P19438 | TNF RI | R & D Systems | DY225 | — | Tumor necrosis factor receptor superfamily member 1A, p55, p60, CD120a |
| P20333 | TNF RII | R & D Systems | DY726 | — | Tumor necrosis factor receptor superfamily member 1B, p75, p80 TNF-alpha receptor, CD120b |
| Q99816 | TSG101 | Abcam | ab117627 | — | Tumor susceptibility gene 101 protein, ESCRT-I complex subunit TSG101 |
| P19075 | Tspan8 | R & D Systems | MAB4734 | 458811 | Tumor-associated antigen CO-029, tetraspanin-8 |
| P35968 | VEGFR2 | Biolegend | 359902 | 7D4-6 | Vascular endothelial growth factor receptor 2, Fetal liver kinase 1, FLK-1, CD309 |
| Q16790 | CAIX | Abcam | ab107257 | — | Carbonic anhydrase 9, P54/58N, Renal cell carcinoma-associated antigen G250, |
| P35613 | CD147 | Abcam | ab11572 | — | Basigin, 5F7, Collagenase stimulatory factor, Extracellular matrix metalloproteinase inducer, EMMPRIN, Leukocyte activation antigen M6, OK blood group antigen, Tumor cell-derived collagenase stimulatory factor, TCSF |

TABLE 1-continued

List of antibodies for use in characterization of extracellular vesicles

| UniProt ID | Antibody target | Antibody Producer | Catalog # | Clone | Alternative names |
|---|---|---|---|---|---|
| O95832 | Claudin-1 | Abcam | ab63070 | — | Senescence-associated epithelial membrane protein, SEMP1 |
| Q07954 | LRP-1 | Abcam | ab20384 | — | Prolow-density lipoprotein receptor-related protein 1, Alpha-2-macroglobulin receptor, A2MR, CD91 |

More specifically, EVs can for example be recognized by detection of tetraspanins, annexins and heat shock proteins. Examples genes, which are expressed in EVs are CD9, CD63, CD62E, CD81, CD142, Flot-1, N-Cad, CD105, CD235a, CD42b, CD138, CD141 and CD162. Thus, in one embodiment, the extracellular vesicles express one or more gene products of a gene selected from the group consisting of CD9, CD63, CD62E, CD81, CD142, Flot-1, N-Cad, CD105, CD235a, CD42b, CD138, CD141 and CD162.

In another preferred embodiment, the at least one member of a plurality of genes or gene products associated with a population of extracellular vesicles and/or physiological or clinical condition are selected from the group consisting of AnnexinV, CD19, CD106, CD142, TNF RI, CD9, CD42a, CD81, Alix, CD63, CD62E, CD3, Flotillin-1, TSG101 and ICAM-1. The presence of these gene products can be detected using one or more antibodies, which are shown in table 2.

To only detect the exosomes captured on such an array, a cocktail of antibodies against the tetraspanins CD9, CD63 and CD81 could be used. These antibodies can ensure that all captured exosomes are detected, and concomitantly excluding the detection of other types of extracellular vesicles. Thus, in one specific embodiment, exosomes are defined as vesicles carrying tetraspanins CD9, CD63 and/or CD81, and the plurality of genes or gene products associated with a population of extracellular vesicles comprises one or more or all of the tetraspanins CD9, CD63 and/or CD81.

TABLE 2

List of preferred antibodies for use in characterization of extracellular vesicles

| Company | Anti-human antibody | Catalogue no. | Clone |
|---|---|---|---|
| R&D Systems (MN, USA) | AnnexinV | AF399 | — |
| | CD19 | MAB4867 | 4G7-2E3 |
| | CD106 | MAB809 | HAE-2Z |
| | CD142 | MAB2339 | 323514 |
| | TNF RI | 840237 | — |
| LifeSpan BioSciences (WA, USA) | CD9 | LS-035418 | — |
| | CD42a | LS-045240 | — |
| | CD81 | LS-B7347 | — |
| Biolegend (CA, USA) | Alix | 634501 | 3A9 |
| | CD63 | 312002 | MEM-259 |
| Thermo Scientific (MA, USA) | CD62E | MA1-22165 | — |
| BD Biosciences (CA, USA) | CD3 | 555337 | Hit3a |
| Abcam (MA, USA) | Flotillin-1 | ab41927 | — |
| | TSG101 | ab117627 | — |
| eBiosciences (CA, USA) | ICAM-1 | BMS1011 | R6.5 |

Protein microarrays are well accepted as powerful tools to search for antigens or antibodies in various sample types. It is used as a high-throughput method to track the interactions and activities of proteins on a large scale. The superiority of protein microarray is that large numbers of proteins can be tracked in parallel; it is a rapid, automated, economical and highly sensitive method consuming only small quantities of samples and reagents.

Protein microarrays for analysis of extracellular vesicles have been developed and shown to be applicable for estimating the content and distribution of vesicles in clinical samples. Thus, in one preferred embodiment, at least one member of a plurality of genes or gene products associated with a population of extracellular vesicles which is associated with a physiological or clinical condition is detected using a protein microarray platform.

A protein microarray consists of a support surface, such as a glass slide, nitrocellulose membrane, bead, or microtitre plate, to which an array of capture proteins is bound. The function of this surface is to provide a support onto which proteins can be immobilized. It should demonstrate maximal binding properties, whilst maintaining the protein in its native conformation so that its binding ability is retained. Microscope slides made of glass or silicon are a popular choice since they are compatible with the easily obtained robotic arrayers and laser scanners that have been developed for DNA microarray technology. However, nitrocellulose film slides can be preferred as a better protein binding substrate for protein microarray applications. The chosen solid surface is then covered with a coating that must serve the simultaneous functions of immobilising the protein, preventing its denaturation, orienting it in the appropriate direction so that its binding sites are accessible, and providing a hydrophilic environment in which the binding reaction can occur. In addition, it also needs to display minimal non-specific binding in order to minimize background noise in the detection systems. Furthermore, it needs to be compatible with different detection systems. Immobilising agents include layers of aluminium or gold, hydrophilic polymers, and polyacrylamide gels, or treatment with amines, aldehyde or epoxy. Thin-film technologies like physical vapour deposition (PVD) and chemical vapour deposition (CVD) are employed to apply the coating to the support surface.

A number of proteins or their ligands are then spotted onto the solid support in a pre-defined pattern. The capture molecules arrayed on the solid surface may be antibodies, antigens, aptamers (nucleic acid-based ligands), affibodies (small molecules engineered to mimic monoclonal antibodies), or full length proteins. Sources of such proteins include cell-based expression systems for recombinant proteins, purification from natural sources, production in vitro by cell-free translation systems, and synthetic methods for peptides.

Detection is preferably achieved by fluorescence labeling which is highly sensitive, safe and compatible with readily available microarray laser scanners. Other labels can be used, such as affinity, photochemical or radioisotope tags. These labels are attached to the probe itself and can interfere with the probe-target protein reaction. Therefore, a number of label free detection methods are available, such as surface plasmon resonance (SPR), carbon nanotubes, carbon nanowire sensors (where detection occurs via changes in conductance) and microelectromechanical system (MEMS) cantilevers. All these label free detection methods are relatively new and are not yet suitable for high-throughput protein interaction detection; however, they do offer much promise for the future.

In one preferred embodiment, the at least one member of a plurality of genes or gene products associated with a population of extracellular vesicles and/or physiological or clinical condition are detected using a protein microarray comprising a ligand or an antibody or a functional fragment thereof, which binds one or more of AnnexinV, CD19, CD106, CD142, TNF RI, CD9, CD42a, CD81, Alix, CD63, CD62E, CD3, Flotillin-1, TSG101 and ICAM-1. Specific examples of preferred antibodies are shown in table 2.

Extracellular vesicles can also be detected using one or more detection members, which recognize one or more membrane components characteristic of the EVs, for example lipids, phospholipids or glycans. In one embodiment, EVs are detected using Lactadherin, which is a protein that binds phosphotiadylserine (PS), which is present in the membranes of the EVs.

In one particular aspect, a use is provided of at least one detection member for detecting in a sample at least one member of a plurality of genes or gene products associated with a population of extracellular vesicles and/or a physiological or clinical condition, wherein the sample is extracted from a dried body fluid card sample, such as a dry blood card sample. The detection member can be any compound capable of detecting one or more gene products associated with a population of extracellular vesicles and/or a physiological or clinical condition. Such detection members include antibodies, antigens, aptamers, affibodies and full length proteins. In one preferred embodiment, the detection member is a group of ligands or antibodies or functional fragments thereof, and in a particularly preferred embodiment, the detection members are provided in the form of a protein microarray.

Clinical Utility

The present disclosure provides methods, wherein at least one member of a plurality of genes or gene products associated with a population of extracellular vesicles is detected. Relevant genes, which are specific for microvesicles and/or exosomes, are mentioned herein above; cf. paragraph "Characterization of extracellular vesicles".

The extracellular vesicles, in particular exosomes, appear to have specialized functions and play key roles in many different physiological processes including coagulation, intercellular signalling and waste management. Exosomes are also recognized as potential markers for prognosis and therapy, and can be used as biomarkers for human health and disease. The methods of the present invention offer an objective and easily manageable approach for collecting samples of extracellular vesicles, such as exosomes from dried body fluid card samples, for example dry blood card samples. In a preferred embodiment, these extracellular vesicles/exosomes are used for further characterization in diagnostic or prognostic or therapeutic approaches. Thus, in one embodiment, a method is provided for diagnosing, prognosing, evaluating and/or monitoring a clinical condition, comprising the following steps
  a. providing a dried body fluid card sample, such as preferably a dry blood card sample,
  b. extracting body fluid/body fluid components, such as blood from said dried body fluid card sample or blood from said dry blood card sample, and
  c. detecting at least one member of a plurality of genes or gene products associated with a population of extracellular vesicles, and
  d. detecting at least one member of a plurality of genes or gene products associated with a clinical condition.

Extracellular vesicles/exosomes can be used for diagnosis, prognosis as well as evaluation or monitoring of different physiological and clinical conditions.

In a preferred embodiment, the clinical condition is a cancer. The cancer is for example an acute lymphoblastic leukemia; acute myeloid leukemia; adrenocortical carcinoma; AIDS-related cancer; AIDS-related lymphoma; anal cancer; appendix cancer; astrocytomas; atypical teratoid/rhabdoid tumor; basal cell carcinoma; bladder cancer; brain stem glioma; brain tumor, brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma; breast cancer; bronchial tumors; Burkitt lymphoma; cancer of unknown primary site (CUP); carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor.

In another embodiment, the cancer is an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumor (GIST), glioblastoma, head and neck squamous carcinoma, leukemia, liver hepatocellular carcinoma, low grade glioma, lung bronchioloalveolar carcinoma (BAC), non-small cell lung cancer (NSCLC), lung small cell cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma.

In another embodiment, the cancer is a breast cancer, triple negative breast cancer, metaplastic breast cancer (MpBC), head and neck squamous cell carcinoma (HNSCC), human papilloma virus (HPV)-positive HNSCC, HPV-negative/TP53-mutated HNSCC, metastatic HNSCC, oropharyngeal HNSCC, non-oropharyngeal HNSCC, a carcinoma, a sarcoma, a melanoma, a luminal A breast cancer, a luminal B breast cancer, HER2+ breast cancer, a high microsatellite instability (MSI-H) colorectal cancer, a microsatellite stable colorectal cancer (MSS), non-small cell lung cancer (NSCLC), chordoma, or adrenal cortical carcinoma. The carcinoma may comprise a carcinoma of the breast, colon, lung, pancreas, prostate, Merkel cell, ovary, liver, endometrial, bladder, kidney or cancer of unknown primary (CUP). The sarcoma may comprise a liposarcoma, chondrosarcoma, extraskeletal myxoid chondrosarcoma or uterine sarcoma. Furthermore, the sarcoma may comprise an alveolar soft part sarcoma (ASPS), angiosarcoma, breast angiosarcoma, chondrosarcoma, chordoma, clear cell sarcoma, desmoplastic small round cell tumor (DSRCT), epithelioid hemangioendothelioma (EHE), epithelioid sarcoma, endometrial stromal sarcoma (ESS), ewing sarcoma, fibromatosis, fibrosarcoma, giant cell tumour, leiomyosarcoma (LMS), uterine LMS, liposarcoma, malignant fibrous histiocytoma (MFH/UPS), malignant peripheral nerve sheath tumor (MPNST), osteosarcoma, perivascular epithelioid cell tumor (PEComa), rhabdomyosarcoma, solitary fibrous tumor (SFT), synovial sarcoma, fibromyxoid sarcoma, fibrous hamartoma of infancy, hereditary leiomyomatosis, angiomyolipoma, angiomyxoma, atypical spindle cell lesion (with fibrohistiocytic differentiation), chondroblastoma, dendritic cell sarcoma, granular cell tumor, high grade myxoid sarcoma, high-grade myoepithelial carcinoma, hyalinizing fibroblastic sarcoma, inflammatory myofibroblastic sarcoma, interdigitating dendritic cell tumor, intimal sarcoma, leiomyoma, lymphangitic sarcomatosis, malignant glomus tumor, malignant myoepithelioma, melanocytic neoplasm, mesenchymal neoplasm, mesenteric glomangioma, metastatic histocytoid neoplasm, myoepithelioma, myxoid sarcoma, myxoid stromal, neurilemmoma, phyllodes, rhabdoid, round cell, sarcoma not otherwise specified (NOS), sarcomatous mesothelioma, schwannoma, spindle and round cell sarcoma, spindle cell or spinocellular mesenchymal tumor.

In a preferred embodiment, the clinical condition is cancer, such as a cancer selected from the group consisting of Non-Small Cell Lung Cancer (NSCLC), Small Cell Lung Cancer (SCLC), prostate cancer, rectal cancer, in particular, locally advanced rectal cancer (LARC), Melanoma, Osteosarcoma, lymphoma, breast cancer, and ovarian cancer.

In another embodiment, the clinical condition is selected from the group consisting of Pneumonia, abortus habitualis, stroke/brain hemorrhage, multiple sclerosis, Chronic Obstructive Pulmonary Disease (COPD), malaria, HPV and side effects thereof, Monoclonal gammopathy of undetermined significance (MGUS), Systemic Lupus Erythematosus (SLE), and Ischemia.

In another preferred embodiment, the clinical condition is lung cancer, and a method is provided for diagnosing and/or prognosing the lung cancer, and/or for evaluating and/or monitoring a treatment of the lung cancer. The most relevant diagnostic and prognostic extracellular vesicle/exosomal markers with respect to lung cancer are CD151, CD171, and tetraspanin 8. The lung cancer is preferably non-small cell lung cancer, and for non-small cell lung cancer the markers are preferably one or more of NY-ESO-1, EGFR, PLAP, EpCam and Alix.

EXAMPLES

Example 1

General Protocol
Sampling:
1) The hands are cleaned and the designated finger swiped with alcohol.
2) Using a lancet device (well known to diabetic patients), a hole is pricked in the fingertip.
3) By massaging the fingertip blood drops will appear, which are placed on one of the indicated circles on the blood card. This is continued until all four circles are saturated with blood.

4) Before the blood card is closed and stored/shipped it is left to dry at room temperature for 1 hour. Afterwards the card is kept in a plastic bag until analysis.

Elution of sample from the blood card:
1) Using a disc punch designed for the purpose a circle is excised from the blood card (12.5 mmØ).
2) The blood disc is wetted with 60 µL of Elution Buffer using a forceps to sustain it.
3) The wetted blood disc is placed in a spin column, which is afterwards placed in a collection tube containing 60 µL Reaction Buffer.
4) The spin column is closed and the assembly is incubated for 1 hour at room temperature.
5) The spin column assembly is centrifuged at 20.000×g for 5 min.
6) The spin column and containing disc is discarded and 60 µL sample is removed from the top and transferred to a new sample tube. At this point, the cell-containing pellet is very diffuse and therefore very fragile. Hence, only the top 60 µL of sample is collected for further use.
7) Subsequently, the sample is ready for analysis by an EV protein microarray without further preparation. Alternatively, the sample can be frozen and analysed later.

Example 2

Comparison of Buffer Compositions

Different buffers for the elution as well as the reaction phase were compared. Following buffers has been tested:

| Buffer no. | Elution phase | Reaction phase |
|---|---|---|
| 1 | Elution buffer (ELU) From ArrayIt's Blood Card Kit-Content unknown | Reaction buffer (REAC) From ArrayIt's Blood Card Kit-Content unknown |
| 2 | ELU | Phosphate Buffered Saline (PBS) 137 mmol NaCl 2.7 mmol KCl 10 mmol $NA_2HPO_4$ 1.8 mmol $KH_2PO_4$ |
| 3 | ELU | PBS + 0.05% Tween20 |
| 4 | ELU | PBS + 0.2% Tween20 |
| 5 | REAC | REAC |
| 6 | PBS | PBS |
| 7 | PBS + 0.05% Tween20 | PBS + 0.05% Tween20 |
| 8 | PBS + 0.2% Tween20 | PBS + 0.2% Tween20 |

The elution process of the protocol is illustrated in FIG. 1.

Even in healthy individuals, the content and composition of extracellular vesicles in the blood vary greatly. Hence, 3 persons were selected to participate in this test. Each person filled out 2 blood cards using blood from the finger tips. Additionally, venous blood were drawn from each person and collected in 4 different blood collection tubes (containing different kinds of anticoagulant agents). Subsequently, all the samples were analyzed using an Extracellular Vesicle (EV) Array (Jørgensen et al., 2013, JEV).

Conclusion

Figure 2:
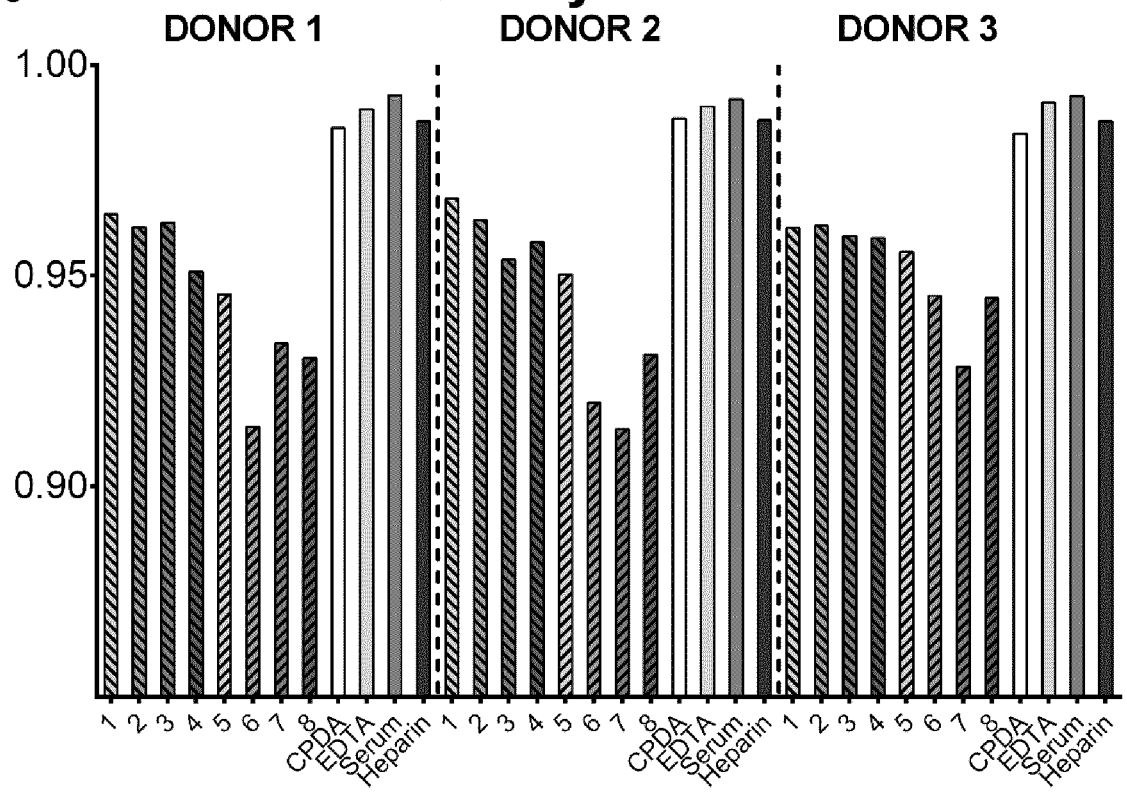
FIG. 2. Quality control; example 2
FIG. 3. Comparison in three donors of the detected expression of CD9.
Figure 3:
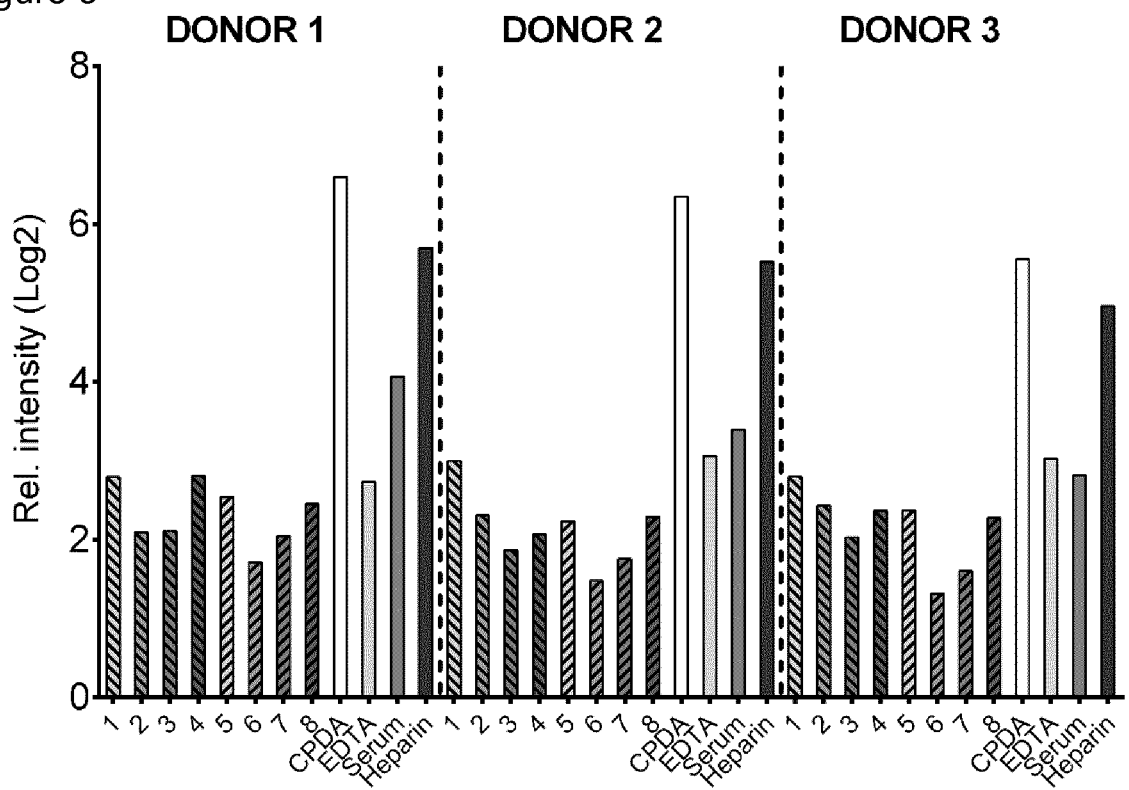
Figure 4:
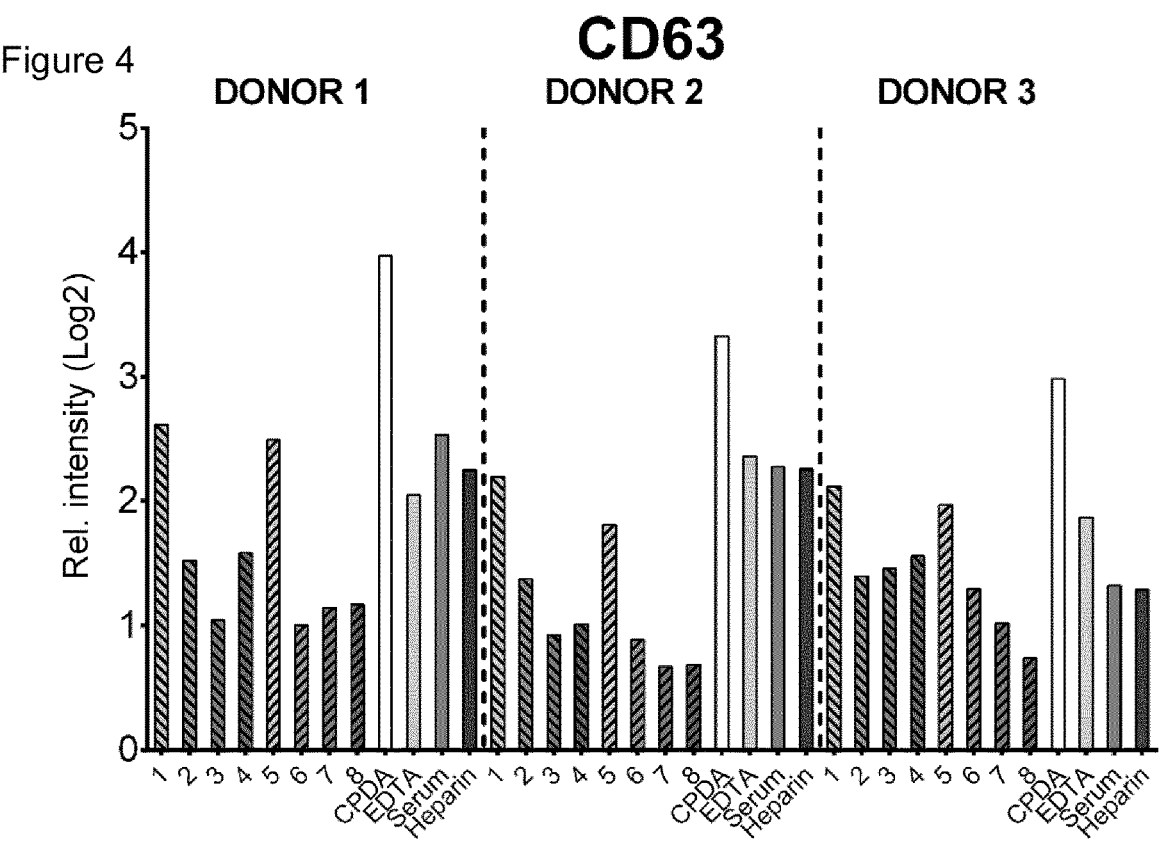
FIG. 4. Comparison in three donors of the detected expression of CD63.
Figure 5:
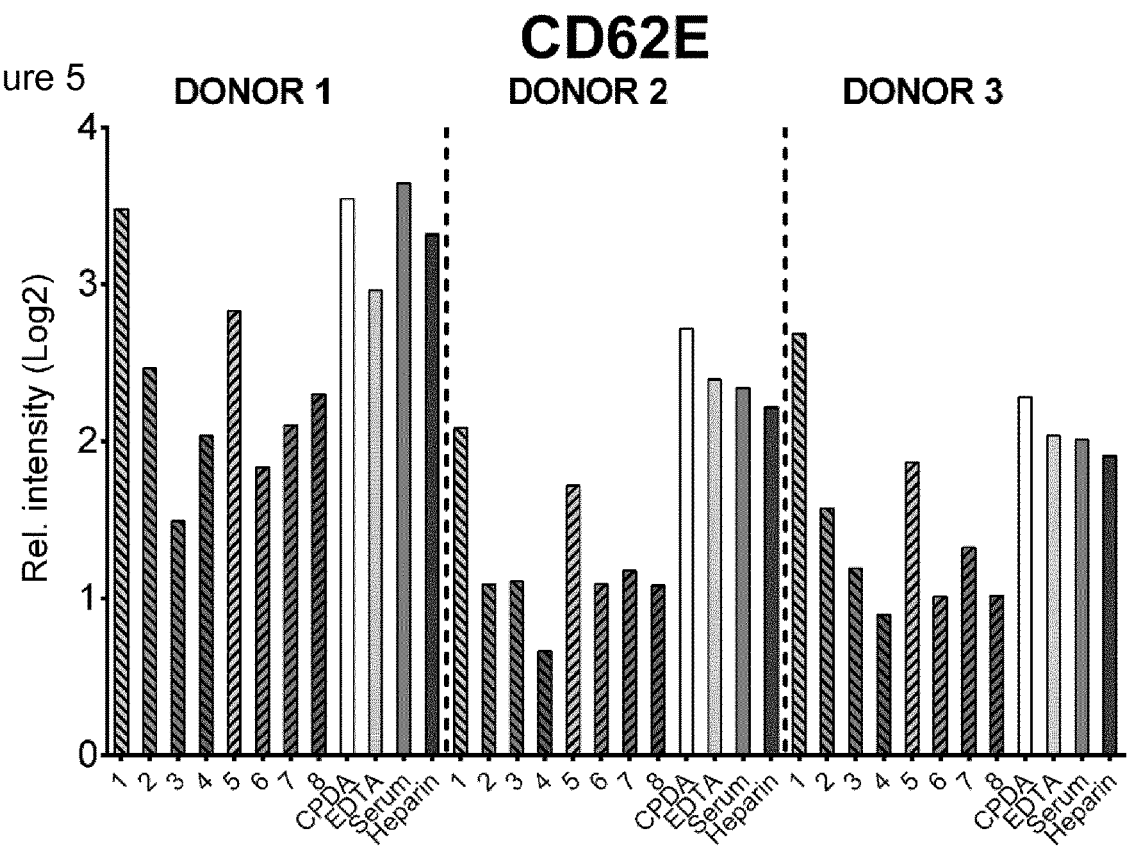
FIG. 5. Comparison in three donors of the detected expression of CD62E.
Figure 6:
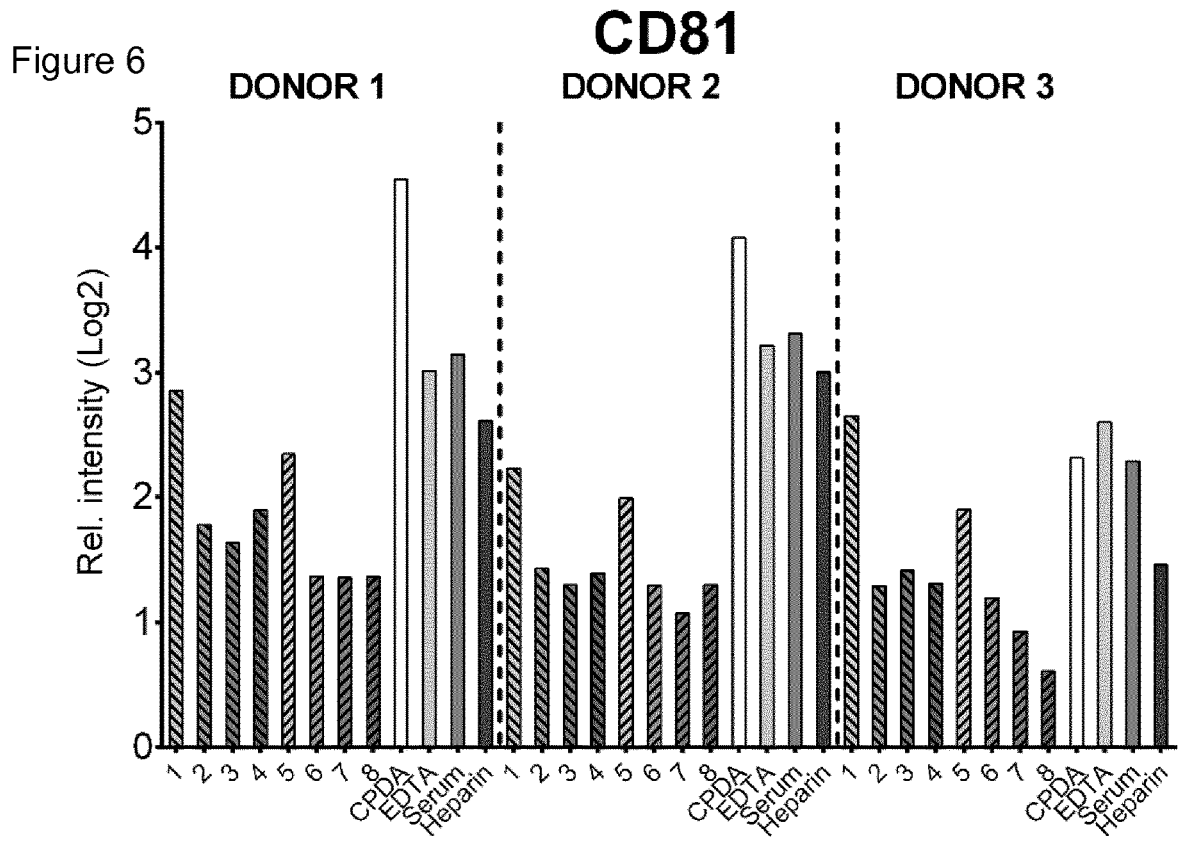
FIG. 6. Comparison in three donors of the detected expression of CD81.
Figure 7:
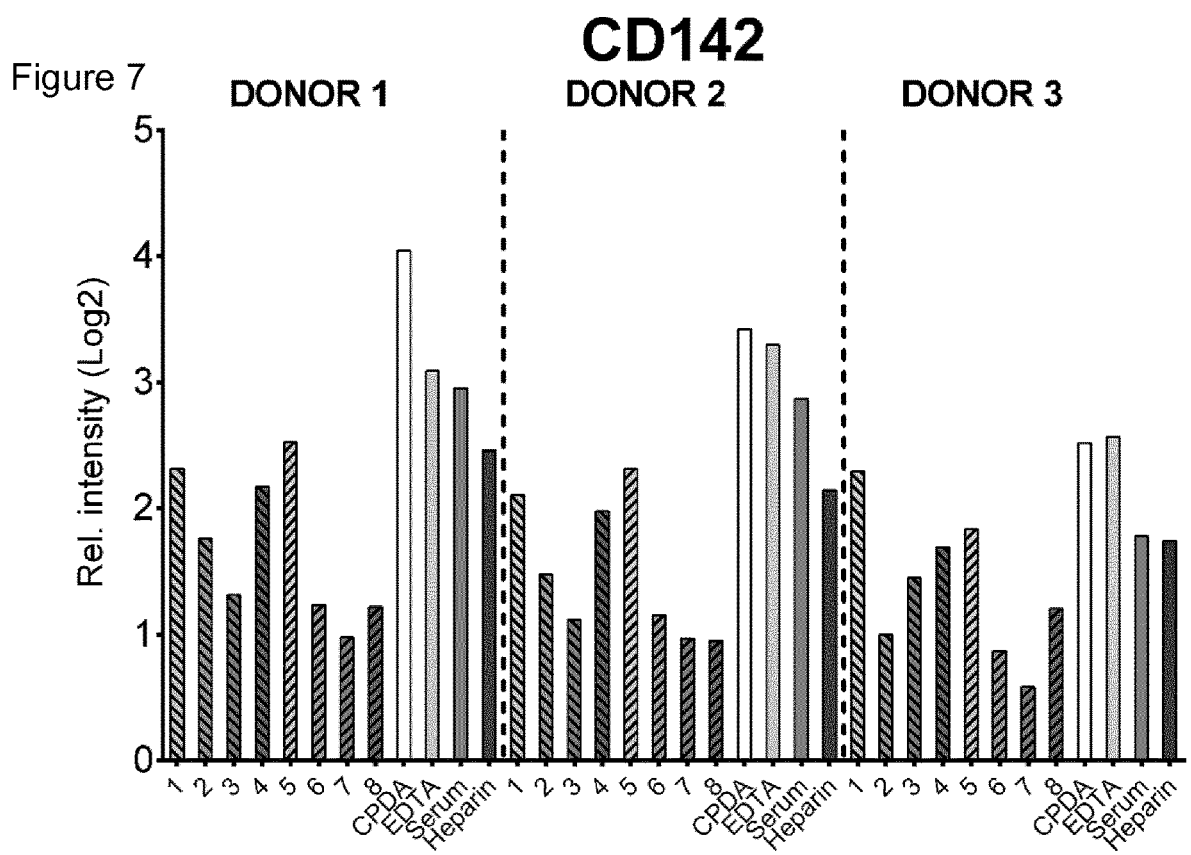
FIG. 7. Comparison in three donors of the detected expression of CD142.
Figure 8:
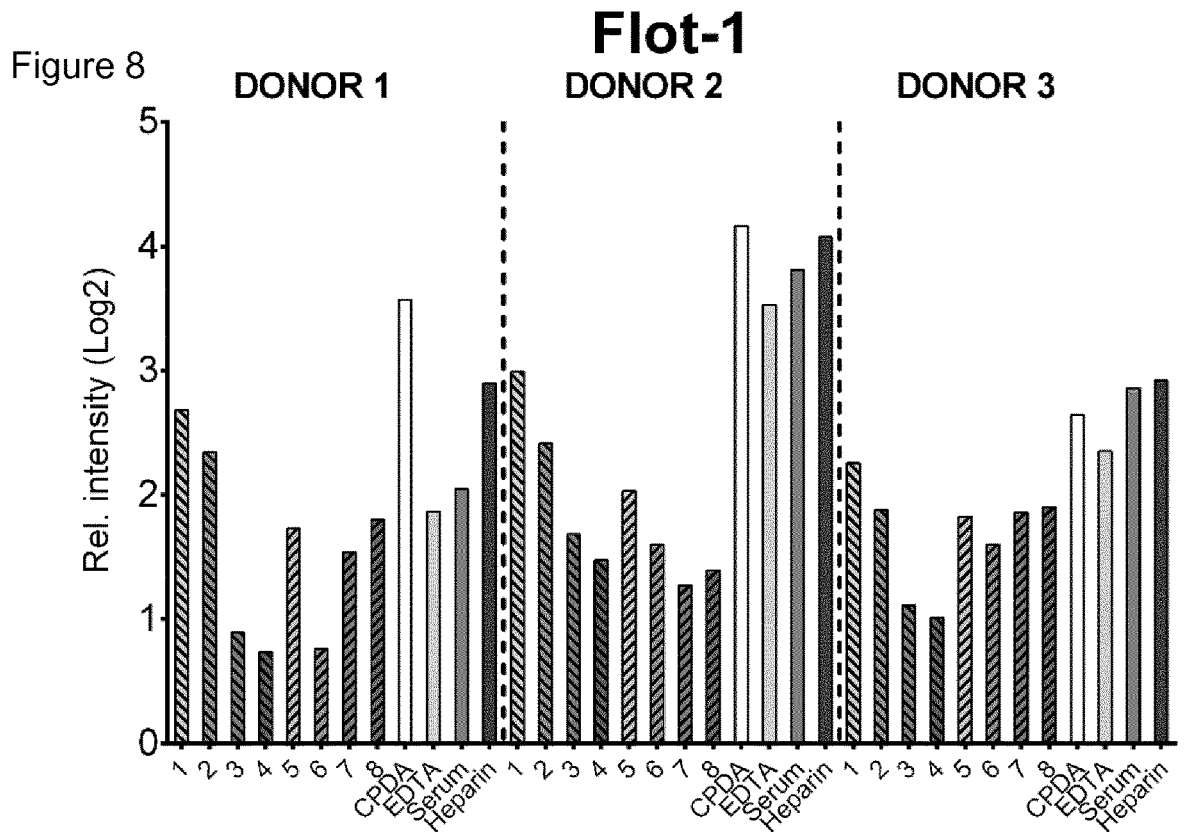
FIG. 8. Comparison in three donors of the detected expression of Flottilin-1.
Figure 9:
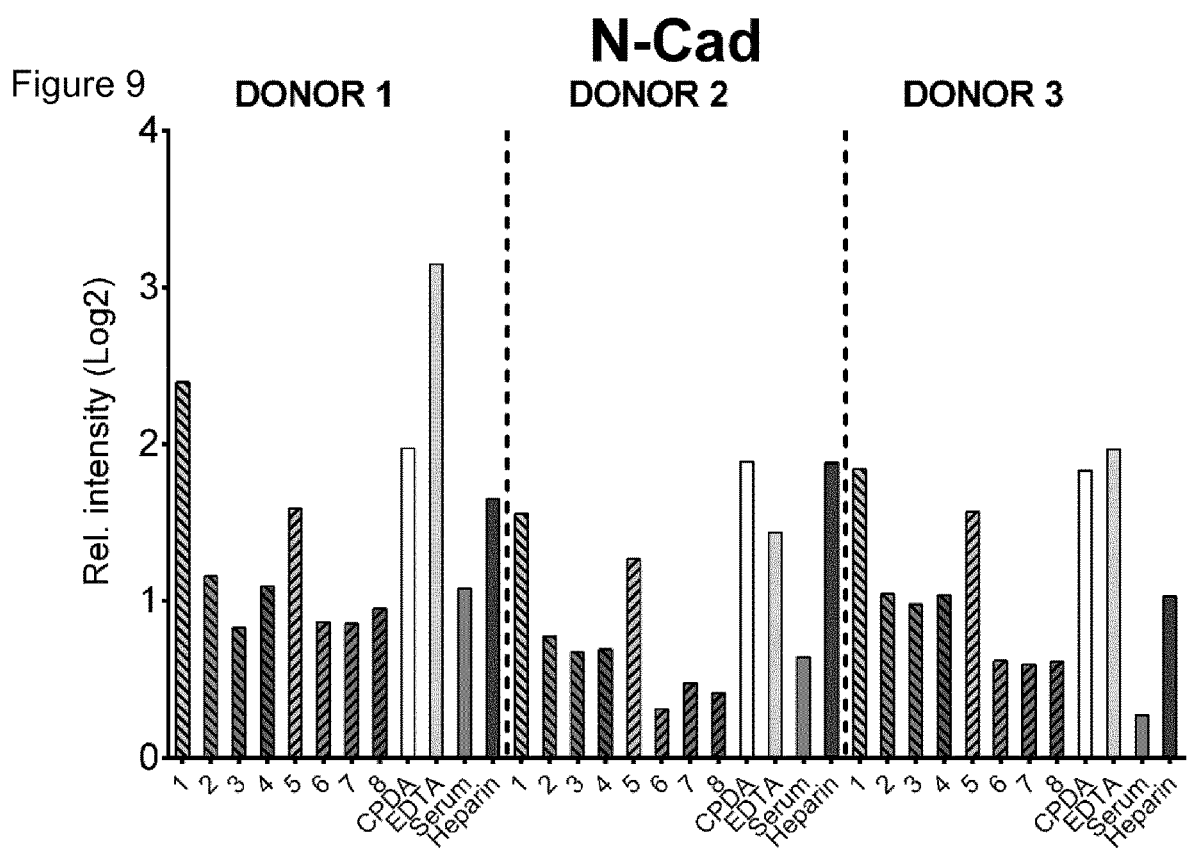
FIG. 9. Comparison in three donors of the detected expression of N-Cadherin.
Figure 10:
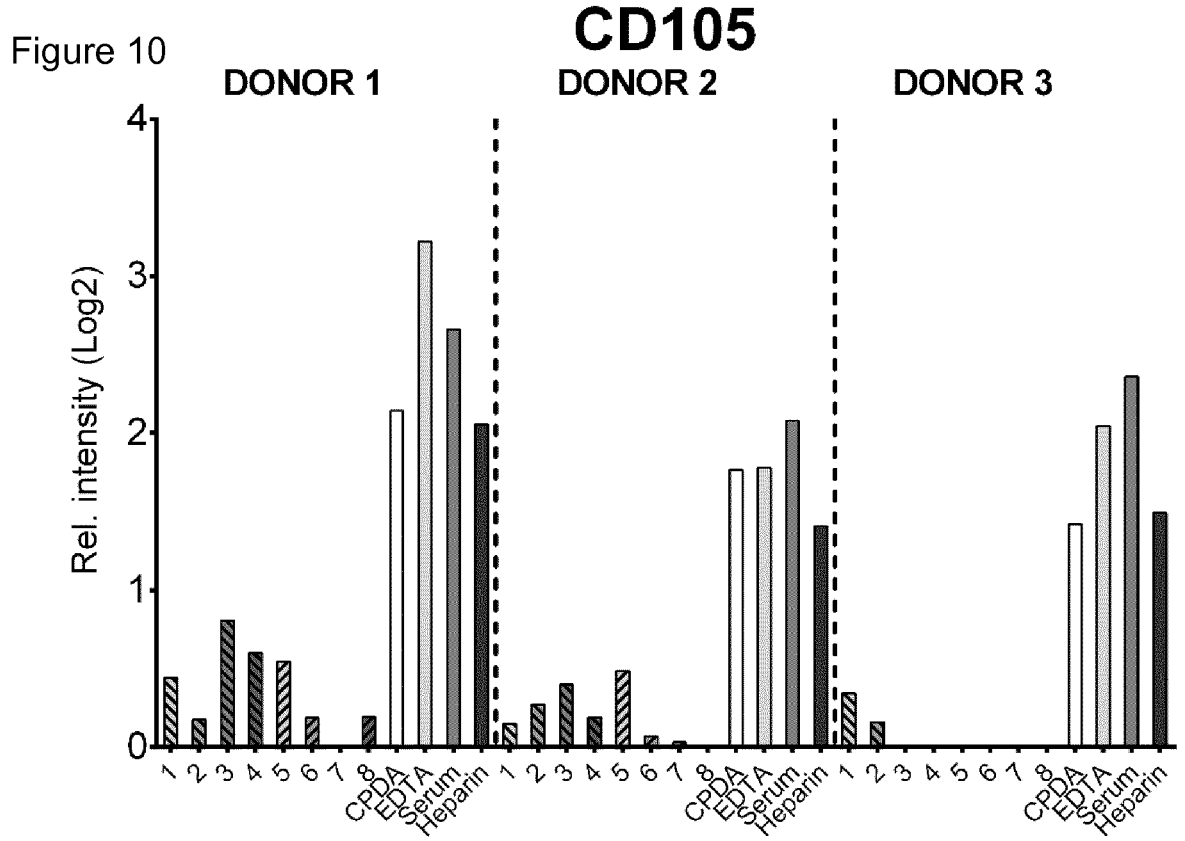
FIG. 10. Comparison in three donors of the detected expression of CD105.
Figure 11:
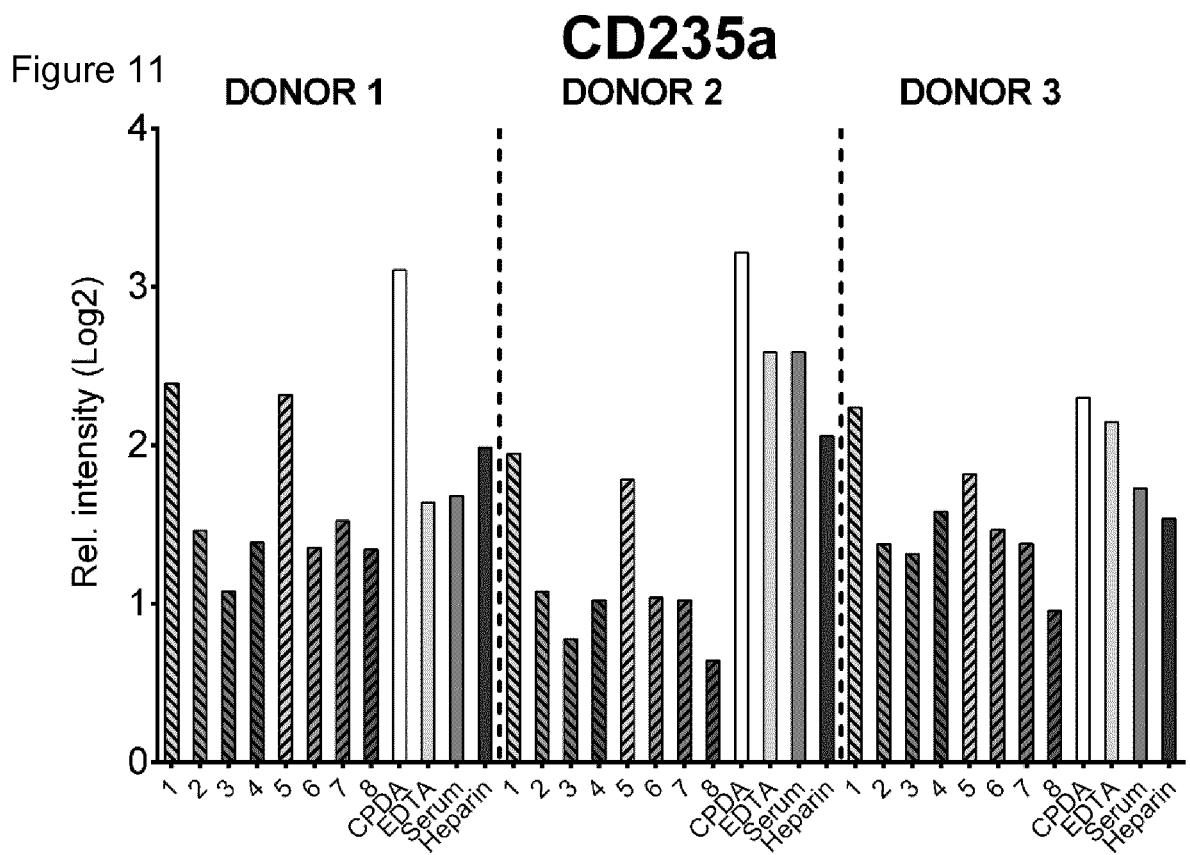
Figure 12:
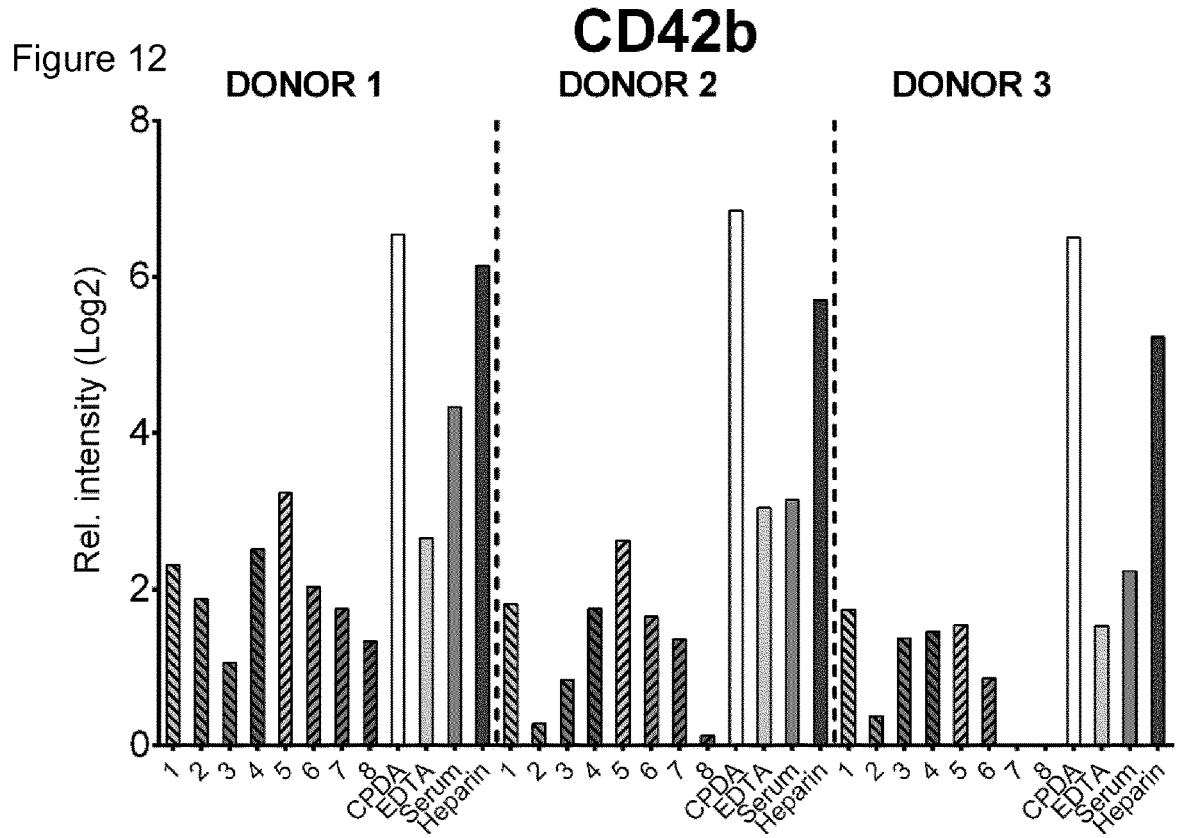
FIG. 12. Comparison in three donors of the detected expression of CD42b.
Figure 13:
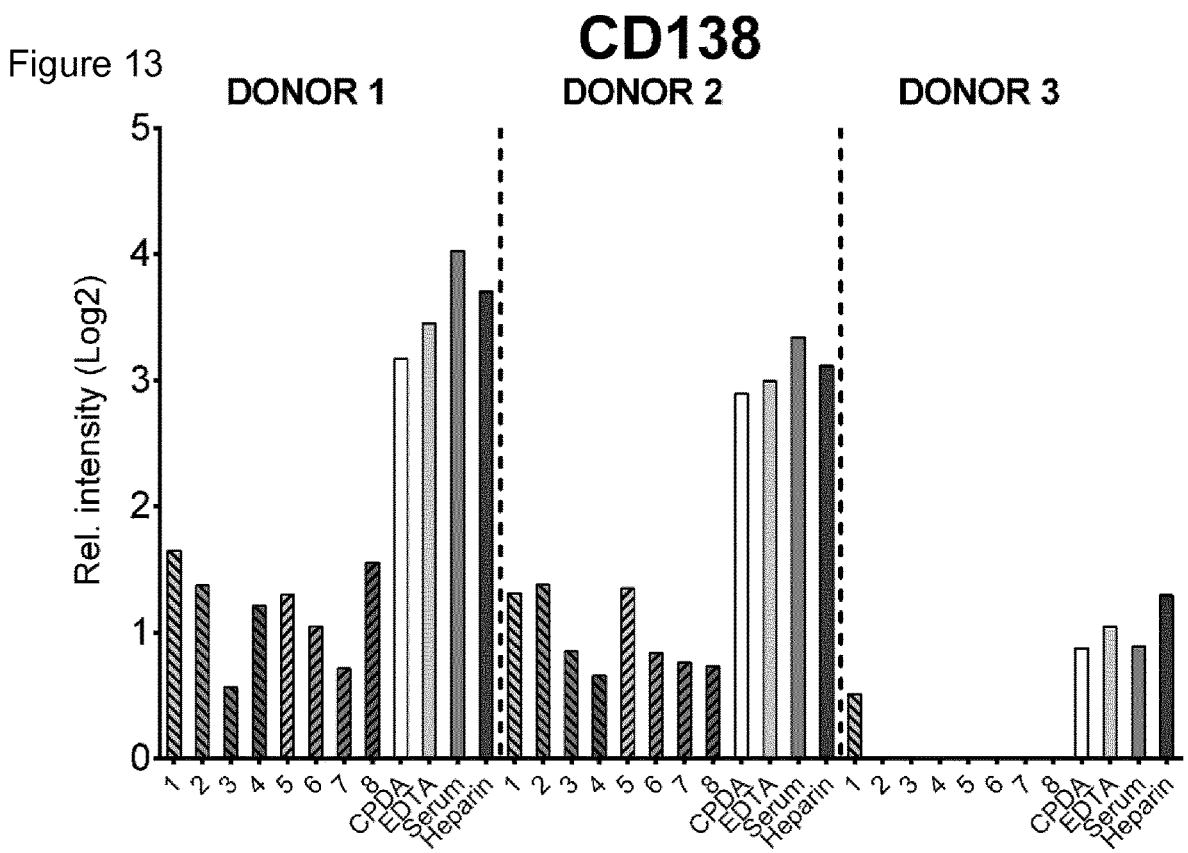
FIG. 13. Comparison in three donors of the detected expression of CD138.
Figure 14:
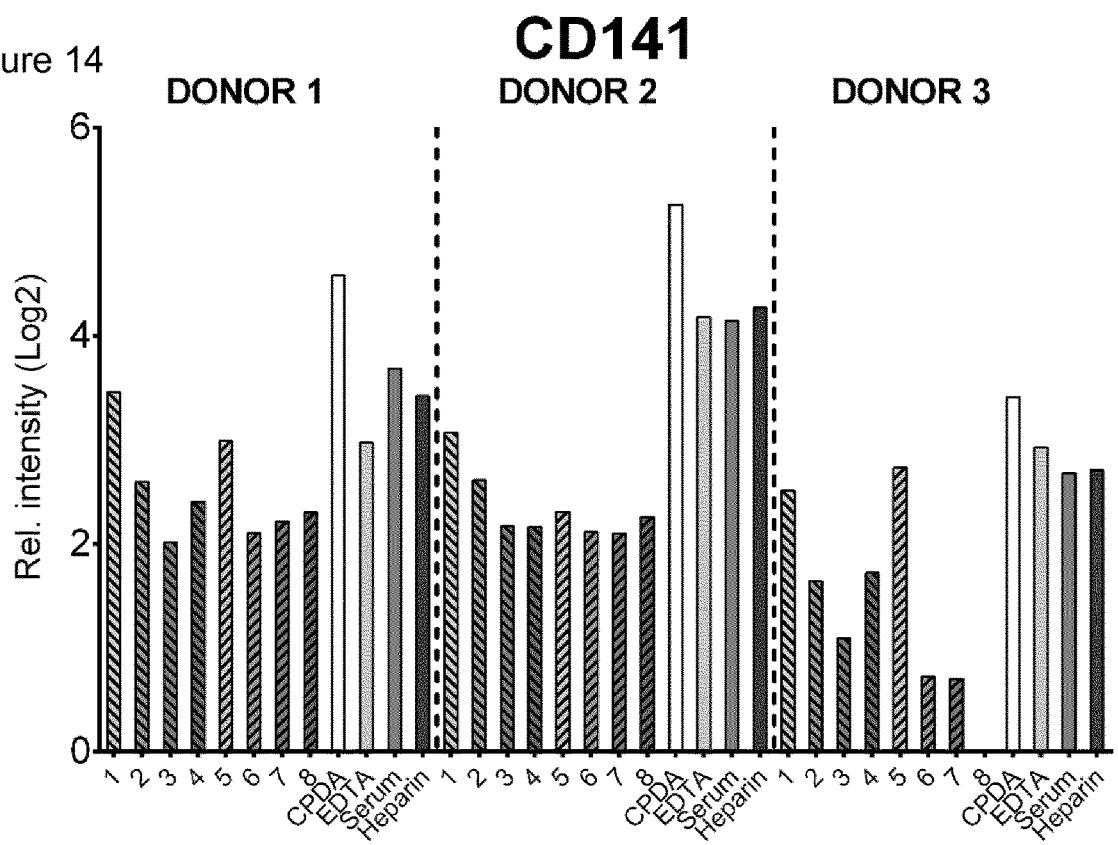
FIG. 14. Comparison in three donors of the detected expression of CD141.
Figure 15:
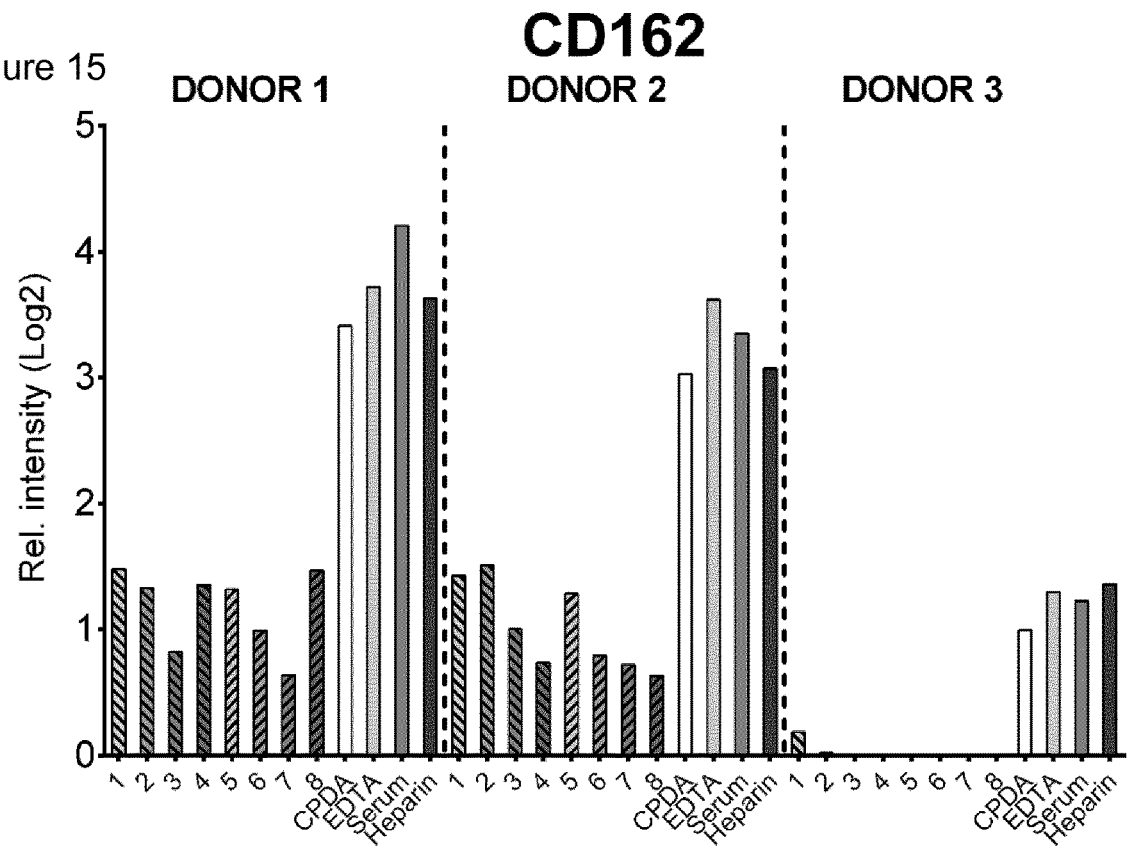
FIG. 15. Comparison in three donors of the detected expression of CD162.

FIG. 2 displays the Quality Control (QC), which is performed in relation to the EV Array analysis. The value on the y-axis outlines the ratio between the printed positive control and the obtained background signal. The ratio is calculated as: (positive control−background signal)/positive control. In practice, if no background is present the value is 1, but increased background will decrease the value (Bæk and Jørgensen, 2017, Meth. Mol. Biol).

The QC graph shows that the reference samples from venous blood have the lowest background, but all samples have a value above 0.9 and thereby clear signals in relation to the background. During the elution from the blood cards, an evident hemolysis is seen. Hemolysis is due to a burst of the erythrocytes which then releases hemoglobin into the liquid. Hereby, the liquid turns red and this coloring is probably the explanation of the increased background levels seen on the EV Array. In the standard treatment of the venous blood the cells are removed by centrifugation and the plasma is isolated prior to the analysis, which is the explanation for the low background signals. The rest of the graphs (FIGS. 3-15) illustrate the results obtained from the vesicles captured on the EV Array. Generally, the venous blood samples show the best results. However, from a quantitative point of view, it is not possible to compare the results directly. In this experiment, 10 µL of the venous blood and 50 µL from the blood card were applied to the EV Array. When the donors fill the blood card they applied blood drops until the indicated circle is red. There are differences in the amount of blood applied in each circle and for some of the donors it was relatively easy to get large blood drops and thereby soaking the blood card. During the procedure of eluting from the blood card, some undefined amount of material will be lost.

The data shown here, clearly show that EVs can be isolated from blood cards. One superior buffer could not be identified on the basis of the present results. However, the buffers from ArrayIt appear to be superior for many of the analytes. This is probably due to a reduced background in relation to the other buffers tested. Still, for other analytes, other buffers appear to perform better.

Example 3

Extraction of Blood From Blood Cards

Based on the above results it was chosen to use buffer no. 8 (PBS with 0.2% Tween20) as both Elution- and Reaction Buffer.

Figure 16:
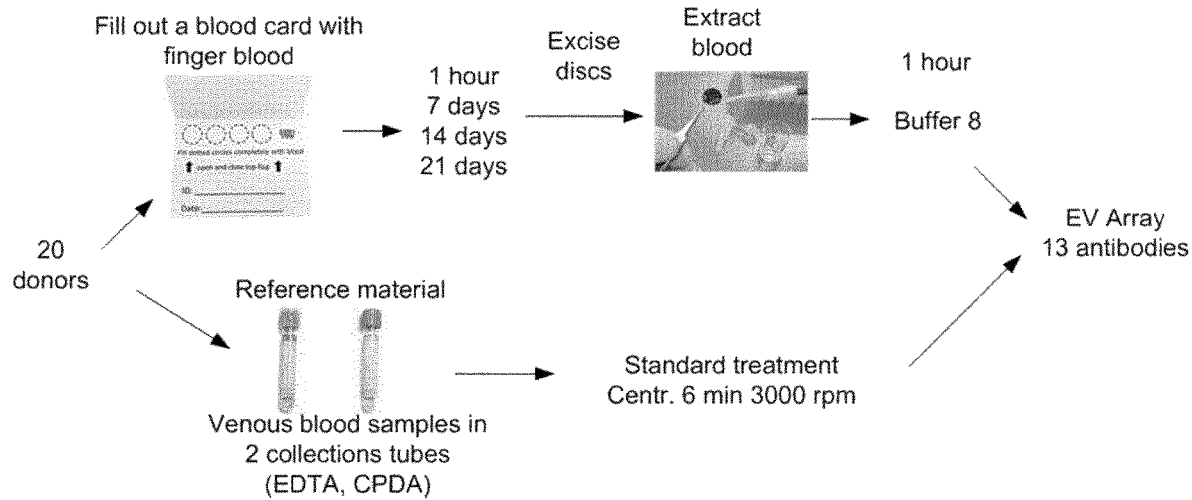
FIG. 16. Overview of experiment, example 3
FIG. 17. Quality control; example 3
FIG. 18. Time course experiment on the detection of CD9 and CD62E/P.
Figure 17:
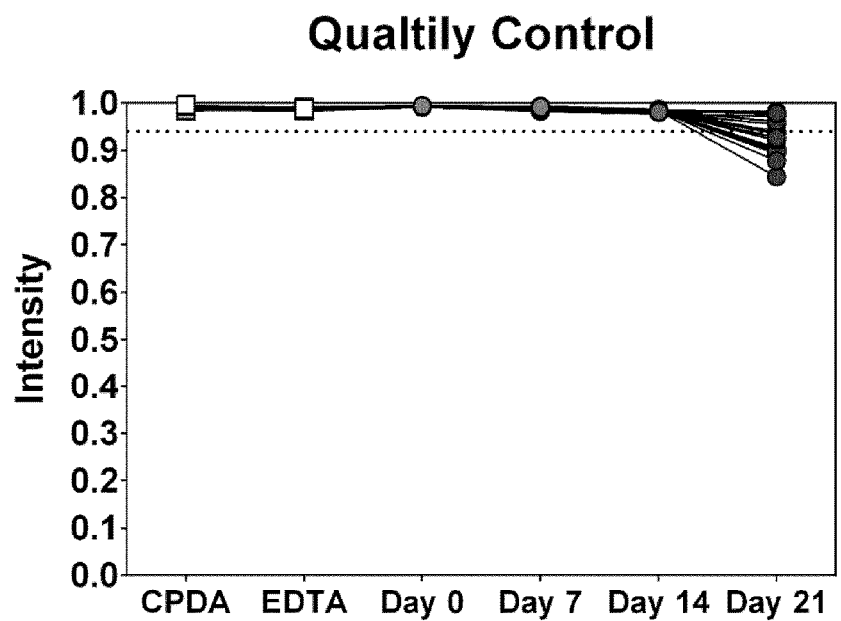
Figure 18:
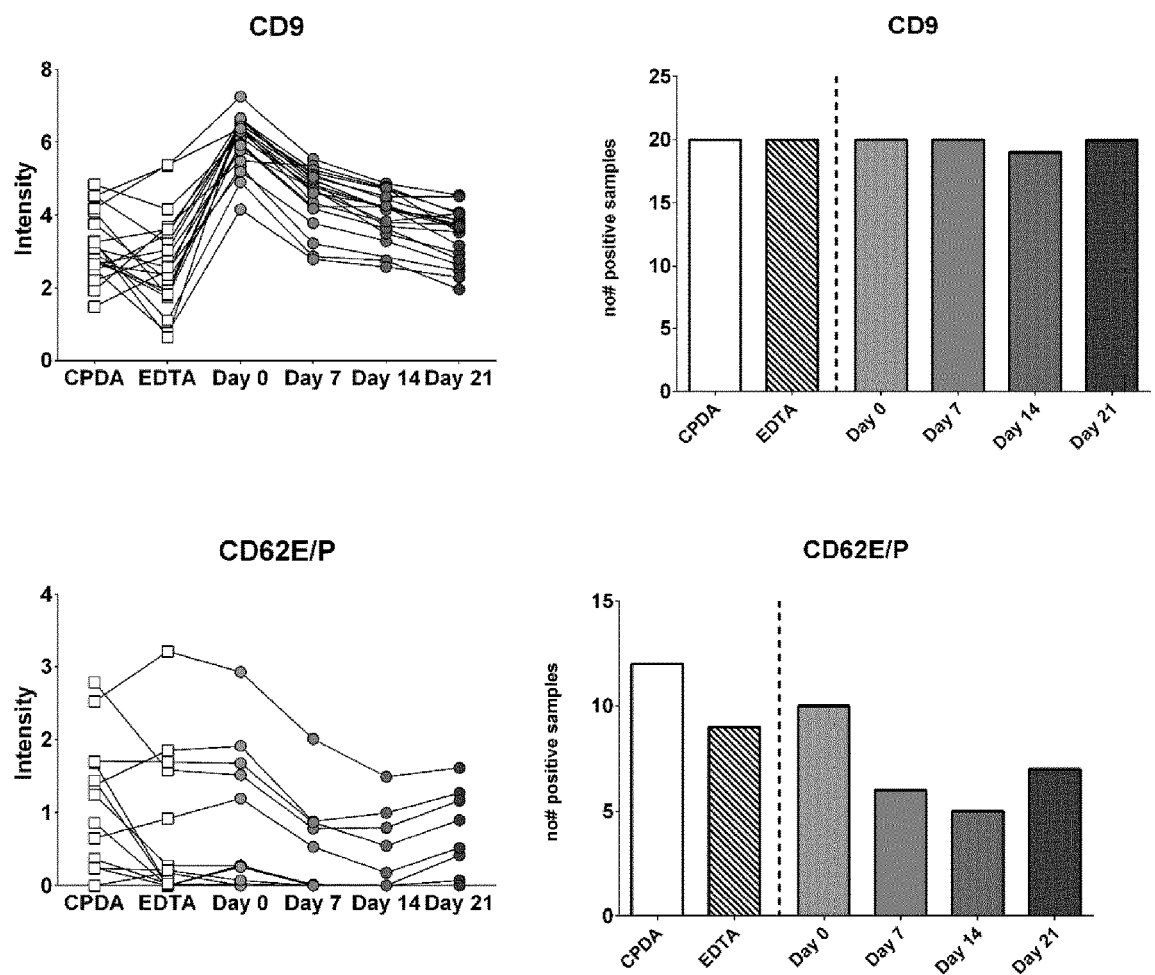
Figure 19:
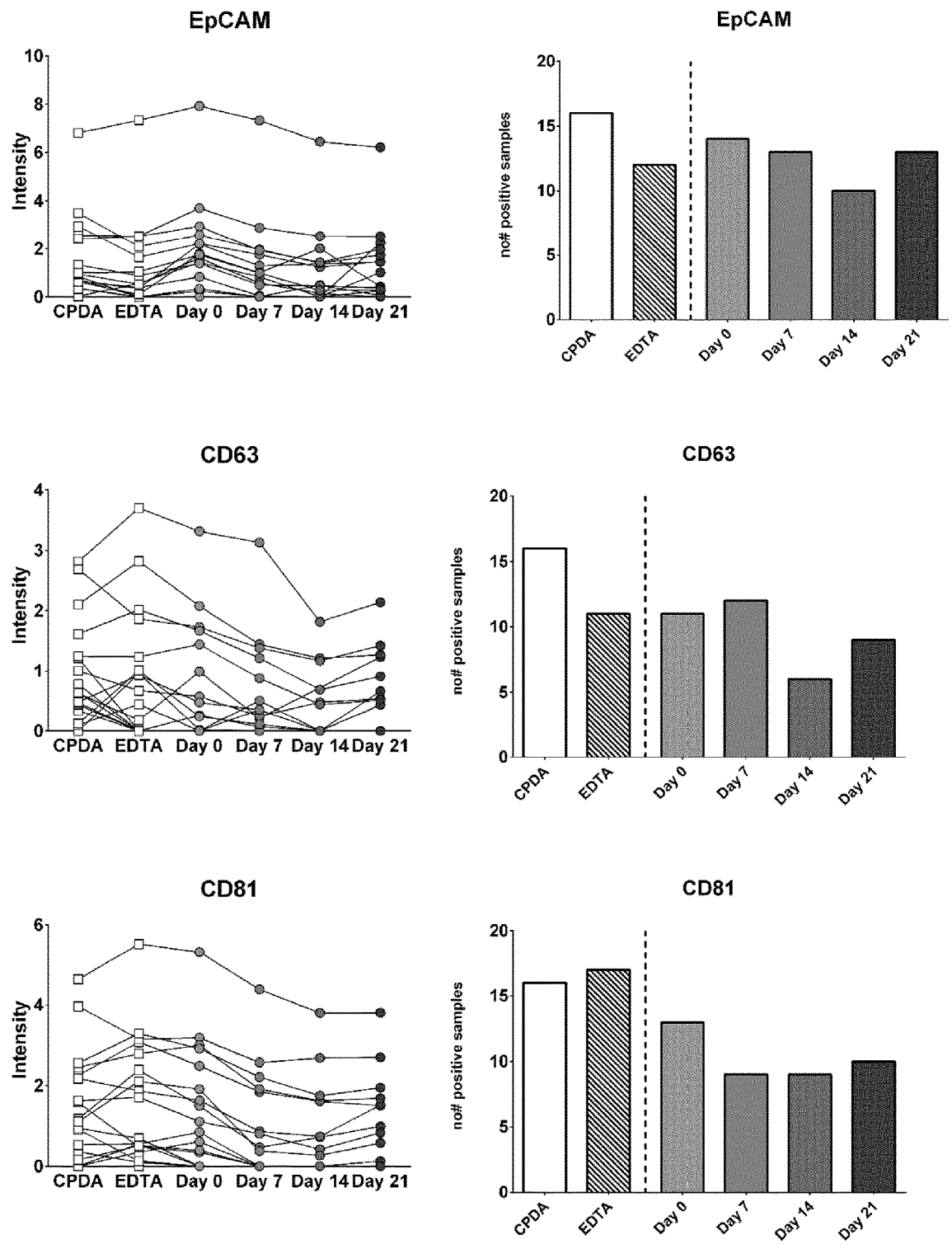
FIG. 19. Time course experiment on the detection of EpCAM, CD63 and CD81.
Figure 20:
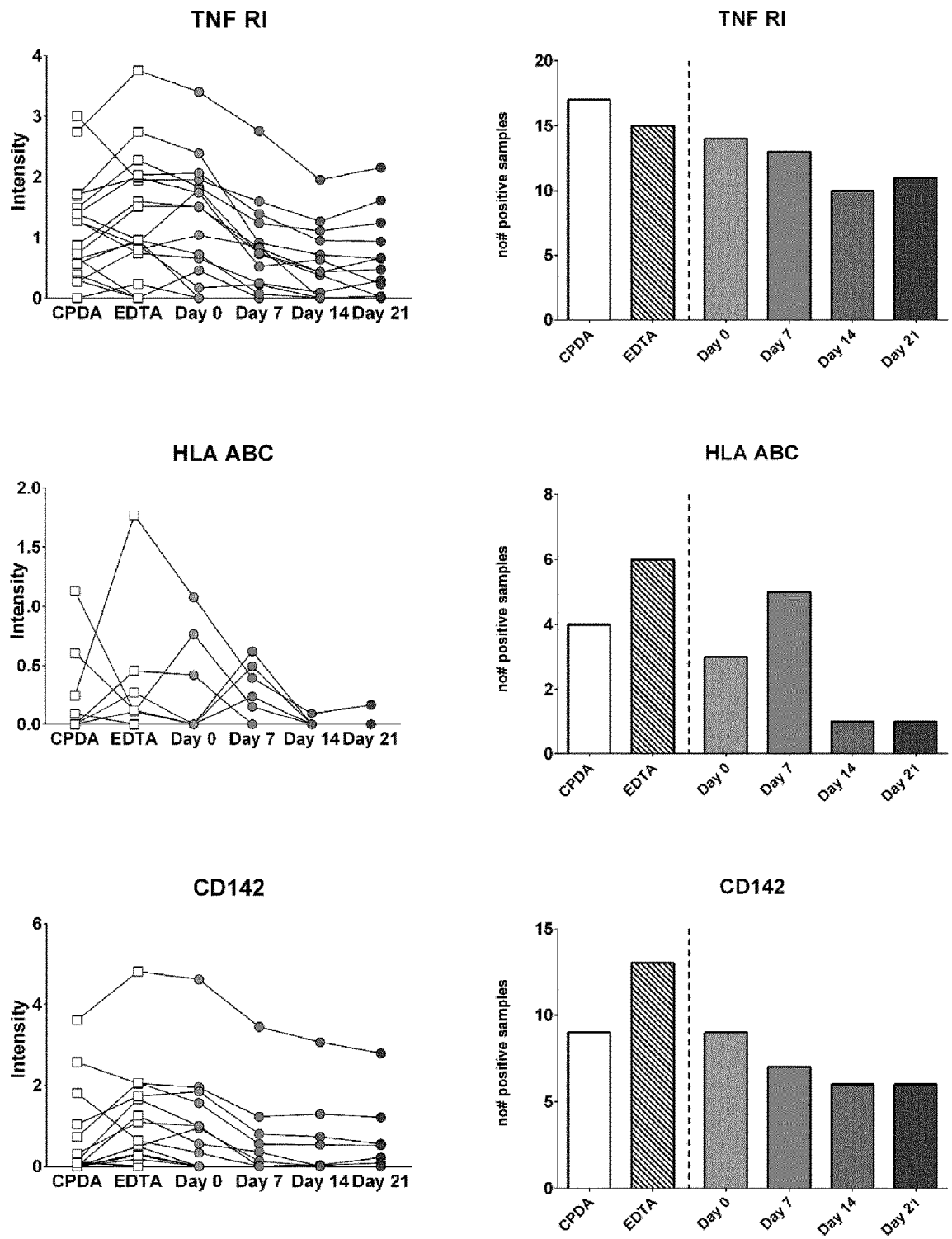
FIG. 20. Time course experiment on the detection of TNF RI, HLA ABC and CD142
FIG. 21. Time course experiment on the detection of Flotilin-1, TSG101 and Alix.
Figure 21:
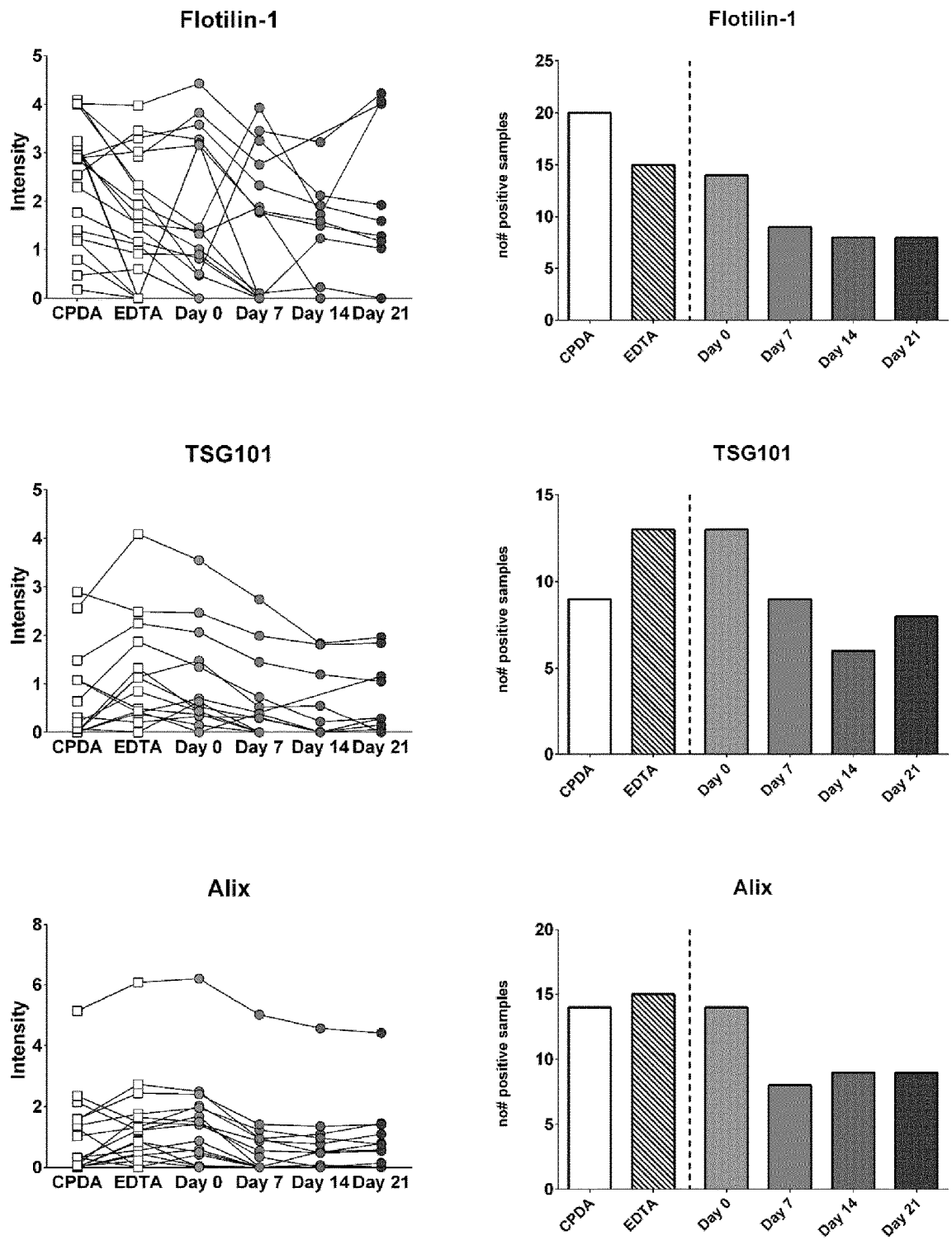
Figure 22:
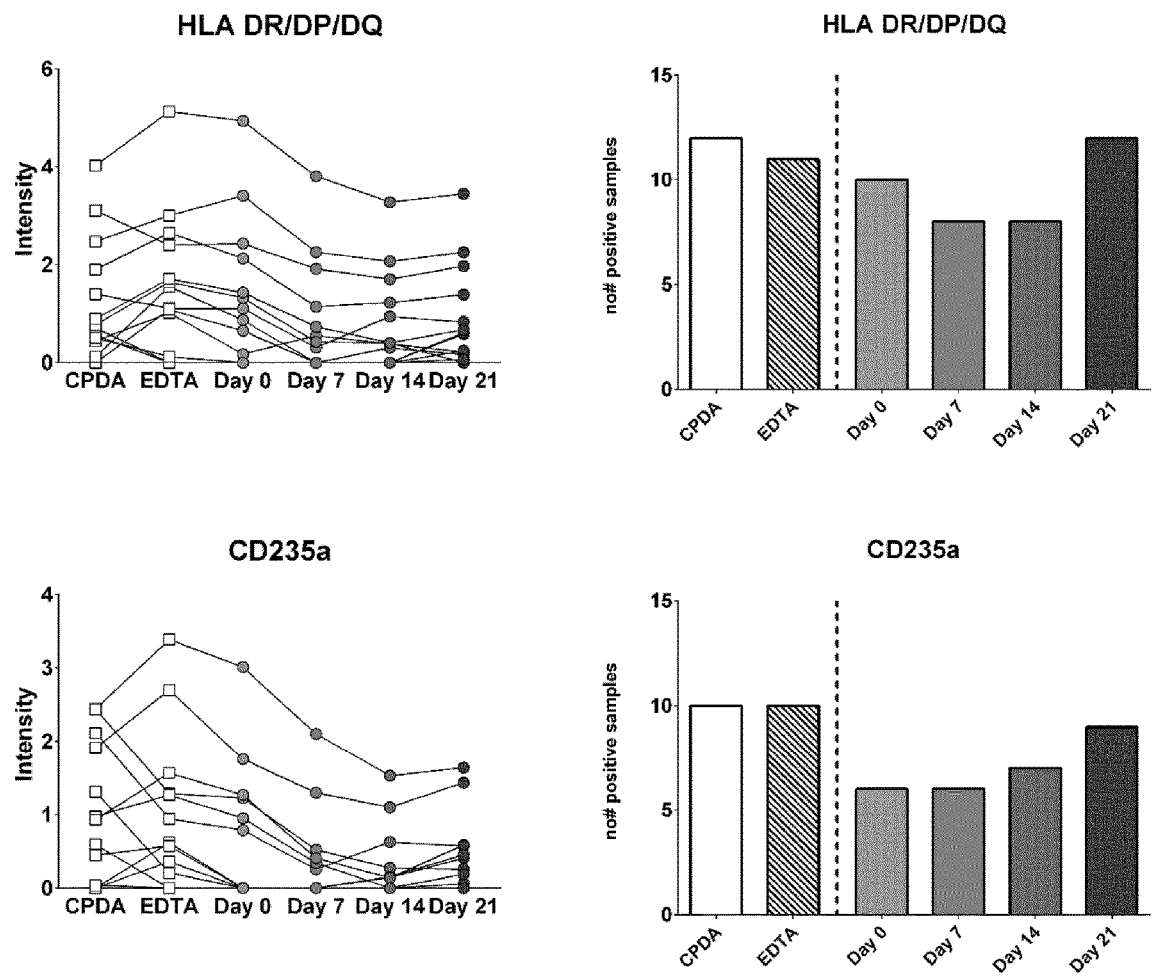

20 donors were asked to fill a blood card each, and to get drawn an ordinary blood sample of venous blood in EDTA and CPDA blood collection tubes. The blood was eluted from the blood card after 1 hour, 7 days, 14 days and 21 days. Buffer 8 (PBS with 0.2% Tween20) was used as both Elution- and Reaction Buffer. The protocol is schematically shown in FIG. 16.

The internal quality control shows a clear tendency of dropping when the vesicles are eluted from the blood card after 3 weeks (21 days) of storage at room temperature. This dropping was also visible during the fluorescent scanning of the slides, where an increased background signal was seen. If the background signal increases, it will influence the signal-to-noise ratio in a negative direction giving a lower analysis response. However, despite the dropping after 21 days, the level of the quality control is still at an acceptable level.

The graphs in FIGS. 18-22 show the results obtained for the vesicle detection. To the left is the quantitative measurements and to the right is the qualitative measurement depicting the number of positive samples obtained.

Conclusion

There are pronounced differences in the contents of vesicles between the donors. This is well-known from an earlier study (Bæk et al., 2016, Transf. Apheresis Sci.) and it was therefore important to test the protocol on a larger panel of donors. The results also showed differences when analyzing EVs obtained from conventional collection tubes (CPDA and EDTA), which is also known from a previously study (Bæk et al., 2016, J Imm. Meth.).

Several of the analytes showed a better signal when using blood eluted from the blood cards compared to normal venous blood samples. However, a quantitative comparison is not fair to the normal collection tubes, as only 10 µL where loaded onto the EV Array, compared to the 50 µL loaded from the blood card elutions (originating from one circleØ12.5 cm of the blood card). In addition, it should be taken into account that the donors have applied various amounts of finger blood onto the card. But the curves clearly show that analysis of EVs obtained from blood cards is possible and can be at least equally efficient as venous blood.

In FIGS. 18-22, the graphs presented to the right illustrate the qualitative data, which are the ones to focus on. These graphs show whether a vesicle type is present or not. There is a tendency that the number of positive samples drops the later the sample was eluted. However, this is not the case for CD235a, which increases the later the sample was eluted; cf. FIG. 22. CD235a is a marker of erythrocytes and a clear hemolysis is seen after elution from the blood cards. During hemolysis the erythrocytes are destroyed and thereby release their content of hemoglobin into the surroundings. In that process, there will also appear fragments of dead cells, which is probably also captured on the EV Array. However, only when the CD235a marker is in complex with at least one of the vesicle markers used for detection, a signal is obtained.

Example 4

Extraction of blood from four filter paper materials (card types) in combination with different buffers.

Four donors were asked to get drawn an ordinary blood sample of venous blood in EDTA, CPDA and serum blood collection tubes. 50 µL of blood from the serum tube was applied to four different card types:

Card type I: ArrayIt (Whole Blood Collection Card)
Card type II: Whatman (903TM Protein Saver Card)
Card type III: Whatman (FTA DMPK-C)
Card type IV: Whatman (ID Bloodstain Card)

Figure 23:
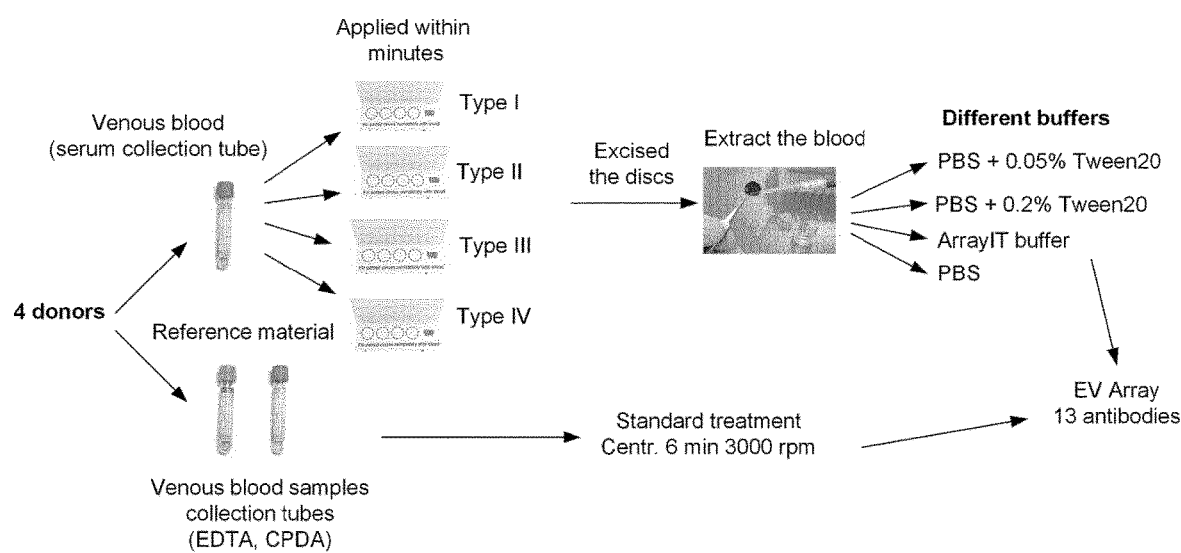
FIG. 23. Overview of experiment, example 4.
Figure 24:
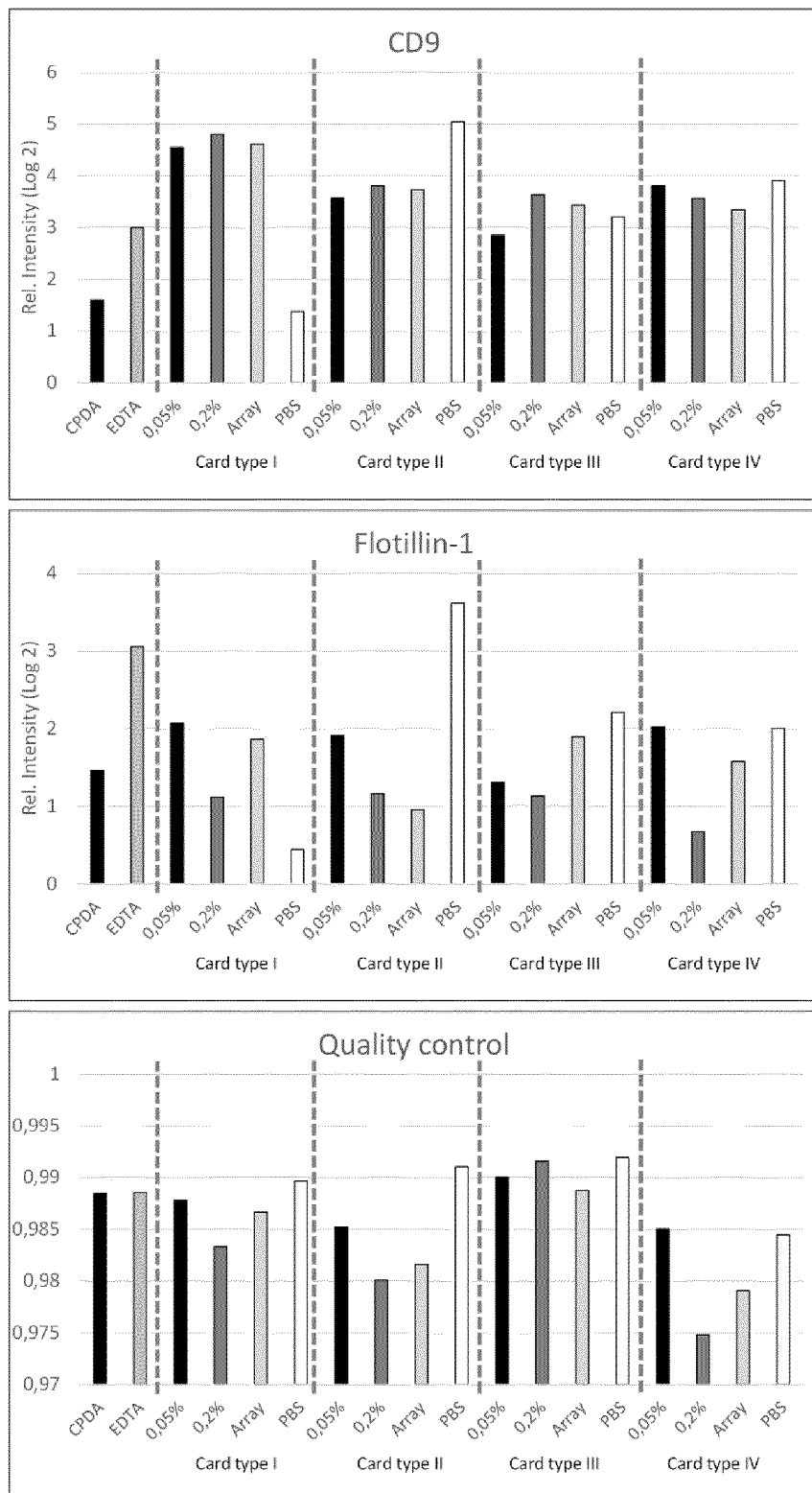
FIG. 24. Comparison of four card types and four buffers on the detection of CD9 and Flotilin-1 together with the quality control for donor #1.
Figure 25:
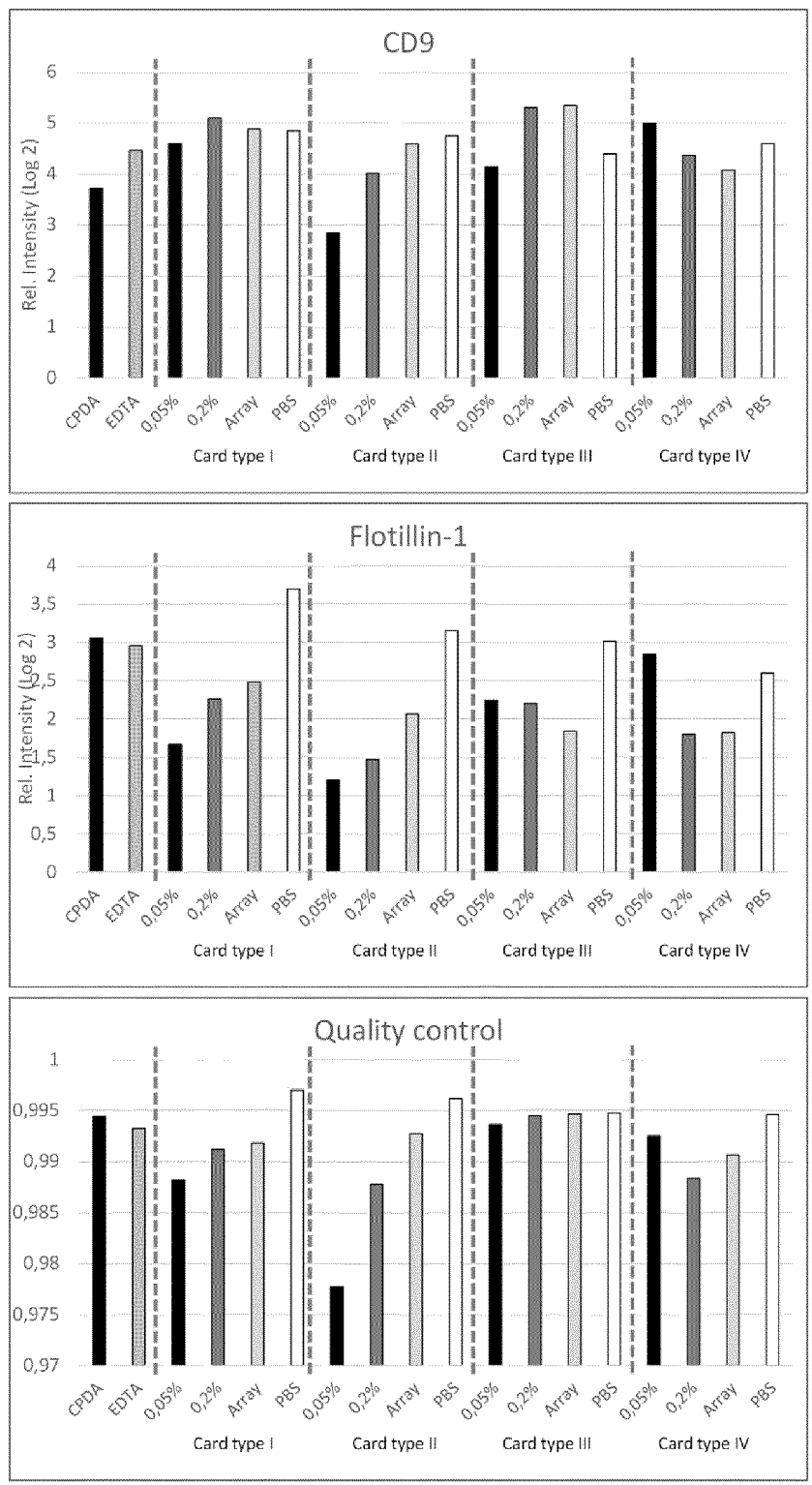
FIG. 25. Comparison of four card types and four buffers on the detection of CD9 and Flotilin-1 together with the quality control for donor #2.
Figure 26:
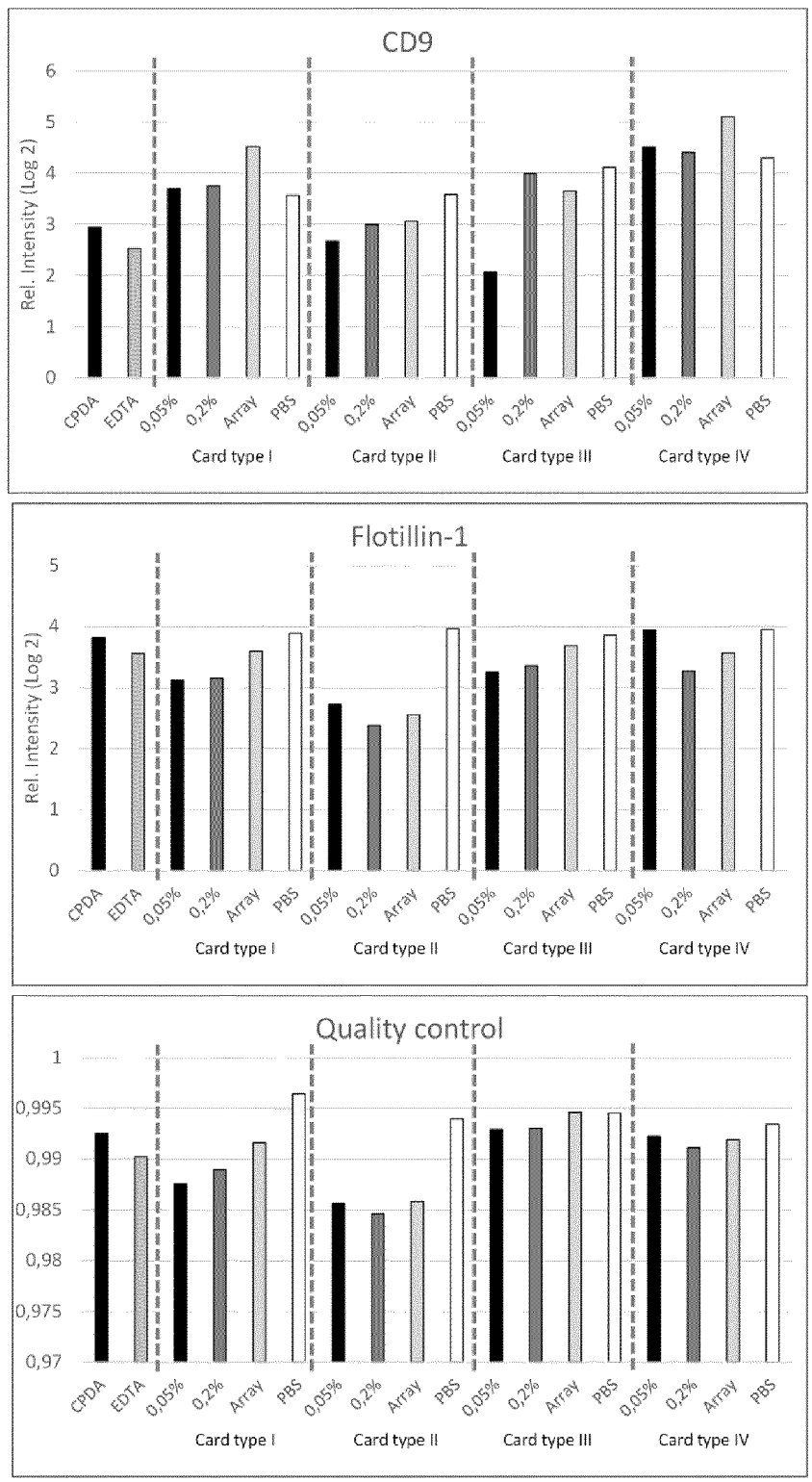
FIG. 26. Comparison of four card types and four buffers on the detection of CD9 and Flotilin-1 together with the quality control for donor #3.
Figure 27:
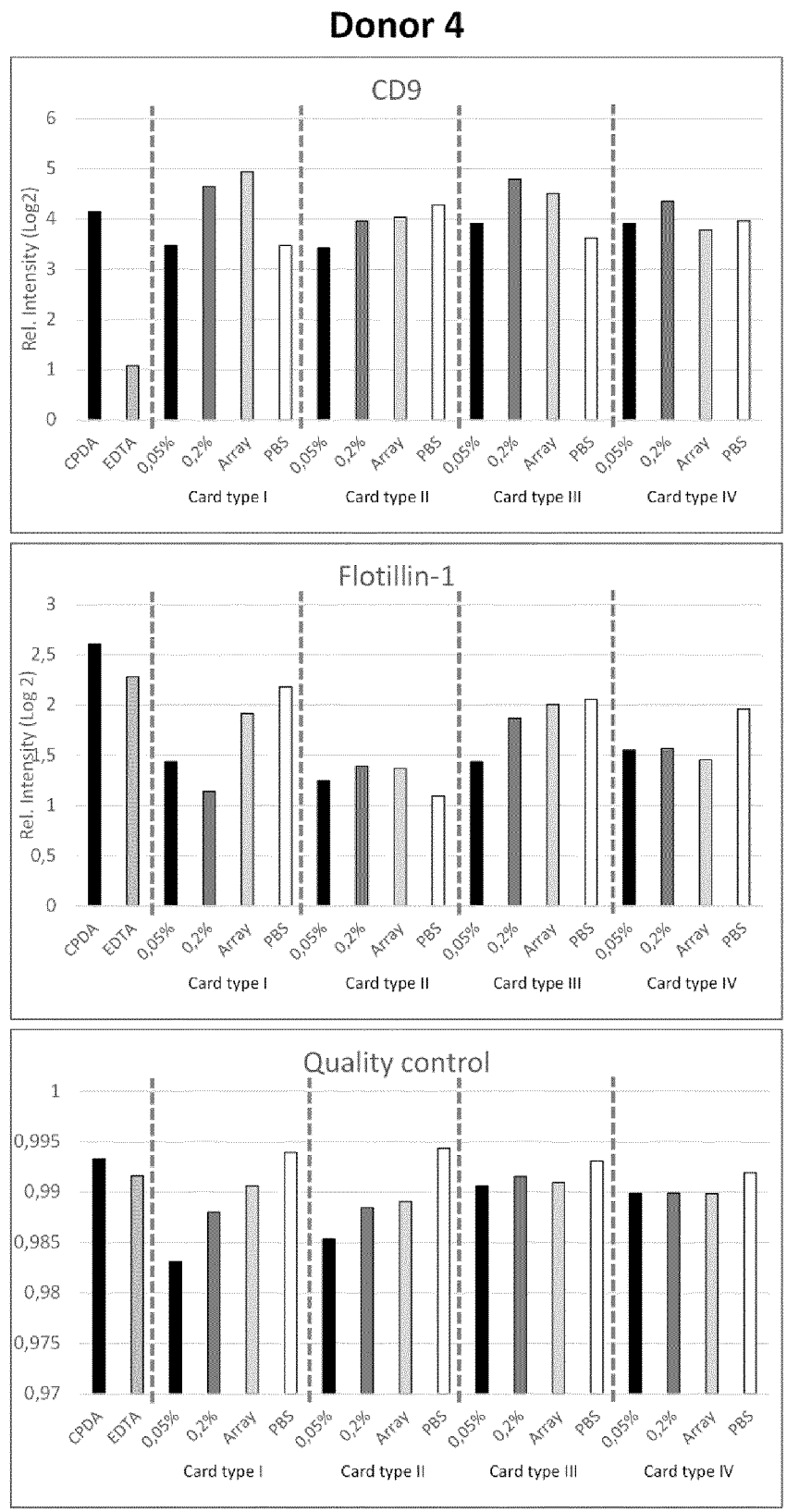
FIG. 27. Comparison of four card types and four buffers on the detection of CD9 and Flotilin-1 together with the quality control for donor #4.

The blood was eluted from the blood card after 1 hour using 4 different buffers as both Elution- and Reaction Buffer:

PBS with 0.2% Tween20; PBS with 0.05% Tween20; ArrayIt Elution Buffer; PBS. The protocol is schematically shown in FIG. 23.

The graphs in FIGS. 24-27 show the results obtained for the vesicle detection from 4 different donors. In the top of each figure is the quantitative measurements represented by CD9 and Flotilin-1 and at the bottom is the qualitative measurement depicting as bars.

Conclusion

From FIG. 24-27 it can be concluded that all the card types can be used ahead of the EV analysis. The different buffers show a variation in regards to be able to eluate the vesicles, but they all succeed in some degree. The quality controls revealed that PBS in general is the buffer that gives the best background (Highest QC value) for all the donors.

Example 5

Extraction of blood from four filter paper materials (card types) in combination with different separation filters.

One donor was asked to get drawn an ordinary blood sample of venous blood in serum blood collection tubes. 50 µL of blood from the serum tube was applied to the four different card types described in example 4.

The blood was eluted from the blood card after 1 hour using PBS as buffer (both Elution- and Reaction Buffer) and three filter types were tested for the separation:

Filter I: ArrayIt spin column (no poresize)
Filter II: Pierce (Spin cups with cellulose acetate filter, 0.45 µm pore size)
Filter III: Pierce (Spin column Snap Cap with polyethylene filter, 30 µm pore size)

Figure 28:
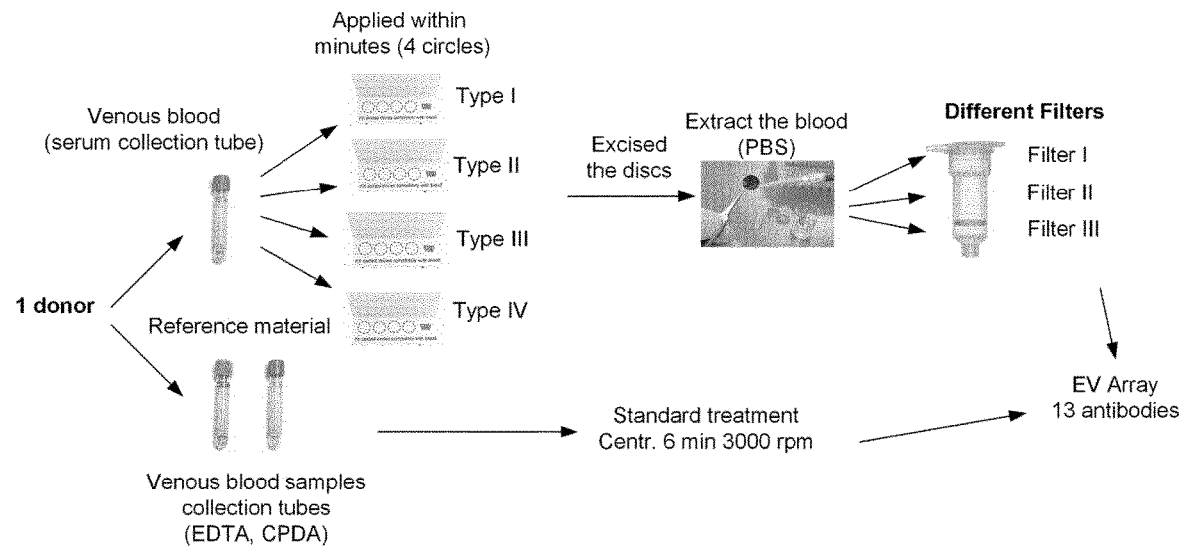
FIG. 28. Overview of experiment, example 5.

The protocol is schematically shown in FIG. 28.

Figure 29:
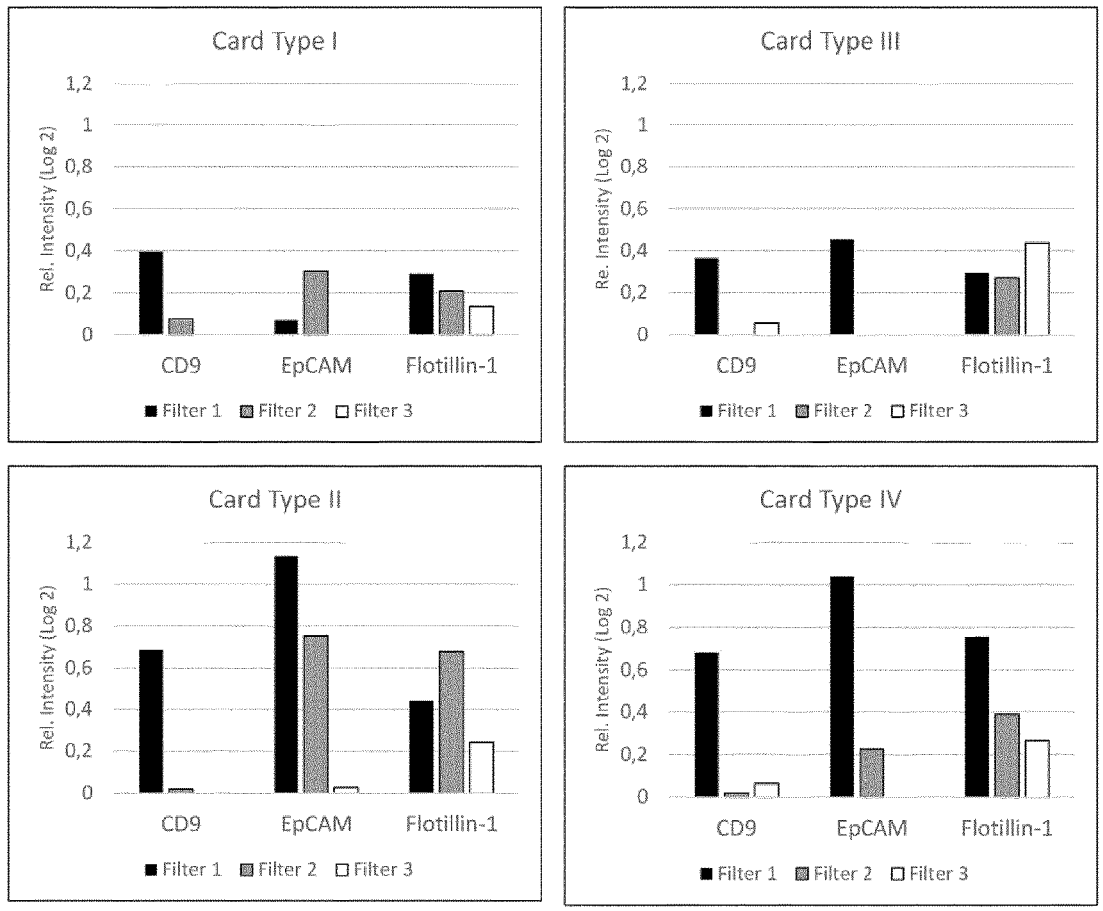
FIG. 29. Comparison of four card types in combination with three filter types on the detection of CD9, EpCAM and Flotilin-1.

The graphs in FIG. 29 show the results obtained for the vesicle detection from 4 different card types. The results are shown for CD9, EpCAM and Flotilin-1 for one donor measured in technical triplicates. The three different filter types are indicated as differently shaded bars.

Conclusion

All the card types and filter types are compatible with the following EV analysis. Although Card type I and III shows significant lower contents of vesicles for the given donor.

Generally, separation filter type I (ArrayIt) gives the most optimal results for all the card types as the results shown has been corrected for background.

Example 6

Time course experiment with extraction of blood from four filter paper materials (card types).

Based on the above results it was chosen to use PBS as buffer and separation filter type I (ArrayIt).

Figure 30:
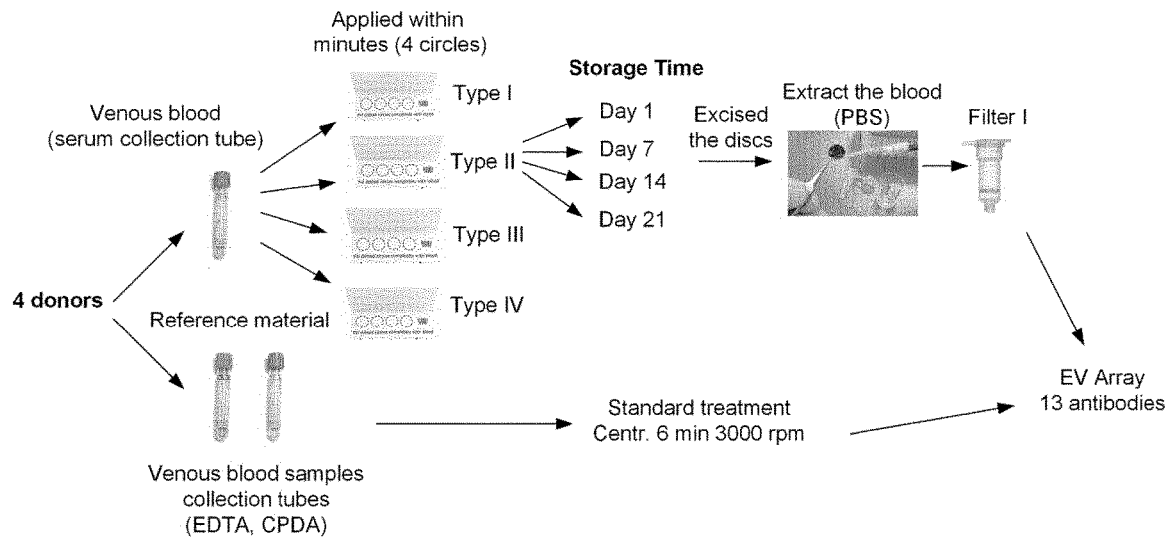
FIG. 30. Overview of experiment, example 6.
Figure 31:
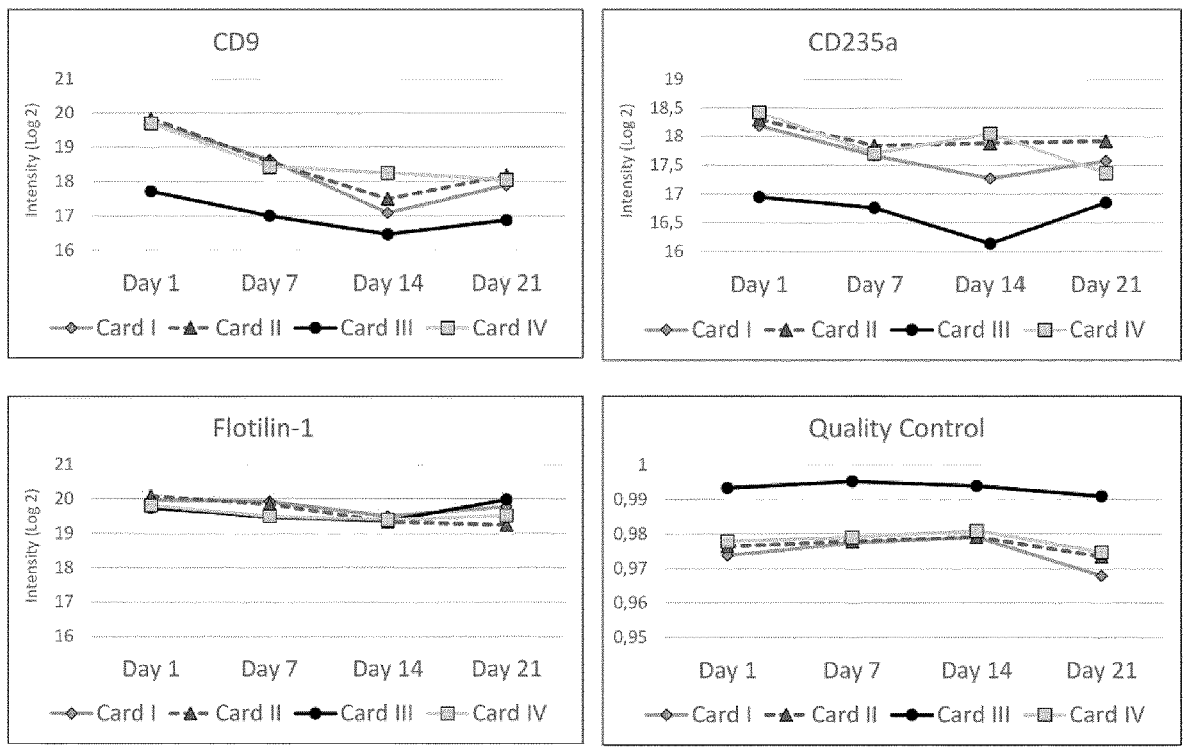
FIG. 31. Time course experiment comparing four card types on the detection of CD9, CD235a, Flotilin-1 together with the quality control for donor #1.
Figure 32:
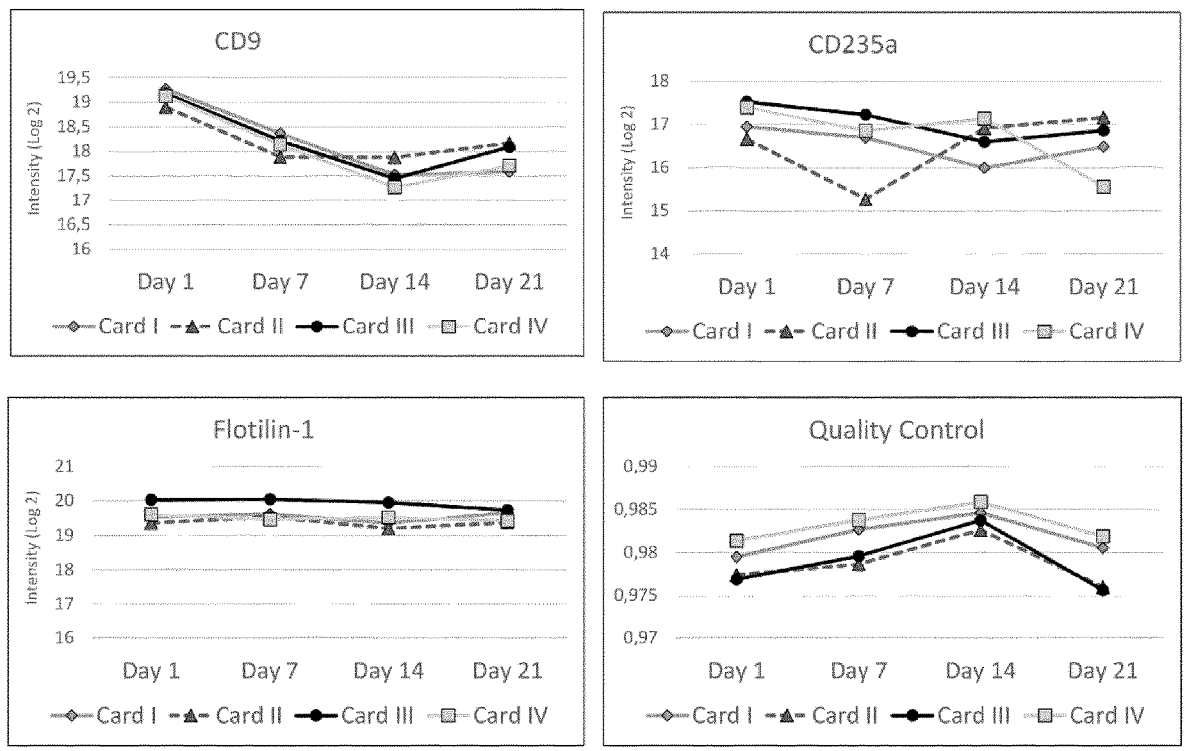
FIG. 32. Time course experiment comparing four card types on the detection of CD9, CD235a, Flotilin-1 together with the quality control for donor #2.
Figure 33:
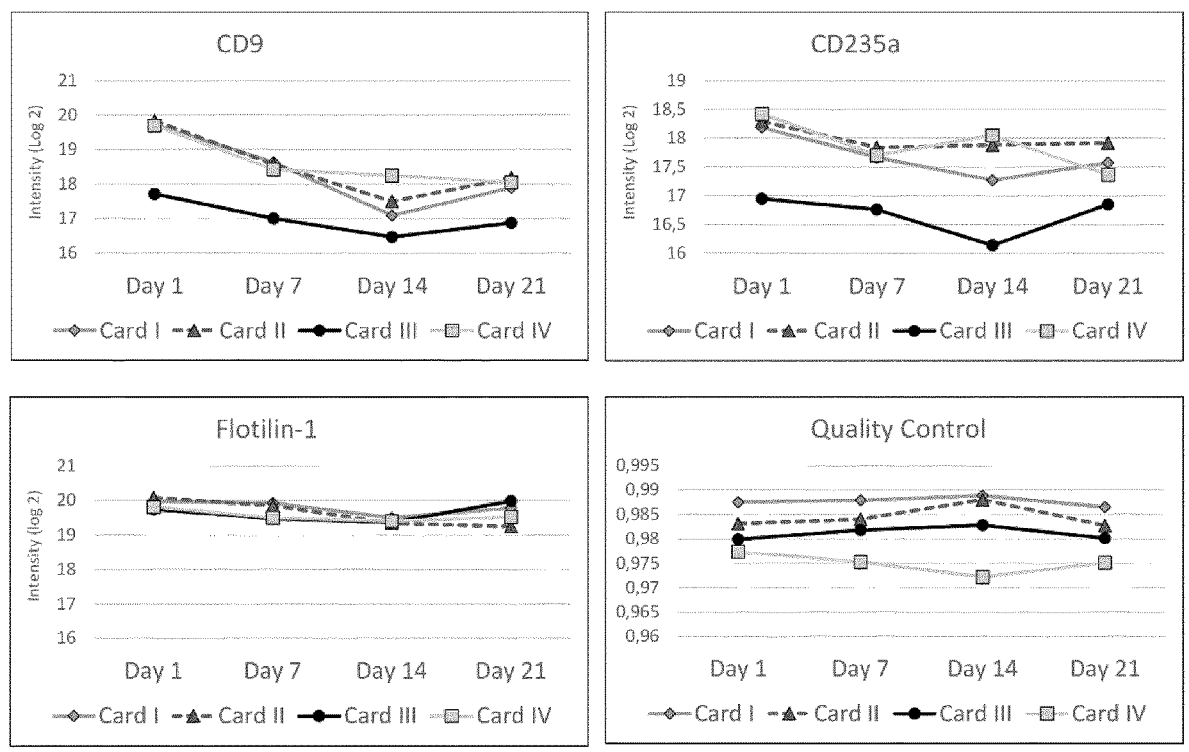
FIG. 33. Time course experiment comparing four card types on the detection of CD9, CD235a, Flotilin-1 together with the quality control for donor #3.
Figure 34:
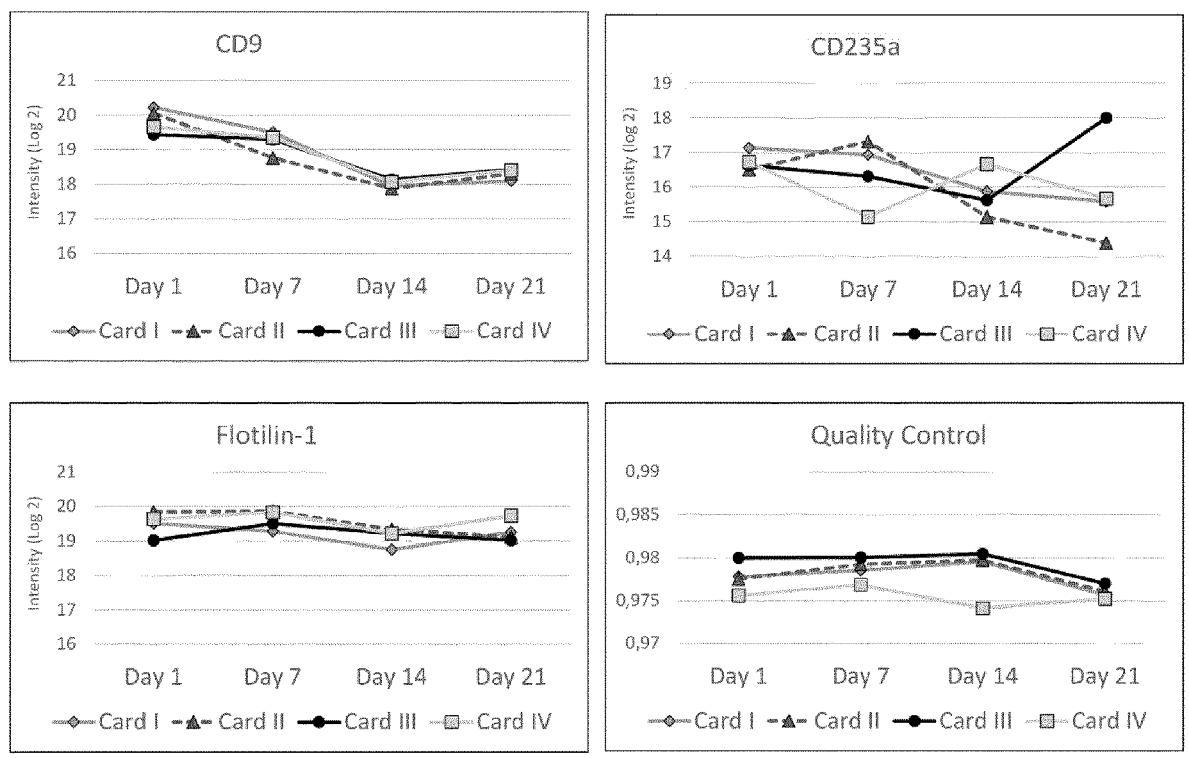
FIG. 34. Time course experiment comparing four card types on the detection of CD9, CD235a, Flotilin-1 together with the quality control for donor #4.

Four donors were asked to get drawn an ordinary blood sample of venous blood in EDTA, CPDA and serum blood collection tubes. 50 µL of blood from the serum tube were within minutes applied to the blood cards. The blood was eluted from the blood card after 1 hour, 7 days, 14 days and 21 days. PBS was used as both Elution- and Reaction Buffer. Everything was carried out with 4 technical replicates. The protocol is schematically shown in FIG. 30.

The results for CD9, Flotilin-1, CD235a together with the QC are presented in FIG. 31-34. The internal QC shows a tendency of dropping when the vesicles are eluted from the blood card after 3 weeks (21 days) of storage at room temperature. If the background signal increases, it will influence the signal-to-noise ratio in a negative direction giving a lower analysis response. However, despite the dropping after 21 days, the level of the QC is still at an acceptable level.

For all the four donors and all the four filter paper materials (card types) it is seen that the vesicles containing CD9 decreases during the time, but still after 21 days it is clearly detectable. This tendency is not seen for Flotilin-1, which have the same level through all the time courses.

Conclusion

All four card types can be used for storage of blood for up to at least 21 days. There are detectable differences between the filter paper materials (card types). Using PBS as buffer seems to have a good effect on the haematolysis of the red blood cells, which is seen as higher values of the QC.

Sequences

TABLE 3 overview of sequences of target proteins

| SEQ ID NO: | PROTEIN TYPE |
|---|---|
| 1 | HUMAN Actin, alpha skeletal muscle (ACTS) |
| 2 | HUMAN A-kinase anchor protein 3 (AKAP3) |
| 3 | HUMAN Programmed cell death 6-interacting protein (PDC6I) |
| 4 | HUMAN Annexin A5 (ANXA5) |
| 5 | HUMAN Amphiregulin (AREG) |
| 6 | HUMAN Actin, cytoplasmic 1 (ACTB) |
| 7 | HUMAN Galactoside 3(4)-L-fucosyltransferase (CA19-9 FUT3) |
| 8 | HUMAN Carbonic anhydrase 12 (CAH12) |
| 9 | HUMAN Endoglin (EGLN) |
| 10 | HUMAN Vascular cell adhesion protein 1 (CD106 VCAM1) |
| 11 | HUMAN Aminopeptidase N (AMPN) |
| 12 | HUMAN Syndecan-1 (SDC1) |
| 13 | HUMAN Monocyte differentiation antigen (CD14) |
| 14 | HUMAN Thrombomodulin (TRBM) |
| 15 | HUMAN Tissue factor (CD142 TF) |
| 16 | HUMAN Cell surface glycoprotein MUC18 (CD146 MUC18) |
| 17 | HUMAN CD151 antigen (CD151) |
| 18 | HUMAN Low affinity immunoglobulin gamma Fc region receptor III-A (CD16 FCG3A) |
| 19 | HUMAN Low affinity immunoglobulin gamma Fc region receptor III-B (FCG3B) |
| 20 | HUMAN P-selectin glycoprotein ligand 1 (SELPL) |
| 21 | HUMAN Scavenger receptor cysteine-rich type 1 protein M130 (C163A) |
| 22 | HUMAN Neural cell adhesion molecule L1 (L1CAM) |
| 23 | HUMAN B-lymphocyte antigen CD19 (CD19) |
| 24 | HUMAN Macrophage mannose receptor 1 (CD206 MRC1) |
| 25 | HUMAN Glycophorin-A (GLPA) |
| 26 | HUMAN CD276 antigen (CD276) |
| 27 | HUMAN T-cell-specific surface glycoprotein CD28 (CD28) |
| 28 | HUMAN T-cell surface glycoprotein CD3 (CD3) |
| 29 | HUMAN Leukocyte antigen CD37 (CD37) |
| 30 | HUMAN T-cell surface glycoprotein CD4 (CD4) |
| 31 | HUMAN Integrin alpha-IIb (ITA2B) |
| 32 | HUMAN Platelet glycoprotein IX (GPIX) |
| 33 | HUMAN Receptor-type tyrosine-protein phosphatase C (PTPRC) |
| 34 | HUMAN Integrin alpha-4 (ITA4) |
| 35 | HUMAN Neural cell adhesion molecule 1 (NCAM1) |
| 36 | HUMAN E-selectin (LYAM2) |
| 37 | HUMAN P-selectin (LYAM3) |
| 38 | HUMAN CD63 antigen (CD63) |
| 39 | HUMAN T-lymphocyte activation antigen CD80 (CD80) |
| 40 | HUMAN CD81 antigen (CD81) |
| 41 | HUMAN CD82 antigen (CD82) |
| 42 | HUMAN CD83 antigen (CD83) |

TABLE 3-continued overview of sequences of target proteins

| SEQ ID NO: | PROTEIN TYPE |
|---|---|
| 43 | HUMAN T-cell surface glycoprotein CD8 alpha chain (CD8A) |
| 44 | HUMAN CD9 antigen (CD9) |
| 45 | HUMAN Carcinoembryonic antigen-related cell adhesion molecule 5 (CEAM5) |
| 46 | HUMAN Hepatocyte growth factor receptor (MET) |
| 47 | HUMAN Coilin (COIL) |
| 48 | HUMAN Cytotoxic T-lymphocyte protein 4 (CTLA4) |
| 49 | HUMAN Epidermal growth factor receptor (EGFR) |
| 50 | HUMAN Epithelial cell adhesion molecule (EPCAM) |
| 51 | HUMAN Tumor necrosis factor ligand superfamily member 6 (TNFL6) |
| 52 | HUMAN Flotillin-1 (FLOT1) |
| 53 | HUMAN 78 kDa glucose-regulated protein (GRP78) |
| 54 | HUMAN Proheparin-binding EGF-like growth factor (HBEGF) |
| 55 | HUMAN Receptor tyrosine-protein kinase erbB-2 (ERBB2) |
| 56 | HUMAN Receptor tyrosine-protein kinase erbB-3 (ERBB3) |
| 57 | HUMAN Receptor tyrosine-protein kinase erbB-4 (ERBB4) |
| 58 | HUMAN Homeobox protein Hox-A7 (HXA7) |
| 59 | HUMAN Heat shock protein HSP 90-beta (HS90B) |
| 60 | HUMAN Intercellular adhesion molecule 1 (ICAM1) |
| 61 | HUMAN Lactadherin (MFGM) |
| 62 | HUMAN Lysosome-associated membrane glycoprotein 2 (LAMP2) |
| 63 | HUMAN Integrin alpha-L (ITAL) |
| 64 | HUMAN MHC class I polypeptide-related sequence A (MICA) |
| 65 | HUMAN MHC class I polypeptide-related sequence B (MICB) |
| 66 | HUMAN Mucin-1 (MUC1) |
| 67 | HUMAN Mucin-16 (MUC16) |
| 68 | HUMAN Cadherin-2 (CADH2) |
| 69 | HUMAN Nucleophosmin (NPM) |
| 70 | HUMAN Cancer/testis antigen 1 (CTG1B) |
| 71 | HUMAN Osteopontin (OSTP) |
| 72 | HUMAN Cellular tumor antigen p53 (p53) |
| 73 | HUMAN Tumor protein p73 (p73) |
| 74 | HUMAN Paired box protein Pax-8 (PAX8) |
| 75 | HUMAN Programmed cell death 1 ligand 1 (PD1L1) |
| 76 | HUMAN Alkaline phosphatase, placental type (PPB1) |
| 77 | HUMAN Pulmonary surfactant-associated protein D (SFTPD) |
| 78 | HUMAN Pulmonary surfactant-associated protein A1 (SFTA1) |
| 79 | HUMAN Toll-like receptor 3 (TLR3) |
| 80 | HUMAN Tumor necrosis factor receptor superfamily member 1A (TNR1A) |
| 81 | HUMAN Tumor susceptibility gene 101 protein (TS101) |
| 82 | HUMAN Tetraspanin-8 (TSN8) |
| 83 | HUMAN Vascular endothelial growth factor receptor 2 (VGFR2) |
| 84 | HUMAN Carbonic anhydrase 9 (CAH9) |
| 85 | HUMAN Basigin (BASI) |
| 86 | HUMAN Claudin-1 (LRP1) |
| 87 | HUMAN Prolow-density lipoprotein receptor-related protein 1 (LRP1) |

The invention claimed is:

1. A method comprising
a) providing a dried body fluid card sample,
b) eluting the sample using an elution buffer, which supports extraction of intact and detectable extracellular vesicles, and
c) detecting at least one member of a plurality of genes or gene products associated with a population of extracellular vesicles.

2. The method according to claim 1, wherein said method further comprises
d) detecting at least one member of a plurality of genes or gene products associated with a clinical condition.

3. The method according to claim 2, wherein said clinical condition is a cancer selected from the group consisting of Non-Small Cell Lung Cancer (NSCLC), Small Cell Lung Cancer (SCLC), prostate cancer, rectal cancer, Melanoma, Osteosarcoma, lymphoma, breast cancer, and ovarian cancer, or wherein said clinical condition is selected from the group consisting of Pneumonia, abortus habitualis, stroke, brain hemorrhage, multiple sclerosis, Chronic Obstructive Pulmonary Disease (COPD), malaria, HPV, Monoclonal gammopathy of undetermined significance (MGUS), Systemic Lupus Erythematosus (SLE), and Ischemia.

4. The method according to claim 3, wherein the rectal cancer is locally advanced rectal cancer (LARC).

5. The method according to claim 2, wherein said clinical condition is non-small cell lung cancer and said at least one member of a plurality of genes or gene products are selected from the group consisting of NY-ESO-1, EGFR, PLAP, EpCam and Alix.

6. The method according to claim 2, wherein said clinical condition is lung cancer and said at least one member of said plurality of genes or gene products are selected from the group consisting of CD151, CD171 and tetraspanin 8.

7. The method according to claim 2, wherein said at least one member of a plurality of genes or gene products associated with a population of extracellular vesicles and/or a clinical conditions are selected from the group consisting of Annexin V, CD19, CD106, CD142, TNF RI, CD42a, CD81, Alix, CD63, CD62E, CD3, Flotillin-1, TSG101, ICAM-1.

8. The method according to claim 2, wherein said at least one member of said plurality of genes or gene products associated with a population of extracellular vesicles and/or at least one member of said plurality of genes or gene products associated with a clinical condition is detected by an antibody.

9. The method according to claim 2, wherein said at least one member of said plurality of genes or gene products associated with a population of extracellular vesicles and/or at least one member of said plurality of genes or gene products associated with a clinical condition is detected by a protein microarray.

10. The method according to claim 1, wherein said body fluid is blood and the sample is a dry blood card sample.

11. The method according to claim 1, wherein said elution buffer is a pH-buffered solution.

12. The method according to claim 11, wherein the pH-buffered solution, is phosphate buffered saline (PBS).

13. The method according to claim 1, wherein said elution buffer comprises one or more ingredients selected from the group consisting of polysorbate 20, Sodium dodecyl sulfate (SDS), CHAPS, N-octylglucoside, octyl phenol ethoxylate, sodium azide ($NaN_3$), sodium chloride (NaCl), potassium chloride (KCl), sodium phosphate ($Na_2HPO_4$), potassium phosphate $NaH_2PO_4$, EDTA, Tris, MES, HEPES, MOPS, Tris-base, polysaccharides, glucose, sucrose, sodium diatrizoate and polysaccharides, and/or iodixanol.

14. The method according to claim 1, wherein said extracellular vesicles are exosomes.

15. The method according to claim 1, wherein said at least one member of a plurality of genes or gene products associated with a population of extracellular vesicles are selected from the group consisting of tetraspanins, annexins and heat shock proteins.

16. The method according to claim 1, wherein said at least one member of a plurality of genes or gene products associated with a population of extracellular vesicles are selected from the group consisting of CD9, CD63, CD62E, CD81, CD142, Flot-1, N-Cad, CD105, CD235a, CD42b, CD138, CD141 and CD162.

17. The method according to claim 1, wherein said at least one member of a plurality of genes or gene products associated with a population of extracellular vesicles are selected from the group consisting of CD9, CD63 and CD81.

18. The method according to claim 1, wherein the material for the dried body fluid card sample is absorbent filter paper, nitrocellulose membrane or polyvinylidene difluoride (PVDF).

* * * * *